(12) United States Patent
Reed et al.

(10) Patent No.: US 11,905,558 B2
(45) Date of Patent: Feb. 20, 2024

(54) SYSTEM AND METHOD FOR SEQUENCING

(71) Applicant: LIFE TECHNOLOGIES CORPORATION, Carlsbad, CA (US)

(72) Inventors: Mark Reed, Menlo Park, CA (US); Chiu Tai Andrew Wong, Orange, CT (US); David Marran, Durham, CT (US)

(73) Assignee: Life Technologies Corporation, Carlsbad, CA (US)

( * ) Notice: Subject to any disclaimer, the term of this patent is extended or adjusted under 35 U.S.C. 154(b) by 311 days.

(21) Appl. No.: 16/994,318

(22) Filed: Aug. 14, 2020

(65) Prior Publication Data

US 2021/0054450 A1  Feb. 25, 2021

Related U.S. Application Data

(60) Provisional application No. 62/890,003, filed on Aug. 21, 2019.

(51) Int. Cl.
*C12Q 1/6874* (2018.01)

(52) U.S. Cl.
CPC .................................. *C12Q 1/6874* (2013.01)

(58) Field of Classification Search
CPC ................ C12Q 1/6874; C12Q 1/6806; C12Q 2535/122; C12Q 2527/113; B01J 2219/00608; B01J 2219/00722; B01J 19/0046; B01J 19/00; G16B 30/00
See application file for complete search history.

(56) References Cited

U.S. PATENT DOCUMENTS

| | | | |
|---|---|---|---|
| 5,223,414 A | 6/1993 | Zarling et al. | |
| 5,273,881 A | 12/1993 | Sena et al. | |
| 5,670,316 A | 9/1997 | Sena et al. | |
| 7,270,981 B2 | 9/2007 | Armes et al. | |
| 7,399,590 B2 | 7/2008 | Piepenburg et al. | |
| 7,435,561 B2 | 10/2008 | Piepenburg et al. | |
| 7,575,865 B2 * | 8/2009 | Leamon ................. | C07H 21/00 435/6.12 |
| 7,666,598 B2 | 2/2010 | Piepenburg et al. | |
| 7,763,427 B2 | 7/2010 | Piepenburg et al. | |
| 8,017,339 B2 | 9/2011 | Piepenburg et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 9,243,085 B2 | 1/2016 | Fonnum et al. | |
| 9,428,807 B2 | 8/2016 | Hubbell et al. | |
| 9,868,826 B2 | 1/2018 | Fonnum et al. | |
| 9,953,130 B2 | 4/2018 | Gottimukkala et al. | |
| 10,241,075 B2 | 3/2019 | Davey et al. | |
| 2012/0046877 A1 | 2/2012 | Hyland et al. | |
| 2012/0077716 A1 * | 3/2012 | Godwin ............. | C12N 15/1079 506/26 |
| 2012/0109598 A1 | 5/2012 | Davey et al. | |
| 2012/0156728 A1 | 6/2012 | Li et al. | |
| 2012/0197623 A1 | 8/2012 | Homer | |
| 2013/0090860 A1 | 4/2013 | Sikora et al. | |
| 2013/0345066 A1 | 12/2013 | Brinza et al. | |
| 2014/0051584 A1 | 2/2014 | Davey et al. | |
| 2014/0052381 A1 | 2/2014 | Utiramerur et al. | |
| 2014/0256571 A1 | 9/2014 | Konvicka | |
| 2014/0296080 A1 | 10/2014 | Hubbell et al. | |
| 2016/0019340 A1 | 1/2016 | Gottimukkala et al. | |
| 2016/0103957 A1 | 4/2016 | Veitch et al. | |
| 2018/0336316 A1 | 11/2018 | Bai | |
| 2019/0087539 A1 | 3/2019 | Gottimukkala et al. | |
| 2019/0194719 A1 | 6/2019 | Rosenbaum et al. | |
| 2019/0255505 A1 | 8/2019 | Rosenbaum et al. | |

FOREIGN PATENT DOCUMENTS

| | | | | |
|---|---|---|---|---|
| CN | 101278295 A | 10/2008 | | |
| CN | 109486902 A | 3/2019 | | |
| EP | 3095879 A1 * | 11/2016 | ................ | B01L 7/00 |
| WO | WO-2014062717 A1 | 4/2014 | | |
| WO | WO-2019094524 A1 | 5/2019 | | |

OTHER PUBLICATIONS

Damerla et al, Ion Torrent sequencing for conducting genome-wide scans for mutation mapping analysis, 2014, Mamm. Genome, 25:120-128 (Year: 2014).*
Loka et al., "Reliable variant calling during runtime of Illumina sequencing", bioRxiv, 9 Aug. 9, 2018,, www.biorxiv.org/content/10.1101/387662v1.full.pdf [retrieved on Nov. 13, 2020].
PCT/US2020/046510, Search Report and Written Opinion, dated Nov. 24, 2020, 13 pages.
Zook et al., "Extensive sequencing of seven human genomes to characterize benchmark reference materials", Scientific Data, vol. 3, Jun. 7, 2016, p. 160025.

* cited by examiner

*Primary Examiner* — Narayan K Bhat

(57) ABSTRACT

A sequencing system includes an automated sequencing instrument adapted to determine variant calls for one or more extracted polynucleotide samples with a performance of at least 98.5% raw read accuracy and a run time in a range of 5 hours to 14 hours to determine variant calls for 4 extracted polynucleotide samples using a targeted assay with one DNA pool per sample and an average amplicon size in a range of 100 to 120 bases.

16 Claims, 45 Drawing Sheets

Specification includes a Sequence Listing.

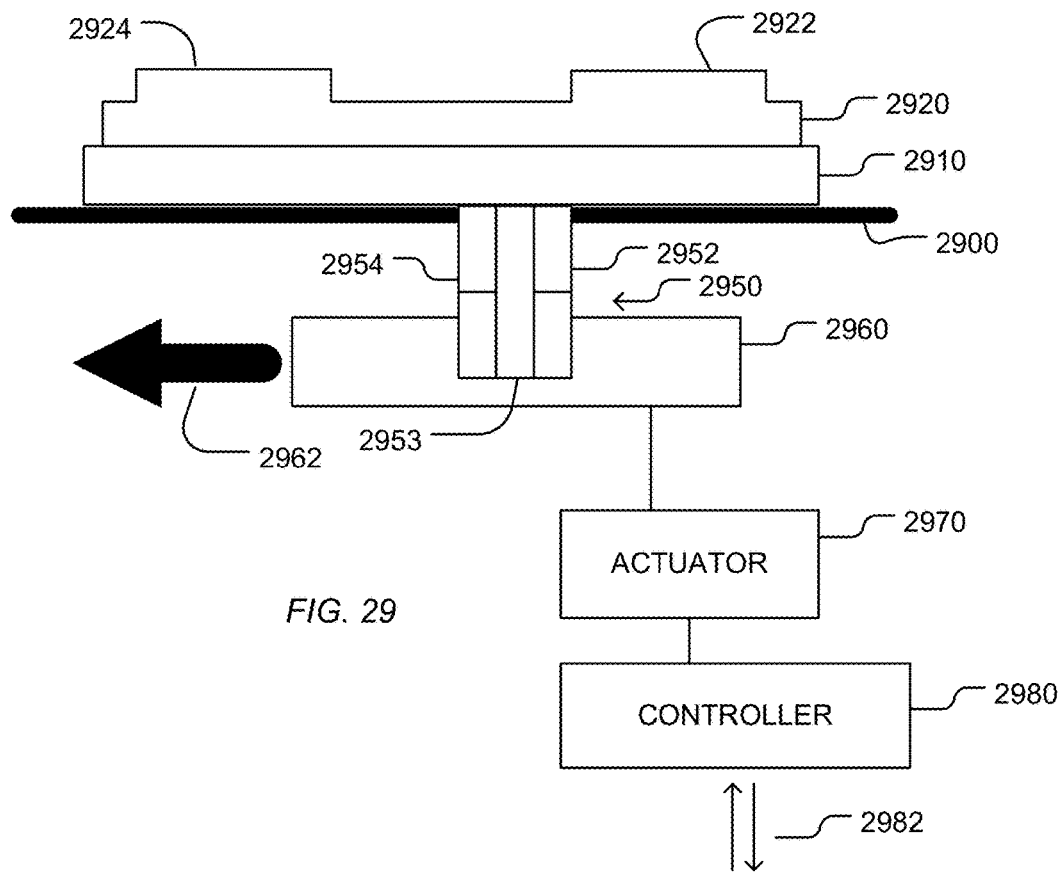
FIG. 29
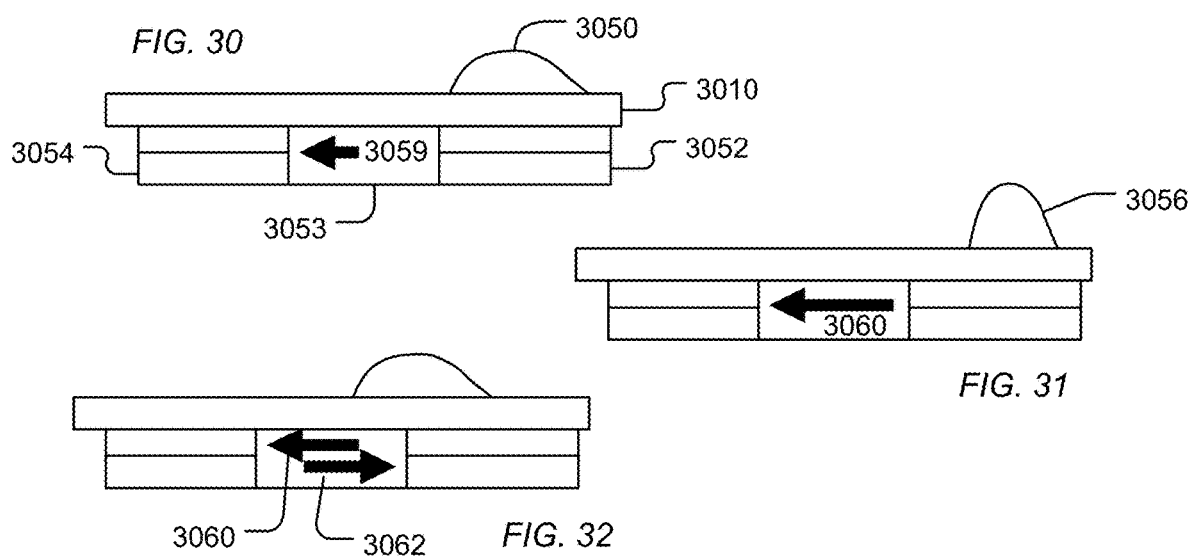
FIG. 30
FIG. 31
FIG. 32

NUMERICAL REFRENCES IN FIG. 39 ARE ASSUMED TO BEGIN WITH 4

NUMERICAL REFRENCES IN FIG. 42 ARE ASSUMED TO BEGIN WITH 4

NUMERICAL REFRENCES IN FIG. 46 ARE ASSUMED TO BEGIN WITH 4

SYSTEM AND METHOD FOR SEQUENCING

CROSS-REFERENCE TO RELATED APPLICATION(S)

This application claims benefit of U.S. Provisional Application No. 62/890,003, filed Aug. 21, 2019, which is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "LT01383_ST25.txt" created on Oct. 12, 2020, and is 2,000 bytes in size. The sequence listing contained in this .txt file is part of the specification and is hereby incorporated by reference herein in its entirety.

FIELD OF THE DISCLOSURE

The present disclosure relates generally to systems and methods for manipulating and analyzing nucleic acids.

BACKGROUND

Increasingly, biological and medical research is turning to nucleic acid sequencing for enhancing biological studies and medicine. For example, biologists and zoologists are turning to sequencing to study the migration of animals, the evolution of species, and the origins of traits. The medical community is using sequencing for studying the origins of disease, sensitivity to medicines, and the origins of infection. As such, sequencing has wide applicability in many aspects of biology, therapeutics, diagnostics, forensics, and research.

Nevertheless, the use of sequencing can be limited by assay availability, sequencing run time, preparation time, and cost. Additionally, quality sequencing has historically been an expensive process, thus limiting its practice.

As such an improved sequencing system would be desirable.

BRIEF DESCRIPTION OF THE DRAWINGS

The present disclosure may be better understood, and its numerous features and advantages made apparent to those skilled in the art by referencing the accompanying drawings.

FIG. 29 includes a schematic presentation of an example magnetic loading system.

FIG. 30 schematically illustrates movement of a solution containing magnetic beads relative to a magnetic package at a first speed.

FIG. 31 schematically illustrates movement of a solution containing magnetic beads relative to a magnetic package at a second speed.

FIG. 32 schematically illustrates movement of a solution containing magnetic beads relative to a magnetic package in reverse direction.

The use of the same reference symbols in different drawings indicates similar or identical items.

DETAILED DESCRIPTION

Figure 1:
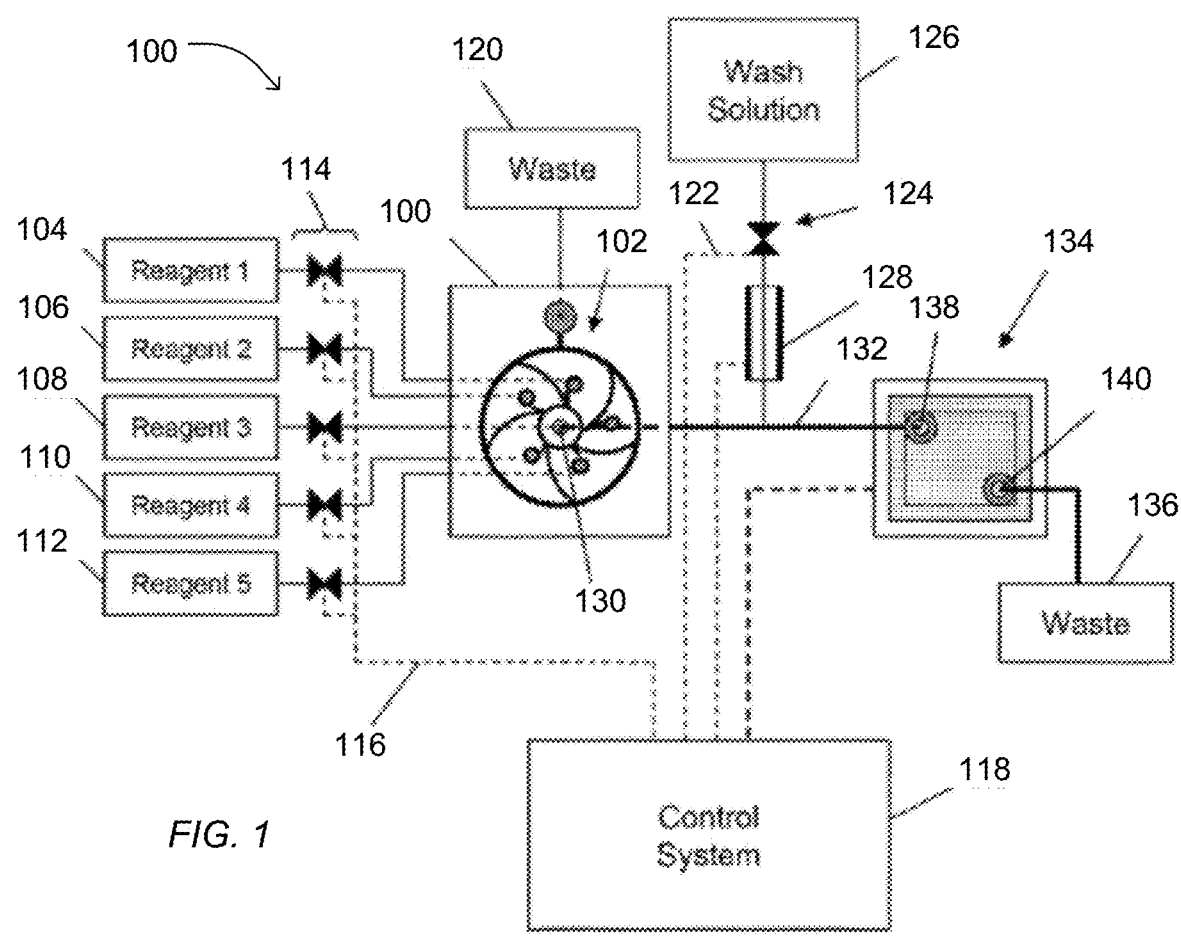
FIG. 1 includes an illustration of an example sequencing system.

In an embodiment, a sequencing system includes an automated sequencing instrument adapted to determine sequences of polynucleotides and variant calls from a set of sample polynucleotides. The system can utilize a targeted assay to generate a library of amplicons or target polynucleotides that are sequenced to provide an aligned sequence listing and optionally, variant calls within a desirable time.

Embodiments of the automated sequencing instruments include a preparation deck for preparing libraries of targeted polynucleotides. In an example, the targeted polynucleotides are seeded onto a substrate, such as a polymeric or hydrogel bead. The automated sequencing instrument can further include a loading device to apply the seeded substrate onto a sensor device and can include a sequencer, for example, to perform sequencing-by-synthesis reactions, detecting nucleotide incorporations. The automated sequencing instrument can further include computational devices to utilize the data from the sequencer to determine base calls, aligned reads, and variant calls. In addition, the system can include user interfaces or network interfaces to communicate reports associated with the base calls, aligned reads, or variant calls to a user.

Definitions

As used herein, the term "nucleic acid" and its variants, which is used interchangeably herein with the term "polynucleotide," refers to a polymer of nucleotides and includes, for example, deoxyribonucleic acid and ribonucleic acid. Nucleic acids include, but are not limited to, DNA, cDNA, RNA, chimeric RNA/DNA, and nucleic acid analogs.

As used herein, a primer is any single-stranded nucleic acid molecule (e.g., an oligonucleotide) that, once hybridized to a complementary nucleic acid sequence, can prime, or initiate, nucleic acid synthesis. Typically, such nucleic acid synthesis occurs in a template-dependent fashion, and nucleotides are polymerized onto at least one end of the primer during such nucleic acid synthesis. Primers typically have a free 3' hydroxyl, however in some embodiments, a primer end is blocked (e.g., to prevent extension from the 3' end) or the primer is a fusion primer in which different portions of the primer are designed to bind to different partners. In a reaction that involves primer extension (e.g., pre-seeding amplification), a blocking moiety at the 3' end of a blocked fusion primer can reduce the level of primer-dimer formation. In some embodiments, blocked or unblocked primers are tailed primers wherein the 5' end includes a sequence that is non-complementary to a target nucleic acid to which the rest of the primer is complementary. This 5' tail can be used as a template for primer extension. In various embodiments of methods provided herein, nucleic acid molecules include a first primer binding sequence and optionally a second primer binding sequence. In some embodiments, reactions described herein include a population of first primers and optionally a population of second primers that bind the forward primer binding and reverse primer binding sequences, respectively, or vice versa. In some embodiments, the first and second primers are referred to as a primer pair. In some embodiments, the first primers or the second primers are universal primers. The first primer can bind to either the forward primer binding sequence or the reverse primer binding sequence and the second primer can bind to either the forward primer binding sequence or the reverse primer binding sequence. Accordingly, the terms "first" and "second" when used herein with reference to a primer are relative terms, and each can refer to a forward or reverse primer depending on the context in which they are used.

As used herein, nucleic acid amplification refers to a process in which a new strand of a nucleic acid is synthesized through nucleotide polymerization and involves one or more cycles of the following: separation, e.g., denaturation or dissociation, of double-stranded nucleic acids into single strands, annealing, e.g., hybridization, of a primer to single strands of the separated double-stranded nucleic acids and extension of the hybridized primers. The term "primer extension" and its variants, as used herein, relates to any method for catalyzing nucleotide incorporation onto a terminal end of a nucleic acid molecule. In some embodiments, a cycle of amplification includes (a) partial, incomplete, or complete denaturation or dissociation of the strands of a double-stranded nucleic acid, (b) hybridization or annealing of a primer to a partially or completely single-stranded nucleic acid, and (c) primer extension to form an extended primer strand. In some embodiments, a cycle of amplification optionally includes (a) hybridization of a first primer to a template nucleic acid strand, (b) primer extension to form a first extended nucleic acid strand, and (c) partial or incomplete denaturation of the extended strand from the template strand. Optionally, the denatured portion of the template strand from step (c) is free to hybridize with a different primer in the next amplification cycle. In some embodiments, primer extension in an amplification cycle involves displacement of one strand of a duplex nucleic from the other strand of the duplex or displacement of the first extended strand from the template strand. A second primer can be included which hybridizes to the 3' end of the first extended strand.

Numerous methods of nucleic acid amplification are known in the art. Some examples include recombinase-polymerase amplification (RPA), template walking and polymerase chain reaction (PCR) amplification. In an RPA reaction, nucleic acid molecules are amplified using a recombinase, polymerase, and optionally a recombinase accessory protein in the presence of primers and nucleotides. The recombinase and optionally the recombinase accessory protein can dissociate at least a portion of a double-stranded template nucleic acid molecules to allow primers to hybridize that the polymerase can then bind to initiate replication. An example of a recombinase accessory protein is a single-stranded binding protein (SSB) that prevents the re-hybridization of dissociated nucleic acid molecules. Typically, RPA reactions are isothermal and performed at isothermal temperatures. In some instances, an RPA reaction can be performed within an emulsion. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are typically dissociated by thermal cycling. After cooling, primers bind to complementary sequences and can be used for replication by the polymerase. In some of the embodiments of methods provided herein, a pre-seeding or templating reaction is performed in a reaction mixture formed with the components necessary for amplification of the template nucleic acid molecules. In any of the disclosed aspects, the reaction mixture includes some or all of the following: a population of template nucleic acid molecules, a polymerase, one or more supports or surfaces (e.g., solid supports) with a population of attached first primers, nucleotides, or a cofactor such as a divalent cation. In some embodiments, the reaction mixture further includes a second primer and optionally a diffusion-limiting agent. In some embodiments, the population of template nucleic acid molecules comprise template nucleic acid molecules joined to at least one adaptor sequence which hybridizes to the first or second primers. In some embodiments, the reaction mixture forms an emulsion, as in emulsion RPA or emulsion PCR. In reactions involving RPA, the reaction mixture includes a recombinase and optionally a recombinase accessory protein. The various components of the reaction mixture are discussed in further detail herein.

As used herein, the terms "identity" and "identical" and their variants, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window or designated region. Sequences are said to be "substantially identical" when there is at least about 80%, or at least about 85%, identity at the amino acid level or at the nucleotide level. In some instances, sequences are "substantially identical" when there is at least 90% identity, at least 91% identity, at least 92% identity, at least 93% identity, at least 94% identity, at least 95% identity, at least 96% identity, at least 97% identity, at least 98% identity, at least 99% identity at the amino acid level or at the nucleotide level. Preferably, the identity exists over a region that is at least about 20, 25, 50, or 100 residues in length, or across the entire length of at least one compared sequence. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences or primers) that can undergo cumulative base pairing at two or more individual corresponding positions in antiparallel orientation, as in a hybridized duplex. Such base pairing can proceed according to any set of established rules, for example according to Watson-Crick base pairing rules. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the sequences where two opposed nucleotides are not complementary. Complementary nucleotides include nucleotides that are efficiently incorporated by DNA polymerases opposite each other during DNA replication under physiological conditions.

As used herein, the term "monoclonal" and its variants, when used in reference to one or more polynucleotide populations, refers to a population of polynucleotides where at about 50-99%, or up to 100%, or 100% of the members of the population share at least 80% identity, or at least 85% identity, or at least 90% identity, or at least 95% identity, or at least 99% identity, or about 100% identity, or 100% identity at the nucleotide sequence level. As used herein, the phrase "substantially monoclonal" and its variants, when used in reference to one or more polynucleotide populations, refer to one or more polynucleotide populations wherein one polynucleotide molecule, e.g., an amplified template polynucleotide molecule, is the single most prevalent polynucleotide in the population. Accordingly, all members of a monoclonal or substantially monoclonal population need not be completely identical or complementary to each other. For example, different portions of a polynucleotide template can become amplified or replicated to produce the members of the resulting monoclonal population; similarly, a certain number of "errors" or incomplete extensions may occur during amplification of the original template, thereby generating a monoclonal or substantially monoclonal population whose individual members can exhibit sequence variability amongst themselves. In some embodiments, a low or insubstantial level of mixing of non-homologous polynucleotides may occur during nucleic acid amplification reactions, and thus a substantially monoclonal population may contain a minority of one or more polynucleotides (e.g., less than 50%, less than 40%, less than 30%, less than 20%, less than 10%, less than 5%, less than 1%, less than 0.5%, less than 0.1%, or less than 0.001%, of diverse polynucleotides). In certain examples, at least 90% of the polynucleotides in the population are at least 90% identical to the original single template used as a basis for amplification to produce the substantially monoclonal population. In certain embodiments, amplifying of a template polynucleotide yields a population of polynucleotides wherein at least 50%, 60%, 70%, 75%, 80%, 85%, 90%, 91%, 92%, 93%, 94%, 95%, 96%, 97%, 98%, 99%, or 100% of the members of a population of polynucleotides share at least 50%, 60%, 70%, 75%, 80%, 85%, 90%, 95%, 96%, 97%, 98%, 99%, or 100% sequence identity to the template nucleic acid from which the population was generated. In certain embodiments, amplifying of a template polynucleotide yields a population of polynucleotides in which a large enough fraction of the polynucleotides share enough sequence identity to allow sequencing of at least a portion of the amplified template using a high-throughput sequencing system.

In some embodiments, at least 50%, 60%, 70%, 75%, 80%, 90%, 95%, or 99%, of the members of the nucleic acid molecules attached to a templated support will share greater than 90%, 95%, 97%, 99%, or 100% identity with the template nucleic acid molecule. In some embodiments, members of a nucleic acid population which are produced using any of the amplification methods, hybridize to each other under high-stringency hybridization conditions.

In some embodiments, amplification methods provided herein, including, for example, amplification processes used in templating nucleic acids, as well as apparatuses, devices, systems, compositions and kits involving the methods, generate a substantially monoclonal population of nucleic acid molecules that includes sufficiently few polyclonal contaminants such that they can be successfully sequenced in a high-throughput sequencing method. For example, the amplification methods can generate a substantially monoclonal population of nucleic acid molecules that provides for the production of a signal (e.g., a sequencing signal, a nucleotide incorporation signal, and the like) that is detected using a particular sequencing system. Such signals include any detectable signal indicative of nucleotide polymerization, including, but are not limited to, optical or optically detectable signals, non-optical signals (or signals detectable by non-optical detection techniques), ion (e.g., hydrogen ion) concentration, pH, electrical signals, voltage, and changes of fluctuations in any such signal. Optionally, the signal can subsequently be analyzed to correctly determine the sequence or base identity of any one or more nucleotides present within any nucleic acid molecule of the population. Examples of suitable sequencing systems for detection or analysis of such signals include, but are not limited to, systems that include ionic sensors, e.g., a field effect transistor (FET), for example a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, is used for measuring ion concentrations in solution; when the ion concentration (such as $H^+$) changes, the current through the transistor changes accordingly. Non-limiting examples of systems that include FET sensors are the Ion Torrent sequencing systems, such as the Ion Torrent PGM™ sequence systems, including the 314, 316 and 318 systems, the Ion Torrent Proton™ sequencing systems, including the Proton I, (Thermo Fisher Scientific, Waltham, Mass.) and the Ion Torrent Proton™ sequencing systems, including Ion S5 and S5XL (Thermo Fisher Scientific, Waltham, Mass.). In one embodiment, an ISFET-based sequencing system for detection or analysis of signals is described in detail herein. In some embodiments, a substantially monoclonal nucleic acid population permits the accurate sequencing of at least 5 contiguous nucleotide residues on a system incorporating FET sensors, e.g., an Ion Torrent sequencing system.

As used herein, the term "clonal amplification" and its variants refer to any process whereby a monoclonal, or substantially monoclonal, polynucleotide population is produced via amplification of a polynucleotide. In some embodiments of clonal amplification, two or more polynucleotides are amplified to produce at least two a monoclonal, or substantially monoclonal, polynucleotide populations.

As used herein, the term "pre-seeding," also referred to herein as "seeding," refers to a process involving the attachment of a polynucleotide to a surface or support. In some embodiments, pre-seeding involves attachment of one or more nucleic acids to a surface or support, or to one or more sites on a surface or support. Pre-seeded surfaces or supports are used, for example, in further manipulation or analysis, e.g., nucleic acid amplification (including, e.g., amplification in a templating process), sequencing or other processes, of the attached nucleic acids. In some embodiments, the pre-seeding process generates one or more surfaces or supports having one or more nucleic acid molecules attached thereto. In some embodiments, pre-seeding generates one or more surfaces or supports having a single polynucleotide attached thereto. The one or more surfaces or supports having one or more nucleic acid molecules attached thereto may be included in a population, plurality or collection of two or more surfaces or supports, in which some, a minority, a majority, or substantially all of the surfaces or supports have one or more nucleic acid molecules attached thereto. In some embodiments, the nucleic acid molecule or molecules attached to different surfaces or supports, or to different sites on a surface or support, are different. In some embodiments, multiple (or a plurality of) substantially identical copies of a nucleic acid molecule (or substantially monoclonal nucleic acids) are attached to a surface or support or multiple (or a plurality of) different nucleic acids are attached to one or more sites on a surface or support(s) in a pre-seeding process. In some embodiments, a limited number of substantially identical copies of a polynucleotide (or substantially monoclonal nucleic acids) is attached to a surface or support to generate a monoclonal, or substantially monoclonal, population of nucleic acids in a pre-seeding process. In some embodiments, pre-seeding of a surface or support includes attachment of a nucleic acid to a surface or support, for example, by hybridization of the nucleic acid to a complementary polynucleotide attached to the support, in a process that does not involve nucleic acid amplification. In some embodiments, pre-seeding of a surface or support includes nucleic acid amplification, e.g., one or more cycles of nucleic acid amplification (e.g., PCR) or isothermal amplification. For example, nucleic acid amplification may be used in a pre-seeding process to generate one or more copies of a nucleic acid that is capable of attaching (e.g., by hybridization) to a surface or support. Typically, pre-seeding that generates a surface or support having more than one nucleic acid, or multiple copies of a nucleic acid, attached thereto includes nucleic acid amplification. A surface or support generated in a pre-seeding or seeding process as provided herein is referred to as a "pre-seeded" or "seeded" support.

As used herein, a "limited number" when referring to a number of nucleic acids (or substantially identical copies of, or substantially monoclonal, nucleic acids) attached to a surface or support in a pre-seeding or templating method typically refers to a number of nucleic acids that is controlled for various purposes. A limited number of copies of a nucleic acid can be, for example, a number sufficient to provide a crowding effect in any subsequent larger scale amplification (e.g., templating) of the nucleic acids on the surface or support to generate a larger substantially monoclonal population of the nucleic acids in order to prevent or reduce polyclonal population formation by preventing or reducing migration of the templates between reaction sites. Such a limited number of template copies can be limited in order to use relatively short nucleic acid amplification times, for example, to prevent or reduce migration of templates between reaction sites but generate a sufficient number of template copies to provide a crowding effect in subsequent amplifications.

As used herein, the term "templating" refers to a process of generating two or more, or a plurality or population, of substantially identical polynucleotides, or of generating a substantially monoclonal population of nucleic acids, that can be used as templates in nucleic acid analysis methods, including, for example, nucleic acid sequencing, such as sequencing by synthesis, of the polynucleotides. The polynucleotides generated in a templating process are typically referred to as nucleic acid templates. In some embodiments, templating involves attachment of polynucleotide templates to a surface or support. In some embodiments, templating involves generating two or more, or a plurality, of separate surfaces or supports, or discrete sites on a surface or support, each having attached thereto two or more, or a plurality or population, of substantially identical polynucleotides, or a substantially monoclonal population of polynucleotides. In some embodiments, templating involves generating one or more surfaces or supports, or discrete sites on a surface or support, having a substantially monoclonal population of polynucleotides attached thereto. In some embodiments, templating generates one or more surfaces or supports having a substantially monoclonal population of at least 50,000, 75,000, 100,000, 125,000, 150,000, 200,000, 250,000, 300,000, 350,000, 400,000, 450,000, 500,000, 600,000, 700,000, 800,000, 900,000 or $10^6$ or more template nucleic acid molecules attached to each templated surface or support. In some embodiments, templating generates surfaces or supports having a substantially monoclonal population of between about 50,000 and 500,000 template nucleic acid molecules attached to each templated surface or support, or, for example, between about 50,000 and 400,000 template nucleic acid molecules, between about 50,000 and 300,000 template nucleic acid molecules, between about 50,000 and 200,000 template nucleic acid molecules, or between about 50,000 and 100,000 template nucleic acid molecules attached to each templated support. In some embodiments, templating generates one or more templated surfaces or supports having a substantially monoclonal population of between about 100,000 and 400,000 template nucleic acid molecules attached to each templated surface or support, between about 100,000 and 300,000 template nucleic acid molecules, between about 100,000 and 200,000 template nucleic acid molecules, or between about 150,000 and 300,000 template nucleic acid molecules attached to each templated support. In some embodiments, templating is performed starting with one or more pre-seeded or seeded surfaces or supports. In such embodiments, templating can generate one or more templated surfaces or supports including at least 1.5 times, at least 2 times, at least 2.5 times, at least 3 times, at least 3.5 times, at least 4 times, at least 4.5 times, at least 5 times, at least 5.5 times, at least 6 times, at least 6.5 times, at least 7 times, at least 7.5 times, at least 8 times, at least 8.5 times, at least 9 times, at least 9.5 times, at least 10 times, at least 25 times, at least 50 times, at least 100 times, at least 250 times, at least 500 times, at least 1000 times, at least 2500 times, at least 5000 times, at least 10,000 times, at least 25,000 times, at least 50,000 times, at least 100,000 times, at least 250,000 times, at least 5000,000 times, or at least $10^6$ times or more as many template nucleic acid molecules on the templated surfaces or supports as were present on the pre-seeded surfaces or supports. In some embodiments, only about 1 or only 1 nucleic acid molecule is present on a pre-seeded support. In some embodiments, at least 50,000, 75,000 or 100,000 substantially monoclonal template nucleic acid molecules or between about 25,000 and 1,000,000 substantially monoclonal template nucleic acid molecules are present on a pre-seeded surface or support, for example between about 25,000 and 500,000, between about 25,000 and 250,000, between about 25,000 and 125,000, or between about 25,000 and 100,000 substantially monoclonal template nucleic acid molecules are present on a pre-seeded surface or support, e.g., a solid surface or support.

In some embodiments, the methods, as well as apparatuses, devices, systems, compositions and kits for performing the methods, provided herein, include supports, e.g., solid supports or semi-solid supports, to confine, enrich, sequester, isolate, localize, amplify or transfer nucleic acids that can be used in analysis methods. A solid surface or support may include a polymeric, a glass, or a metallic material. Examples of solid supports include a membrane, a planar surface, a microtiter plate, a bead, a filter, a test strip, a slide, a cover slip, and a test tube. A solid surface or support means any solid phase material upon which an oligomer is synthesized, attached, ligated, or otherwise immobilized. A support can optionally include a "resin", "phase", "surface", and "support". A support may be composed of, for example, organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of, for example, beads, spheres, particles, granules, a gel, or a surface. Surfaces may be, for example, planar, substantially planar, or non-planar, as well as concave, convex, or any combination thereof. Supports may be porous, semi-porous or non-porous, and may have swelling or non-swelling characteristics. A support can be shaped to include one or more wells, depressions or other containers, vessels, features, or locations. One or more supports may be configured in an array at various locations. A support is optionally addressable (e.g., for robotic delivery of reagents), or by detection means including scanning by laser illumination and confocal or deflective light gathering. A support (e.g., a bead) can be placed within or on another support (e.g., within a well of a second support). Examples of bead materials include, but are not limited to, gels, hydrogels, or acrylamide polymers. In some embodiments, a support is an Ion Sphere Particle (Thermo Fisher Scientific, Waltham, Mass.). Examples of solid supports include, but are not limited to, a "microparticle," "bead," "microbead" (optionally but not necessarily spherical in shape) sphere, filter, flow cell, well, groove, channel reservoir, gel, or inner wall of a capillary. In some embodiments, a surface includes texture (e.g., etched, cavitated, pores, three-dimensional scaffolds, or bumps). Sizes of supports include, but are not limited to, supports having a smallest cross-sectional length (e.g., diameter) of 50 microns or less, 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Also included in surfaces or solid supports are magnetic or paramagnetic beads (e.g., magnetic or paramagnetic nanoparticles or microparticles). For example, paramagnetic microparticles include paramagnetic beads attached with streptavidin (e.g., Dynabeads™ M-270 from Invitrogen, Carlsbad, Calif.). Particles can have an iron core, or can be a hydrogel or agarose (e.g., Sepharose™). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). A bead surface can be functionalized for attaching one, or more, or a plurality, or a population of primers. In some embodiments, a bead is any size that can fit into a reaction chamber. For example, one bead can fit in a reaction chamber. In some embodiments, more than one bead fit in a reaction chamber. In some embodiments, the methods, as well as apparatuses, devices, systems, compositions, and kits for performing the methods, provided herein, include supports or surfaces having one, two or more, a plurality or a population of oligonucleotides (e.g., primers) attached thereto. A support or surface can be coated with an acrylamide, carboxylic, or amine compound for attaching a nucleic acid molecule (e.g., a first primer or second primer). For example, an amino-modified nucleic acid molecule (e.g., primer) can be attached to a support that is coated with a carboxylic acid. A primer can be attached to an acrylamide compound coating on a surface. Particles can be coated with an avidin-like compound (e.g., streptavidin) for binding biotinylated nucleic acids. In some embodiments, the oligonucleotides attached to a support or surface are substantially identical or include a primer sequence that is substantially identical in all the oligonucleotides. In some embodiments, two or more different oligonucleotides are attached to a support or surface. In some embodiments, a surface has attached a population of first primers, the first primers of the population sharing a common first primer sequence. In some embodiments, a surface has attached a population of first primers and a population of second primers, the first primers of the population sharing a common first primer sequence and the second primers of the population of second primers sharing a common second primer sequence. In some embodiments, the surface has immobilized thereon a population of first primers. In other embodiments, the surface has immobilized thereon a population of first primers and a population of second primers.

Overview

In FIG. 1, a system 100 containing fluidics circuit 102 is connected by inlets to at least two reagent reservoirs (104, 106, 108, 110, or 112), to waste reservoir 120, and to biosensor 134 by fluid pathway 132 that connects fluidics node 130 to inlet 138 of biosensor 134 for fluidic communication. Reagents from reservoirs (104, 106, 108, 110, or 112) can be driven to fluidic circuit 102 by a variety of methods including pressure, pumps, such as syringe pumps, gravity feed, and the like, and are selected by control of valves 114. Reagents from the fluidics circuit 102 can be driven through the valves 114 receiving signals from control system 118 to waste container 120. Reagents from the fluidics circuit 102 can also be driven through the biosensor 134 to the waste container 136. The control system 118 includes controllers for valves 114, which generate signals for opening and closing via electrical connection 116.

The control system 118 also includes controllers for other components of the system, such as wash solution valve 124 connected thereto by electrical connection 122, and reference electrode 128. Control system 118 can also include control and data acquisition functions for biosensor 134. In one mode of operation, fluidic circuit 102 delivers a sequence of selected reagents 1, 2, 3, 4, or 5 to biosensor 134 under programmed control of control system 118, such that in between selected reagent flows, fluidics circuit 102 is primed and washed, and biosensor 134 is washed. Fluids entering biosensor 134 exit through outlet 140 and are deposited in waste container 136 via control of pinch valve regulator 144. The valve 144 is in fluidic communication with the sensor fluid output 140 of the biosensor 134.

Figure 2:
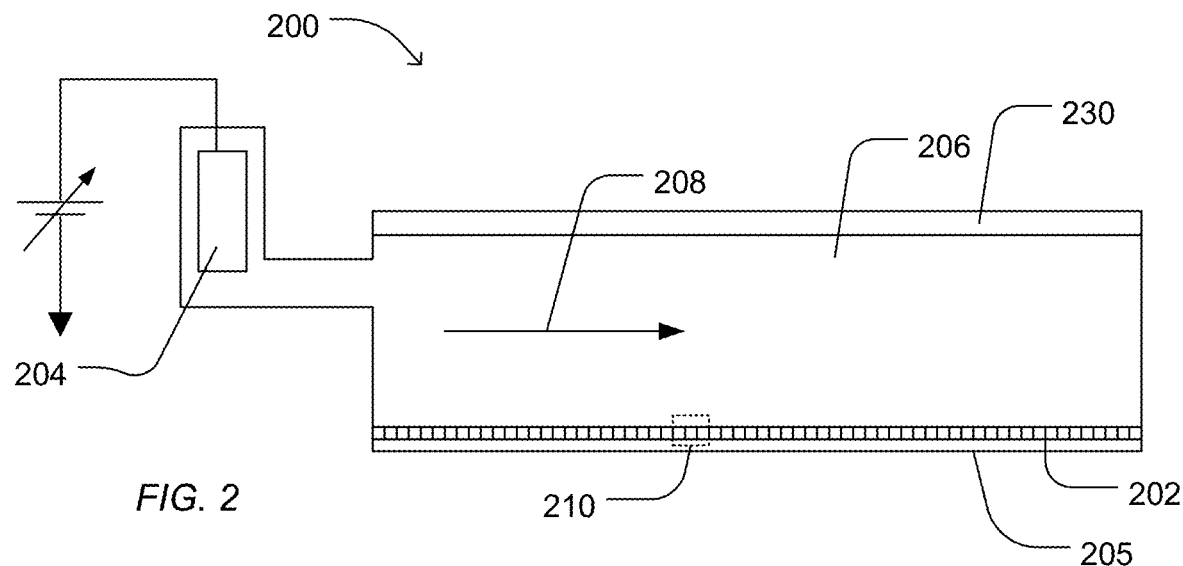
FIG. 2 includes an illustration of an example system including a sensor array.

The device including the dielectric layer defining the well formed from the first access and second access and exposing a sensor pad finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 2 illustrates an expanded and cross-sectional view of a flow cell 200 and illustrates a portion of a flow chamber 206. A reagent flow 208 flows across a surface of a well array 202, in which the reagent flow 208 flows over the open ends of wells of the well array 202. The well array 202 and a sensor array 205 together may form an integrated unit forming a lower wall (or floor) of flow cell 200. A reference electrode 204 may be fluidly coupled to flow chamber 206. Further, a flow cell cover 230 encapsulates flow chamber 206 to contain reagent flow 208 within a confined region.

Figure 3:
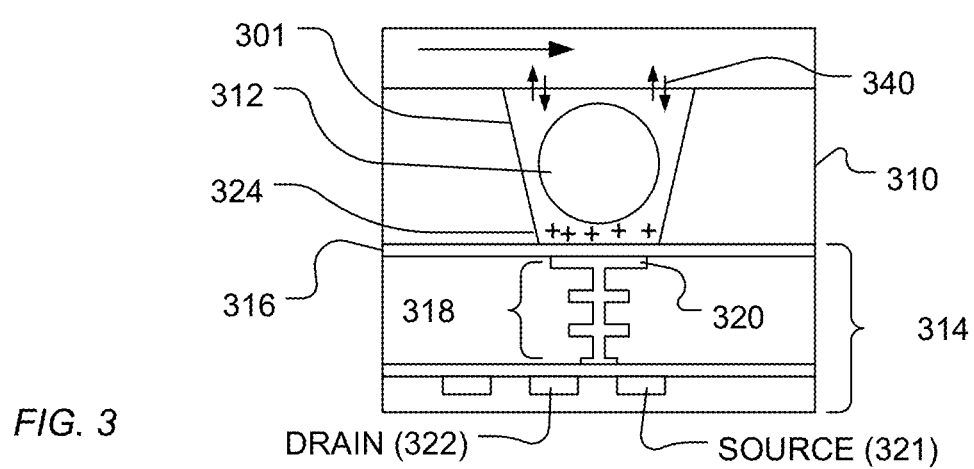
FIG. 3 includes an illustration of an example sensor and associated well.

FIG. 3 illustrates an expanded view of a well 301 and a sensor 314, as illustrated at 210 of FIG. 2. The volume, shape, aspect ratio (such as base width-to-well depth ratio), and other dimensional characteristics of the wells may be selected based on the nature of the reaction taking place, as well as the reagents, byproducts, or labeling techniques (if any) that are employed. The sensor 314 can be a chemical field-effect transistor (chemFET), more specifically an ion-sensitive FET (ISFET), with a floating gate 318 having a sensor plate 320 optionally separated from the well interior by a material layer 316. The sensor 314 can be responsive to (and generate an output signal related to) the amount of a charge 324 present on the material layer 316 opposite the sensor plate 320. The material layer 316 can be a ceramic layer, such as an oxide of zirconium, hafnium, tantalum, aluminum, or titanium, among others, or a nitride of titanium. Alternatively, the material layer 316 can be formed of a metal, such as titanium, tungsten, gold, silver, platinum, aluminum, copper, or a combination thereof. In an example, the material layer 316 can have a thickness in a range of 5 nm to 100 nm, such as a range of 10 nm to 70 nm, a range of 15 nm to 65 nm, or even a range of 20 nm to 50 nm.

While the material layer 316 is illustrated as extending beyond the bounds of the illustrated FET component, the material layer 316 can extend along the bottom of the well 301 and optionally along the walls of the well 301. The sensor 314 can be responsive to (and generate an output signal related to) the amount of a charge 324 present on the material layer 316 opposite the sensor plate 320. Changes in the charge 324 can cause changes in a current between a source 321 and a drain 322 of the chemFET. In turn, the chemFET can be used directly to provide a current-based output signal or indirectly with additional circuitry to provide a voltage-based output signal. Reactants, wash solutions, and other reagents may move in and out of the wells by a diffusion mechanism 340.

The well 301 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 301 of array 202 can have a characteristic diameter, defined as the square root of 4 times the cross-sectional area (A) divided by P1 (e.g., sqrt(4*A/π)), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 301 can have a characteristic diameter of at least 0.01 micrometers. Ina further example, the well 301 can define a volume in a range of 0.05 fL to 10 pL, such as a volume in a range of 0.05 fL to 1 pL, a range of 0.05 fL to 100 fL, a range of 0.05 fL to 10 fL, or even a range of 0.1 fL to 5 fL.

In an embodiment, reactions carried out in the well 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, then multiple copies of the same analyte may be analyzed in the well 301 at the same time in order to increase the output signal generated. In an embodiment, multiple copies of an analyte may be attached to a solid phase support 312, either before or after deposition into the well 301. The solid phase support 312 may be microparticles, nanoparticles, beads, solid or porous comprising gels, or the like. For simplicity and ease of explanation, solid phase support 312 is also referred herein as a particle or bead. For a nucleic acid analyte, multiple, connected copies may be made by rolling circle amplification (RCA), exponential RCA, or like techniques, to produce an amplicon without the need of a solid support.

In particular, the solid phase support, such a bead support, can include copies of polynucleotides. In a particular example illustrated in FIG. 4, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

A bead support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Supports may be porous or non-porous, and may have swelling or non-swelling characteristics. In some embodiments, a support is an Ion Sphere Particle. Example bead supports are disclosed in U.S. Pat. No. 9,243,085, titled "Hydrophilic Polymeric Particles and Methods for Making and Using Same," and in U.S. Pat. No. 9,868,826, titled "Polymer Substrates Formed from Carboxy Functional Acrylamide," each of which is incorporated herein by reference.

In some embodiments, the solid support is a "microparticle," "bead," "microbead," etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). In an example, the support is at least 0.1 microns. Microparticles or bead supports may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments, a population of microparticles having different shapes sizes or colors is used. The microparticles can optionally be encoded, e.g., with quantum dots such that each microparticle or group of microparticles can be individually or uniquely identified.

Magnetic beads (e.g., Dynabeads from Dynal, Oslo, Norway) can have a size in a range of 1 micron to 100 microns, such as 2 microns to 100 microns. The magnetic beads can be formed of inorganic or organic materials including, but not limited to, glass (e.g., controlled pore glass), silica, zirconia, cross-linked polystyrene, polystyrene, or a combination thereof.

In some embodiments, a bead support is functionalized for attaching a population of first primers. In some embodiments, a bead is any size that can fit into a reaction chamber. For example, one bead can fit in a reaction chamber. In some embodiments, more than one bead fit in a reaction chamber. In some embodiments, the smallest cross-sectional length of a bead (e.g., diameter) is about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In general, the bead support can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

Figure 4:
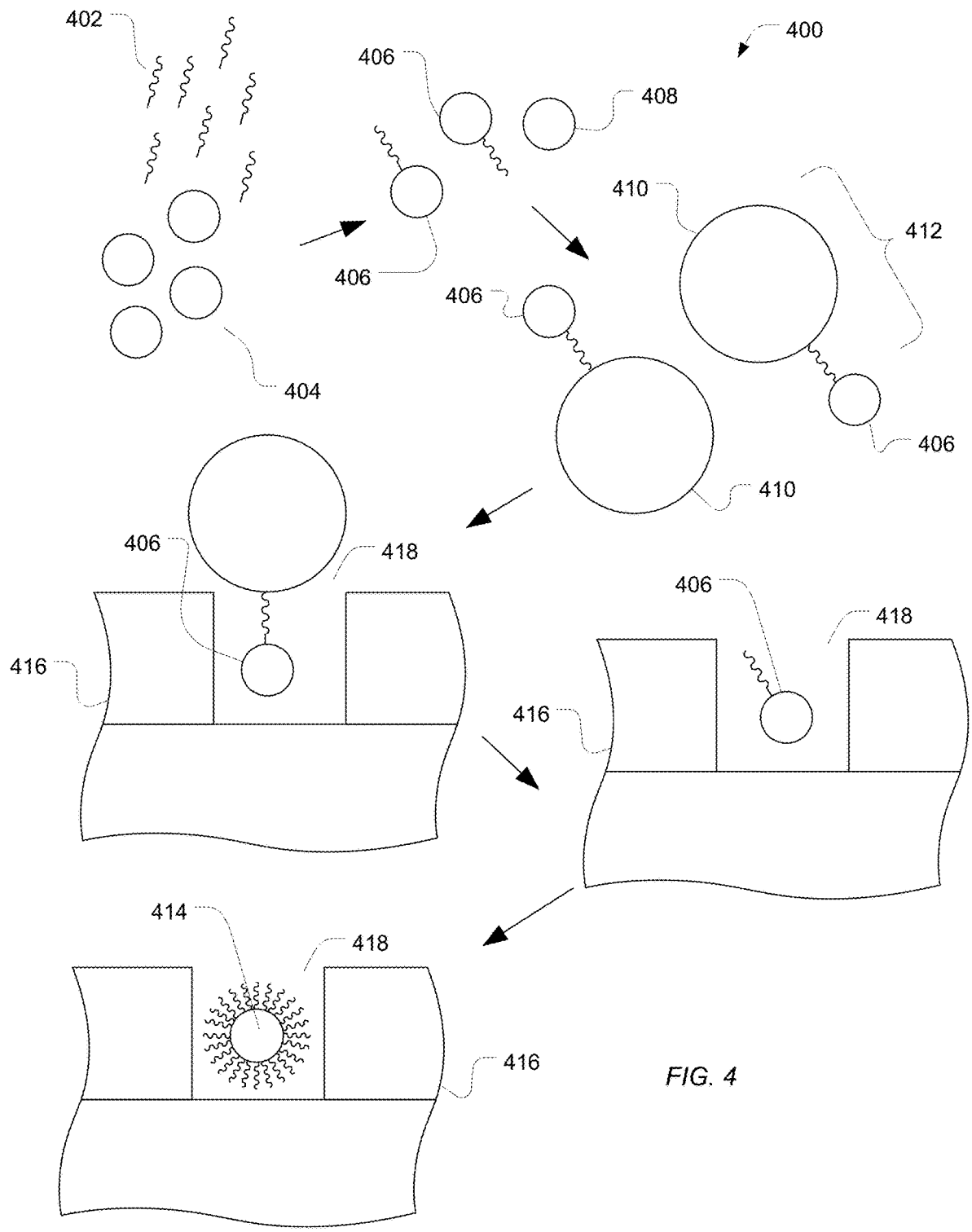
FIG. 4 includes an illustration of an example method for preparing a sequencing device.

As illustrated in FIG. 4, a plurality of bead supports 404 can be placed in a solution along with a plurality of polynucleotides 402 (target or template poylnucleotides). The plurality of bead supports 404 can be activated or otherwise prepared to bind with the polynucleotides 402. For example, the bead supports 404 can include an oligonucleotide (capture primer) complementary to a portion of a polynucleotide of the plurality of polynucleotides 402. In another example, the bead supports 404 can be modified with target polynucleotides 402 using techniques such as biotin-streptavidin binding.

In some embodiments, the template nucleic acid molecules (template polynucleotides or target polynucleotides) can be derived from a sample that can be from a natural or non-natural source. The nucleic acid molecules in the sample can be derived from a living organism or a cell. Any nucleic acid molecule can be used, for example, the sample can include genomic DNA covering a portion of or an entire genome, mRNA, or miRNA from the living organism or cell. In other embodiments, the template nucleic acid molecules can be synthetic or recombinant. In some embodiments, the sample contains nucleic acid molecules having substantially identical sequences or having a mixture of different sequences. Illustrative embodiments are typically performed using nucleic acid molecules that were generated within and by a living cell. Such nucleic acid molecules are typically isolated directly from a natural source such as a cell or a bodily fluid without any in vitro amplification. Accordingly, the sample nucleic acid molecules are used directly in subsequent steps. In some embodiments, the nucleic acid molecules in the sample can include two or more nucleic acid molecules with different sequences.

The methods can optionally include a target enrichment step before, during, or after the library preparation and before a pre-seeding reaction. Target nucleic acid molecules, including target loci or regions of interest, can be enriched, for example, through multiplex nucleic acid amplification or hybridization. A variety of methods can be used to perform multiplex nucleic acid amplification to generate amplicons, such as multiplex PCR, and can be used in an embodiment. Enrichment by any method can be followed by a universal amplification reaction before the template nucleic acid molecules are added to a pre-seeding reaction mixture. Any of the embodiments of the present teachings can include enriching a plurality of at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 target nucleic acid molecules, target loci, or regions of interest. In any of the disclosed embodiments, the target loci or regions of interest can be at least 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, 500, 600, 700, 800, 900, or 1,000 nucleotides in length and include a portion of or the entirety of the template nucleic acid molecule. In other embodiments, the target loci or regions of interest can be between about 1 and 10,000 nucleotides in length, for example between about 2 and 5,000 nucleotides, between about 2 and 3,000 nucleotides, or between about 2 and 2,000 nucleotides in length. In any of the embodiments of the present teachings, the multiplex nucleic acid amplification can include generating at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 copies of each target nucleic acid molecule, target locus, or region of interest.

In some embodiments, after the library preparation and optional enrichment step, the library of template nucleic acid molecules can be templated onto one or more supports. The one or more supports can be templated in two reactions, a seeding reaction to generate pre-seeded solid supports and a templating reaction using the one or more pre-seeded supports to further amplify the attached template nucleic acid molecules. The pre-seeding reaction is typically an amplification reaction and can be performed using a variety of methods. For example, the pre-seeding reaction can be performed in an RPA reaction, a template walking reaction, or a PCR. In an RPA reaction, template nucleic acid molecules are amplified using a recombinase, polymerase, and optionally a recombinase accessory protein in the presence of primers and nucleotides. The recombinase and optionally the recombinase accessory protein can dissociate at least a portion of a double stranded template nucleic acid molecules to allow primers to hybridize that the polymerase can then bind to initiate replication. In some embodiments, the recombinase accessory protein can be a single-stranded binding protein (SSB) that prevents the re-hybridization of dissociated template nucleic acid molecules. Typically, RPA reactions can be performed at isothermal temperatures. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are dissociated by thermal cycling. After cooling, primers bind to complementary sequences and can be used for replication by the polymerase. In any of the aspects of the present teachings, the pre-seeding reaction can be performed in a pre-seeding reaction mixture, which is formed with the components necessary for amplification of the template nucleic acid molecules. In any of the disclosed aspects, the pre-seeding reaction mixture can include some or all of the following: a population of template nucleic acid molecules, a polymerase, one or more solid supports with a population of attached first primers, nucleotides, and a cofactor such as a divalent cation. In some embodiments, the pre-seeding reaction mixture can further include a second primer and optionally a diffusion-limiting agent. In some embodiments, the population of template nucleic acid molecules comprise template nucleic acid molecules joined to at least one adaptor sequence which can hybridize to the first or second primers. In some embodiments, the reaction mixture can form an emulsion, as in emulsion RPA or emulsion PCR. In pre-seeding reactions carried out by RPA reactions, the pre-seeding reaction mixture can include a recombinase and optionally a recombinase accessory protein. The various components of the reaction mixture are discussed in further detail herein.

In a particular embodiment of seeding, the hydrophilic particles and polynucleotides are subjected to polymerase chain reaction (PCR) amplification or recombinase polymerase amplification (RPA). In an example, the particles 404 include a capture primer complementary to a portion of the template polynucleotide 402. The template polynucleotide can hybridize to the capture primer. The capture primer can be extended to form beads 406 that include a target polynucleotide attached thereto. Other beads may remain unattached to a target nucleic acid and other template polynucleotide can be free floating in solution.

In an example, the bead support 406 including a target polynucleotide can be attached to a magnetic bead 410 to form a bead assembly 412. In particular, the magnetic bead 410 is attached to the bead support 406 by a double stranded polynucleotide linkage. In an example, a further probe including a linker moiety can hybridize to a portion of the target polynucleotide on the bead support 406. The linker moiety can be attached to a complementary linker moiety on the magnetic bead 410. In another example, the template polynucleotide used to form the target nucleic acid attached to beads 406 can include a linker moiety that attaches to the magnetic bead 410. In another example, the template polynucleotide complementary to target polynucleotide attached to the bead support 406 can be generated from a primer that is modified with a linker that attaches to the magnetic bead 410.

The linker moiety attached to the polynucleotide and the linker moiety attached to the magnetic bead can be complementary to and attach to each other. In an example, the linker moieties have affinity and can include: an avidin moiety and a biotin moiety; an antigenic epitope and an antibody or immunologically reactive fragment thereof, an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement. In a particular example, the linker moiety attached to the polynucleotide includes biotin and the linker moiety attached to the magnetic bead includes streptavidin.

The bead assemblies 412 can be applied over a substrate 416 of a sequencing device that includes wells 418. In an example, a magnetic field can be applied to the substrate 416 to draw the magnetic beads 410 of the bead assembly 412 towards the wells 418. The bead support 406 enters the well 418. For example, a magnet can be moved in parallel to a surface of the substrate 416 resulting in the deposition of the bead support 406 in the wells 418.

The bead assembly 412 can be denatured to remove the magnetic bead 410 leaving the bead support 406 in the well 418. For example, hybridized double-stranded DNA of the bead assembly 412 can be denatured using thermal cycling or ionic solutions to release the magnetic bead 410 and template polynucleotides having a linker moiety attached to the magnetic bead 410. For example, the double-stranded DNA can be treated with low ion-content aqueous solutions, such as deionized water, to denature and separate the strands. In an example, a foam wash can be used to remove the magnetic beads.

Optionally, the target polynucleotides 406 can be amplified, referred to herein as templating, while in the well 418, to provide a bead support 414 with multiple copies of the target polynucleotides. In particular, the bead 414 has a monoclonal population of target polynucleotides. Such an amplification reactions can be performed using polymerase chain reaction (PCR) amplification, recombination polymerase amplification (RPA) or a combination thereof. Alternatively, amplification can be performed prior to depositing the bead support 414 in the well.

In a particular embodiment, an enzyme such as a polymerase is present, bound to, or is in close proximity to the particles or beads. In an example, a polymerase is present in solution or in the well to facilitate duplication of the polynucleotide. A variety of nucleic acid polymerase may be used in the methods described herein. In an example embodiment, the polymerase can include an enzyme, fragment, or subunit thereof, which can catalyze duplication of the polynucleotide. In another embodiment, the polymerase can be a naturally occurring polymerase, recombinant polymerase, mutant polymerase, variant polymerase, fusion or otherwise engineered polymerase, chemically modified polymerase, synthetic molecules, or analog, derivative or fragment thereof. Example enzymes, solutions, compositions, and amplification methods can be found in WO2019/094,524, titled "METHODS AND COMPOSITIONS FOR MANIPULATING NUCLEIC ACIDS", which is incorporated herein by reference in its entirety.

While the polynucleotides of bead support 414 are illustrated as being on a surface, the polynucleotides can extend within the bead support 414. Hydrogel and hydrophilic particles having a low concentration of polymer relative to water can include polynucleotide segments on the interior of and throughout the bead support 414 or polynucleotides can reside in pores and other openings. In particular, the bead support 414 can permit diffusion of enzymes, nucleotides, primers, and reaction products used to monitor the reaction. A high number of polynucleotides per particle produces a better signal.

In an example embodiment, the bead support 414 can be utilized in a sequencing device. For example, a sequencing device 416 can include an array of wells 418.

In an example, a sequencing primer can be added to the wells 418 or the bead support 414 can be pre-exposed to the primer prior to placement in the well 418. In particular, the bead support 414 can include bound sequencing primer. The sequencing primer and polynucleotide form a nucleic acid duplex including the polynucleotide (e.g., a template nucleic acid) hybridized to the sequencing primer. The nucleic acid duplex is an at least partially double-stranded polynucleotide. Enzymes and nucleotides can be provided to the well 418 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 416 and can migrate to the well 418. Excitation energy can be also provided to the well 418. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 418 can change. Such a change in pH can be detected by ion sensitive field effect transistors (ISFET). As such, a change in pH can be used to generate a signal indicating the order of nucleotides complementary to the polynucleotide of the particle 410.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET may be a FET array. As used herein, an "array" is a planar arrangement of elements such as sensors or wells. The array may be one or two dimensional. A one-dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In embodiments, one or more microfluidic structures can be fabricated above the FET sensor array to provide for containment or confinement of a biological or chemical reaction. For example, in one implementation, the microfluidic structure(s) can be configured as one or more wells (or wells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 4, in another example, a well 418 of the array of wells can be operatively connected to measuring devices. For example, for fluorescent emission methods, a well 418 can be operatively coupled to a light detection device. In the case of ionic detection, the lower surface of the well 418 may be disposed over a sensor pad of an ionic sensor, such as a field effect transistor.

One example system involving sequencing via detection of ionic byproducts of nucleotide incorporation is the Ion Torrent PGM™, Proton™ or S™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™, or S5™ sequencer detects the nucleotide incorporations by detecting the hydrogen ion byproducts of the nucleotide incorporations. The Ion Torrent PGM™, Proton™ or S5™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Seeding the bead supports and capture by the magnetic beads can be performed through various methods. For example, turning to FIG. 5 at 502, a template polynucleotide (B'-A) can be captured by a capture probe (B) attached to a bead support 510. The capture probe (B) can be extended complementary to the template polynucleotide. Optionally, the resultant double-stranded polynucleotide can be denatured removing the template nucleic acid (B'-A) and leaving a single-stranded (B-A') attached to the bead support 510. As illustrated at 504, a primer (A) modified with a linker moiety, such as biotin, can be hybridized to a portion (A') of the nucleic acid (B-A') attached to the bead support 510. Optionally, the primer (A) can be extended to form a complementary nucleic acid (A-B').

As illustrated 506, a magnetic bead 512 can be introduced to the solution. The magnetic bead 512 can include a linker complementary to the linker moiety attached to the primer (A). For example, the linker attached to the primer (A) can be biotin and the magnetic bead 512 can be coated with streptavidin. As described above, the magnetic bead 512 can be utilized to clean the solution and to assist with deposition of the bead support 510 and the attached nucleic acid (B-A') into a well of a sequencing device. As illustrated 508, double-stranded polynucleotide can be denatured, resulting in the dehybridization of the nucleic acid (B'-A) from the nucleic acid (B-A') attached to the bead support 510. As such, the bead support 510 is deposited into the wells of the sequencing device and has a single stranded target nucleic acid (B-A'). Alternatively, the linker modified probe (A) may not be extended to form a complementary polynucleotide with a length the polynucleotide (B-A'). Extension reactions can be carried out using polymerase chain reaction (PCR), recombinase polymerase amplification (RPA), or other amplification reactions.

Instrument

Figure 6:
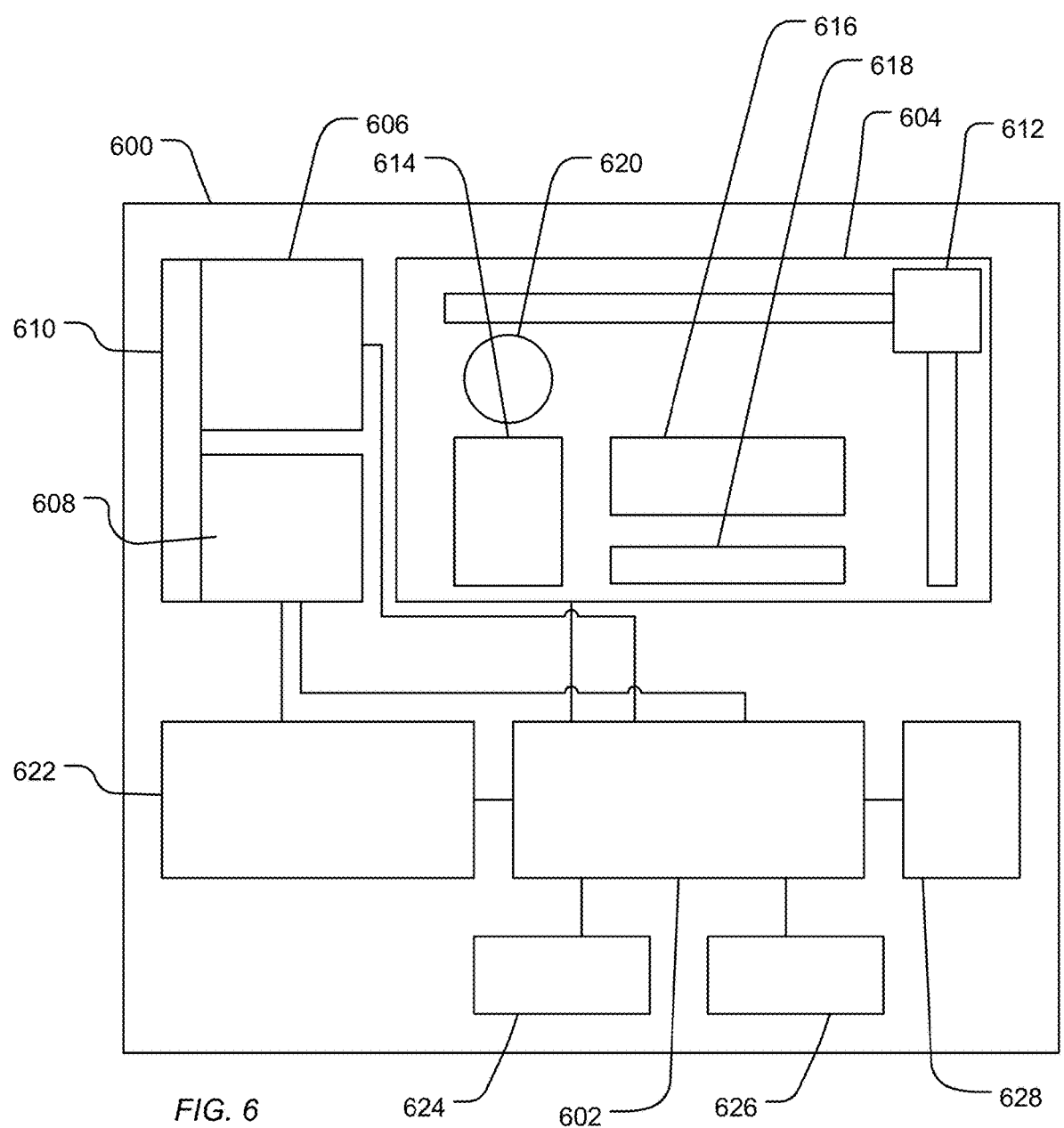
FIG. 6 includes an illustration of an example sequencing system.

FIG. 6 includes an illustration of an exemplary sequencing instrument system 600, which includes a controller 602 in communication with a preparation deck 604, a loading station 606, and a sequencing station 608. The preparation deck 604 can include a pipetting robot 612 that can access samples 614, reagents and solutions 616, a thermocycler 618 and other devices 620, such as a magnetic separator or a centrifuge. Target sequences prepared at the preparation deck 604 can be provided to the loading station 606. For example, the preparation deck 604 can provide seeded substrates including target sequences that are provided to the loading station 606 to be loaded onto a sensor device.

Once loaded, the sensor device including the target sequences can be transported to the sequencing station 608 utilizing the slide mechanism 610. The sequencing station 608 can include fluidics and an electronic interface to interact with the sensor device to sense the addition of nucleotides during a sequencing-by-synthesis reaction. Data gathered from the sensing device can be provided to a sequencing computer 622 which can perform base calling, read alignment, and variant calling.

The controller 602 can further communicate with a user interface 624 such as a monitor, keyboard, mouse, touchscreen, or any combination thereof, among other interfaces. Further, the controller 602 can communicate with a network interface that may access a local area network, wide area network, or global network. The network interface 626 can be a wired interface or a wireless interface using various standard communication protocols. Further, the system can be powered by a power source 628.

Figure 7:
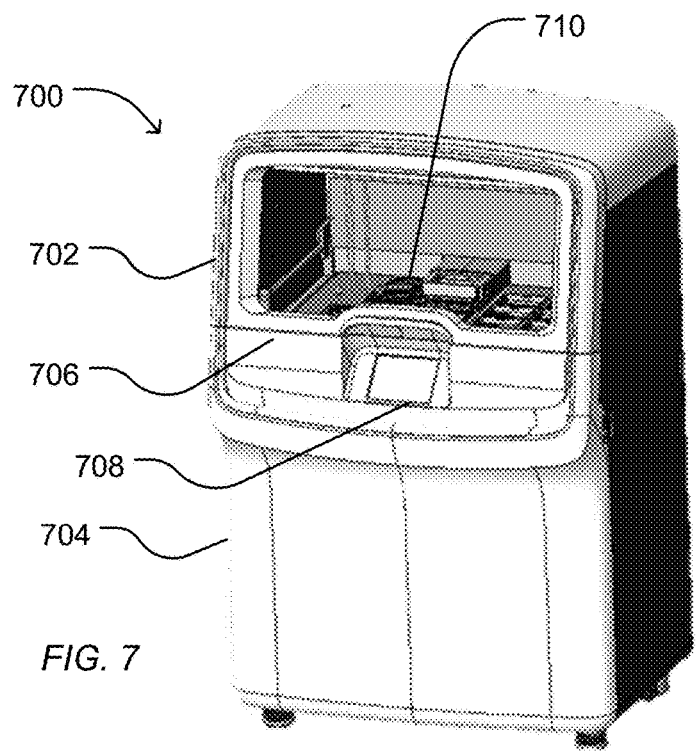
FIG. 7 includes an illustration of an example instrument.

FIG. 7 includes an illustration of an example instrument 700 incorporating a three-axis pipetting robot. In an example, the instrument 700 can be a sequencer incorporating a sample prep preparation platform. For example, the instrument 700 can include an upper portion 702 and a lower portion 704. The upper portion can include a door 706 to access a deck 710 on which samples, reagent containers, and other consumables are placed. The lower portion can include a cabinet for storing additional reagent solutions and other parts of the instrument 700. In addition, the instrument can include a user interface, such as a touchscreen display 708.

In a particular example, the instrument 700 can be a sequencing instrument. In some embodiments, the sequencing instrument includes a top section, a display screen, and a bottom section. In some embodiments, the top section may include a deck supporting components of the sequencing instrument and consumables, including a sample preparation section, a sequencing chip and reagent strip tubes and carriers. In some embodiments, the bottom section may house reagent bottles used for sequencing and a waste container.

In some embodiments, one or more cameras mounted in a cabinet of the top section of the instrument is oriented towards the deck to monitor what items are in place in preparation for a sequencing run. The camera can acquire video or images at time intervals. For example, images may be acquired at 1-4 second intervals or any suitable interval. In another example, frames of a video stream can be extracted at intervals such as in a range of 0.5 seconds to 4 seconds. A computer or processor analyses images to detect the completion of a task by the user. The computer or processor may provide feedback and instructions for the next task in the preparation via the display screen. The display screen may present graphical representations of the instrument components and consumables in order to illustrate instructions for the user.

Figure 8:
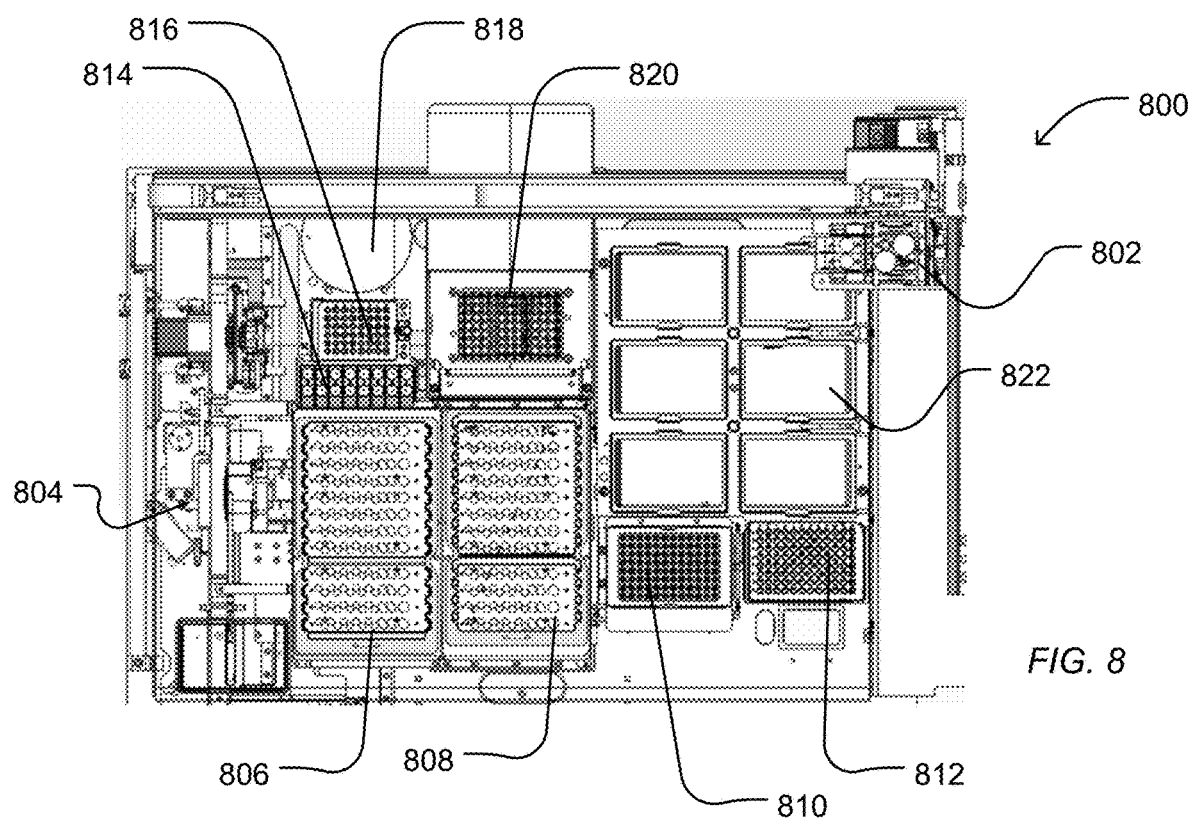
FIG. 8 includes an illustration of an example deck of an instrument.

An example instrument deck 710 is illustrated in FIG. 8 as instrument deck 800. The deck 800 is housed in the top section of the instrument in the view of the camera or cameras. The sample preparation deck may include a plurality of locations configured to receive reagent strips, supplies, a sequencing chip, and other consumables. As used herein, consumables are components used by the instrument that are replaced periodically as they are used. For example, consumables include reagent and solution strips or containers, pipette tips, microwell arrays, and flow cells and associated sensors, among other disposable components not part of the permanent components of the instrument.

In an example, the system 800 includes a pipetting robot 802 that accesses various reagent strips and containers, pipette tips, microwell arrays, and other consumables to implement a test. Further, the system can include mechanisms 804 for carrying out testing. Example mechanisms 804 include mechanical conveyors or slides and fluidic systems.

In an example, the deck 800 includes trays 806 or 808 to receive solution or reagent strips of a particular configuration. In an example of a sequencing instrument, the tray 806 can be used for library and template solutions in appropriately configured strips, and the tray 808 can receive library and template reagents in the appropriate configuration.

Further, the instrument can be configured to receive microwell arrays 810 and 812 at particular locations on the deck. For example, a sample can be supplied in an array of wells, such as microwell array 812. In another example, the system can be configured to receive additional reagents 814 in a different strip configuration. In another example, reagent solutions can be provided in an array 816. In a further example, container arrays 820 can be provided in conjunction with instrumentation, such as a thermocycler. Further, the system can include other instrumentation, such as a centrifuge, that may be supplied with consumables, such as tubes. Further, trays can be provided to receive pipetting tips 822.

The appropriate provisioning of consumables in each of these locations can be monitored by a vision system including one or more cameras. The deck may be provided with one or more cameras to track provisioning and securing of reagents and other consumables. The user can be prompted through the user interface when a reagent is missing that is to be utilized to perform one plan or when a reagent consumable is present in a used state.

Figure 9:
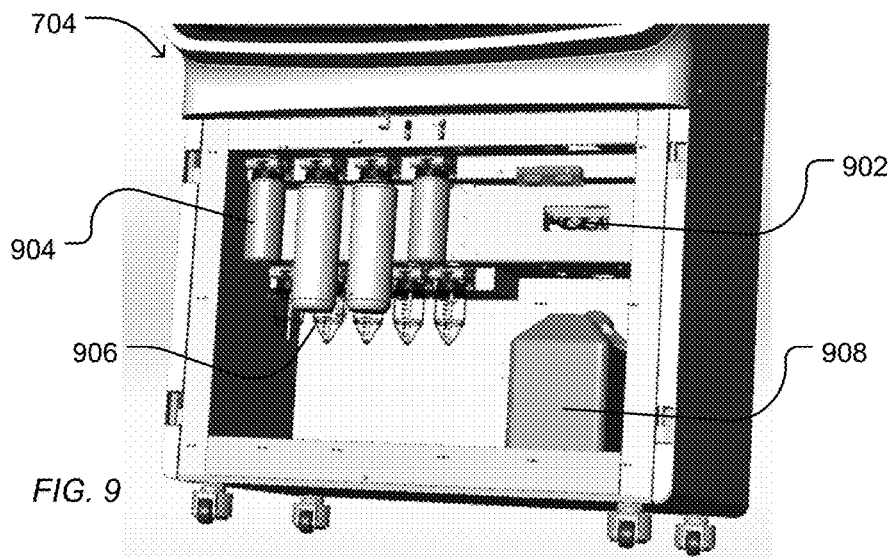
FIG. 9 includes an illustration of an example reagent storage for an instrument.

FIG. 9 includes an illustration of a reagent storage cabinet 704 to store larger volume reagent and solution containers. For example, the cabinet storage 704 includes an interface 902 to receive a reagent cartridge. In another example, the storage 704 can provide space for containers 904 or 906. In a further example, the storage 704 can include space for a waste container 808.

Figure 10:
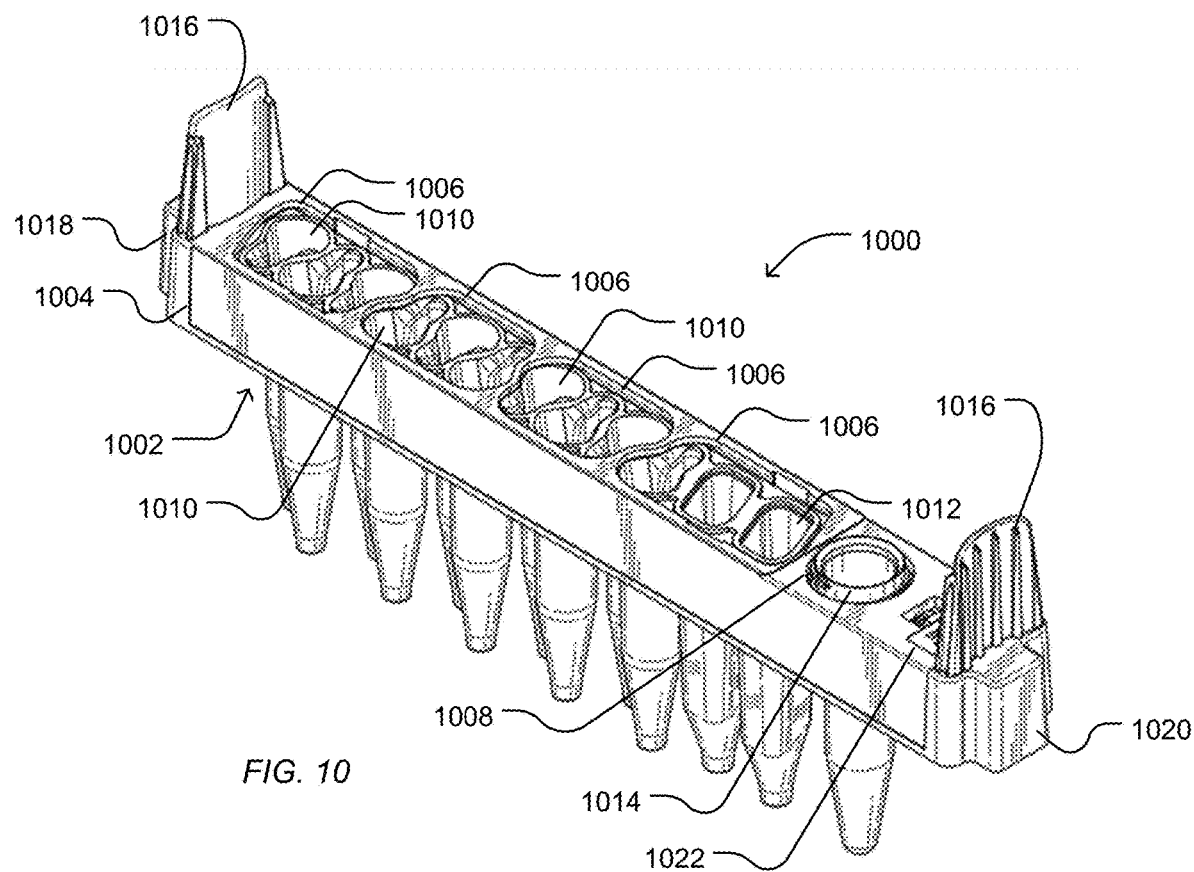
FIG. 10 includes an illustration of an example consumable.

An example consumable, such as a solution or reagent strip configured to fit in slot 1002 is illustrated in FIG. 10. In an example, the strip includes a base 1002 and a top 1004 coupled to the base 1002. The top 1004 includes windows 1006 that provide access to wells 1010 or 1012. Optionally, the top 1004 can provide a window 1008 to provide access to tube 1014 inserted into a tube receptacle of the base 1002.

The top can further include grips 1016. For example, the grips 1016 can be used to hold the reagent container 1000 when inserting or removing the reagent container 1000 from an analytical device. Further, the top 1004 can define end structures 1018 or 1020 configured to engage a complementary structure on the instrument and limit an orientation of the strip in relation to a position within the instrument. Further, a code 1022, such as a bar code or QR code, can be present on the top 1004.

Flow Through Initialization

In an example system for preparing reagent solutions in a sequencing device, a source of an initial solution can be connected to containers within a cartridge. The initial solution can include salts, surfactants, and preservatives.

The cartridge can include containers storing a concentrate of reagents to be used in the sequencing reaction. For example, the containers can include a concentrated nucleotide, a concentrated modified nucleotide, or a blend of nucleotides. In another example, the container can include cofactors and enzymes useful in sequencing.

The concentrated nucleotide can be blended with the initial solution, yielding a nucleotide solution to be stored in separate containers. In particular, the reagent storage container can be part of the system illustrated in FIG. 1, having reagent storage containers 104, 106, 108, 110, or 112.

The source can be a pressurized system to instigate flow through the cartridge. Alternatively, solutions can be pumped to the cartridge from the source. In another example, a vacuum may be drawn in the containers to draw solution through the cartridge and into the containers. In another example, flow can be instigated by both drawing a vacuum and pressurizing or pumping.

Figure 11:
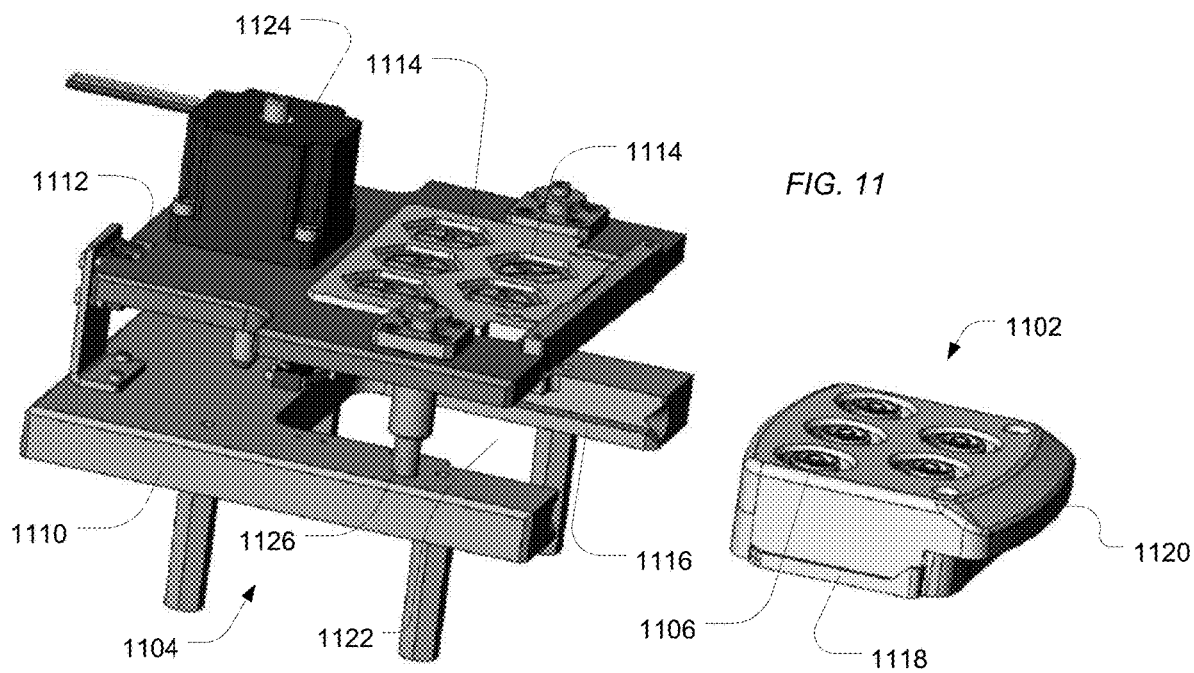
FIG. 11 and FIG. 12 include illustrations of example cartridge system.
Figure 12:
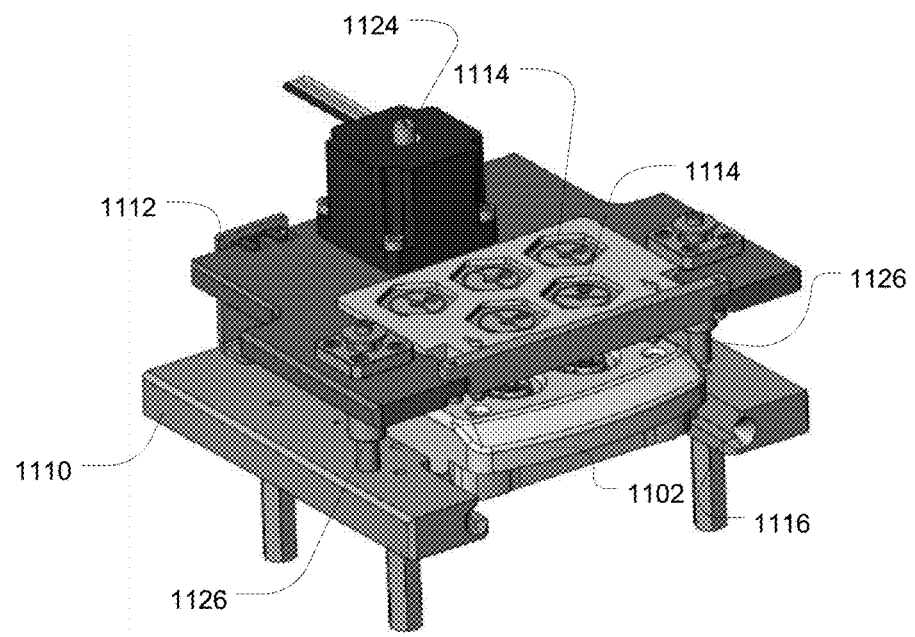

FIG. 11 illustrates an example cartridge system including a cartridge 1102 and a docking station 1104. The cartridge 1102 can fit in a docking area 1122 of a primary platform 1110 of the docking station 1104. In particular, the docking station 1104 can include guides, such as rails 1116, that cooperate with other guides, such as rails 1118 on the cartridge 1102, to position the cartridge 1102 in the docking station 1104, for example as illustrated in FIG. 12. The cartridge 1102 can further include a handle 1120 to assist with inserting the cartridge 1102 and removing the cartridge 1102 from the dock 1104.

The docking station 1104 includes a second platform 1112 movable relative to the first platform 1110. For example, the platform 1112 can be driven relative to the platform 1110 by a driver 1124, such as a motor or screw mechanism. In particular, the platform 1112 can be guided up and down by guides 1126.

The platform 1112 includes fluid couplers 1114 that can be attached to tubing on the top side and interface with the containers 1106 of the cartridge 1102. When the cartridge 1102 is inserted into the dock 1104, and secured by the platform 1110, the platform 1112 can be driven downward or towards the platform 1110 by driver 1124 so that the fluidic couplers 1114 can engage the containers 1106 of the cartridge 1102. In particular, guides 1126 can ensure positioning of the fluidic couplers 1114 relative to the cartridge 1102.

The cartridge 1102 includes a plurality of containers 1106. For example, the cartridge can include a number of containers 1106 at least equal to the number of nucleotides (i.e., 4). As illustrated, the cartridge 1102 has 5 container and may have more or fewer than 5. The cartridge 1102 can further include additional reagent concentrate containers, for example including a combination of nucleotides, other ionic compositions, enzymes, or surfactants.

The cartridge 1102 also includes a guide 1118, illustrated as a rail, to guide the cartridge 1102 when engaging the dock 1104. The cartridge also can include a handle 1120 to assist with insertion and removal of the cartridge from the docking station 1104. Further, the cartridge can include positioning features, such as indentations, useful in ensuring that the fluidic couplers 1114 are positioned properly to engage the containers 1106.

Figure 13:
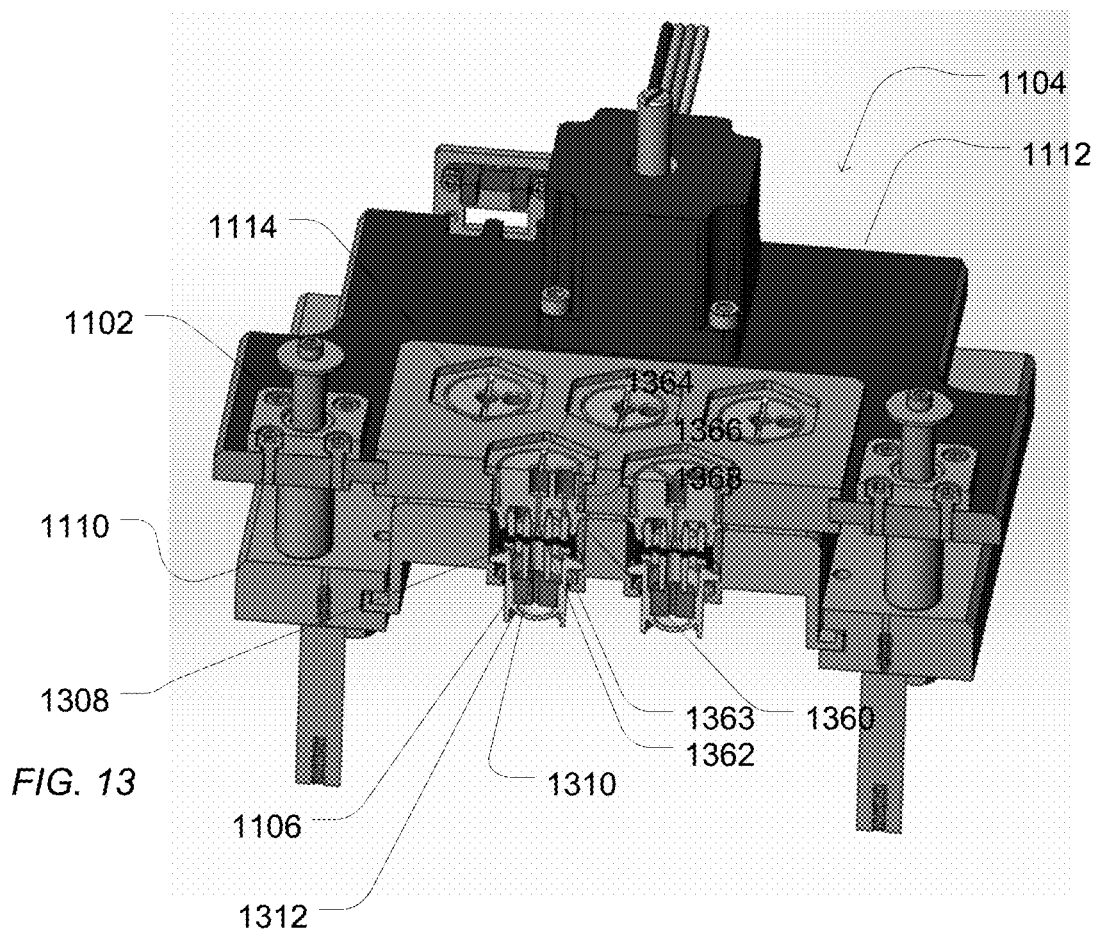
FIG. 13 includes an illustration of an example docking station to receive a cartridge.

As illustrated in FIG. 13, The container 1106 includes a receiver, a clip, and a seal. The seal includes a central bore 1310 and at least one peripheral bore 1308 positioned radially outward from the central bore 1310.

In cross-section, the containers 1106 can further include a frit 1312 disposed in a cavity of the receiver. The frit 1312 can include a central bore aligned with the central bore 1310 of the seal. The cavity can also be in fluidic communication with the peripheral openings 1308. Fluid can be applied to the central bore 1310, which flows down through the frit 1312 and into the cavity. The fluid then flows out of the outer holes 1308 and into a channel of the seal.

A frit 1312 can include a protrusion at a top surface configured to engage the central bore of the seal. In particular, the protrusion of the frit can enter a central bore of the seal at the protrusion of the seal. The frit can be fluid permeable. For example, the frit 1312 can be formed of a porous material, such as a porous ceramic or metallic material. In another example, the frit 1312 can be formed of a porous polymeric material or a water permeable polymer or fibrous material. The frit 1312 can include a central bore extending at least partially into the frit 1312 or completely through the frit 1312. In addition, the frit 1312 includes a larger surface area at the top through which a solution can flow through the frit to remove concentrated nucleotide solution or reagent solution from the frit and into the cavity of the receiver.

As illustrated in FIG. 13, when the cartridge 1102 is inserted into the dock 1104 and the platform 1112 is positioned proximity to the platform 1110, the fluidic couplers 1114 engage the containers and in particular, the seal of the container 1106. A central tube of the fluidic couplers 1114 enters the central bore 1310 of the seal. The outer concentric ring 1360 engages the seal radially outward of the channel, enclosing the channel. The fluidic couplers 1114 further include openings to engage tubes 1364 and 1366. In an example, an opening 1364 is positioned at an axial center of the fluidic couplers 1114 and a second opening 1366 is disposed radially outwardly from the central axis of the fluidic couplers 1114.

In a particular example, fluid can flow into the opening 1364 and be driven down the tube 1360 into the central bore 1310 of the seal. The fluid flows through the frit 1312 and into the cavity of the receiver. The fluid can flow through the openings 1308 into the channel enclosed by the fluidic coupler 1114. The fluid can leave the channel through a hole 1368 connected to the opening 1366. Alternatively, the flow can be reversed.

Chip and Slide Mechanism

Figure 14:
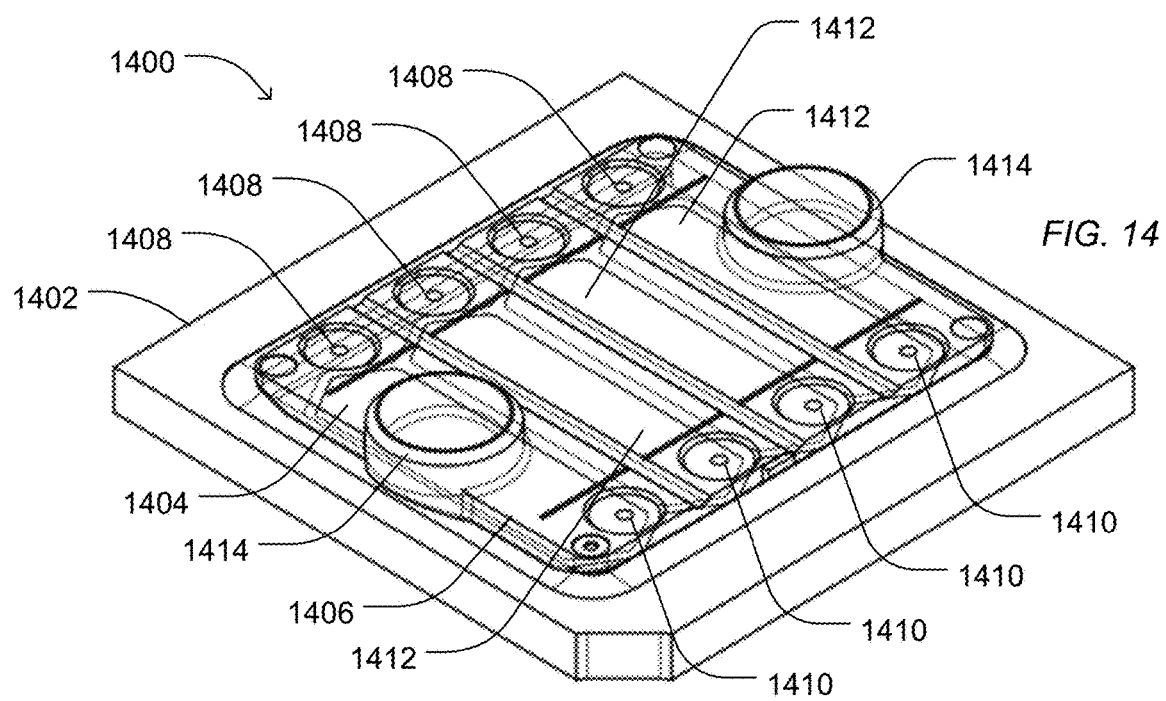
FIG. 14 and FIG. 15 include illustrations of an example sensor device.
Figure 15:
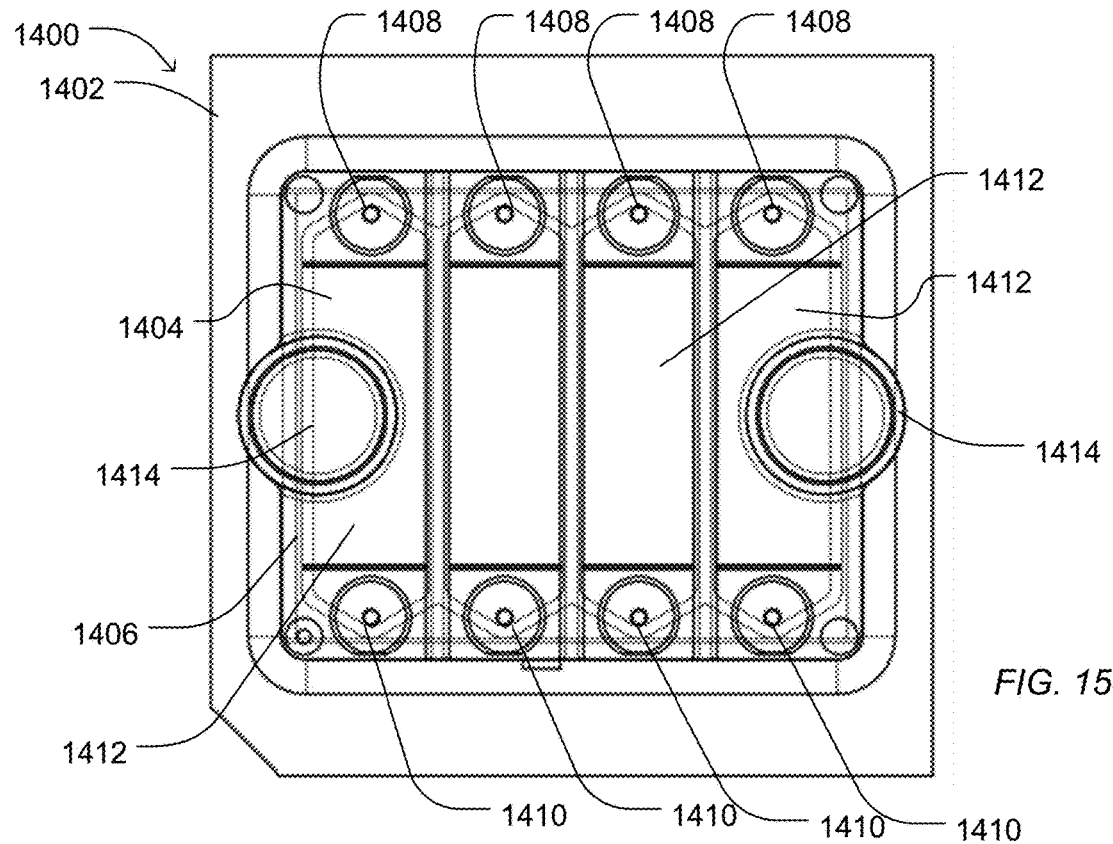

In an example, the biosensor and flow cell are an example of a sensor device. FIG. 14 and FIG. 15 illustrate an example sensor device 1400, such as a microchip including a flow cell. For example, the sensor device 1400 includes a substrate 1402 securing a die 1404 that has a plurality of microwells in fluid communication with a sensor array. A flow cell 1406 is secured over the substrate, providing a volume over the die 1404.

In an example, the flow cell 1406 includes a set of fluid inlets 1408 and a set of fluid outlets 1410. In particular, the flow cell 1406 can be divided into lanes 1412. Each lane is individually accessed by a respective fluid inlet 1408 and fluid outlet 1410.

As illustrated, the sensor device 1400 includes four lanes 1412. Alternatively, the sensor device 1400 can include less than four lanes or more than four lanes. For example, the sensor device 1400 can include between 1 and 10 lanes, such as between 2 and 8 lanes, or 4 to 6 lanes. The lanes 1412 can be fluidically isolated from each other. As such, the lanes 1412 can be used at separate times, concurrently, or simultaneously, depending upon aspects of a run plan.

The sensor device 1400 can further include guides structures 1414, for example, formed as part of the flow cell 1406, to engage complementary structures on a fluidic coupler. Such guide structures 1414 assist with aligning the fluid inlets 1408 and fluid outlet 1410 with associated ports on a fluidic coupler.

Figure 16:
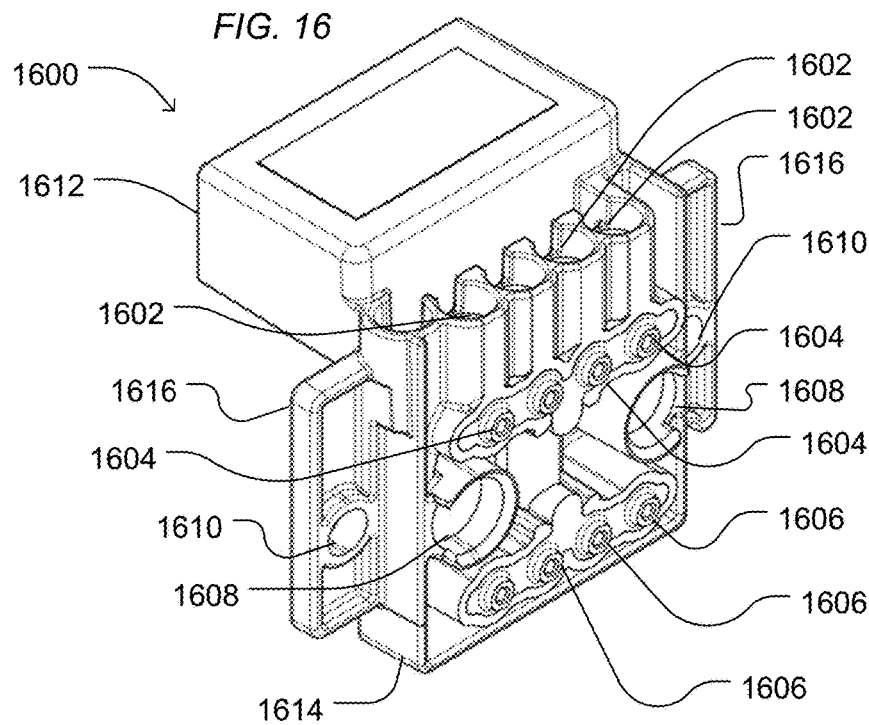
FIG. 16, FIG. 17, and FIG. 18 include illustrations of an example fluidic coupler.
Figure 17:
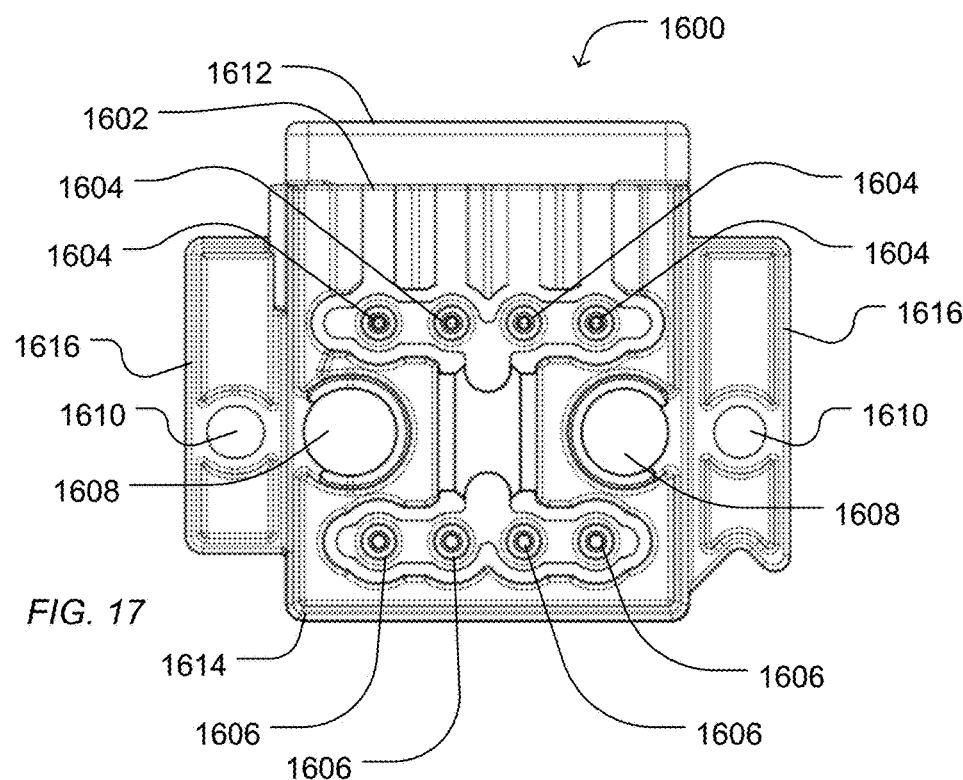
Figure 18:
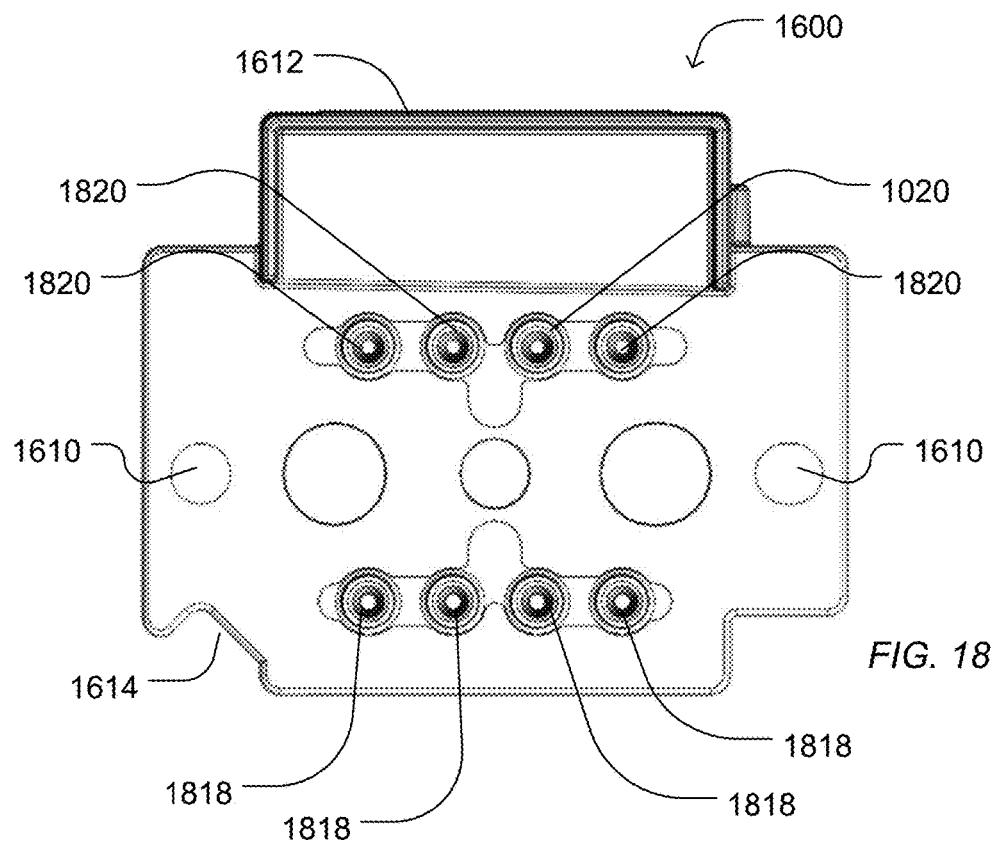

FIG. 16, FIG. 17, and FIG. 18 include illustrations of an example fluidic coupler 1600. The fluidic coupler 1600 includes a body 1614 defining fluidic pathways between sets of ports. Further, the fluidic coupler 1600 can include a connector section 1612 to engage a mechanical assembly and assist with positioning the fluidic coupler 1600 relative to the mechanical assembly. In another example, the fluidic coupler 1600 can include wings 1616 defining reference holes 1610 to engage guide rods of a mechanical assembly, further assisting with positioning the fluidic coupler 1600 relative to a sensor device.

The body 1614 of the fluidic coupler 1600 can define openings 1602 that are in fluidic communication with a first set of ports 1604. The openings 1602 can be sized to receive an end of a pipette tip and allow pipetting of a fluid composition into the opening 1602. The openings 1602 are in fluidic communication with a set of ports 1604, which are configured to engage inlets 1408 of a sensor device 1400 (FIG. 14). The fluidic coupler 1600 can further define a second set of ports 1606 that can engage and provide fluidic communication with outlets 1410 of the sensor device 1400 (FIG. 14).

As illustrated in FIG. 18, the system can further include a third set of ports 1818 that are in fluidic communication with the second set of ports 1606. The third set of ports 1818 can engage with a fluidic manifold of a mechanical assembly, such as the fluidic manifold 2540 illustrated in FIG. 26 and FIG. 27. Optionally, the fluidic coupler 1600 can include a fourth set of ports 1820, which can connect with a fluidic manifold or can be blocked depending upon the configuration of the mechanical assembly.

The ports 1604, 1606, 1818 or 1820 can be formed of a resilient material, such as a rubber or elastomeric polymer. In an example, the ports can be formed as an overmold using the resilient material.

Returning to FIG. 16, the body 1614 of the fluidic coupler 1600 can further include guide features 1608 complementary to guide features 1414 of the sensor device 1400 (FIG. 14).

Figure 19:
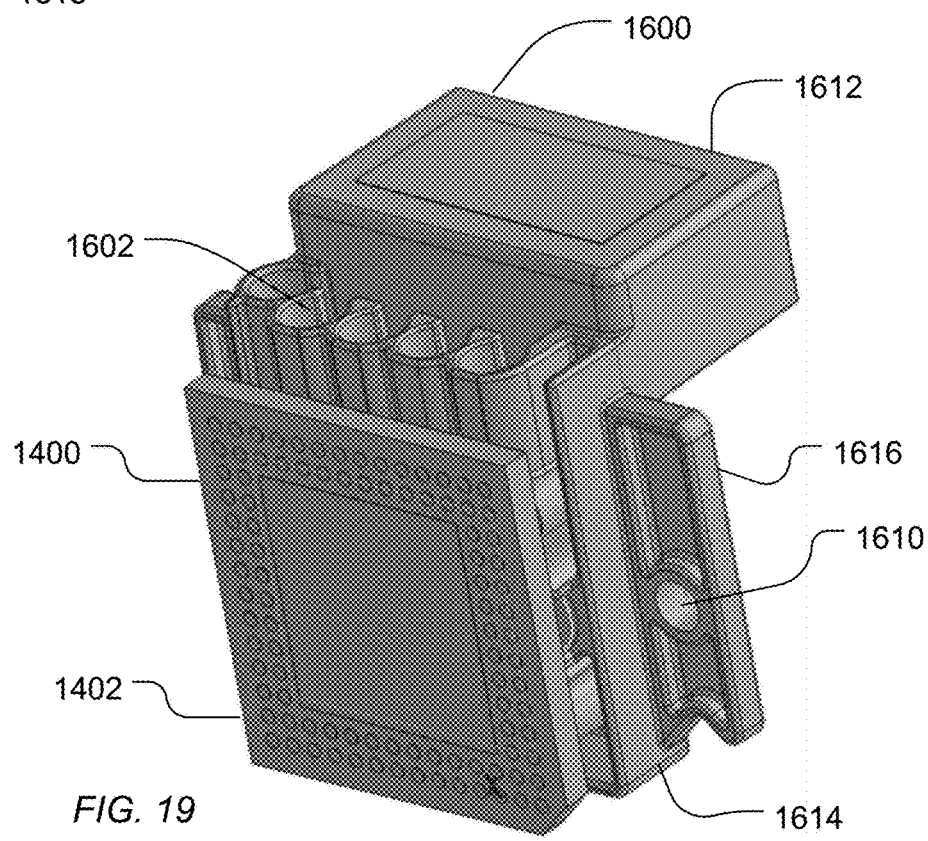
FIG. 19 and FIG. 20 include illustrations of an example interconnection between a sensor device and a fluidic coupler.
Figure 20:
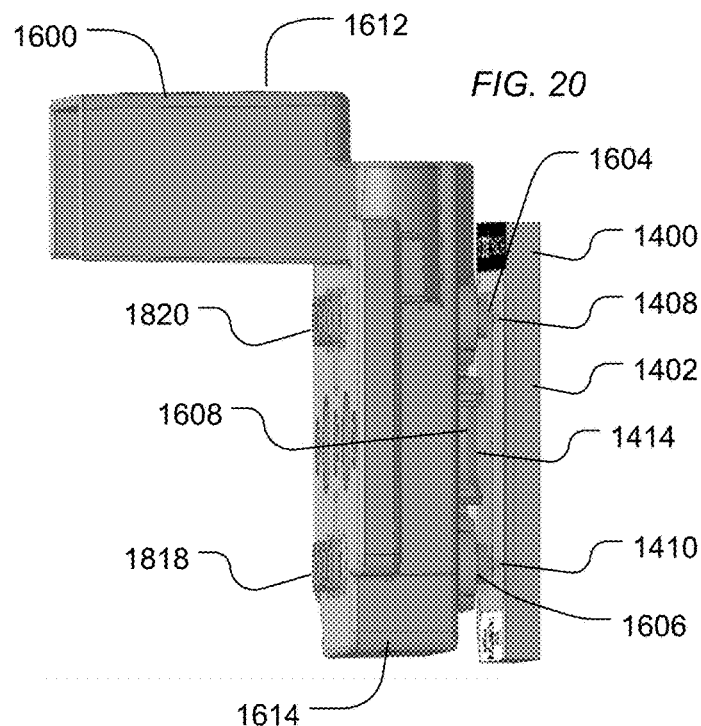

As illustrated in FIG. 19 and FIG. 20, the fluidic coupler 1600 can engage the sensor device 1400. The body 1614 of the fluidic coupler 1600 can be aligned with the substrate 1402 of the sensor device 1400 to allow the first set of ports 1604 of the fluidic coupler 1600 to be in fluid communication with the inlets 1408 of the sensor device 1400. Further, the second set of ports 1606 can be in fluidic communication with the outlets 1410 of the sensor device 1400. For example, the guide structures 1414 and 1608 can engage to align the ports with the inlets and outlets. Optionally, a third set of ports 1818 can be in fluid communication with a manifold. In a further example, a set of fluid ports 1820, optionally in fluid communication with the second set of port 1608, can be in fluid communication with a fluidic manifold.

Accordingly, fluid compositions can be pipetted into the openings 1602 in fluid communication with the first set of ports 1604, which provide the fluidic composition to the flow cell 1406 of the sensor device 1400 via the inlets 1408 of the flow cell 1406. After processing, the remainder of the fluidic composition can be drawn out of the outlet 1410 of the sensor device 1400 through the second set of ports 1606 and the third set of ports 1818 into a fluid manifold.

Figure 21:
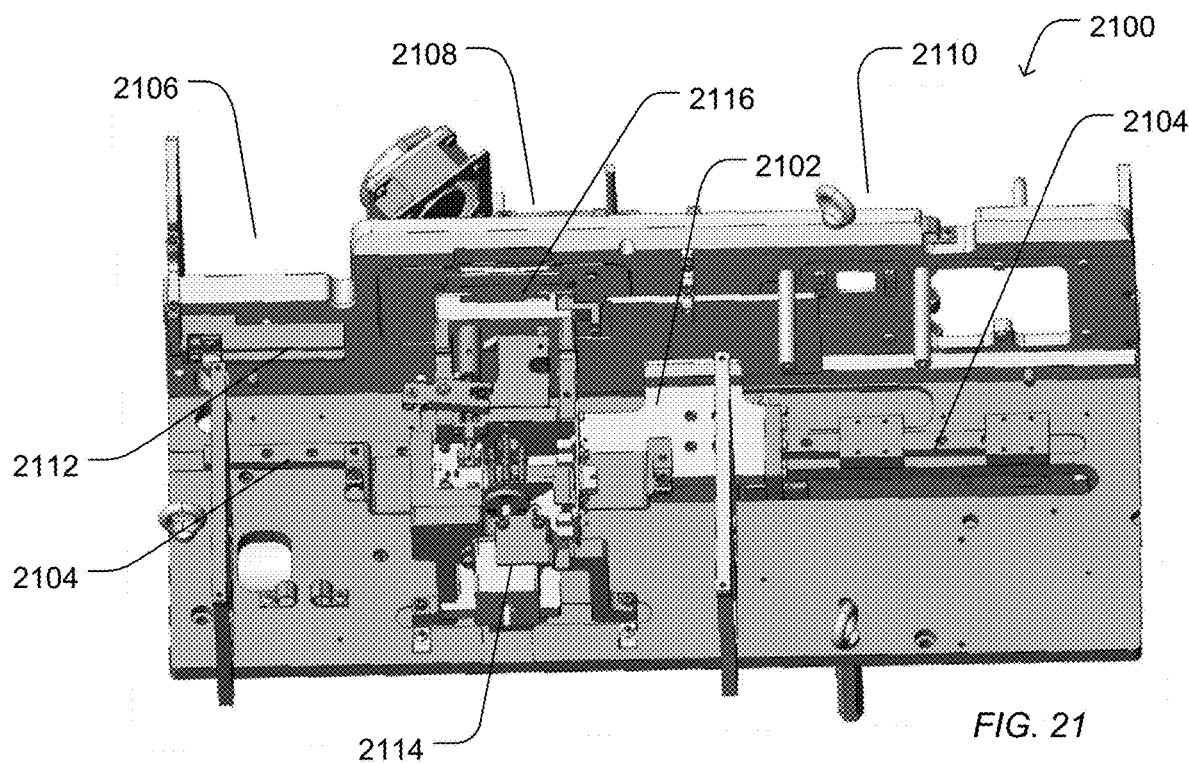
FIG. 21 and FIG. 22 include illustrations of an example mechanical system to interact with a sensor device.
Figure 22:
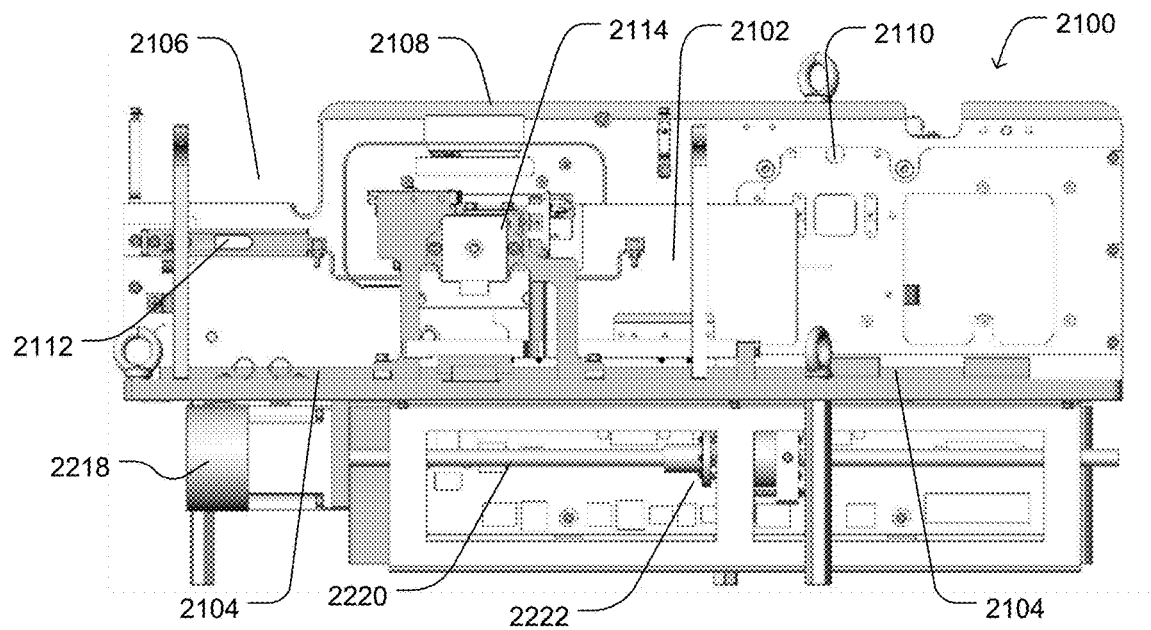

FIG. 21 and FIG. 22 include illustrations of an example mechanical system 2100 for moving a sensor device between various stations within the system. For example, a slide mechanism 2102 can move along a rail 2104 to guide a sensor device (e.g., sensor device 1400 in FIG. 14) between stations 2106, 2108, and 2110. For example, a sensor device can be inserted into the slide mechanism 2102 at station 2106. In an example, the sensor device can be inserted in a vertical orientation in which the inlet and outlet are directed to a side in contrast to upward. A sensor 2112 can detect the presence of the sensor device and allow the slide mechanism 2102 to move when the sensor device is present. For example, the slide mechanism 2102 can move the sensor device to station 2108 where the sensor device can be loaded with samples, such as through a magnetic loading method described above in relation to FIG. 4. In particular, a fluidic coupler can be inserted into space 2116 provided by the mechanical assembly 2114, which can press the fluidic coupler against the sensor device and engage the fluidic coupler with a manifold. When the magnetic loading technique is complete, the mechanical assembly 2114 can detach from the fluidic coupler, and the slide 2102 can move the sensor device to a subsequent station 2110, such as a fluidic station providing reagents and other conditions for sequencing.

As illustrated in FIG. 22, a drive 2218, such as a screw drive, can include a screw 2220 that engages a clutch 2222 to move the slide 2102 and thus the sensor device between the stations 2106, 2108, and 2110.

Figure 23:
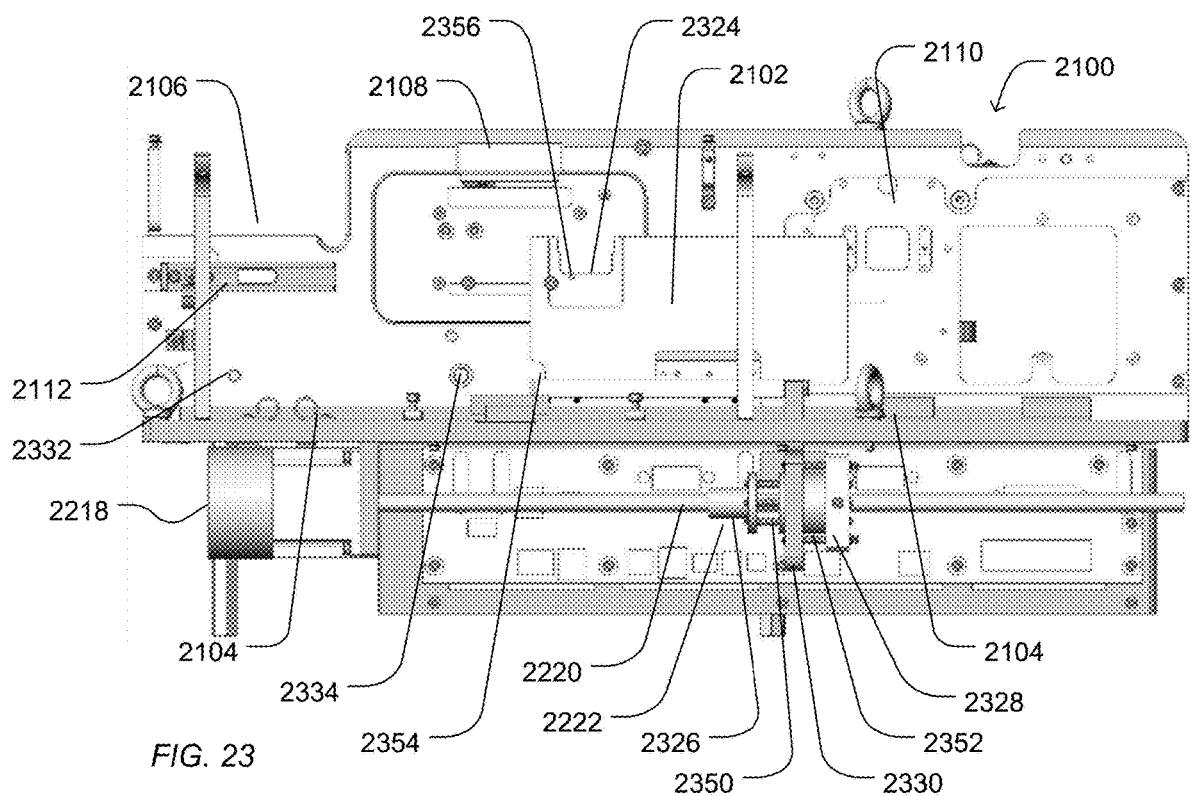
FIG. 23 and FIG. 24 include illustrations of example slide mechanism for use with the mechanical system.
Figure 24:
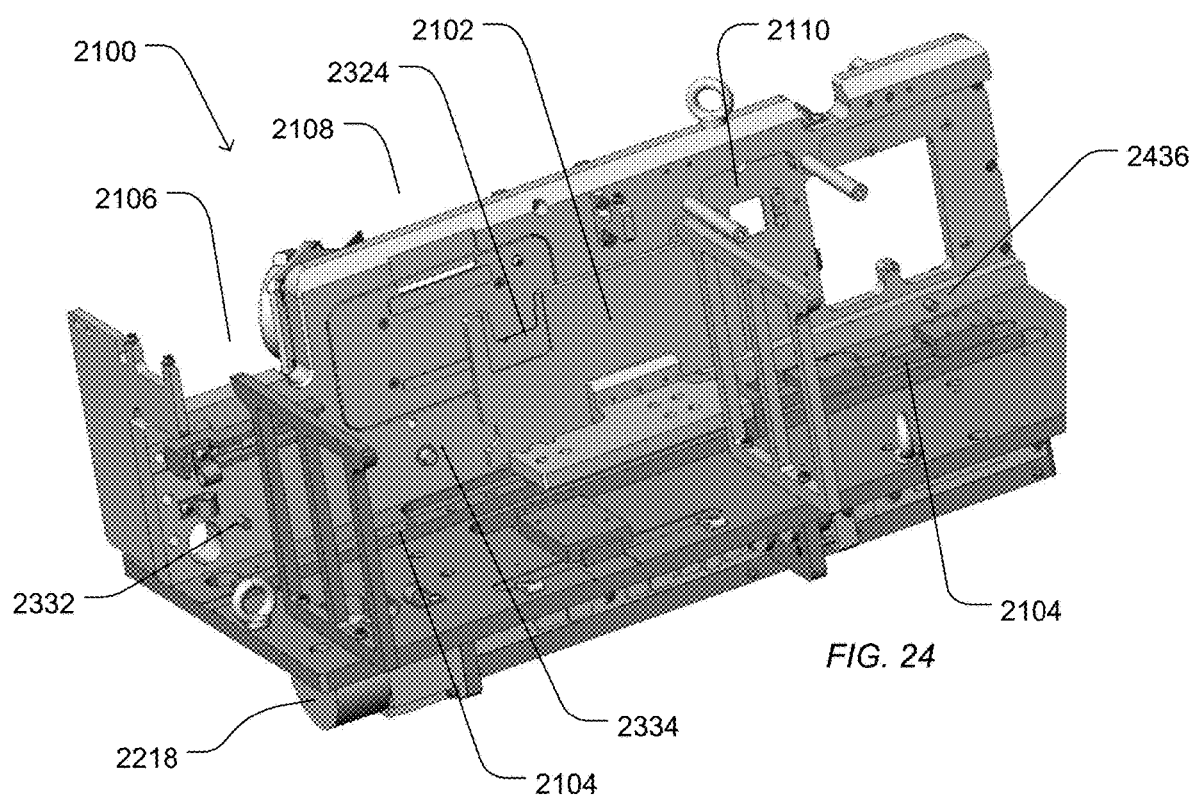

As illustrated in FIG. 23, the slide 2102 can be positioned at station 2106 in which a stop post 2332 engages the slide 2102 at feature 2354. Further, the slide 2102 can move forward from station 2106 to station 2108 at which a solenoid stop post 2334 can be engaged, and the slide moved backwards (left as illustrated) to engage the solenoid stop 2334 with the feature 2354. In addition, the slide 2102 can be moved along the rail 2104 to engage a forward stop 2436, illustrated in FIG. 24, aligning the slide and sensor receptacle 2324 with the station 2110. To return the slide 2102 back to station 2106, the solenoid stop post 2334 can be disengaged to permit the slide 2102 to pass.

When a sensor device is inserted into the receptacle 2324 at station 2106, a sensor 2112 can sense the presence of the sensor device in the receptacle 2324 through opening 2356. For example, the sensor device 2112 can be an optical sensor that optically detects the presence of the sensor device within the receptacle 2324 through the opening 2356.

The clutch 2222 can be used to provide both a backwards force (illustrated as toward the left) against stops 2324 or 2334 and a forward force (illustrated as toward the right) against the stop 2436. For example, the clutch system 2222 includes a nut 2326 to engage the screw 2220 of the screw drive mechanism 2218. The nut 2326 is engaged with a coupling 2328 having a central bore that allows the screw 2220 to pass through the coupling 2328. The coupling 2328 is attached to the nut 2326 using pin and spring system 2350. The pins are movably connected to the nut so that when the springs of the pin and spring system 2350 compress, the pins move through the nut 2326.

The coupling 2328 is also connected to a connector plate 2330 using pin and spring systems 2352. The pins of the pin and spring system 2352 can be configured to move through the connector plate 2330 when the springs of the pin and springs system 2352 are compressed. Alternatively or in addition, the pins of the pin and spring system 2352 can be configured to move through the coupling 2328.

The connector plate 2330 is coupled to the slide 2102 moving back and forth in response to a rotation of the screw 2220. When the slide 2102 is moved backwards (illustrated as left in FIG. 23) against the stop 2332 or 2334, the springs of the pin and spring system 2352 can compress, and the pins can move through either the connector plate 2330 or the coupling 2328. As such, rotation of the screw 2220 provides a known force backwards against the rods 2332 or 2334, providing for precise positioning of the sensor device within the receptacle 2324. In a further example, as the slide 2102 is moved forward to engage the stop 2436, the slide 2102 stops moving. Additional rotation of the screw 2220 moves the nut further forward (illustrated as right in FIG. 23). The springs of the pin and springs system 2350 compress, and the pins of the pin and spring system 2350 move through the nut 2326, providing a known force of the slide 2102 against the forward stop 2436. Such a force and positioning provides precise location of the sensor device receptacle 2324 and sensor device at station 2110.

Figure 25:
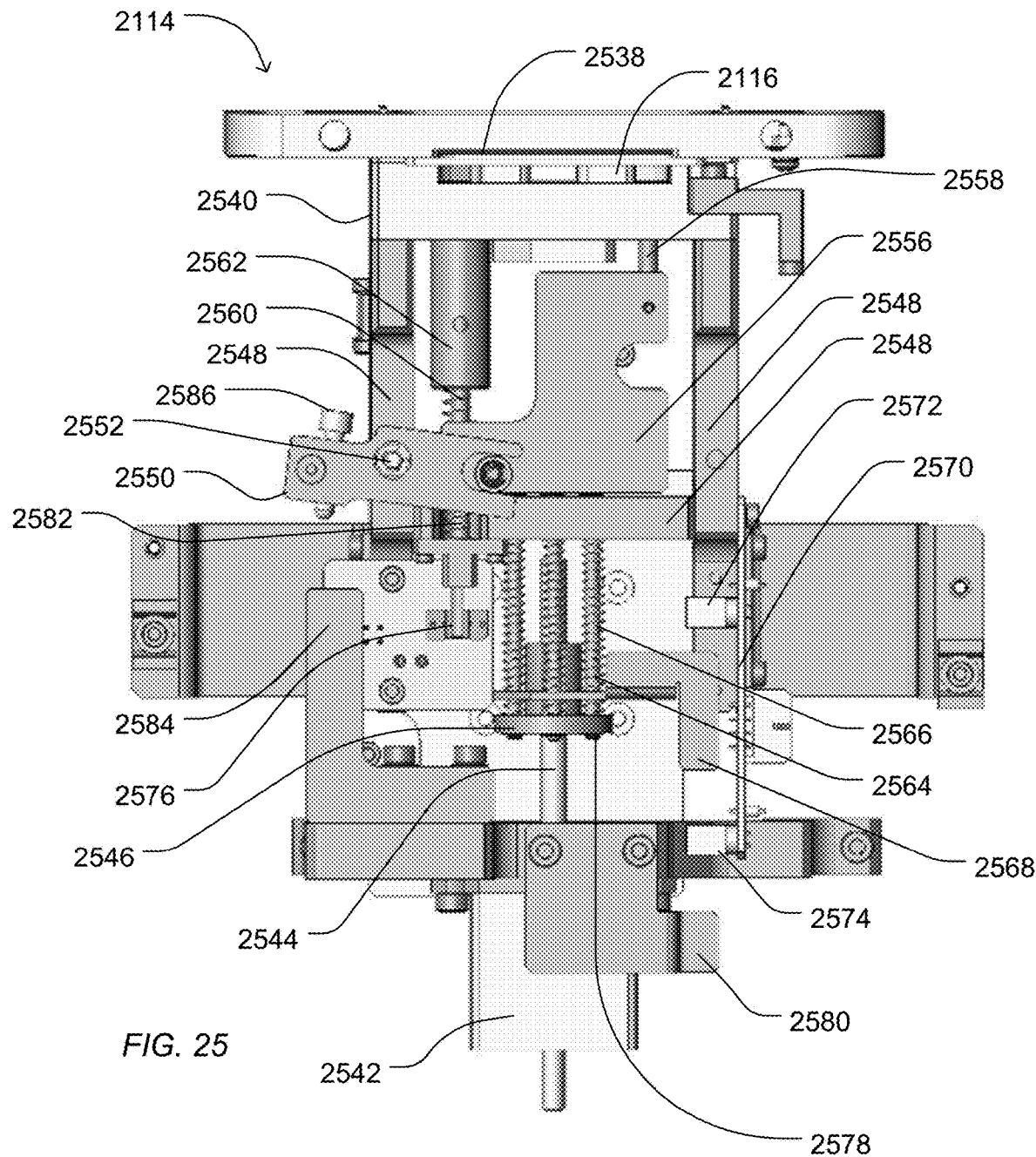
FIG. 25 includes an illustration of an example mechanical assembly to provide fluidic connection between the fluidic coupler and the sensor device.

FIG. 25 includes an illustration of an example mechanical assembly 2114 to provide a fluidic coupling between the sensor device and a fluidic coupler. When the slide is in position, a space 2538 is provided for the sensor device. Further, a space 2116 is provided for a fluidic coupler. When engaged by the mechanical assembly 2114, a fluidic coupler is pressed in fluid communication with the sensor device and with the manifold 2540. The drive mechanism 2542 utilizing, for example, a screw drive with a screw 2544, can move a frame 2548 of the mechanical assembly 2114 forward (illustrated as up in FIG. 25) and backwards (illustrated is down in FIG. 25) utilizing clutch system having a nut 2546 and coupled to the frame 2548 by pins 2564 and springs 2566. The pins 2564 can be movably coupled with the nut 2546 such that the heads 2578 of the pins 2564 are positioned against the nut 2546 until the manifold 2540 is pressed against a fluidic coupler. Additional movement of the nut 2546 forward causes the pins 2564 to move through the nut 2546, allowing the springs 2566 to compress.

The frame components 2548 can move together forward and back in response to the movement of the nut 2546. A lever 2550 is rotatably coupled to the frame 2548 at fastener 2552. When the assembly is in a rearward position, an adjustment screw 2586 attached to the lever 2550 engages a stop 2584, pivoting an opposite side of the lever 2550 rearward (downward as illustrated). As the nut 2546 moves forward, the adjustment screw 2586 gradually disengages from the stop 2584, and the opposite side of the lever 2550 is pivoted forward, for example, motivated by a spring 2582. The pivoting of the lever 2550 moves a guide plate 2556 forward relative to the frame 2548 that is also moving forward (upward as illustrated). The guide plate 2556 is connected to guide rods 2558 and 2560 that move forward with the guide plate 2556 to engage reference holes of a fluidic coupler. The guide rod 2560 can be further guided by a guide 2562 that engages a portion of the manifold 2540. As the guide rod 2560 moves forward, it can disengage from a sensor 2576, indicating that the guide rod 2560 is engaging the reference hole of the fluidic coupler.

When the manifold 2540 and the guide rods 2558 and 2560 engage the fluidic coupler, the nut 2546 can continue forward while the frame 2546 remains stationary. The pins 2564 can move through the nut 2546 and the springs 2566 compress, providing a known force against the fluidic coupler and against the sensor device in fluid communication with the fluidic coupler. Such force provides a desirable leak-free fluidic coupling between the sensor device and the fluidic coupler.

A circuit board 2570 including sensors 2572 and 2574 can be connected to the movable frame 2548 and can move with the frame 2548. A flag 2568 can be connected to the nut 2546. From the rearward position to a second position in which the manifold 2540 and frame 2548 connect with the fluidic coupler, the position of the flag 2568 remains constant relative to the position sensor 2572. Once the manifold 2540 is positioned against the fluidic coupler and a sensor device, the nut 2546 moves forward relative to the frame 2548. Thus, the flag 2568 moves forward towards the sensor 2572. When the flag 2568 is detected by the sensor 2572, the forward drive of the nut 2546 can be stopped. As such, a known compression of the springs 2566 is achieved, and a known force is applied against the frame 2548, manifold 2540, and fluidic coupler.

As the nut 2546 is moved rearward from the forward position, the flag 2568 disengages from the sensor 2572 until the pins 2564 at their head 2578 are secured against the nut 2546. As the nut 2546 continues to move backwards, the frame 2548 and manifold 2540 are drawn rearward along with the sensor circuit board 2570. The adjustable screw 2586 engages the stop 2584, withdrawing the guide rods 2558 and 2560 from the reference holes of the fluidic coupler. As the guide rods are withdrawn from the fluidic coupler, the reference rod 2560 engages the sensor 2576 indicating it has been withdrawal from the reference hole of the fluidic coupler. The sensor 2574 continues to move backwards with the sensor circuit board 2570 attached to the frame 2548 until the sensor 2574 engages a flag 2580 indicating that the nut 2546 is in the rearward most position. The fluidic coupler is disengaged from the mechanical assembly 2114 and can be removed. Further, the slide mechanism 2102 can move the sensor device to the next station 2110.

Figure 26:
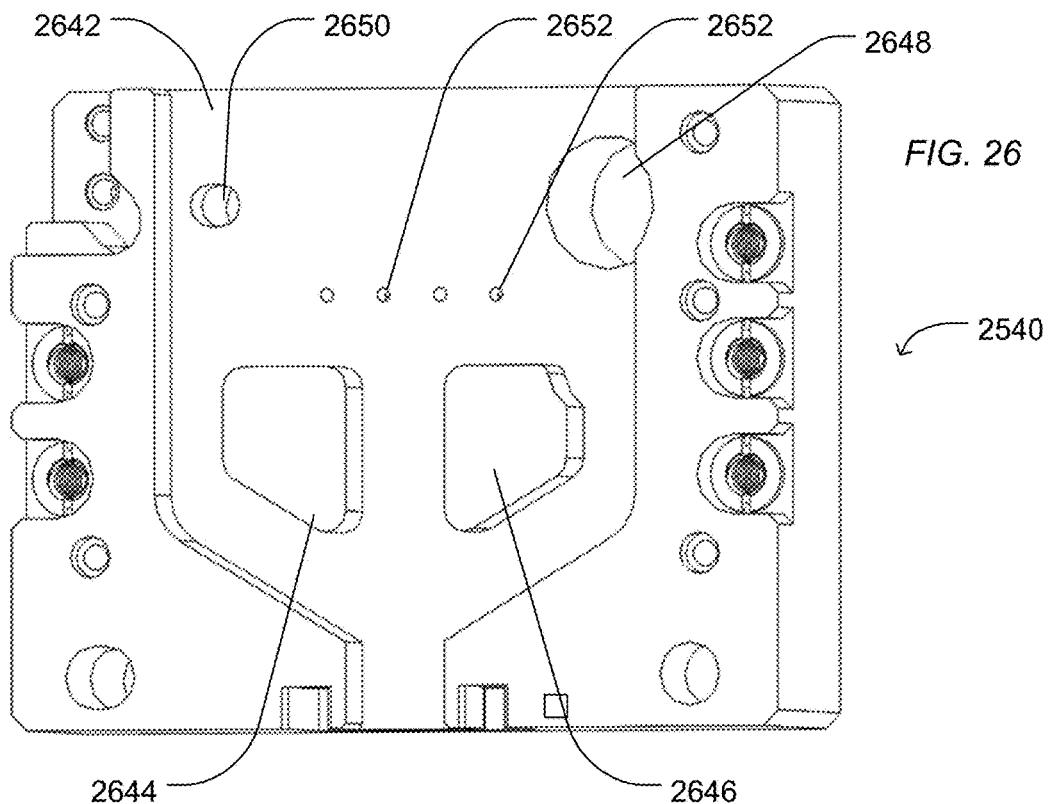
FIG. 26 and FIG. 27 include illustrations of example fluidic manifold.
Figure 27:
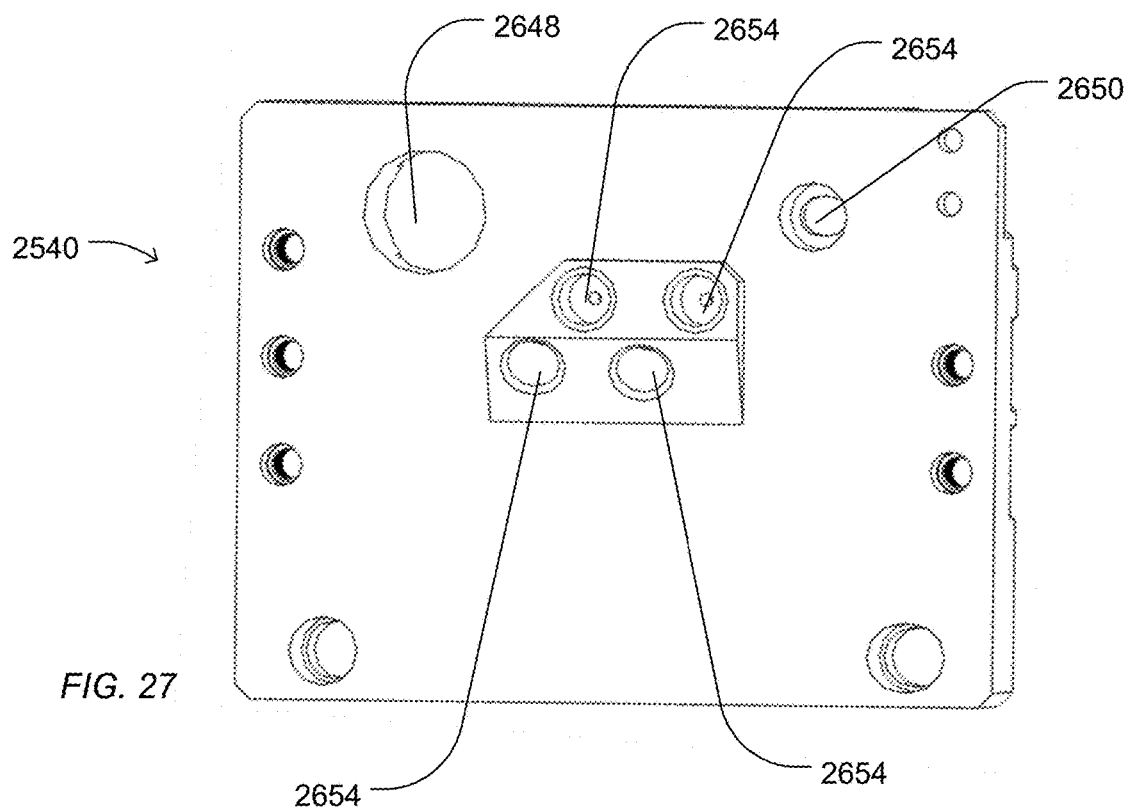

FIG. 26 and FIG. 27 include illustrations of an example manifold 2540 for use with the mechanical assembly 2114. The manifold 2540 can include at a front surface a slot 2642 to receive the fluidic coupler. The slot 2642 along with rest structures 2644 and 2646 can set a vertical position of a fluidic coupler, such as the fluidic coupler 1600 illustrated in FIG. 16. The connector section 1612 of the fluidic coupler 1600 can extend over the manifold 2540 towards the rear surface of the manifold. The manifold 2540 can further include reference holes 2650 and 2648 that align with the reference holes 1610 of the fluidic coupler 1600. The reference hole 2650 can be sized to receive the guide rod 2558. The reference hole 2648 can be sized to receive the guide rod 2560 and optionally the guide 2562.

In particular, the manifold 2540 includes a set of fluid openings 2652 to engage the third ports 1818 of the fluidic coupler 1600 (illustrated in FIG. 18). The set of openings 2652 are in fluid communication with a set of ports 2654 disposed on a rearward surface of the fluid manifold 2540. Such ports 2654 can be connected to a vacuum to allow fluid to be drawn through the ports 2654, the openings 2652, the third set of ports 1818 of a fluidic coupler 1600, and the second set of ports 1606 of a fluidic coupler 1600. Optionally, an additional set of fluid openings and flow ports can be provided to connect with the fourth set of fluid ports 1820 of the fluidic coupler 1600.

Figure 28:
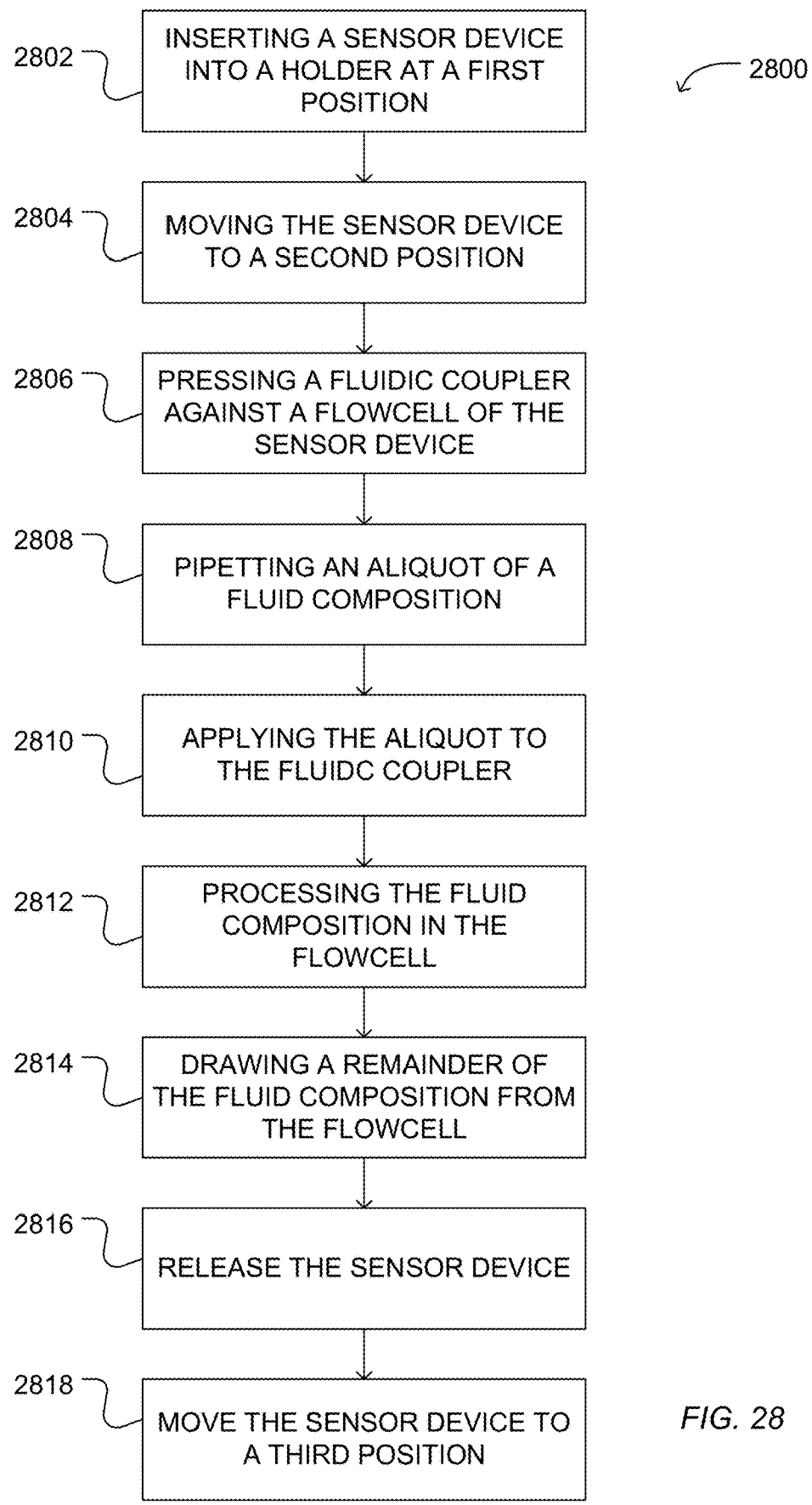
FIG. 28 includes a block flow diagram of an example method for interacting with a sensor device using the mechanical system.

FIG. 28 includes a block flow diagram illustrating a method 2800 for fluidically engaging a sensor device. For example, as illustrated at block 2802, a sensor device can be inserted into a holder or receptacle of the slide when the slide is in a first position. Optionally, a detector can determine whether the sensor device is properly positioned within the holder or receptacle prior to allowing movement of the slide to a second position.

As illustrated at block 2804, the sensor device and slide can be moved to a second position. In an example system, the second position can represent a position in which a sample is loaded onto the sensor device. For example, a fluidic coupler can be pressed against a flow cell of the sensor device, as illustrated at block 2806. The fluidic coupler can include openings that allow fluid compositions to be pipetted into the openings and through ports of the fluidic coupler that are engaged with inlets of the flow cell of the sensor device.

For example, a pipette can draw an aliquot of a fluid composition, as illustrated at block 2808. The aliquot can be applied to the openings of the fluidic coupler, as illustrated at block 2810. The aliquot can pass through the opening of the fluidic coupler, through the first set of ports, and through the inlet of the sensor device and into the flow cells of the sensor device.

In an example, the fluid composition can be processed within the flow cell, as illustrated at block 2812. For example, a magnetic loading technique can be applied to load samples within wells of the sensor device.

As illustrated at block 2814, the remainder of the fluid composition can be drawn from the flow cells of the sensor device. For example, a vacuum attached to the manifold pressed against the fluidic coupler and in fluid communication with the outlets of the flow cells can draw the remainder of the fluid composition from the flow cells. The process of pipetting an aliquot of fluid composition, applying the aliquot, processing the fluid composition, and drawing the remainder of the fluid composition can be repeated, for example, to apply additional samples or wash the flow cell.

Once the process of loading is complete, the sensor device can be released from the mechanical assembly, as illustrated at block 2816. For example, the mechanical assembly can be drawn to a rearward position, releasing the sensor device and the fluidic coupler, and permitting the sensor device to move to a subsequent station.

The slide and sensor device can move to a third position, as illustrated at block 2818. For example, sensor device can be moved to a sequencing section of the system.

Magnetic Loading

FIG. 29 is a schematic presentation of an example magnetic loading system. Specifically, FIG. 29 shows substrate 2900 supporting chip surface 2910 and flow cell 2920. Magnetic package 2950 is arranged in tray 2960 proximal to substrate 2900.

Magnetic package 2950 is shown with two magnets 2952 and 2954. Although the embodiment of FIG. 29 shows magnets 2952 and 2954, the disclosed principles are not limited thereto and may include more or less magnets than shown in FIG. 29. The magnets 2952, 2954 may be separated with an inert material 2953. The inert material 2953 can act a non-conductive insulator. In certain embodiments, magnets 2952 and 2954 can be arranged such that the north pole of magnet 2952 is immediately across from the south pole of magnet 2954. With this arrangement, substrate 2900 is simultaneously exposed to the north and the south poles of magnets 2952 and 2954. In other embodiments, magnets 2952 and 2954 may be arranged such that substrate 2900 is exposed only to the north or the south pole of the magnets.

Substrate 2900 may comprise any material configured to receive microchip 2910 (interchangeably, chip or sensor device). Microchip 2910 may comprise a top surface having a plurality of receptacles, such as microwells, cavities, divots, dimples, or other receptacles, configured to receive one or more sequencing beads. In one embodiment, chip 2900 may comprise microwells configured to receive a sequencing bead. One such example microchip is supplied by Ion Torrent® as the Ion 541 Chip™. An example microchip is discussed in reference to FIG. 14.

Flow cell 2920 is positioned over the upper surface of microchip 2910 to enable fluid communication to the surface of the microchip. The fluid may be communicated through ports 2922 and 2924 formed on top of chip 2910. Magnetic beads and sequencing beads (not shown) may be communicated along with one or more reagents to the surface of microchip 2910 through ports 2922 and 2924. Once the sequencing beads have been loaded onto the surface of microchip 2910, a wash reagent may be communicated through ports 2922 and 2924 to remove unwanted particles or reagents.

Tray 2960 (and magnetic package 2950) may move relative to substrate 2900, as indicated by arrow 2962. While the movement and orientation of the substrate are illustrated as being horizontal, in alternative examples, the substrate may be oriented vertically, and the movement may be up and down. The movement may be arranged by an actuator 2970 in combination with a programmable processor or controller 2980 that designates the speed and direction of movement for tray 2960. The actuator 2970 may include, for example, a motor or a solenoid controlled by a controller 2980 having one or more of a processor circuitry and a memory circuitry. The controller 2980 may be a programmable controller. In one embodiment of the disclosure, the controller 2980 may be configured to receive input information 2982 from auxiliary source(s) to indicate when tray 2962 should be moved relative to substrate 2900 (which may be stationary). The information 2982 may also include data related to the moving speed of tray 2960 as a function of the type of particle being loaded on to the chip. Such data may be stored at one or more memory circuitry associated with the controller 2980.

FIG. 30 schematically shows movement of a solution containing magnetic beads relative to a magnetic package at a first speed. In FIG. 30, the uppers surface of microchip 3010 is exposed to a reagent (or, solution) 3050. Reagent 3050 may include magnetic beads as well as sequencing beads. The magnetic beads may comprise any beads having an affinity or being reactive to a magnetic field. In one embodiment, the magnetic bead size is selected so as not to allow it to enter into the microwell, cavity or a divot formed on the surface of the microchip. Example magnetic beads may be substantially spherical with a diameter of about 1 μm to 100 μm.

Magnets 3052 and 3054 are separated by inert material 3053 to form a magnetic package. Arrow 3059 shows the direction of movement of magnetic package 3050 relative to microchip 3010. Reagent 3050 is disposed on top of microchip 3010. Reagent 3050 may comprise one or more magnetic beads coupled to sequencing beads. Reagent 3050 may be a liquid, a gel, or any material with texotropic and viscosity to move over a solid surface. A plurality of magnetic beads (not shown) may be disposed in reagent 3050 in a manner such that the magnetic beads may freely move or rotate relative to each other.

FIG. 31 schematically shows movement of a solution containing magnetic beads relative to a magnetic package at a second speed. FIG. 31 schematically shows a faster magnet motion (as shown by arrow 3060) relative to that of FIG. 31. Whereas the shape of reagent 3050 shows a relatively wider dispersion of reagent 3050 (containing magnetic beads), the shape of reagent 3056 suggest a narrower and densely packed reagent (containing magnetic beads). FIGS. 30 and 31 also show that when the relative movement is slow, the reagent/bead leading edge aligns with the lagging magnet's inner or leading edge. When the relative movement is fast, the reagent/bead pile falls behind the lagging magnet's front edge.

FIG. 32 schematically shows movement of a solution containing magnetic beads relative to a magnetic package reversing direction. Arrow 3062 shows the reversal of movement direction for the magnets. As seen in FIG. 32, when the magnets switch movement direction, the reagent/bead pile remains at the same location until picked up by the new lagging magnet's (3054) inner edge. Reversing direction on the magnets' movement may aid in loading the beads into the microwells or allow multiple sweeps of the reagent pile across the surface of the array on the microchip.

In an example, the magnet can be cycled between 5 and 50 sweeps (across and back), such as between 5 and 35 sweeps or 10 and 30 sweeps. In an example, each sweep takes 1 minute to 5 minutes, such as 1 minute to 3 minutes. Once bead supports load into wells, the bead assemblies can be denatured and the surface can be foam washed to remove the magnetic beads.

Figure 33:
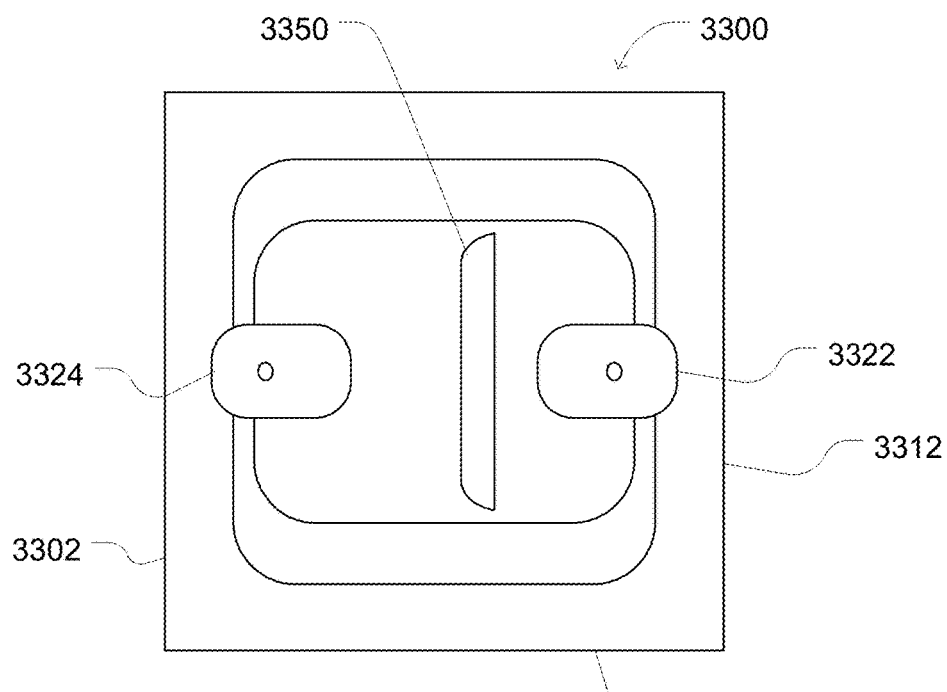
FIG. 33 illustrates a microchip having beads loaded thereon.

When implemented on a microchip, a suspension including the bead complexes is deposited into a flow cell over the microchip surface. FIG. 33 illustrates a microchip having magnetic beads loaded thereon according to one embodiment of the disclosure. More specifically, FIG. 33 shows microchip 3302 having flow cell 3312 positioned thereon. Flow cell 3312 includes ports 3322 and 3324 for receiving and discarding reagents. The flow cell 3312 may have more than two ports, for example, as illustrated in FIG. 14. Microchip 3302 is placed over substrate 3310. One or more magnets (not shown) are placed below substrate 3310. The magnets create a magnetic field which causes a line of magnetic beads 3350 to form on the surface of microchip 3302. Movement of the magnets causes movement of line 3350 (i.e., magnetic beads) along the surface of microchip 3302. As the magnetic beads move along the surface, the sequencing beads coupled to the magnetic beads in the reagent enter wells or cavities on the surface of the microchip 3302.

Figure 34:
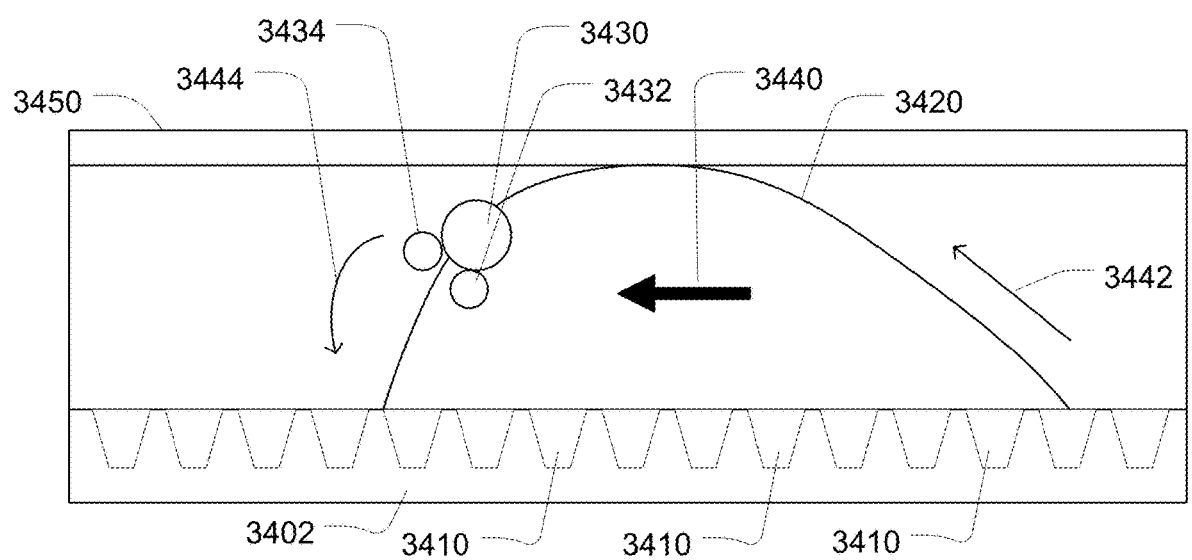
FIG. 34 schematically illustrates a magnetic loading model.
Figure 35:
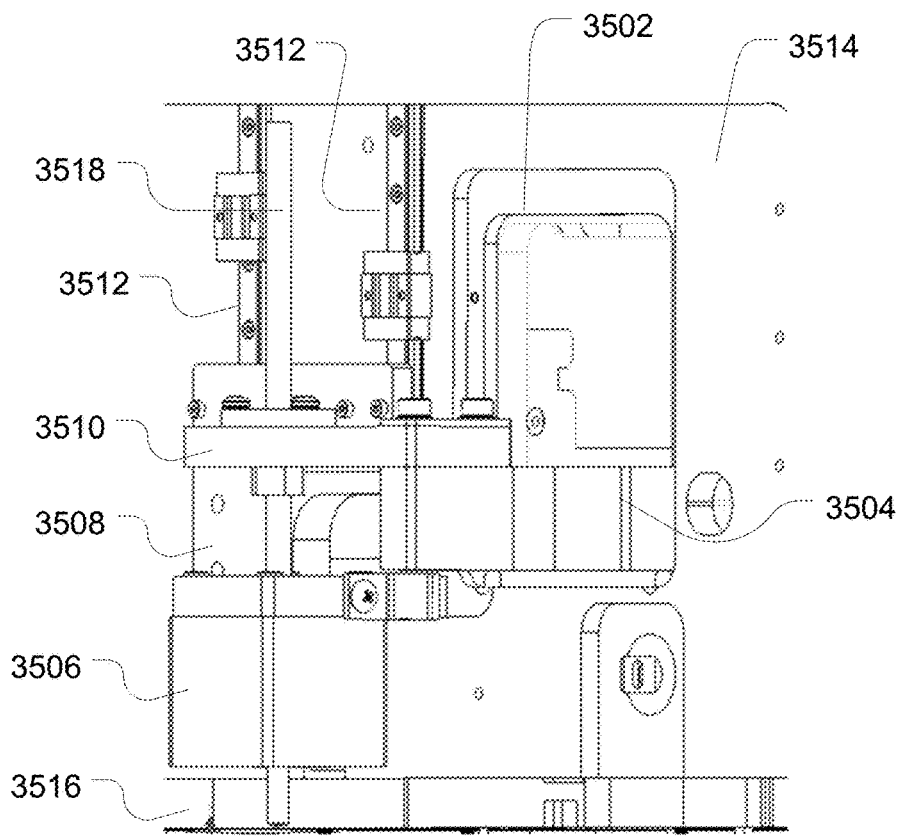
FIG. 35, FIG. 36, FIG. 37, and FIG. 38 include illustrations of an example loading device.

FIG. 34 schematically illustrates a magnetic bead loading model. In FIG. 34, the microchip surface 3402 is shown with multiple microwells 3410. Stream 3420 contains, among others, sequencing beads 3432, 3434 attached to magnetic beads 3430. As illustrated in FIG. 34, sequencing beads 3432 and 3434 can have a smaller diameter than magnetic bead 3430. Microwells 3410 are sized so as to receive sequencing beads 3432, 3434. Each microwell 3410 may be configured to receive at least one sequencing bead 3432, 3434 and exclude magnetic beads 3430. While not shown, each microwell 3410 may be coupled to a sensing circuitry comprising one or more electrode, as well as electronic circuitry configured to detect presence of an analyte in microwell 3410. The analyte may be coupled to the sequencing bead or may be released as a result of one or more reaction inside the well. Surface 3450 schematically illustrates flow cell surface having input and output ports (not shown).

The sequencing beads may have different sizes. In one embodiment, the sequencing beads 3432, 3434 are selected such that at least one sequencing bead may enter a microwell. In other words, the sequencing bead diameters may be selected to be smaller than the microwell opening. While microwells 3410 are shown with tapered sidewalls, the claimed embodiment is not limited thereto and the microwells may have different shapes and forms without departing from the disclosed principles.

As shown, stream 3420 may comprise a plurality of beads. Magnetic beads 3430 may include magnetic properties. In certain embodiments, stream 3420 may comprise other reagents in addition to the beads. Magnetic beads 3430 may comprise Dynabeads® M-270 or Dynabeads® M-280, supplied by Thermo Fisher Scientific, having bead diameter of about 2.8 µm. Each magnetic bead 3430 may have, for example, streptavidin for coupling with biotinylated nucleic acids, antibodies, or other biotinylated ligands and targets. The magnetic beads 1530 can be attached to the sequencing beads 3432, 3434 using such a biotin/streptavidin binding.

Such methods of loading may be implemented in hardware having a horizontal or vertical configuration. For example, the hardware can hold a substrate on to which beads are being deposited horizontally. In another example, the hardware can hold the substrate vertically in which the plane of the substrate is approximately parallel to gravity. As used herein, vertical refers to an orientation in which a plane of a major surface of a substrate is closer to being parallel with gravity than perpendicular to gravity. In an example illustrated in FIG. 35, FIG. 36, FIG. 37, and FIG. 38, a magnetic loading system 3500 includes a plate 3502 and a magnet holder 3504 that guides magnets along the plate 3502. In the illustrated example, the plate 3502 is secured to a vertical structure 3514 that is secured to a horizontal structure 3516. The magnet holder 3504 can move magnets up and down along the plate 3502 to facilitate loading of beads supports, such as sequencing beads, into wells of a substrate disposed on opposite side of the plate 3502.

In a particular example, a drive mechanism 3506 can facilitate movement of the magnet holder 3504 up and down along the plate 3502. For example, the drive mechanism 3506 can rotate a threaded screw 3518 to drive a connector plate 3510 up and down along the screw 3518. The connector plate 3510 is connected to the magnet holder 3504. Optionally, the connector plate 3510 can be coupled with a guide plate 3508. The guide plate 3508 can slide along rails 3512, providing stability to the movement of the connector plate 3510 and the magnetic holder 3504.

Figure 36:
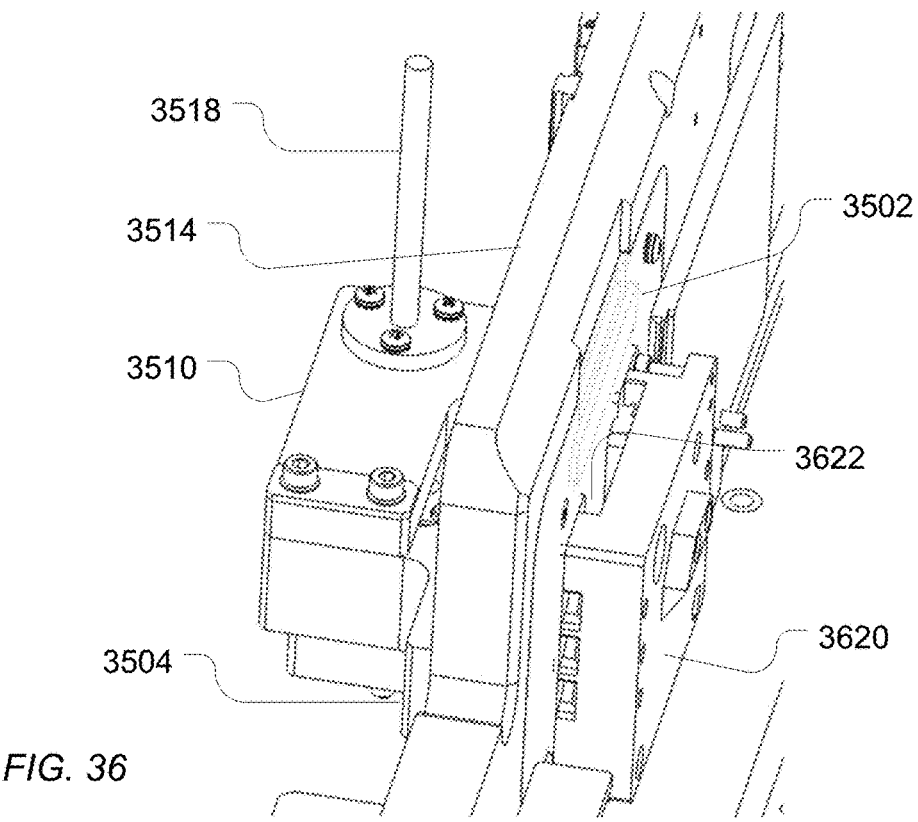

As illustrated in FIG. 36, a substrate holder 3620 (e.g., the manifold of FIG. 26 or FIG. 27) provides space 3622 for a substrate or sensor device, such as a microchip with a flow cell, to be inserted and held against the plate 3502. As the magnets attached to the holder 3504 moved up and down along the vertical surface of the plate 3502, bead supports attached to magnetic beads in solution are deposited into wells of the substrate. In an example, the substrate is a sequencing chip having a flow cell in which the solution is disposed.

Figure 37:
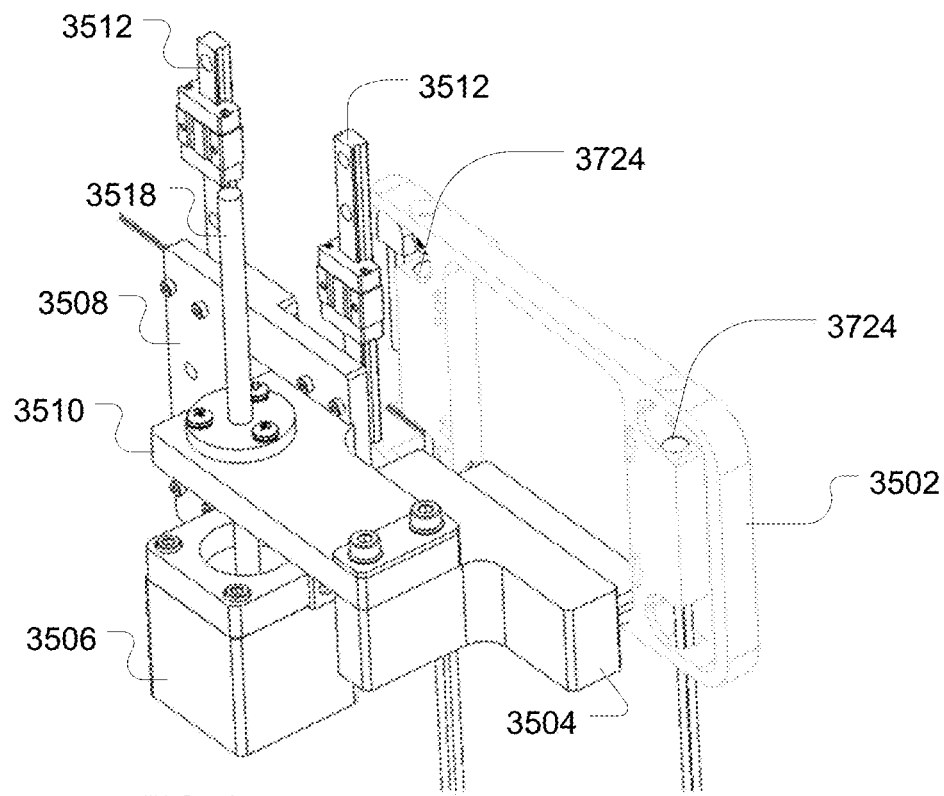

As illustrated in FIG. 37, the plate 3502 can optionally include recesses to receive heaters 3724. The heaters 3724 can be utilized to control the temperature of the plate 3502 and optionally the substrate positioned adjacent to the surface of the plate 3502. Alternatively, the heaters 3724 can be utilized to facilitate melt off of double-stranded nucleic acids or control a temperature for amplification.

Figure 38:
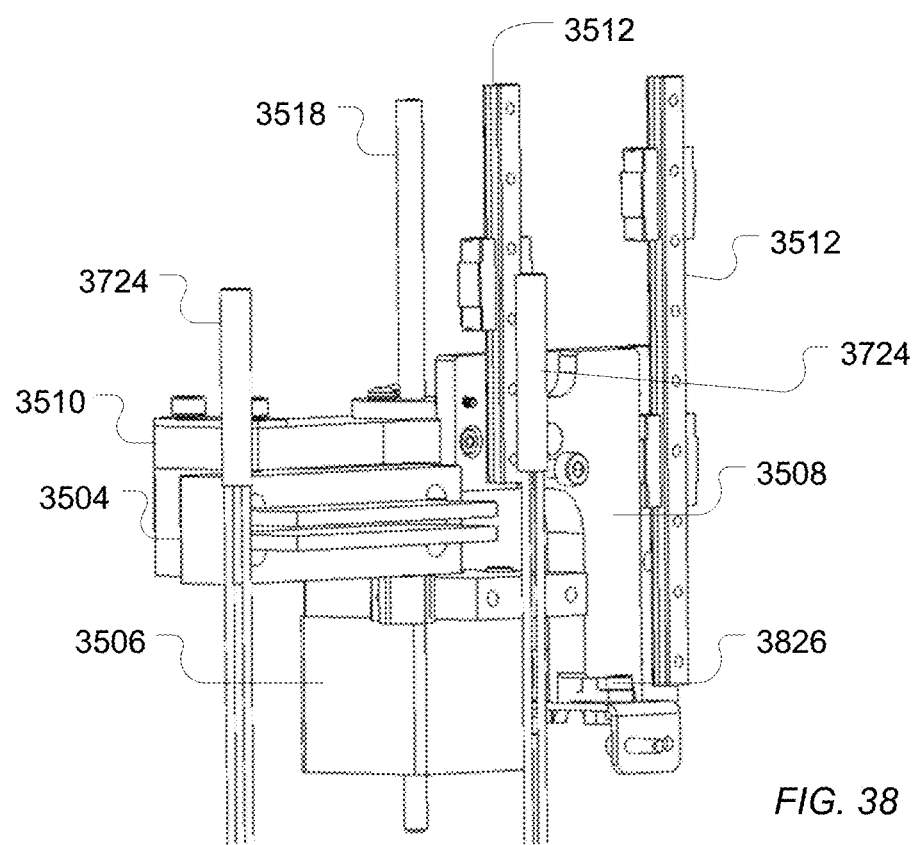

The magnetic holder 3504 can include one or more magnets. For example, as illustrated in FIG. 38, the magnetic holder 3504 can include a magnet 3828 and a magnet 3830. The magnets 3828 or 3830 can be separated by air. Alternatively, the magnets can be separated by a paramagnetic material or insulative material.

In an example, the magnets are configured such that different polls of the magnets are positioned against the plate 3502. For example, the magnet 3828 may be configured to have a north pole positioned adjacent the plate 3502, and the magnet 3830 can be configured to have a south pole adjacent to the plate 3502. Alternatively, the south pole of the magnet 3828 and the north pole of the magnet 3830 can be positioned adjacent to the plate 3502. In a further alternative, the same pole of each magnet can be positioned adjacent the plate 3502.

The system can further include a sensor 3826 that detects a position of the magnets, for example, a lower boundary. As illustrated in FIG. 38, the guide plate 3508 can interfere with an optical sensor 3826 when the magnets are in their lower position. Alternatively, other sensors can be used to determine the position of the plates and associated magnets.

Following loading beads into wells of a sensor device or microchip, polynucleotides on the sequencing beads can be amplified to form monoclonal populations of polynucleotide on the sequencing beads. The monoclonal populations of polynucleotides can be sequenced using, for example, ion-based sequencing techniques.

Multilane Fluidics

Figure 39:
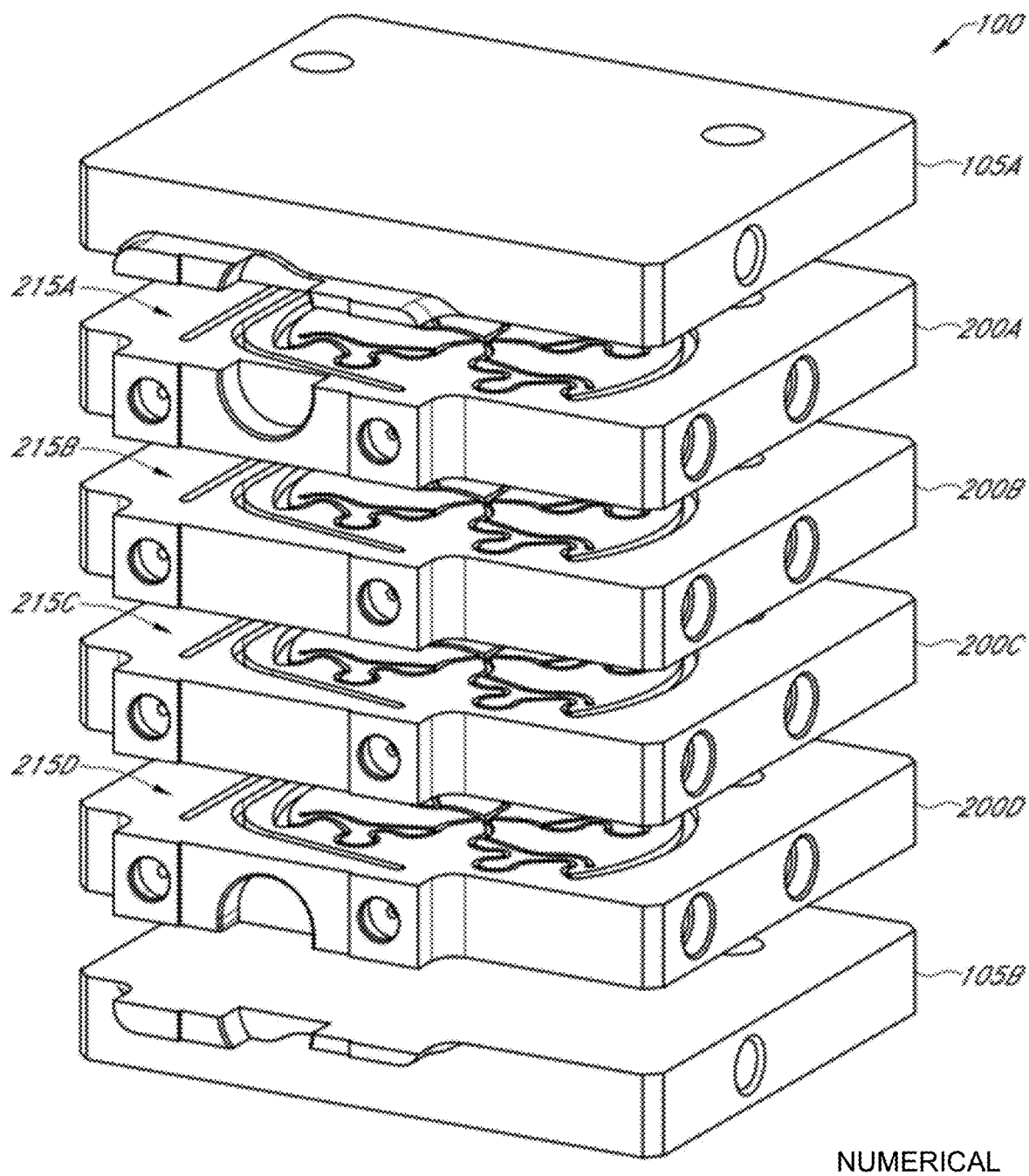
FIG. 39 is an exploded view that illustrates generally a fluidic multiplexer block of the present teachings.

FIG. 39 illustrates generally an exploded view of fluidic multiplexer block 39100, which as a component of a fluidic system of an integrated next generation sequencing system, can provide distribution of various solutions used during analysis to a multi-lane sensor array device. According to the present teachings, various embodiments of a fluidic system disclosed herein are configured to execute a sequence of fluidic operations for the sequential delivery of various solutions to a multi-lane sensor array device over the course of a next generation sequencing analysis. Exemplary fluidic operations include washing, priming and nucleotide reagent delivery through a fluidic multiplexer block, such as fluidic multiplexer block 39100 of FIG. 39. Such a fluidic multiplexer block is configured to provide independent fluid distribution to each lane of a multi-lane sensor array device used for detection during an analysis. According to the present teachings, any number or combination of lanes can be used during an analysis, so that during an analysis one lane in any position can be used singly during a run, all four lanes can be used simultaneously during a run, or any combination of lanes can be used simultaneously during a run. Using a fluidic multiplexer block of the present teachings for fluid distribution to a multi-lane sensor array device during a sequence of fluidic operations can avoid cross-contamination of solutions used during analysis in various fluidic compartments, as well as providing sharp transitions between reagent fluid streams during an analysis. Additionally, various embodiments of fluidic systems of the present teachings provide a constant electrolyte fluidic environment for a reference electrode, thereby providing a constant stable reference voltage for a multi-lane sensor array device.

As depicted in FIG. 39, fluidic multiplexer block 4100 includes fluidic multiplexer units 4200A through 4200D, as well as first end cover 4105A and second end cover 4105B. According to the present teachings, each fluidic multiplexer unit has a fluidic multiplexer circuit formed within the body of fluidic multiplexer unit. Accordingly, as depicted in FIG. 39, each of fluidic multiplexer units 4200A through 4200D has a fluidic multiplexer circuit 4215A through 4215D formed within the body of each fluidic multiplexer unit. As will be disclosed in more detail herein, each fluidic multiplexer unit in fluidic multiplexer block 100 is independently in controllable fluid communication with one of each of a flow cell lane of a multi-lane sensor array device. Accordingly, a first lane of a multi-lane sensor array device can be fluidically integrated to fluidic multiplexer unit 4200A, while a second lane can be fluidically integrated to fluidic multiplexer unit 4200B, and a third lane can be fluidically integrated to fluidic multiplexer unit 4200C, while a fourth lane can be fluidically integrated to fluidic multiplexer unit 4200D. Moreover, any number or combination of lanes can be used during an analysis, so that during the set-up of an analysis, an end-user can select one lane in any position used singly during a run, all four lanes used simultaneously during a run, or any combination of lanes to be used simultaneously during a run.

Figure 40:
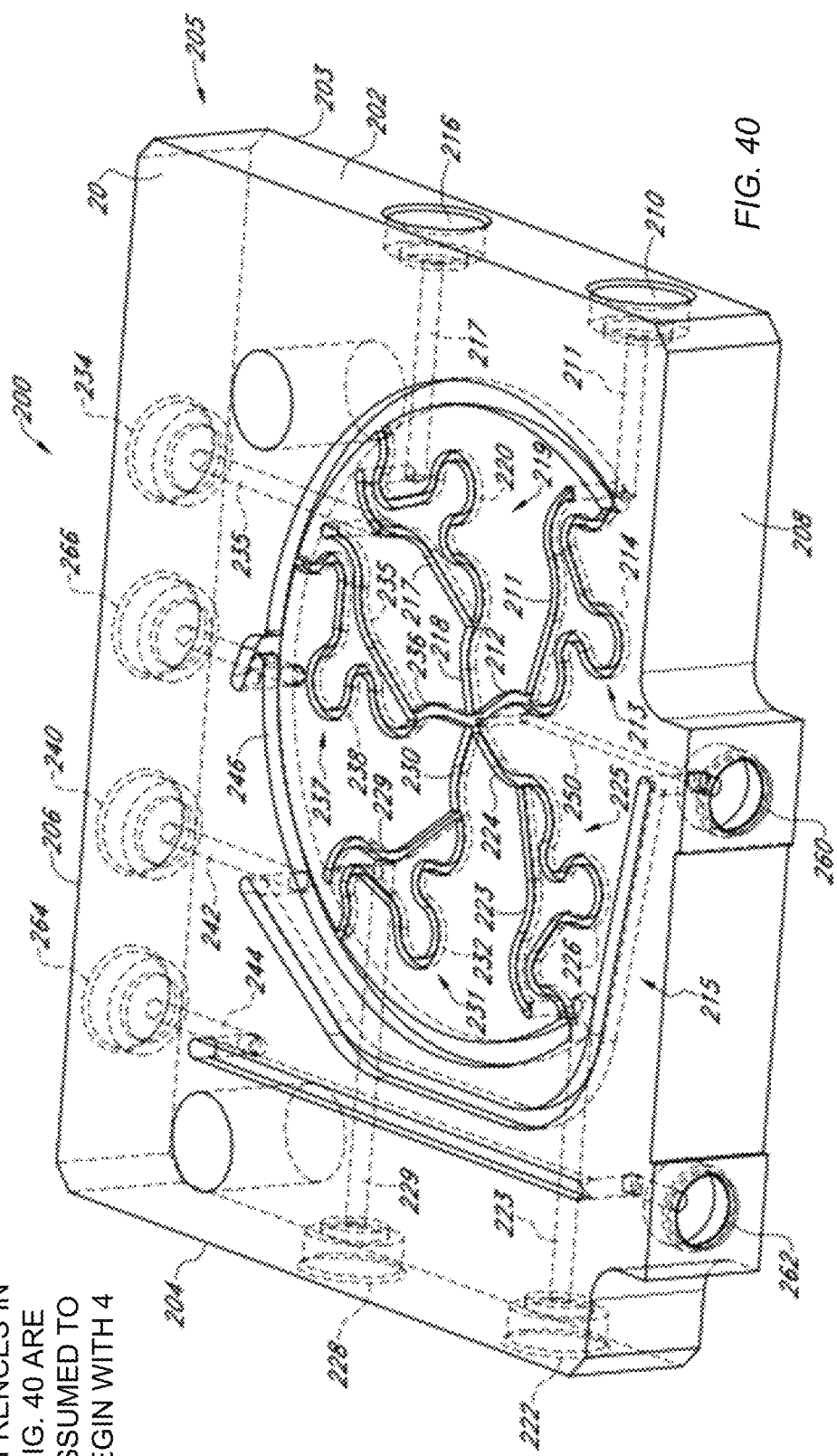
FIG. 40 is an isometric view that illustrates generally a fluidic multiplexer unit of a fluidic multiplexer block, such as the fluidic multiplexer block of FIG. 1.

FIG. 40 illustrates generally an embodiment of fluidic multiplexer unit 4200 that accommodates four input reagents, and a calibration solution in each of five fluidic branches, as well as having a distribution channel for a wash solution. Fluidic circuit 4215 is formed in substrate 4205, which has first surface 4201 and opposing second surface 4203. As depicted in FIG. 40, first surface 4201 and opposing second surface 4203 are substantially parallel to one another. Fluidic multiplexer unit 4200 can have first fluidic interface side 4202, with opposing second fluidic interface side 4204. As depicted in FIG. 40, third fluidic interface side 4206 joins the first and second interface edges on one side, while fourth fluidic interface side 4208 joins first and second interface edges on the opposing side. Substrate 4205 can be constructed from a variety of materials, such as glass, ceramics, and plastics. Exemplary polymeric materials include polycarbonate, polymethyl methacrylate, polyether imide and polyimide. Reagent Inlet ports 4210, 4216, 4222, and 4228, as well as calibration solution inlet port 4234 are in fluid communication with inlet channels 4211, 4217, 4223, 4229, and 4235, respectively. Inlet channels 4211, 4217, 4223, 4229, are in fluid communication with curvilinear channels 4213, 4219, 4225, 4231, and 4235, respectively of each of five fluidic branches. Finally, wash solution inlet port 4240 is in fluid communication with wash solution channel 4242.

As depicted in FIG. 40, each inlet channel forms a tee junction with each curvilinear channel, so that each curvilinear channel consists of two branches. Such a tee junction forming two branches is depicted in FIG. 40, in which inlet channel 4211 tees into curvilinear channel 4213, forming first branch channel 4212 and second branch channel 4214. Similarly, inlet channel 4217 tees into curvilinear channel 4219, forming first branch channel 4218 and second branch channel 4220, while inlet channel 4223 tees into curvilinear channel 4225, forming first branch channel 4224 and second branch channel 4226. Additionally, inlet channel 4229 tees into curvilinear channel 4231, forming first branch channel 4230 and second branch channel 4232. Finally, inlet channel 4235 tees into curvilinear channel 4237, forming first branch channel 4236 and second branch channel 4238. First branch channels 4212, 4218, 4224, 4230 and 4236 of curvilinear channels 4213, 4219, 4225, 4231, and 4237, respectively, of the five fluidic branches are in fluid communication with center channel 4250. As depicted in FIG. 40, central channel 4250 is in fluid communication with sensor interface inlet connector port 4260, which is in fluid communication with a sensor inlet port (not shown). Additionally, wash solution inlet port 4240 is in fluid communication with wash solution channel 4242, which is also in fluid communication with sensor interface inlet connector port 4260. Sensor interface outlet connector port 4262 is in fluid communication with a sensor outlet port (not shown), as well as sensor waste channel 4244. Sensor waste channel 4244 is in fluid communication with a sensor waste receptacle (not shown), which is connected to fluidic multiplexer unit 4200 through sensor waste port outlet 4264. Each of second branch channels 4214, 4220, 4226, 4232, and 4238 of curvilinear channels 4213, 4219, 4225, 4231, and 4237, respectively, are in fluid communication with main waste channel 4246, which is in fluid communication with a main waste receptacle (not shown), which is connected to fluidic multiplexer unit 4200 through main waste outlet port 4266.

Figure 41:
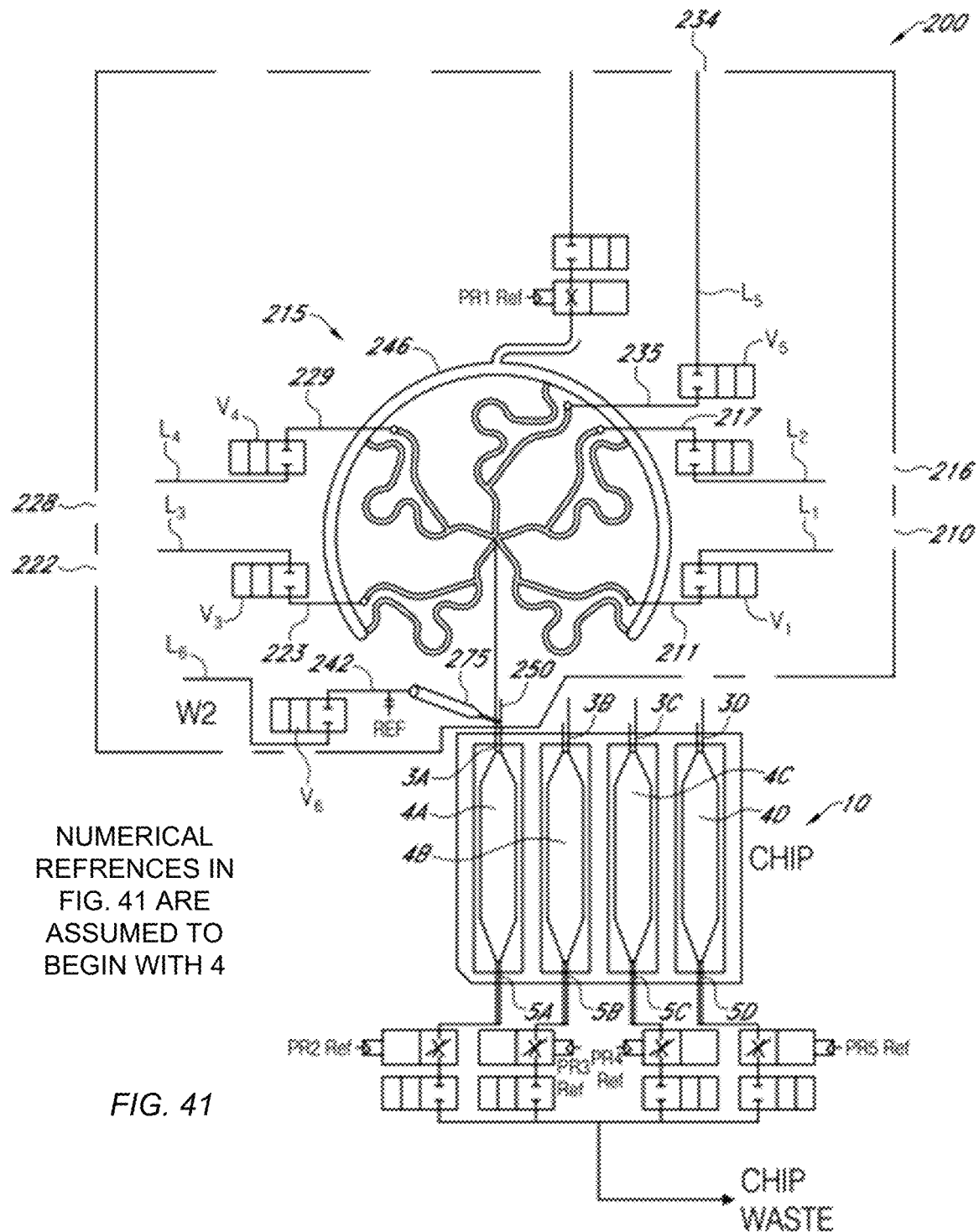
FIG. 41 is a schematic representation that illustrates generally the fluidic integration between a fluidic multiplexer unit and a selected lane of a multi-lane sensor device of the present teachings.

FIG. 41 illustrates generally a schematic representation of the fluidic integration of fluidic multiplexer unit 4200 of fluidic multiplexer block 4100 of FIG. 39 with a multilane sensor device.

Regarding fluidic delivery and control for performing various analyses on a multi-lane sensor array device, such as sensor array device 10 of FIG. 41, fluidic circuit 4215 of fluidic multiplexer unit 4200 can be in fluid communication with one flow cell lane of sensor array device 10. For the purpose of illustration, one fluidic multiplexer unit is shown fluidically integrated with one flow cell lane in FIG. 41. However, an end-user can select any number or combination of lanes during an analysis, as each lane is fluidically integrated with one of a fluidic multiplexer unit, such as fluidic multiplexer units 4200A through 4200D of FIG. 39. By way of a non-limiting example, a first flow cell lane, such as flow cell lane 4A of sensor array device 10 of FIG. 41, can be fluidically integrated with a first fluidic multiplexer, such as fluidic multiplexer unit 4200A of FIG. 39, while a second flow cell lane, such as flow cell lane 4B of sensor array device 10 of FIG. 41 can be fluidically integrated to a second fluidic multiplexer, such as fluidic multiplexer unit 4200B of FIG. 39. Similarly, a third flow cell lane, such as flow cell lane 4C of sensor array device 10 of FIG. 41, can be fluidically integrated with a third fluidic multiplexer, such as fluidic multiplexer unit 4200C of FIG. 39, while a fourth flow cell lane, such as flow cell lane 4D of sensor array device 10 of FIG. 41 can be fluidically integrated to a fourth fluidic multiplexer, such as fluidic multiplexer unit 4200D of FIG. 39. In that regard, what is described herein for illustrative purposes for FIG. 41 discloses generally how each fluidic multiplexer unit 41200 is fluidically integrated with each of a corresponding flow cell lane of a multi-lane sensor device.

As such, during the set-up of an analysis, an end-user can select one lane in any position used singly during a run, all four lanes used simultaneously during a run, or any combination of lanes to be used simultaneously during a run. As will be disclosed in more detail subsequently, a fluidic system of a sequencer instrument of the present teachings can include a plurality of solution containers providing a variety of solutions for use over the course of an analysis. For example, various solutions can include various nucleotide reagents used in analysis, a calibration solution, a diluent (wash) solution, and a cleaning solution. Various solutions used over the course of an analysis can be in controllable fluid communication with any flow cell lane of sensor array device 10 via a flow cell inlet, such as flow cell inlet 3A of flow cell lane 4A of FIG. 41. A fluidic system of a sequencer instrument of the present teachings can include a reagent fluid line from each reagent container, which can be selectively placed in fluid communication with an inlet channel of fluidic circuit 4215, such as inlet channels 4211, 4217, 4223, 4229, 4235, and 4242. Additionally, as depicted in FIG. 41, each of various solutions used over the course of an analysis can have fluid flow controlled by a valve, such as fluid line valves $V_1$ through $V_6$ for each of reagent fluid lines $L_1$ through $L_4$, as well as for calibration solution line $L_5$ and wash solution line $L_6$, respectively. It should be noted that calibration fluid line valve $V_5$ is generally in a closed position except during a calibration sequence before a run is initiated for calibrating a sensor array selected for use during a run. Accordingly, calibration fluid line valve $V_5$ is closed during a sequencing run.

In conjunction with controllable flow of various solutions used over the course of an analysis, fluidic multiplexer unit 4200 of FIG. 41 can perform fluidic operations that include, for example, but not limited by, providing selected reagent delivery to a flow cell lane of sensor array device 10, washing of fluidic multiplexer circuit 4215, as well as a flow cell, such as flow cell lane 4A of sensor array device 10, and priming of fluidic multiplexer circuit 4215 with a selected reagent. Such fluidic operations can provide for cross contamination-free delivery of reagents to a flow cell, such as flow cell lane 4A of FIG. 41, can provide for sharp transitions between reagent fluid streams, as well as providing a constant electrolyte fluidic environment for reference electrode 4275, shown in FIG. 41 to be in fluid communication with central channel 4250, thereby providing a constant stable reference voltage to sensor array device 10.

For example, fluidic multiplexer unit 4200 of FIG. 41 can selectively provide fluid communication between any of reagent fluid lines $L_1$ through $L_4$ and first flow cell inlet 3A of first flow cell lane 4A, thereby providing selective reagent flow through first flow cell lane 4A of sensor array device 10. A non-limiting illustrative reagent fluidic path of the present teachings is given by a reagent delivery operation in which wash solution fluid line valve $V_6$ is in a closed state, and one of reagent fluid line valves $V_1$ through $V_4$ is in an open state, providing that one of a selected reagent is in fluid communication with fluidic multiplexer circuit 4215. Under such a condition, a selected reagent can flow through fluidic multiplexer circuit 4215 and then through waste channel 4246 to waste. Additionally, a selected reagent can flow through fluidic multiplexer circuit 4215 to first flow cell inlet 3A of first flow cell lane 4A, where it can then flow through first flow cell lane 4A to first outlet port 5A, and finally through a flow cell outlet line (see FIG. 40) to a flow cell waste container.

With respect to fluidic control of a wash solution, fluidic multiplexer unit 4200 of FIG. 41 can selectively provide fluid communication between a wash solution and first flow cell lane 4A. As such, with wash solution fluid line valve $V_6$ in an open state, a wash solution line $L_6$ can be in fluid communication with fluidic multiplexer waste channel 4246, as well as with flow cell waste channel (see FIG. 39), providing that washing of fluidic multiplexer circuit 4215 and first flow cell lane 4A can be done. A non-limiting illustrative wash solution fluidic path of the present teachings is given by a washing operation in which wash solution fluid line valve $V_6$ is in an open state, and each of reagent fluid line valves $V_1$ through $V_4$ is in a closed state, providing that a wash solution can flow through wash solution fluid channel 4242 to a tee junction with central channel 4250. As central channel 4250 is in fluid communication with waste channel 4246 through fluidic multiplexer circuit 4215, wash solution can flow to fluidic multiplexer waste through waste channel 4246. As will be disclosed in more detail herein, wash solution can through first flow cell lane 4A from first inlet port 3A to first outlet port 5A, and then to a flow cell waste container.

According to the present teachings, priming of fluidic multiplexer circuit 4215 of fluidic multiplexer unit 4200 can be done with a selected reagent, for example, in sequence after a washing operation and before the selected reagent is placed in fluid communication with first flow cell lane 4A of FIG. 41. A non-limiting example illustrative of reagent priming is given by a reagent priming operation in which solution fluid line valve $V_6$ is in an open state, and one of reagent fluid line valves $V_1$ through $V_4$ is selected to be in an open state, providing that one of a selected reagent is in fluid communication with fluidic multiplexer circuit 4215 of fluidic multiplexer unit 4200. Under such an operation, the flow rate of the wash solution relative to the flow rate of the reagent is selected so that wash solution flows through wash channel 4242 and through first flow cell lane 4A of sensor array device 10 to chip waste. Under such conditions, the selected reagent circulates through fluidic multiplexer circuit 4215, as it is blocked from flowing through sensor array device 10 by the wash solution flow through the device. As such, the selected reagent flows through fluidic multiplexer circuit 4215 through waste channel 4246 to a main waste. Accordingly, when a reagent delivery operation as previously described herein is initiated, the reagent selected in the reagent priming operation is in direct flow communication with first flow cell inlet 3A.

As such, various embodiments of fluidic systems of the present teachings are configured to execute a sequence of operations for the sequential delivery of various solutions to a sensor array device over the course of a next generation sequencing analysis. For example, a sequence of operations can include washing, priming and nucleotide reagent delivery through a fluidic multiplexer block unit to a sensor array device, such as depicted in FIG. 41. Using a fluidic multiplexer block of the present teachings for fluid distribution to a sensor array device during a sequence of fluidic operations can avoid cross-contamination of reagents in various fluidic compartments, as well as provide sharp transitions between reagent fluid streams. Additionally, as will be disclosed in more detail herein, various embodiments of fluidic systems of the present teachings provide a constant electrolyte fluidic environment for a reference electrode, thereby providing a constant stable reference voltage to a sensor array device.

Figure 42:
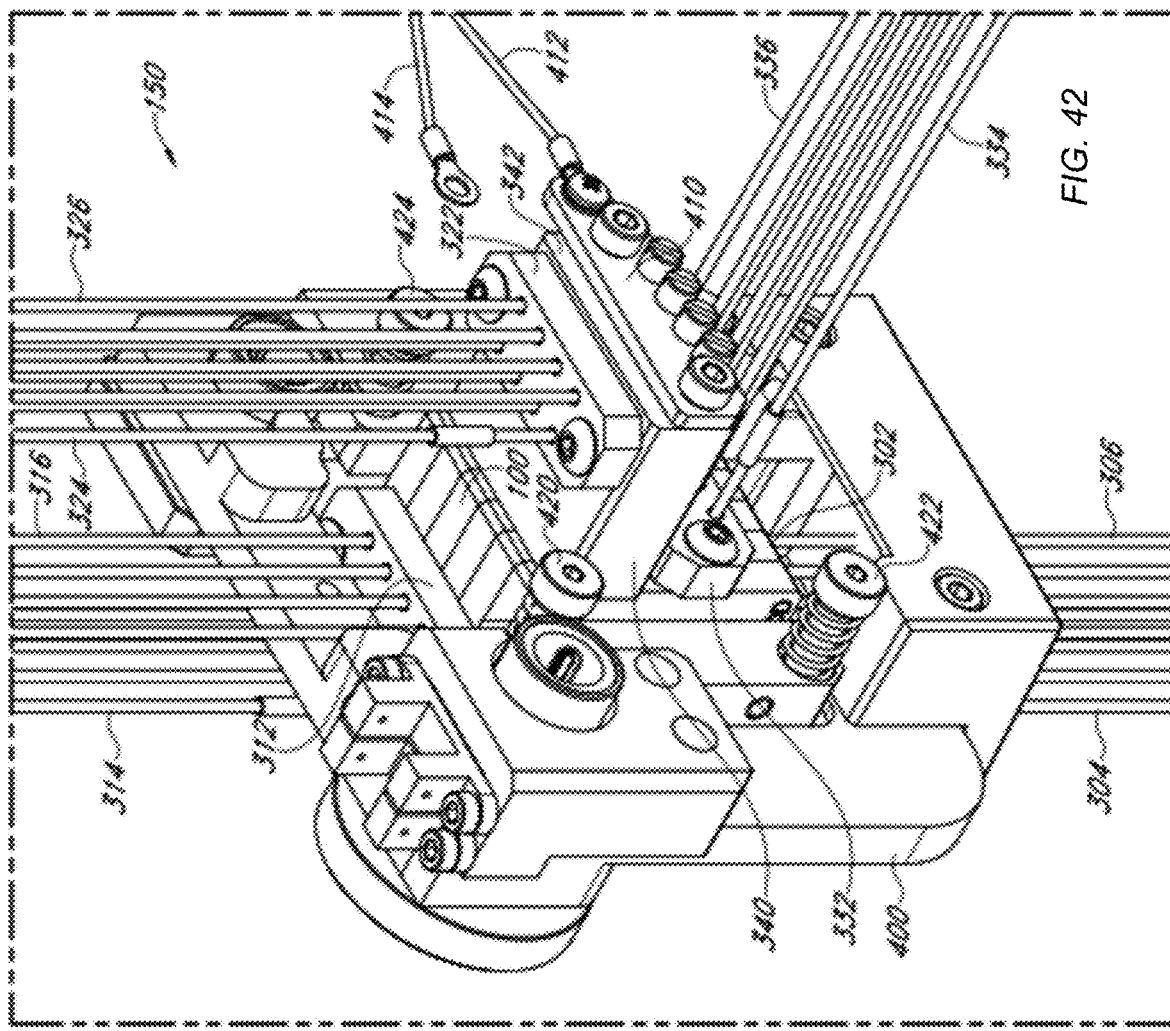
FIG. 42 is aback isometric view that illustrates generally a fluidic multiplexer block clamp assembly that includes a fluidic multiplexer block clamp with a fluidic multiplexer block assembly mounted therein.

FIG. 42 is a back isometric view that illustrates generally fluidic multiplexer block clamp assembly 4150. As depicted in FIG. 42, fluidic multiplexer block clamp assembly 4150 includes fluidic multiplexer block clamp 4400 with fluidic multiplexer block assembly 4110 mounted therein. Fluidic multiplexer block clamp 4400 can include electrode connection mounting plate 4410 mounted on side 4342 of electrode adapter fluidic interface block 4340. Electrode connection mounting plate 4410 enables connection of electrical lead 4412 and ground lead 4414 to electrode adapter fluidic interface block 4340 of fluidic multiplexer block clamp assembly 4150. Fluidic multiplexer block clamp 4400 also includes shoulder screws 4420, 4422, and 4424, as well as a fourth shoulder screw that is placed below shoulder screw 4424 and opposite shoulder screw 4422. The force on the shoulder screws of fluidic multiplexer block clamp 4400 is set to provide four degrees of movement to a fluidic multiplexer block mounted therein to provide flexibility of the docking of a fluidic multiplexer block to a multi-lane sensor array device.

Regarding fluidic multiplexer block assembly 4110 mounted in fluidic multiplexer block clamp 4400, as depicted in FIG. 42, the orientation of fluidic multiplexer block 4100 and fluidic block connections shows fluidic interface block 4312 mounted to fluidic multiplexer block 4100 at the top of fluidic multiplexer block clamp assembly 4150, while fluidic interface block 4302 is mounted to fluidic multiplexer block 4100 at the bottom of fluidic multiplexer block clamp assembly 4150. As depicted in FIG. 42, the orientation of first and second flexible tubing sets 4314 and 4316 emanate likewise from the top of fluidic multiplexer block clamp assembly 4150, while first and second flexible tubing sets 4304 and 4306 emanate likewise from the bottom of fluidic multiplexer block clamp assembly 4150. Similarly, fluidic interface block 4332 is mounted to fluidic multiplexer block 4100 at the back of fluidic multiplexer block clamp assembly 4150, and below electrode adapter fluidic interface block 4340. As depicted in FIG. 42, the orientation of first and second flexible tubing sets 4334 and 4336 emanate likewise from the back of fluidic multiplexer block clamp assembly 4150. Finally, fluidic interface block 4322 is mounted to fluidic multiplexer block 4100 at the back of fluidic multiplexer block clamp assembly 4150, and upon electrode adapter fluidic interface block 4340. As depicted in FIG. 42, the orientation of first and second flexible tubing sets 4324 and 4326 emanate likewise from the top of electrode adapter fluidic interface block 4340.

Figure 43:
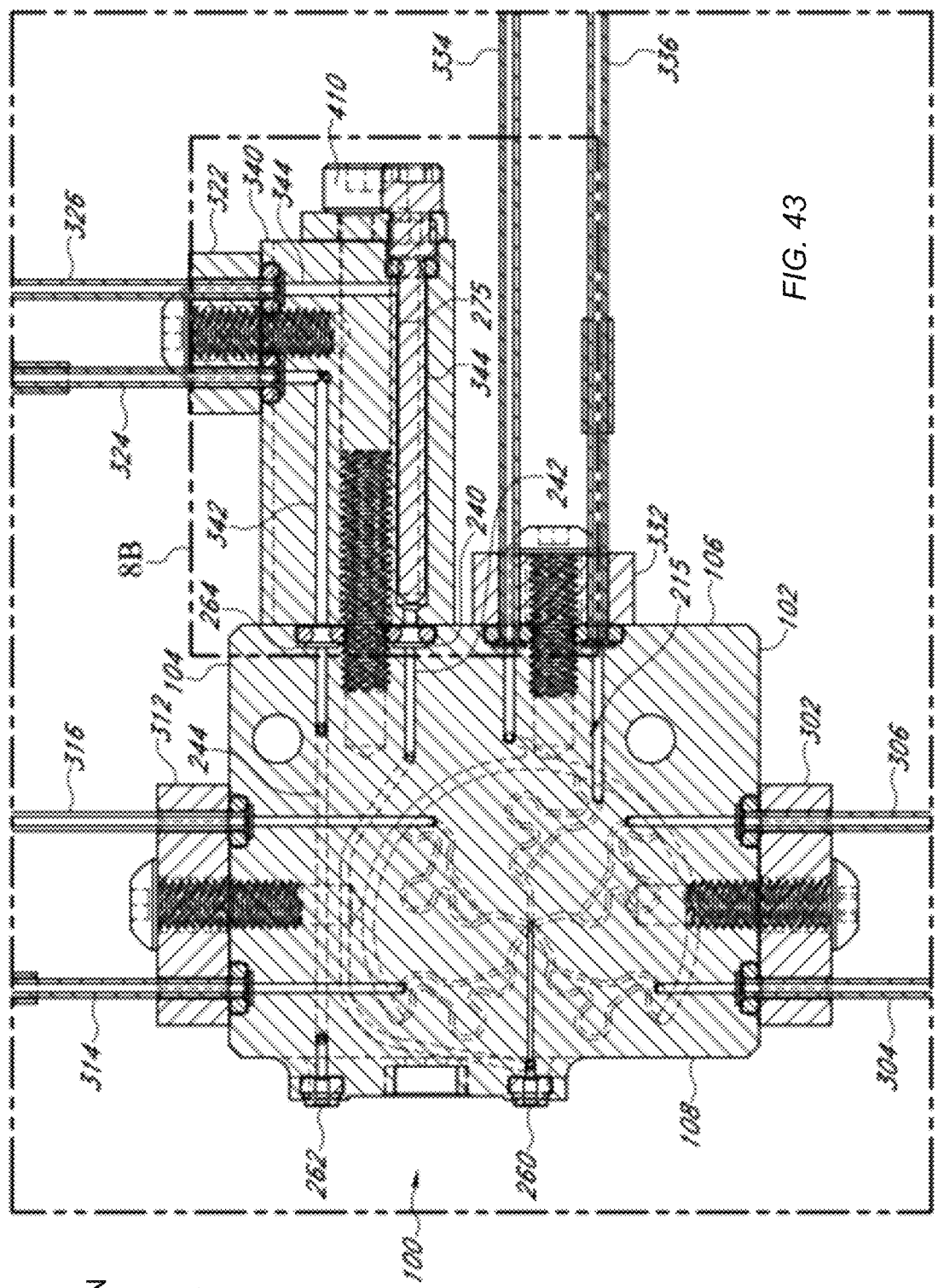
FIG. 43 is a section view that illustrates generally the integration of an electrode into a fluidic multiplexer unit.

FIG. 43 is a section view that illustrates generally orientation of fluidic multiplexer block 4100 as it is mounted in a fluidic multiplexer block clamp assembly, as well as the integration of an electrode into a fluidic multiplexer unit. Fluidic multiplexer block first face 4102 is depicted with fluidic interface block 4302 mounted thereupon and with first and second flexible tubing sets 4304 and 4306 connected to fluidic interface block 4302, while fluidic multiplexer block second face 4104 is depicted with fluidic interface block 4312 mounted thereupon and with first and second flexible tubing sets 4314 and 4316 connected to fluidic interface block 4312. Similarly, fluidic multiplexer block third face 4106 is depicted with fluidic interface block 4332 mounted thereupon and with first and second flexible tubing sets 4334 and 4336 connected to fluidic interface block 4332. Additionally, fluidic multiplexer block third face 4106 is depicted with electrode adapter fluidic interface block 4340 mounted thereupon. As depicted in FIG. 43, fluidic interface block 4322 is mounted upon electrode adapter fluidic interface block 4340 so that first and second flexible tubing sets 4324 and 4326 connected to fluidic interface block 4332 are in fluid communication with electrode adapter fluidic interface block inlet channels 4342 and 4344, respectively. In that regard, electrode adapter fluidic interface block 4340 is mounted to fluidic multiplexer block third face 4106, so that electrode adapter fluidic interface block inlet channels 4342 and 4344 are coupled and sealed to sensor waste outlet port 4264 and wash solution inlet port 4240, respectively. Finally, as depicted in FIG. 43, fluidic multiplexer block fourth face 4108 has sensor interface inlet connector port 4260 and sensor interface outlet connector port 4262. As previously disclosed herein, fluidic multiplexer block fourth face 4108 has a corresponding set of sensor interface inlet connector ports and sensor interface outlet connector ports for each fluidic multiplexer unit of fluidic multiplexer block 4100. As will be disclosed in more detail subsequently herein, sensor interface inlet connector port 4260 and sensor interface outlet connector port 4262 are coupled and sealed to an inlet port and outlet port, respectively, of a multi-lane sensor device.

Regarding providing an electrode connection to each fluidic multiplexer unit, which provides a constant, stable reference electrode voltage to a multi-lane sensor array device, FIG. 43 depicts a section view of electrode adapter fluidic interface block 4340 with electrode connection mounting plate 4410 mounted thereupon. FIG. 43 depicts electrode 4275 in an enlarged bore of in a section of electrode adapter fluidic interface block inlet channel 4344, which provides for fluid passage through electrode adapter fluidic interface block inlet channel 4344, which is in fluid communication with wash solution channel 4242. Electrode 4275 is electrically coupled to a voltage source connected to electrode connection mounting plate 4410 through electrical lead 4412 and ground lead 4414 (see FIG. 42). As was previously disclosed herein, second flexible tubing set 4326 is in fluid communication with a source of a wash solution of stable electrolyte composition. As such, electrode 4275 is in a fluidic environment that provides a constant, stable reference electrode voltage to a multi-lane sensor array device.

Figure 44:
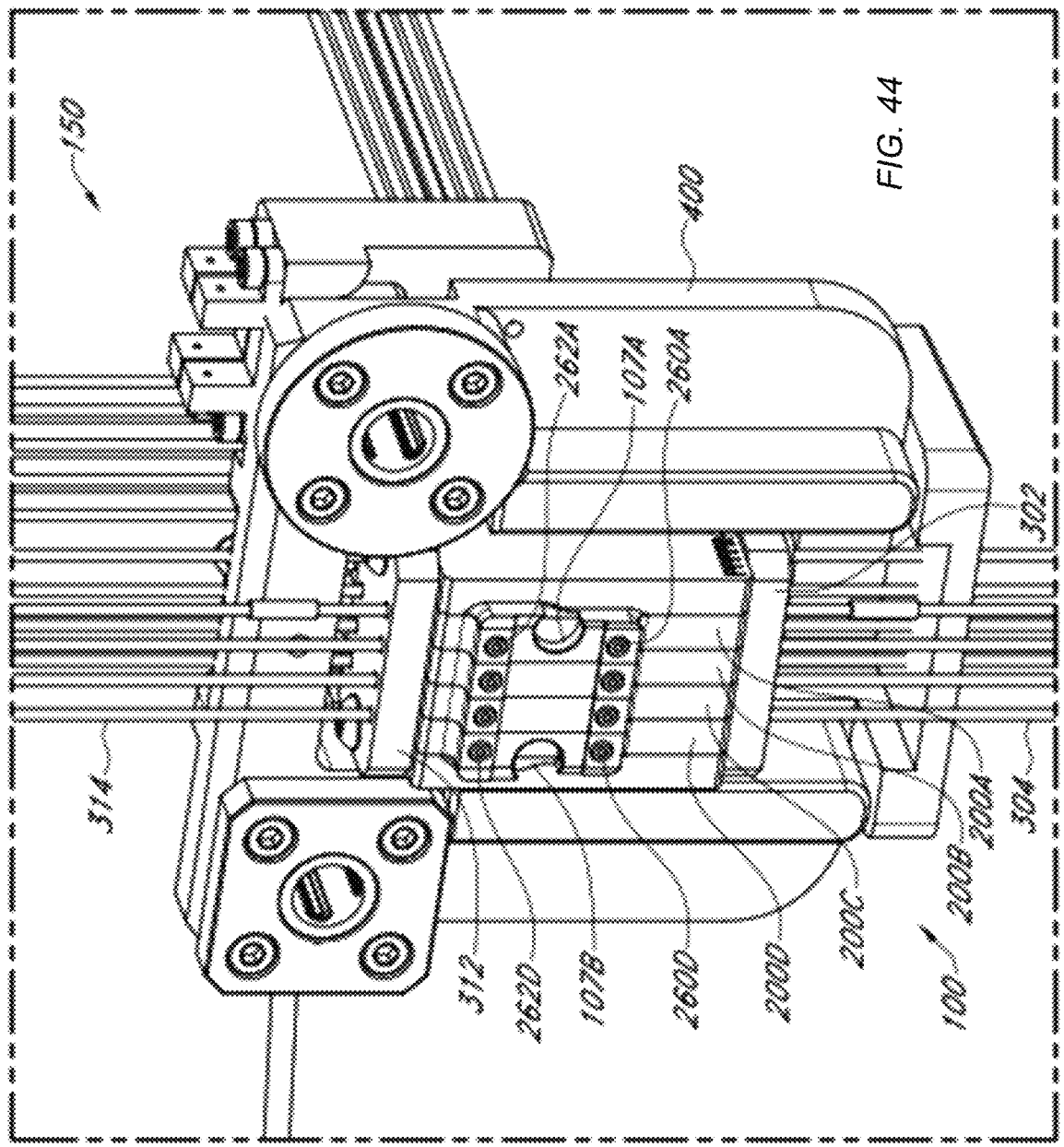
FIG. 44 is a front isometric view that illustrates generally a fluidic multiplexer block clamp assembly that includes a fluidic multiplexer block clamp with a fluidic multiplexer block assembly mounted therein.

FIG. 44 is a front isometric view that illustrates generally fluidic multiplexer block clamp assembly 4150 that includes fluidic multiplexer block clamp 4400 with fluidic multiplexer block assembly 4110 mounted therein. As depicted in FIG. 44, fluidic multiplexer block fourth face 4108 of fluidic multiplexer block 4100 has sensor interface inlet connector ports 4260A though 4260D and sensor interface outlet connector ports 4262A though 4262D for each fluidic multiplexer unit 4200A, 4200B, 4200C and 4200D, respectively. First alignment notch 4107A of first fluidic manifold unit 4200A, and second alignment notch 4107B of fourth fluidic manifold unit 4200D are configured to assist in the alignment and sealing process of fluidic multiplexer block clamp assembly 4150 to a multi-lane sensor array device. As previously disclosed herein, fluidic multiplexer block clamp 4400 provides four degrees of movement to a fluidic multiplexer block mounted therein to provide flexibility of the docking of the fluidic multiplexer block to a multi-lane sensor array device. Additionally, first alignment notch 4107A and second alignment notch 4107B are configured to provide self-alignment of a multi-lane sensor array device to a multi-lane sensor array device, so that sealing of sensor interface inlet connector ports and sensor interface outlet connector ports, such as sensor interface inlet connector ports 4260A though 4260D and sensor interface outlet connector ports 4262A though 4262D can be done to the respective inlet ports and outlet ports of a multi-lane sensor array device.

Figure 45:
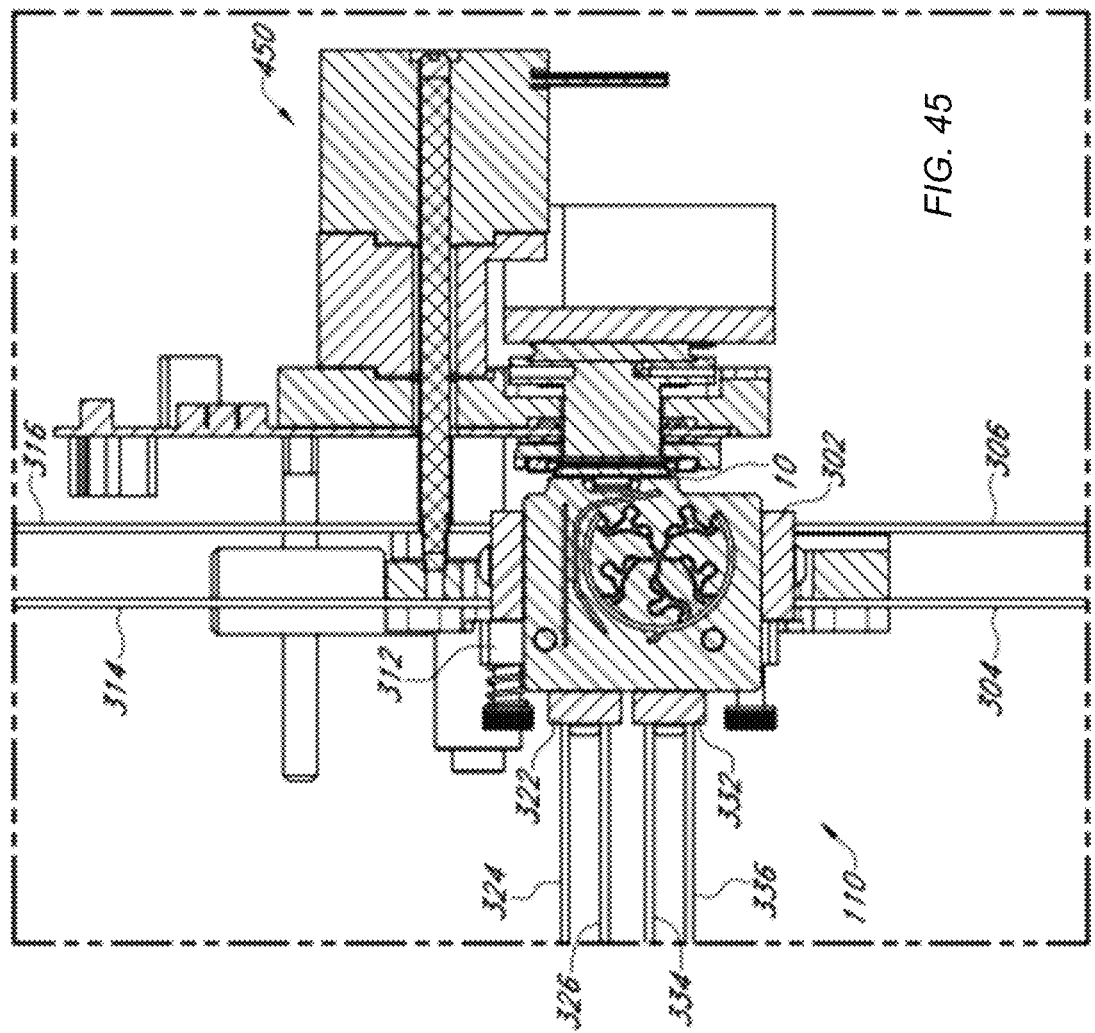
FIG. 45 is a section view that illustrates generally an assembly of a fluidic multiplexer block in a fluidic multiplexer block clamp mounted to a multi-lane sensor device that is positioned in a sensor device mounting assembly.
Figure 46:
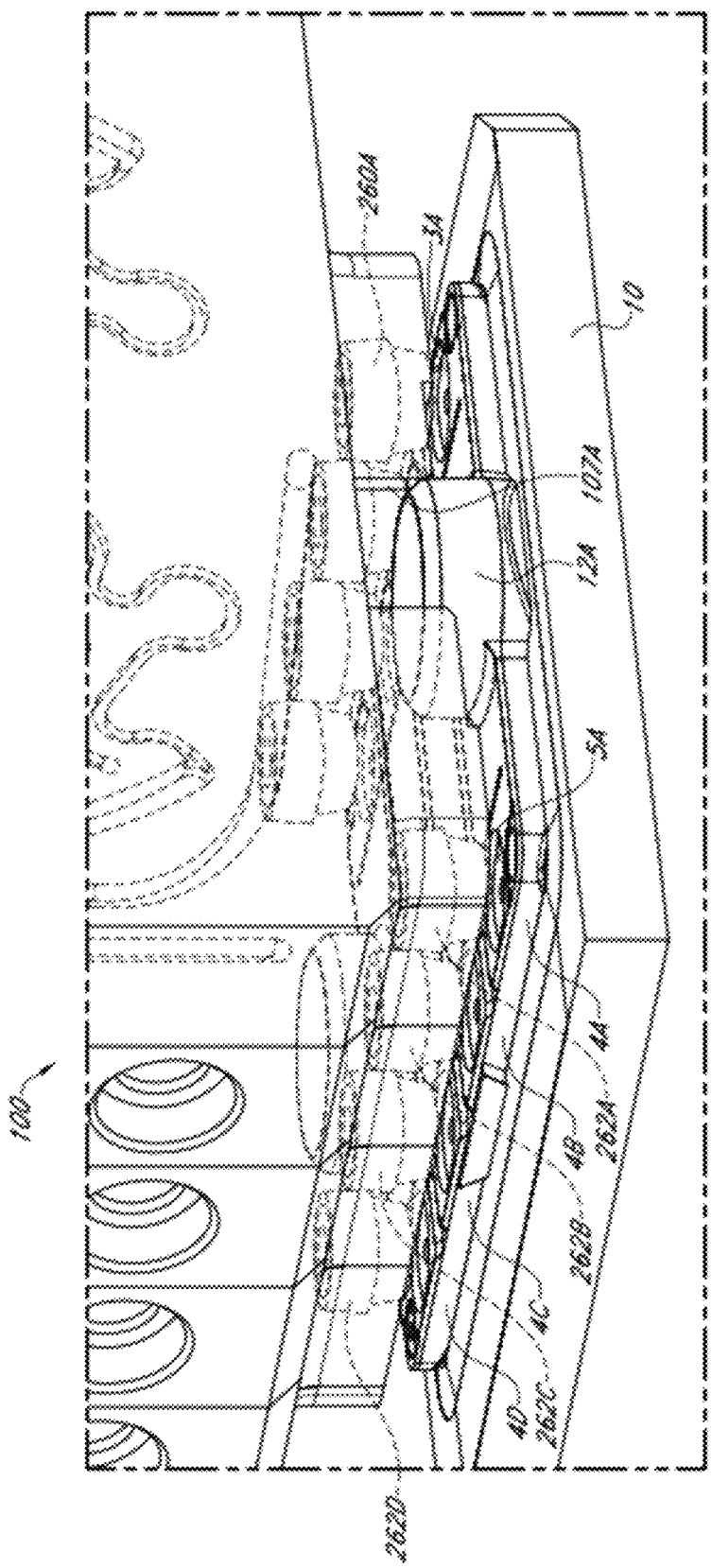
FIG. 46 is an expanded isometric view that illustrates generally the mounting of a fluidic multiplexer block to a multi-lane sensor array device.

FIG. 45 is a section view that illustrates generally fluidic multiplexer block assembly 4110 mounted to multi-lane sensor device 10, such as multi-lane sensor device 10 schematically depicted in FIG. 41. As depicted in FIG. 45, multi-lane sensor device 10 which is mounted to sensor device mounting and positioning assembly 4450. The positions of fluidic interface blocks 4302, 4312, 4322, and 4332 of fluidic multiplexer block assembly 4110 are also evident in the section view of FIG. 45. When fluidic multiplexer block assembly 4110 is mounted to multi-lane sensor device 10, for each lane of a multi-lane sensor array device, coupling and sealing of each sensor interface inlet connector port and each sensor interface outlet connector port to each corresponding sensor array inlet port and each sensor array outlet port, respectively, is done. In that regard, FIG. 46 is an expanded isometric view that illustrates generally the mounting and sealing of a fluidic multiplexer block to a multi-lane sensor array. As depicted in FIG. 46, sensor array device 10 has lanes 4A through 4D, each lane having an inlet port and an outlet port, as exemplified for lane 4A with inlet port 3A and outlet port 5A. In FIG. 46, the juxtaposition of first alignment pin 12A of sensor array device 10 and first alignment notch 4107A of fluidic multiplexer block 4100 shows how the complementary pair engage for alignment of sensor array device 10 with fluidic multiplexer block 4100. Additionally, FIG. 46 depicts how each inlet port and each outlet port of sensor array device 10 can be coupled and sealed to each corresponding sensor interface inlet connector port and each sensor interface outlet connector port of fluidic multiplexer block 4100. In FIG. 46, this is exemplified for lane 4A, in which the juxtaposition of first inlet port 3A to sensor interface inlet connector port 4260A and first outlet port 5A to sensor interface outlet connector port 4262A can be coupled and sealed to each once sensor array device 10 and fluidic multiplexer block 4100 have been completely engaged with one another.

Figure 47:
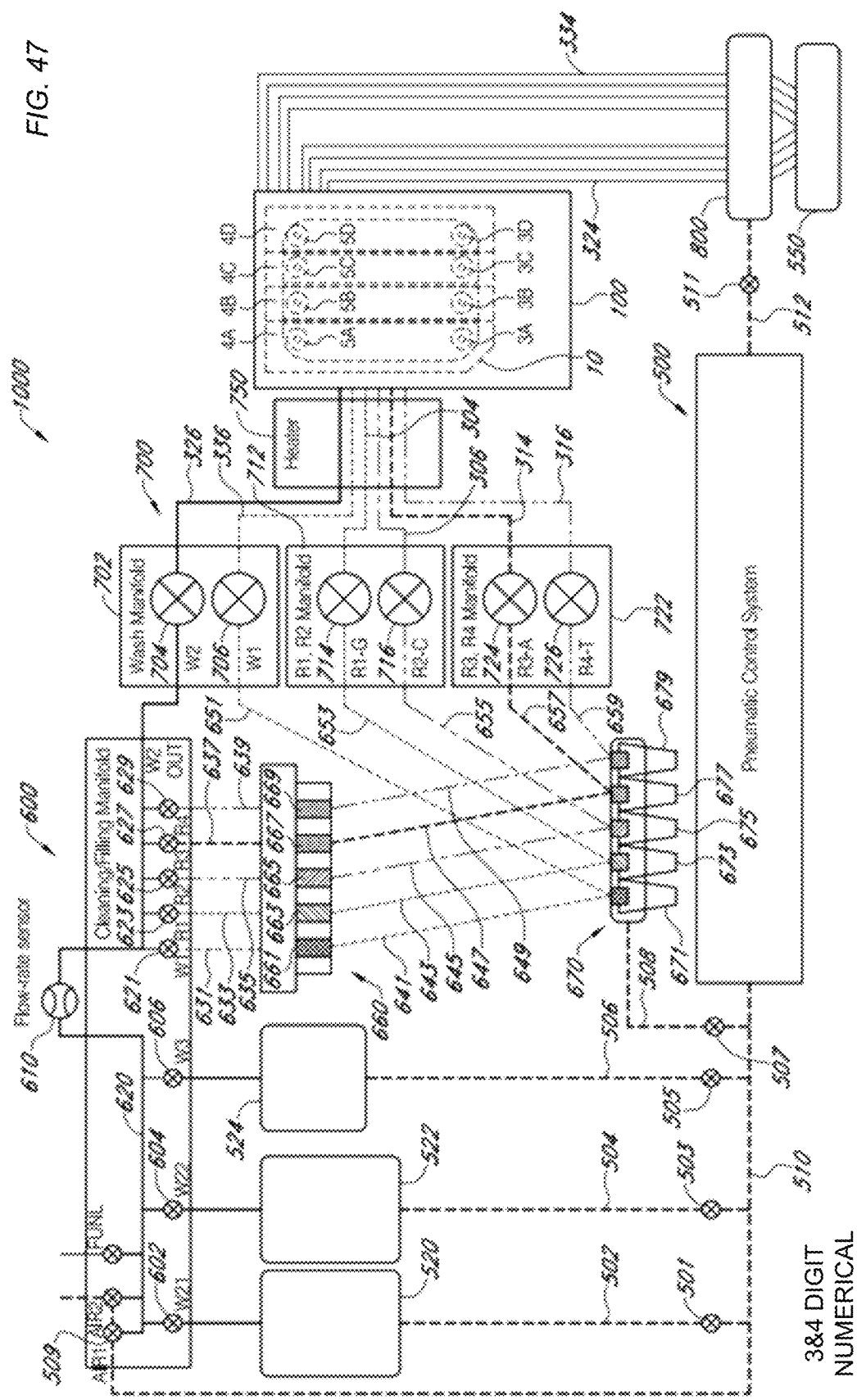
FIG. 47 is a schematic representation that illustrates generally a fluidic system of a sequencing system of the present teachings.

FIG. 47 is a schematic representation that illustrates generally fluidic system 41000 of a sequencing system of the present teachings. As depicted in FIG. 47, fluidic system 41000 has pneumatic control system 4500, as well as liquid handling control systems, such as solution handling manifold 4600 and reagent distribution manifold assembly 4700.

In that regard, pneumatic control system 4500 is in fluid communication with first wash solution container 4520 through first pneumatic inlet line that is controlled via valve 4501, with second wash solution container 4522 through second pneumatic inlet line 4504 that is controlled via valve 4503, and with cleaning solution container 4524 through third pneumatic inlet line 4506 that is controlled via valve 4505. Similarly, pneumatic control system 4500 is in fluid communication with reagent container assembly 4670 via fourth pneumatic inlet line 4508 that is controlled via valve 4507. With respect to fluidic system control, pneumatic control system 4500 is in fluid communication with solution handling manifold 4600 via fifth pneumatic inlet line 4510 that is controlled via valve 4509. Finally, pneumatic control system 4500 is in fluid communication with pinch manifold 4800 via sixth pneumatic inlet line 4512 that is controlled via valve 4511. As will be disclosed in more detail herein, pneumatic control system 4500 and pinch manifold 4800, in conjunction with flow rate sensor 4610 provide system regulation and control between solution input sources and waste. According to the present teachings, fluidic system regulation and control of fluidic system 41000 provides a defined and controllable pressure difference between solution input sources, such as first wash solution container 4520, second wash solution container 4522, cleaning solution container 4524, and reagent container assembly 4670, and waste container 4550. As such, a defined and controlled pressure difference provides a defined and controlled flow rate of various solutions used over the course of an analysis through various liquid circuits of fluidic system 41000. Flow rates may include rates of approximately 15 µl/s for single lane chip flow, 45 µl/s for single lane chip and main waste flow, 180 µl/s for full chip and main waste flow, or over 300 µl/s during system cleaning operations.

Solution handling manifold 4600 provides control for the distribution of various solutions used in cleaning and filling. As depicted in FIG. 47, solution handling manifold 4600 has solution handling manifold line 4620 which is in fluid communication with flow rate sensor 4610. According to the present teachings, flow rate sensor 4610 provides dynamic input to pneumatic control system 4500 for calibrating a defined flow rate for various liquid circuits of fluidic system 41000 using pinch manifold 4800, and for providing a defined volume of flow when filling nucleotide containers. With respect to liquid input sources, first wash solution container 4520 is in fluid communication with solution handling manifold 4600 through first wash solution outlet line 4530, while second wash solution container 4522 is in fluid communication with solution handling manifold 4600 through second wash solution outlet line 4532 and cleaning solution container 4524 is in fluid communication with solution handling manifold 4600 through calibration solution outlet line 4534.

In order to provide sufficient reagent volume for the massively parallel processing performed during next generation sequencing, fluidic system 41000 is configured to provide a substantial volume of various solutions used over the course of an analysis. In that regard, reagent concentrate cartridge 4660 is in fluid communication with wash solution containers 4520 and 4522. As used herein, a wash solution is an aqueous-based solution of stable electrolyte composition, which can be used as a solvent in the preparation of a calibration solutions and sequencing reagents, for a washing operation as previously described herein, as well as used for continually refreshing electrolyte solution around a reference electrode. Reagent concentrate cartridge 4660 can include calibration solution concentrate container 4661, while the remaining concentrates are nucleotide reagent concentrates. For example, first nucleotide reagent concentrate container 4663 can contain a deoxyguanosine triphosphate (dGTP) reagent concentrate, while second nucleotide reagent concentrate container 4665 can contain a deoxycytidine triphosphate (dCTP) reagent concentrate, and third nucleotide reagent concentrate container 4667 (e.g., the cartridge of FIG. 11) can contain a deoxyadenosine triphosphate (dATP) reagent concentrate, while fourth nucleotide reagent concentrate container 4669 can contain a deoxythymidine triphosphate (dTTP) reagent concentrate. Reagent concentrate cartridge 4660 is also in fluid communication with reagent container assembly 4670. Each container of reagent container assembly 4670 holds a substantial volume of calibration solution and dNTP reagents used in high-throughput next generation sequencing-by-synthesis analysis systems of the present teachings. Each reagent container can have a volume of approximately 225 ml, to support a diluted solution volume of approximately 150 ml. In the preparation of bulk calibration solution and bulk nucleotide reagents, the concentrated reagents are diluted by a factor of about 100 when mixed in the reagent containers.

Before the initiation of sequencing runs, the bulk preparation of a calibration solution and nucleotide reagents can be done. Regarding the bulk preparation of a calibration solution, with valves 4602 and 4621 of solution handling manifold 4600 open, and all other solution handling manifold valves closed, wash solution in wash solution container 4520 can flow into solution handling manifold line 4620 through wash solution outlet line 4530 and into calibration solution concentrate container 4661 through calibration concentrate line 4631, and then into calibration solution container 4671 through calibration solution inlet line 4641. Wash solution can continue to flow through calibration solution concentrate container 4661 to calibration solution container 4671 for a predetermined fill volume of calibration solution container 4671, at which point calibration solution concentrate container 4661 has been effectively exhausted of calibration solution concentrate.

Next, the bulk preparation of a first nucleotide solution can be done by having valves 4602 and 4623 of solution handling manifold 4600 open, and all other solution handling manifold valves closed, so that wash solution in wash solution container 4520 can flow into solution handling manifold line 4620 and into first nucleotide reagent concentrate container 4663 through first nucleotide reagent concentrate line 4633, and then into first nucleotide reagent container 4673 through first nucleotide reagent inlet line 4643 until first nucleotide reagent container 4673 is filled.

After the bulk preparation of the first nucleotide solution is complete, the bulk preparation of a second nucleotide solution can be done by having valves 4602 and 4625 of solution handling manifold 4600 open, and all other solution handling manifold valves closed, so that wash solution in wash solution container 4520 can flow into solution handling manifold line 4620 through wash solution outlet line 4530 and into second nucleotide reagent concentrate container 4665 through second nucleotide reagent concentrate line 4635, and then into second nucleotide reagent container 4675 through second nucleotide reagent inlet line 4645 until second nucleotide reagent container 4675 is filled.

Following the bulk preparation of a second nucleotide reagent, the bulk preparation of a third nucleotide solution can be done by having valves 4602 and 4627 of solution handling manifold 4600 open, and all other solution handling manifold valves closed, so that wash solution in wash solution container 4520 can flow into solution handling manifold line 4620 through wash solution outlet line 4530 and into third nucleotide reagent concentrate container 4667 through third nucleotide reagent concentrate line 4637, and then into third nucleotide reagent container 4677 through third nucleotide reagent inlet line 4647 until third nucleotide reagent container 4677 is filled.

Finally, the bulk preparation of a fourth nucleotide solution can be done by having valves 4602 and 4629 of solution handling manifold 4600 open, and all other solution handling manifold valves closed, so that wash solution in wash solution container 4520 can flow into solution handling manifold line 4620 through wash solution outlet line 4530 and into fourth nucleotide reagent concentrate container 4669 through fourth nucleotide reagent concentrate line 4639, and then into fourth nucleotide reagent container 4679 through fourth nucleotide reagent inlet line 4649 until fourth nucleotide reagent container 4679 is filled.

With sufficient calibration solution and nucleotide reagents prepared for high-throughput next generation sequencing-by-synthesis run, reagent distribution manifold assembly 4700 can control the distribution of various solutions in reagent container assembly 4670 through fluidic multiplexer block 4100 and into sensor array device 10, and finally into waste 4530 through chip waste lines 4324 or main waste lines 4334 (see, for example, FIG. 43).

As depicted in FIG. 47, reagent distribution manifold assembly 4700 can include reagent distribution manifold 4702, reagent distribution manifold 4712, and reagent distribution manifold 4722. Heater block 4750 of FIG. 47 can be in contact with flexible tubing sets 4304, 4306, 4314, 4316, 4326, and 4336 to ensure uniform temperature of solutions and reagents before flowing through fluidic multiplexer block 4100 and sensor array device 10.

Reagent distribution manifold 4702 can have a first set of valves in valve block 4704, which can individually control the fluid communication between solution handling manifold line 4620 and flexible tubing set 4326. As depicted for fluidic multiplexer block assembly 43110 of FIG. 43, each tube of flexible tubing set 4326 is connected to a corresponding wash solution inlet port of a corresponding fluidic multiplexer unit, such as wash solution inlet port 40240 of fluidic multiplexer unit 40200 of FIG. 40. Additionally, reagent distribution manifold 4702 can have a second set of valves in valve block 4706, which can individually control the fluid communication between calibration solution line outlet 4651 and flexible tubing set 4336. As depicted for fluidic multiplexer block assembly 4110 of FIG. 43, each tube of flexible tubing set 4336 is connected to a corresponding calibration solution inlet port of a corresponding fluidic multiplexer unit, such as calibration solution inlet port 4234 of fluidic multiplexer unit 4200 of FIG. 40.

To provide a flow of wash solution through a selected lane or through selected lanes of a multi-lane sensor array device, either of valves 4602 or 4604 of solution handling manifold 4600 can be open, while all other valves in solution handling manifold 4600 are closed. Either one valve, all four valves or any combination of valves in valve block 4704 of reagent distribution manifold 4702 can be open, so wash solution from either containers 4520 and 4522 can flow into solution handling manifold line 4620 through either wash solution outlet line 4530 or 4532, respectively, to be distributed by a corresponding fluidic multiplexer block unit to one lane, all four lanes or any combination of lanes, depending on the selection of valves in valve block 4704. To provide a flow of calibration solution through a selected lane or through selected lanes of a multi-lane sensor array device, all valves in solution handling manifold 4600 are closed. Either one valve, all four valves or any combination of valves in valve block 4706 of reagent distribution manifold 4702 can be open, so calibration solution from calibration solution container 4671 can flow into calibration solution line outlet 4651 to be distributed by a corresponding fluidic multiplexer block unit to one lane, all four lanes or any combination of lanes, depending on the selection of valves in valve block 4706.

Reagent distribution manifold 4712 can have a first set of valves in valve block 4714, which can individually control the fluid communication between first nucleotide reagent outlet line 4653 and flexible tubing set 4304. As depicted for fluidic multiplexer block assembly 4110 of FIG. 43, each tube of flexible tubing set 4304 is connected to a corresponding first nucleotide reagent inlet port of a corresponding fluidic multiplexer unit, such as first nucleotide reagent inlet port 4210 of fluidic multiplexer unit 4200 of FIG. 40. Additionally, reagent distribution manifold 4712 can have a second set of valves in valve block 4716, which can individually control the fluid communication between second nucleotide reagent outlet line 4655 and flexible tubing set 4306. As depicted for fluidic multiplexer block assembly 4110 of FIG. 43, each tube of flexible tubing set 4306 is connected to a corresponding second nucleotide reagent inlet port of a corresponding fluidic multiplexer unit, such as second nucleotide reagent inlet port 4216 of fluidic multiplexer unit 4200 of FIG. 40.

To provide a flow of first nucleotide reagent through a selected lane or through selected lanes of a multi-lane sensor array device, all valves in solution handling manifold 4600 are closed. Either one valve, all four valves or any combination of valves in valve block 4714 of distribution manifold 4712 can be open, so first nucleotide reagent from first nucleotide reagent container 4673 can flow into first nucleotide reagent outlet line 4653 to be distributed by a corresponding fluidic multiplexer block unit to one lane, all four lanes or any combination of lanes, depending on the selection of valves in valve block 4714. To provide a flow of second nucleotide reagent through a selected lane or through selected lanes of a multi-lane sensor array device, all valves in solution handling manifold 4600 are closed. Either one valve, all four valves or any combination of valves in valve block 4716 of distribution manifold 4712 can be open, so second nucleotide reagent from second nucleotide reagent container 4675 can flow into second nucleotide reagent outlet line 4655 to be distributed by a corresponding fluidic multiplexer block unit to one lane, all four lanes or any combination of lanes, depending on the selection of valves in valve block 4716.

Reagent distribution manifold 4722 can have a first set of valves in valve block 4724, which can individually control the fluid communication between third nucleotide reagent outlet line 4657 and flexible tubing set 4314. As depicted for fluidic multiplexer block assembly 4110 of FIG. 43, each tube of flexible tubing set 4314 is connected to a corresponding third nucleotide reagent inlet port of a corresponding fluidic multiplexer unit, such as third nucleotide reagent inlet port 40222 of fluidic multiplexer unit 40200 of FIG. 40. Additionally, reagent distribution manifold 4722 can have a second set of valves in valve block 4726, which can individually control the fluid communication between fourth nucleotide reagent outlet line 4659 and flexible tubing set 4316. As depicted for fluidic multiplexer block assembly 4110 of FIG. 43, each tube of flexible tubing set 4316 is connected to a corresponding fourth nucleotide reagent inlet port of a corresponding fluidic multiplexer unit, such as fourth nucleotide reagent inlet port 4228 of fluidic multiplexer unit 4200 of FIG. 40.

To provide a flow of third nucleotide reagent through a selected lane or through selected lanes of a multi-lane sensor array device, all valves in solution handling manifold 4600 are closed. Either one valve, all four valves or any combination of valves in valve block 4724 of distribution manifold 4722 can be open, so third nucleotide reagent from third nucleotide reagent container 4677 can flow into third nucleotide reagent outlet line 4657 to be distributed by a corresponding fluidic multiplexer block unit to one lane, all four lanes or any combination of lanes, depending on the selection of valves in valve block 4724. To provide a flow of fourth nucleotide reagent through a selected lane or through selected lanes of a multi-lane sensor array device, all valves in solution handling manifold 4600 are closed. Either one valve, all four valves or any combination of valves in valve block 4726 of distribution manifold 4722 can be open, so fourth nucleotide reagent from fourth nucleotide reagent container 4679 can flow into fourth nucleotide reagent outlet line 4659 to be distributed by a corresponding fluidic multiplexer block unit to one lane, all four lanes or any combination of lanes, depending on the selection of valves in valve block 4726.

A schedule of cleaning for all fluidic components in fluidic system 41000 can be performed. Such cleaning is typically performed after all four lanes of a chip have been sequenced, or prior to a new chip being installed on the system. Cleaning can be performed with an exhausted reagent concentrate cartridge and a used multi-lane sensor array device in place. With valve 4606 open, each of valves 4623 through 4629 of solution handling manifold 4600 can be sequentially opened, and all of the valves in a set of valves of a corresponding valve block of distribution manifold assembly 4700 can be opened. With such a flow path sequentially executed for each fluidic path of the calibration solution and of each nucleotide reagent as previously described herein, cleaning solution from cleaning solution container 4524 can flow sequentially through every fluidic component of fluidic system 41000 to waste container 4550. Finally, a drying procedure is done in order to leave the system ready for next use. For a drying procedure, valves 4602, 4604 and 4606 closed and all other valves of solution handling manifold 4600 are open, and all valves of reagent distribution manifold assembly 4700 are open. In that configuration, clean dry air is passed through the liquid handling components of fluidic system 41000 to drive remaining liquid to waste container 4550.

As previously disclosed herein, pneumatic control system 4500 and pinch manifold 4800, in conjunction with flow rate sensor 4610 provide system regulation and control between solution input sources and waste. Pinch manifold 4800 contains eight pinch regulators, each constructed as described in U.S. Pat. No. 9,375,716. These devices operate essentially as three port pressure followers, with an input fluidic port, output fluidic port, and control pneumatic port. With a defined waste line fluidic resistance connected between the pinch regulator output fluidic port and waste container 4550, the pressure on the output fluidic port will be approximately equal to the pressure on the pinch regulator control pneumatic port, regardless of the pressure on the input fluidic port. The flow rate through the pinch regulator will then be equal to the output fluidic port pressure divided by the waste line fluidic resistance. In order to precisely calibrate the flow rates, the fluidic control system 41000 is configured to allow wash solution to flow to the desired pinch regulator on pinch manifold 4800. A set of known pneumatic pressures are applied to each pinch regulator pneumatic control port, and the flow sensor 4610 measures the precise flow rate corresponding to the pneumatic control pressure. A table of flow rates vs. pneumatic control pressures is then stored for each pinch regulator, which can be utilized by the instrument software to deliver any desired flow rate precisely.

Figure 48:
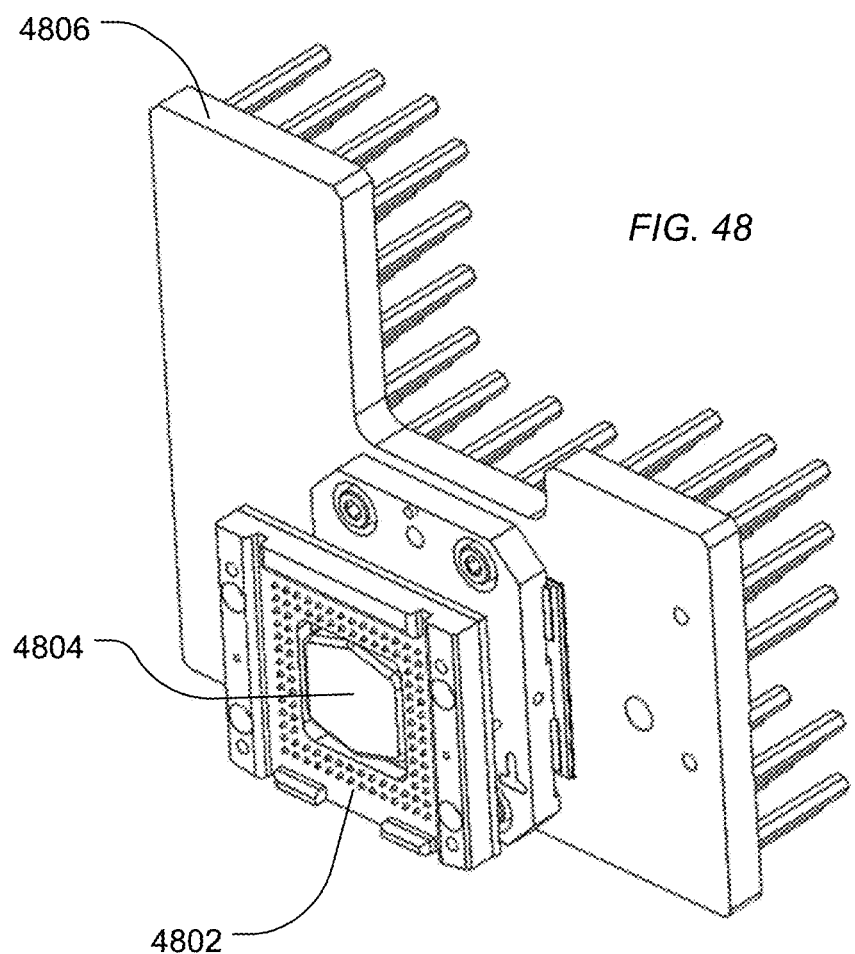
FIG. 48 includes an illustration of an example electronic interface.

FIG. 48 includes an illustration of an exemplary electronic interface 4802 for interfacing with the sensor device. For example, the electronic interface 4802 can include pins to interact with an electronic interface of the sensor device. Optionally, the interface 4802 can include a mechanism 4804 to disengage the sensor device from the electronic interface 4802. For example, when a fluidic manifold is pressed against the sensor device (as illustrated in FIG. 46), mechanism 4804 can depress. When the fluidic manifold is disconnected from the sensor device, the mechanism 4804 can push the sensor device away from the electronic interface 4802. Optionally, the system can further include mechanisms for controlling temperature, such as a heatsink 4806. The heatsink 4806 can include fins. Alternatively, the heatsink 4806 can be liquid cooled heatsink.

In particular, the fluidic system and the electronic interface are used to detect nucleotide incorporations during a sequencing-by-synthesis reaction. The data is collected and provided to a sequencing instrument server system.

Sequencer Software

In some embodiments, a nucleic acid sequencing instrument maybe interfaced with a server system for control of various components of the sequencing instrument and processing of data output from sequencing runs on the sequencing instrument. The server system software may include a web application, databases and analysis pipeline and support connections from a sequencing instrument (e.g., FIG. 6). The server system software may provide the following major functionalities and application program interfaces (APIs):

1. APIs for user authentication, reagent tracking, run information and run tracking/logging. Supported instruments may include the sequencing instrument and extraction instrument.
2. APIs for a LIMS (Laboratory Information Management System) for creation of samples, libraries, plan run and retrieve the run status of the plan.
3. Support for management of samples and run data.
4. Support for assay configuration and execution of the analysis pipeline for data analysis and reporting.
5. Interface to a software update server for software updates and maintenance.
6. Supports configuration to connect to an annotation and reporting system, such as Ion Reporter from Thermo Fisher Scientific, deployed in a cloud-based system or a local system, and establishes secure and authenticated connection with the cloud-based system to transfer mapped or unmapped BAM files.
7. Supports configuration to connect to a resource system in a cloud computing environment, such as the Thermo Fisher Cloud, and establishes secure and authenticated connection with the cloud resource system to download software and system contents and to send telemetry data.

Figure 49:
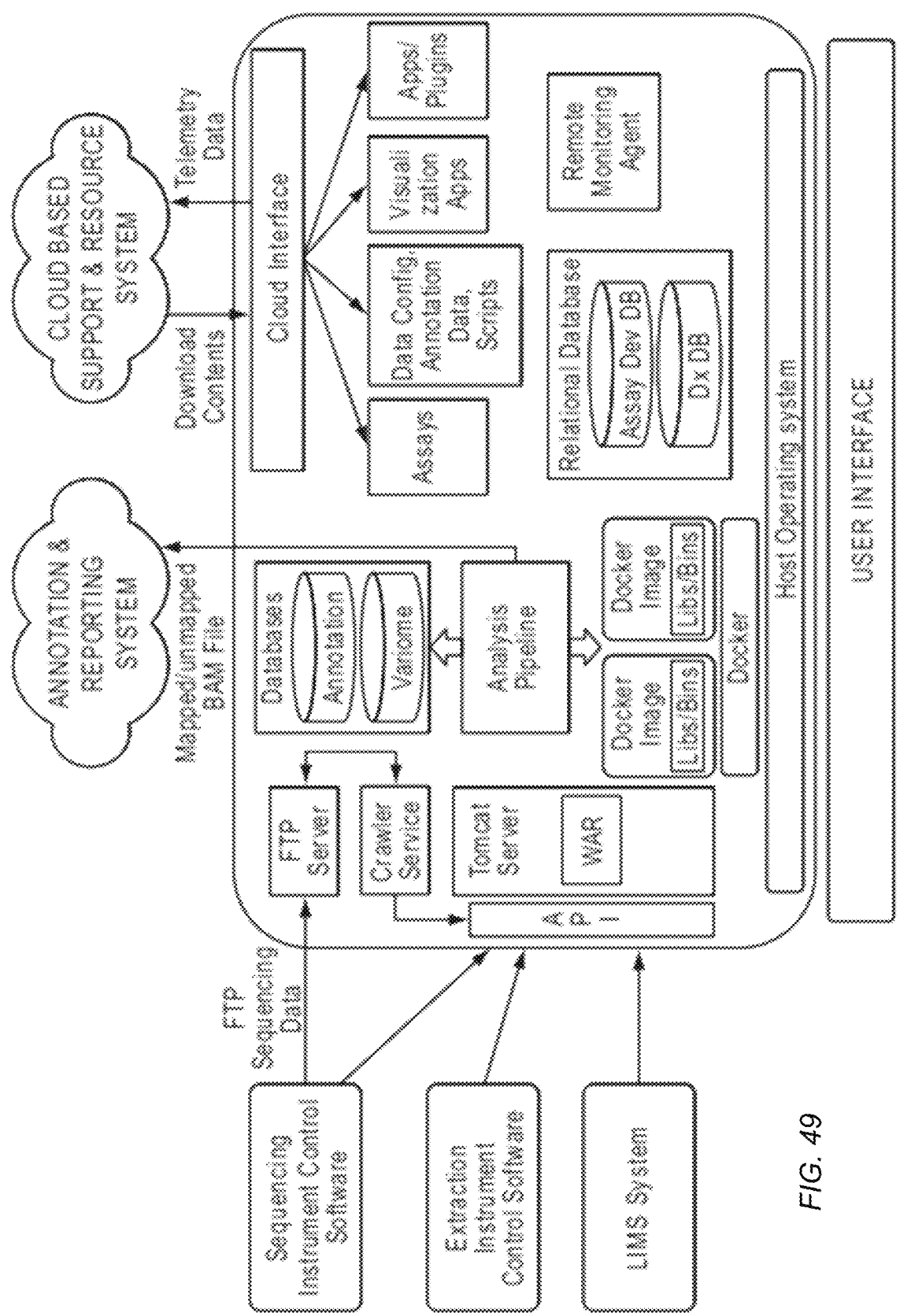
FIG. 49 shows a schematic diagram of server system components.

FIG. 49 shows a schematic diagram of the server system components. In some embodiments, the basic software architecture may comprise a web interface, remote monitoring agent, databases, APIs to the instruments, analysis pipeline, containerization of the analysis pipeline (using Docker, for example), connectivity to an annotations and reporting system (e.g. Ion Reporter from Thermo Fisher Scientific) and a cloud-based support and resource system (e.g. Thermo Fisher Cloud). The cloud-based support and resource system, or cloud-based resource system, may be implemented in a cloud computing and storage system. The cloud-based support and resource system stores content including assay definition files. A server of the cloud computing and storage system may download contents, such as assay definition files, to the local server system. The cloud-based support and resource system may receive telemetry data from the local server system. Server system, local server system and user's server system are used interchangeably herein.

In some embodiments, a user interface (UI) may be implemented via web application software. The UI may provide sample management pages. The sample management UI pages allow the user to enter sample information into the system. Sample information includes unique sample identifier (ID), sample name and sample preparation reagent tracking information. Validation logic is built into the sample management flow that locks the sample preparation step to the pre-defined assay workflow. The UI may provide assay management pages. Assay management UI pages allow the user to view assays, and create assays. The assays lock the workflows to pre-defined parameters for each step of the process. Validation logic may be built in to ensure the assay configuration. The UI may provide run plan and monitor pages. The run plan and monitor UI pages allow the user to plan for a run and monitor the run in progress. The UI may provide output data pages. The output data UI pages allow the user to view the analysis results along with quality control (QC) metric evaluation, log and audit trail of the results generated. The UI may provide configuration pages. The configuration UI pages allow users to view and configure the system.

In some embodiments, application programming interfaces (APIs) may be provided through a Java platform. For example, the Java platform may include a Tomcat server that may be used to build a Web ARchive (WAR) file for web-based applications.

Code modules for various steps of the analysis pipeline may be referred to as actors in the context of a Kepler workflow engine. For example, a code module for an analysis step may implemented by Java program binary code included in an actor jar. A Kepler workflow engine defines processing components of a workflow as "actors" and chains the steps for execution by a processor of the algorithm or analysis pipeline. (kepler-project.org). For example, a Kepler workflow engine may be used to configure the workflow of the analysis pipeline in FIG. 49.

The server system may include one or more databases. For example, the server system may include a relational database for storing sample data, run data and system/user configuration. The relational database may include two separate databases: assay development database and Dx database. The assay development database may store sample data, run data and system/user configuration for RUO, or assay development, mode of operation. The Dx database may store sample data, run data and system/user configuration for the IVD, or Dx, mode of operation.

The server system may include an annotations database, AnnotationDB, for storing annotation source data. For example, the annotations database may be implemented as NoSQL, or non-relational, database, e.g. a MongoDB database. Each annotation source may be stored as a JSON (JavaScript Object Notation) string with meta information indicating source name and version. Each annotation source may contain a list of annotations keyed to annotation IDs. The server system may include a variome database, VariomeDB, for storing variant information. For example, the variome database may be implemented as a NoSQL, or non-relational, database, e.g. a MongoDB database. The VariomeDB may store a collection of variant call results on a particular sample. For example, a JSON formatted record may contain meta information for identifying the sample.

For example, the AnnotationDB database may store one or more of the following annotation sources:
1. RefGene Model: hg19_refgene_63, version 63
2. RefGene Functional Canonical Transcripts Scores: hg19_refgeneScores_4, version 4
3. dbSNP: dbsnp_138, version 138
4. Canonical RefSeq Transcripts: hg19_refgene_63, version 63
5. 5000Exomes: hg_esp6500_1, version 1
6. ClinVar: clinvar_1, version 1
7. DGV: dgv_20130723, version 20130723
8. OMIM: omim_03022014, version 03022014

Other annotation sources may be included. Other versions of the above annotation sources may be included. The annotation source may provide public annotation information content or proprietary annotation information content.

For each call in Variome database, and each annotation source may be queried for annotations matching the variant and matching annotations may be stored as key-value pairs in Variome database with the variant. Annotated variants may be included in a results file, e.g. an annotated VCF file, for the user. VCF files are tab-separated text files used for storing gene sequence variants. In some embodiments, the annotation methods for use with the present teachings may include one or more features described in U.S. Pat. Appl. Publ. No. 2016/0026753, published Jan. 28, 2016, incorporated by reference herein in its entirety.

In some embodiments, the server system may include an analysis pipeline to process sequencing data generated during a sequencing run for an assay performed by a sequencing instrument. The sequencer transfers sequencing data files and experiment log files to the server system memory, for example in raw .dat files, already processed .dat files producing block wise 1.wells files, and thumbnail data. The analysis pipeline accesses the data files from memory and starts data analysis for the run.

In some embodiments, a Docker container and Docker images may be used for packaging the analysis pipeline and operating system specific binaries. The Docker is a tool used to create, deploy, and run applications by using containers. Containers enable an application with all the parts it needs, such as libraries and other dependencies, to be bundled as one package. This allows applications software to use the same Linux kernel as the host system. The Docker image files may be packaged with libraries and binaries needed by the analysis pipeline code. The Docker may be used to adapt an application or algorithm to a new or different version of an operating system (OS) to create a Docker image of the application that is compatible with the OS version.

In some embodiments, the server system may include a crawler service for data transfer from the sequencing instrument to the analysis pipeline. The crawler is an event-based service that may be developed using JAVA NIO watcher API (application programming interface). NIO (Non-blocking I/O) is a collection of Java programming language APIs that offer features for intensive input/output (I/O) operations. The crawler may monitor the FTP directory configured for the sequencing instrument to transfer run data from the sequencing instrument to the analysis pipeline.

Figure 50:
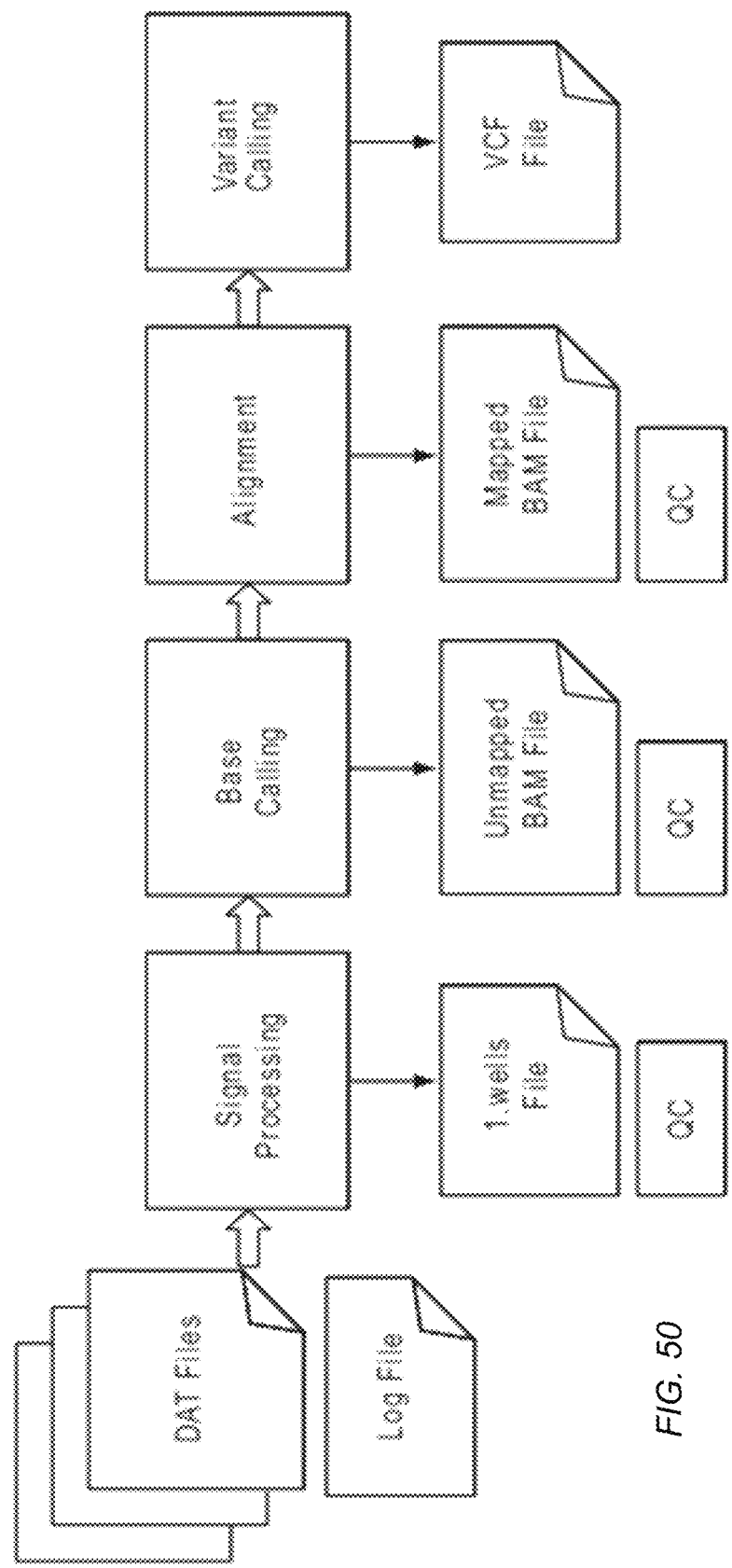
FIG. 50 is a block diagram of the analysis pipeline.

FIG. 50 is a block diagram of the analysis pipeline, in accordance with an embodiment. The sequencing instrument generates raw data files (DAT, or .dat, files) during a sequencing run for an assay. Signal processing may be applied to raw data to generate incorporation signal measurement data for files, such as the 1.wells files, which are transferred to the server FTP location along with the log information of the run. The signal processing step may derive background signals corresponding to wells. The background signals may be subtracted from the measured signals for the corresponding wells. The remaining signals may be fit by an incorporation signal model to estimate the incorporation at each nucleotide flow for each well. The output from the above signal processing is a signal measurement per well and per flow, that may be stored in a file, such as a 1.wells file.

In some embodiments, the base calling step may perform phase estimations, normalization, and runs a solver algorithm to identify best partial sequence fit and make base calls. The base sequences for the sequence reads are stored in unmapped BAM files. The base calling step may generate total number of reads, total number of bases and average read length as QC measures to indicate the base call quality. The base calls may be made by analyzing any suitable signal characteristics (e.g., signal amplitude or intensity). The signal processing and base calling for use with the present teachings may include one or more features described in U.S. Pat. Appl. Publ. No. 2013/0090860 published Apr. 11, 2013, U.S. Pat. Appl. Publ. No. 2014/0051584 published Feb. 20, 2014, and U.S. Pat. Appl. Publ. No. 2012/0109598 published May 3, 2012, each incorporated by reference herein in its entirety.

Once the base sequence for the sequence read is determined, the sequence reads may be provided to the alignment step, for example, in an unmapped BAM file. The alignment step maps the sequence reads to a reference genome to determine aligned sequence reads and associated mapping quality parameters. The alignment step may generate a percent of mappable reads as QC measure to indicate alignment quality. The alignment results may be stored in a mapped BAM file. Methods for aligning sequence reads for use with the present teachings may include one or more features described in U.S. Pat. Appl. Publ. No. 2012/0197623, published Aug. 2, 2012, incorporated by reference herein in its entirety.

The BAM file format structure is described in "Sequence Alignment/Map Format Specification," Sep. 12, 2014 (github.com/samtools/hts-specs). As described herein, a "BAM file" refers to a file compatible with the BAM format. As described herein, an "unmapped" BAM file refers to a BAM file that does not contain aligned sequence read information and mapping quality parameters and a "mapped" BAM file refers to a BAM file that contains aligned sequence read information and mapping quality parameters.

In some embodiments the variant calling step may include detecting single-nucleotide polymorphisms (SNPs), insertions and deletions (InDels), multi-nucleotide polymorphisms (MNPs) and complex block substitution events. In various embodiments, a variant caller can be configured to communicate variants called for a sample genome as a *.vcf, *.gff, or *.hdf data file. The called variant information can be communicated using any file format as long as the called variant information can be parsed or extracted for analysis. The variant detection methods for use with the present teachings may include one or more features described in U.S. Pat. Appl. Publ. No. 2013/0345066, published Dec. 26, 2013, U.S. Pat. Appl. Publ. No. 2014/0296080, published Oct. 2, 2014, and U.S. Pat. Appl. Publ. No. 2014/0052381, published Feb. 20, 2014, and U.S. Pat. No. 9,953,130 issued Apr. 24, 2018, each of which is incorporated by reference herein in its entirety. In some embodiments, the variant calling step may be applied to molecular tagged nucleic acid sequence data. Variant detection methods for molecular tagged nucleic acid sequence data may include one or more features described in U.S. Pat. Appl. Publ. No. 2018/0336316, published Nov. 22, 2018, incorporated by reference herein in its entirety.

In some embodiments, the analysis pipeline may include a fusion analysis pipeline for fusion detection. Fusion detection methods may include one or more features described in U.S. Pat. Appl. Publ. No. 2016/0019340, published Jan. 21, 2016, incorporated by reference herein in its entirety. In some embodiments, the fusion analysis pipeline may be applied to molecular tagged nucleic acid sequence data. Fusion detection methods for molecular tagged nucleic acid sequence data may include one or more features described in U.S. Pat. Appl. Publ. No. 2019/0087539, published Mar. 21, 2019, incorporated by reference herein in its entirety.

In some embodiments, the analysis pipeline may include a copy number variants analysis pipeline for detection of copy number variations. Methods for detection of copy number variation may include one or more features described in U.S. Pat. Appl. Publ. No. 2014/0256571, published Sep. 11, 2014, U.S. Pat. Appl. Publ. No. 2012/0046877, published Feb. 23, 2012, and U.S. Pat. Appl. Publ. No. US2016/0103957, published Apr. 14, 2016, each of which is incorporated by reference herein in its entirety.

In some embodiments, the server system software may support an encapsulated assay configuration that includes assay name, assay type, panel, hotspot file if any, reference name, control names if any, quality control QC thresholds, assay description if any, data analysis parameters and values, instrument run script names and other configurations that define the assay. The entire set of the information is called an assay definition. The assay configuration content and corresponding workflows may be delivered to the user as modular software components in an assay definition file (ADF). The server system software may import an assay definition file that contains the assay configuration. The import process may be initiated by zip file import which includes an encrypted Debian file and triggers an installation process. The user interface may provide a page for the user to select an ADF for import. An application store in the cloud-based support and resource system may store ADFs supporting various assays, panels, and workflows available for selection by the user for download to the user's local server system.

An assay definition file (ADF) is an encapsulated file that defines configurations for the molecular test or assay, including assay name, technology platform configuration (for example, next generation sequencing (NGS), chip type, chemistry type), workflow steps (sample prep, instrument scripts, analytics, reporting), analysis algorithms, regulatory labels (for example, research use only (RUO), in vitro diagnostics (IVD), Central Europe in vitro diagnostics (CE-IVD, internal use only (IUO), etc.), targeted markers (panel), reference genome version, consumables, controls, QC thresholds, reporting genes and variants. The ADFs provide a modular approach to building assay capabilities for the local sequencing instrument. The assay software may be provided by the ADF separately from the platform software of the sequencing instrument.

The advantages of using the ADF for assay configuration include the following:
Encapsulation of the assay workflow and analysis
Single click for installation
No revalidation required after software update for assay configuration because of the modular structure of the software by the Docker implementation allowing separation from the platform software
Multi-tiered encryption for secure delivery
Streamlined support of assay configurations for original equipment manufacturers (OEM)
Streamlined customization of reporting
Support of regional regulatory requirements
Plug-n-play format supports technology agnostic workflows
Enables rapid expansion of molecular test menu and assay adoption by laboratories In some embodiments, the assay definition file (ADF) may include software code modules for one or more of the following steps 1) library preparation; 2) templating; 3) sequencing; 4) analysis; 5) variant interpretation; and 6) report generation. For the workflow steps of library preparation and templating, the ADF may include scripts for preparing libraries, templating, and enrichment of templated beads. For the workflow steps of sequencing and analysis the ADF may include Docker image packages of algorithm binary code and parameters for the analysis pipeline described with respect to FIG. 50. For the workflow step of variant interpretation, the ADF may include a list of annotation sources that may be used for analyzing and annotating variants. For the workflow step of report generation, the ADF may include report templates and image files for use when a generating a report.

The ADF may include for the instrument scripts for control of workflow steps on the sequencing instrument. For example, scripts may include parameters controlling the amount of pipetting and robotic control. The instrument scripts may be customized for the particular assay.

For example, for the sequencing and analysis steps, the ADF may include a Docker image of the end to end analysis pipeline. The Docker image may include OS specific libraries and binaries for the algorithms each step of analysis pipeline. The algorithm binaries may include steps of the analysis pipeline including signal processing, base calling, alignment, and variant calling, such as those described with respect to FIG. 50. In another example, the ADF Debian file may package certain code modules for a particular assay, such as code modules for signal processing, base calling and RNACounts.

The ADF may include scripts for configuration of reagent kits. These scripts support calculation of the consumables needed for a sequencing run. The configurations scripts included in the ADF may include one or more of the following:

Barcode set and chip

Library kit and consumables, including capability to associate sample control configuration, (e.g. sample inline control) and its QC parameters Templating kit and consumables, including capability to associate internal controls and QC parameters Sequencing kit, including capability to associate internal controls and QC parameters The ADF may include one or more reference genome files. Examples of reference genomes include hg19 and GRCH38. The reference genome file may be packaged in the main ADF with the workflow information. Alternatively, the reference genome file may be packaged in a separate ADF that is supplementary to the main ADF.

The ADF may include code modules for workflows of fusion panels and fusion target region panels. The ADF may include fusion target region reference files and hotspot files for analysis.

The ADF may include assay parameters at various points of the workflow that may be configured by the user. The configurable parameters may be displayed in the user interface for adjustment by the user. New parameters may be added at any actor level. The configurable parameters may be passed to the analysis pipeline. Input formats for the configurable assay parameters may include one or more single string text, Boolean, multiline text, floating point, radio buttons, drop downs, and file uploads. For example, the file uploads may use file formats such as properties and .json.

The ADF may include QC parameters used for quality control and assay performance thresholds at various points in the workflow. For example, types of QC parameters include run QC parameters, sample QC parameters, internal control QC parameters and assay specific QC parameters. A QC parameter may be defined by one or more of a data type (e.g. integer, floating point), lower bound, upper bound and default value.

The ADF may include specified data tab columns for results presentation that are selected from the database for a given assay. The selected data tab columns support configuration of the user interface display of results and the columns to be included in the PDF reports for the assay. The ADF may include image files for results presentation for a given assay. The ADF may include support for multiple languages for the PDF reports. The ADF may include a download file list for any files to be generated by the analysis pipeline for a given assay. The file list for the sample or run may be displayed at the user interface. The ADF may include a gene list. The gene list may be used to display the known list of genes for a given cancer type at the user interface and in a PDF report.

The ADF may include a set of plugins to be used for a given assay. The ADF may specify a set of plugins and their versions. If the ADF does not specify a version of a plugin, the latest version of the plugin installed on the server system may be used for the given assay.

The ADF may include a new workflow template to support custom assay creation. The new workflow template may include a set of assay chevron steps. Parameters for the steps may be displayed.

The ADF may include a list of annotation sources and sets to support the configuration of new annotation sets. The ADF may include filter chains to be applied to variants detected by the analysis pipeline of a given assay. The ADF may include rulesets for annotation of variants.

The ADFs can be configured to support a number of different types of assays. Examples include, but are not limited to, oncology related assays (e.g., Oncomine assays from Thermo Fisher Scientific), immuno-oncology related assays (e.g., T-cell receptor (TCR), microsatellite instability (MSI) and tumor mutation load (TML)), infectious diseases related assays (e.g. microbiome), reproductive health related assays and exome related assays. The ADF can also be configured for a custom assay.

Figure 51:
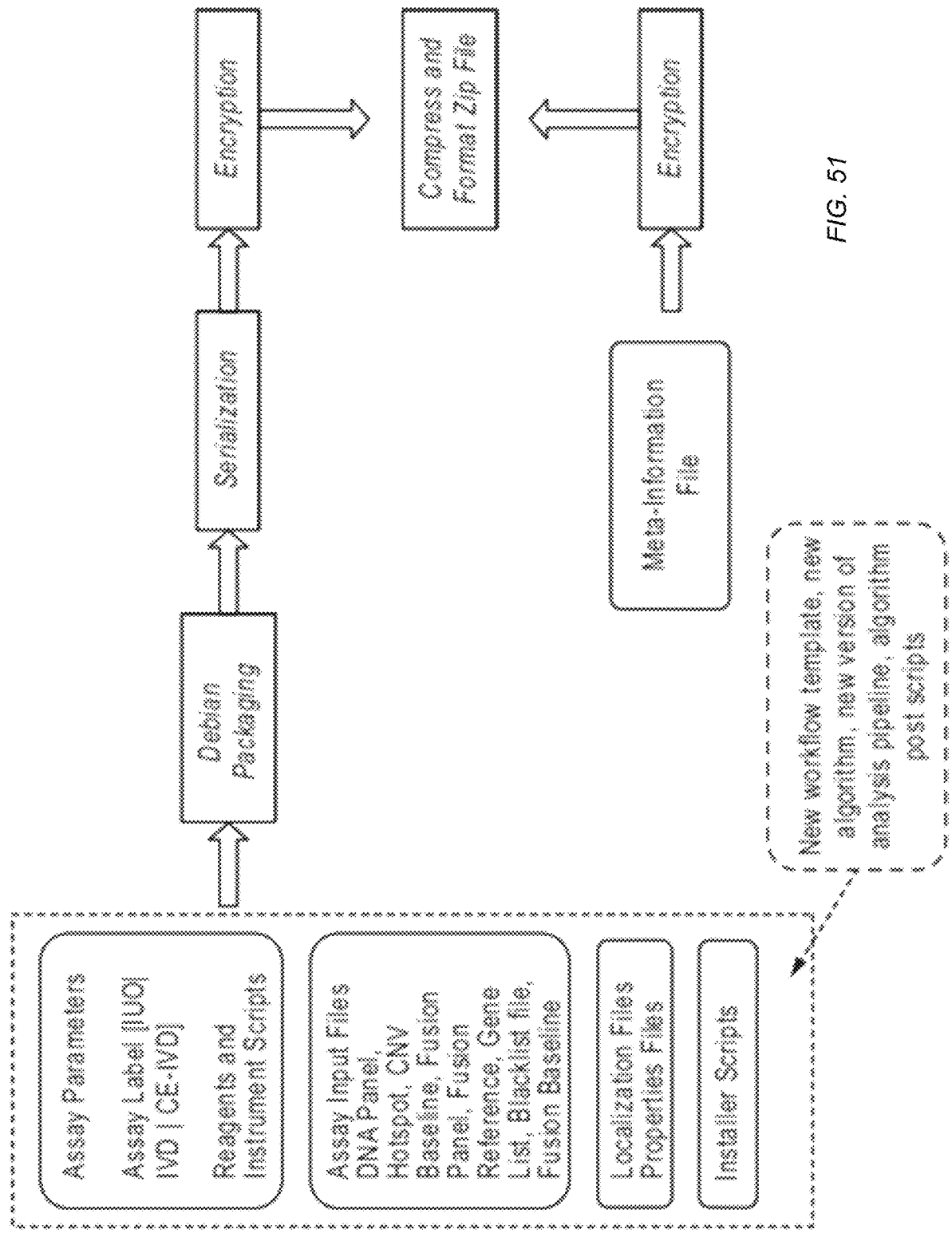
FIG. 51 is a schematic diagram of generating an assay definition file.

FIG. 51 is a schematic diagram of generating an assay definition file, in accordance with an embodiment. The assay definition may be generated by build.sh, debscripts and makedeb.sh that initiate file copying and database population of assay information to form a Debian file. The assay definition content may include assay parameters, BED files (Browser Extensible Data file—BED file—defines chromosome positions or regions), panel files, gene lists, hotspot files (a BED or a VCF file that defines regions in the gene that typically contain variants), and seed data containing allowable reagents. The assay definition content may contain localized versions of an assay name, description and report messages that support assay information display in different languages. The assay definition file may support the packaging of a new analysis pipeline. The ADF may include an optional post processing script which may be executed for variant calling, fusion calling and CNV calling based on the type of assay. The ADF may include an optional Docker container image of updates to the binaries for a specific analysis pipeline. The Docker container image may be packaged with the ADF to ensure that platform changes such as operating system or third-party library do not impact the results of the assays or functioning of the system.

The Debian file may be serialized to prevent unauthorized modifications. The serialized assay definition may be further encrypted using Advanced Encryption Standard (AES), a symmetric-key algorithm. A text file containing assay meta-information may also be encrypted using AES and the same encryption key. The encrypted assay definition file, together with the encrypted meta-information file may be compressed into zip format. Other encryption formats may also be applied to the serialized assay definition information. For example, the meta-information may include one or more of the following:

Analysis pipeline version,

Reference genome path for the reference genome file location,

Assay unique name—the assay's internal name for checking the unique occurrence in the system, Docker image name—to be used for launching analysis and installing assay dependent file references, Any dependency package names needed for analysis pipeline launch.

Figure 52:
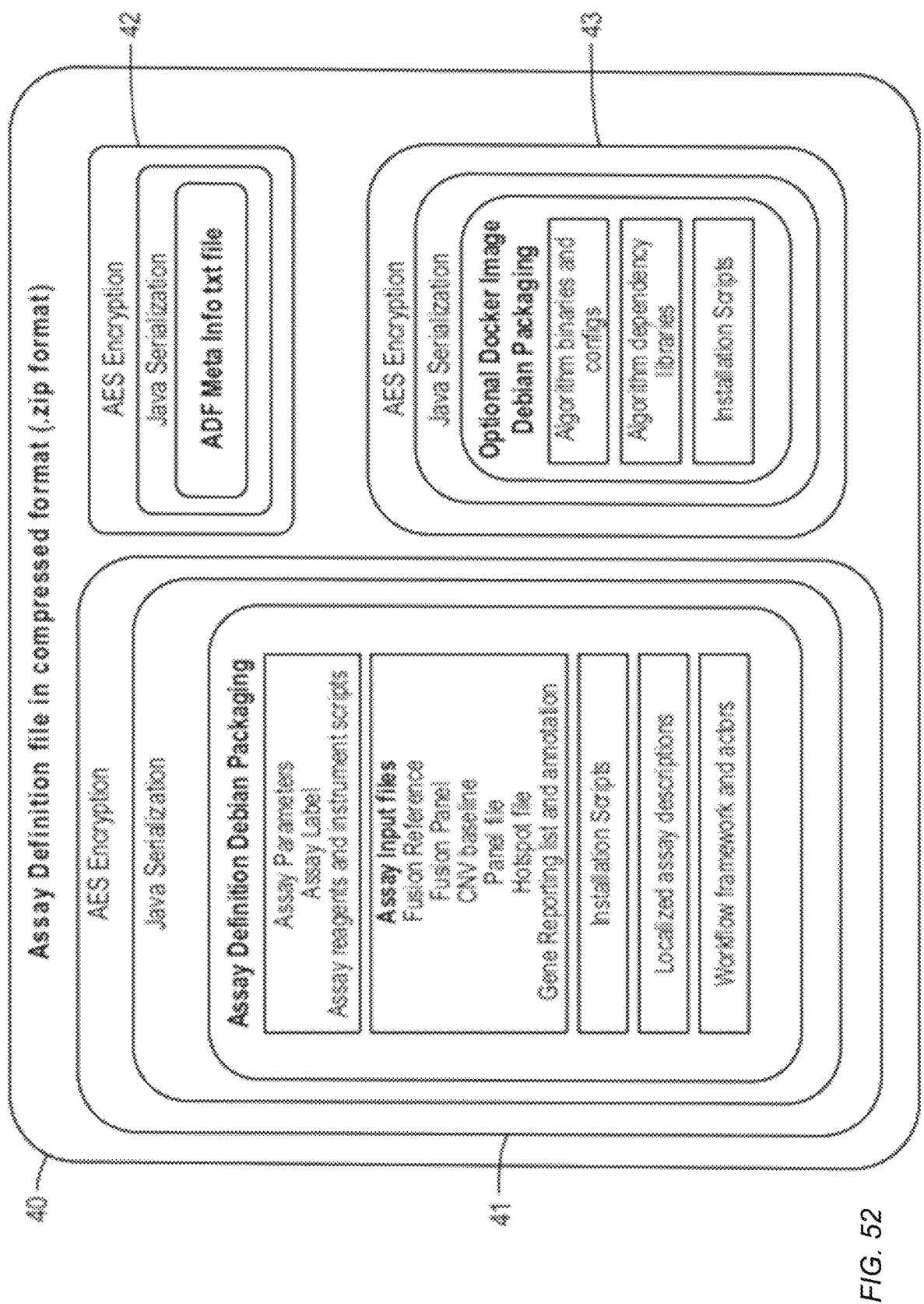
FIG. 52 is a schematic diagram of an example of the assay definition file packaging.

FIG. 52 is a schematic diagram of an example of the assay definition file packaging. The compressed assay definition file in zipped format 40 may include the serialized and encrypted assay definition Debian packaging 41, the serialized and encrypted meta-information text file 42, and serialized and encrypted optional Docker image Debian packaging 43. The server system may decrypt both the meta-information text file 42 and the assay definition serialized file 41 before installing the assay definition Debian file.

The server system and modular software components may be configured to control multiple functional modes, including an RUO, or AD, mode and an IVD, or Dx, mode. Referring to FIG. 1, the Tomcat Server may be configured to include a Web ARchive (WAR) file for the RUO mode and a WAR file for the IVD mode. The server system may be configured to include a RUO variome database for the variants detected by RUO assays and an IVD variome database for the variants detected by IVD assays. The server system may be configured to include separate analysis pipelines and associated Kepler workflow engines for the RUO mode and the IVD mode. The RUO Docker image files for the RUO assays may be configured as separate files from the IVD Docker image files for the IVD assays. The relational databases may be configured to have separate databases: an assay development (AD) database for the RUO mode and a Dx database for the IVD mode. A server system that initially supports only a RUO mode may be configured to support RUO and IVD modes by a software update.

ADFs may be generated separately for RUO mode assays and IVD mode assays. The RUO mode ADFs may include assay definitions for assays used in research. The RUO mode ADFs may be developed by a third party. The IVD mode ADFs include assay definitions for assays compliant with regional regulatory requirements for diagnostic use.

Assays

The automated sequencing instrument can be adapted for use with a variety of targeted assays. Example, targeted assays can utilize chemistries, such as Ion Ampliseq, Ion Ampliseq HD, among other chemistries. For example, the automated sequencing instrument can be adapted for use with assays such as RNA-seq, Diff-Seq, or S1-seq, among other library preparation assays. Other example assays include Oncomine Cancer Assays, e.g., OCAv3, Oncomine Focus Assays, or an Oncomine TCR Beta-LR assay, among others.

The assays can be used with nucleic acids sourced from swabs, blood, FFPE tissue samples, cfTNA, among other sources. The nucleic acids can be in the form of DNA or RNA, optionally converted to CDNA.

The assays can have a number of primer pairs, for example, in a range of 10 to 24000. In an example, the number of primer pairs can be in a range of 100 to 1000, such as a range of 100 to 500 or a range of 150 to 300. In another example, the number of primer pairs is in a range of 300 to 5000, such as a range of 400 to 4000.

The assays can produce libraries having an average amplicon size in a range of 50 to 500, such as a range of 50 to 200 or a range of 75 to 125. In another example, the amplicon size can be in a range of 200 to 500, such as 200 to 400 or 200 to 300.

The assays can be performed in a single pool or can utilize multiple pools. For example, an assay can use a single DNA pool. In another example, an assay utilizes two DNA pools. In a further example, an assay utilizes two RNA pools. In a particular example, an assay utilizes two DNA pools and two RNA pools.

Pre-Seeding (or Seeding) and Templating

Generally, prior to the analysis (e.g., sequencing) of a nucleic acid, the amount of the nucleic acid is increased for optimal detection of signals generated in the analysis. Typically, many copies of the nucleic acid, referred to as amplicons, are generated through amplification. These copies are often referred to as templates for analysis. For example, in sequencing by synthesis methods, the amplicons serve as templates for the polymerization of nucleotides, which is detected and provides data for sequence determination. In some instances, two or more, or a plurality of different nucleic acid sequences are amplified simultaneously and may also then be sequenced simultaneously. For example, in some methods of simultaneous amplification of different nucleic acids, the amplification is conducted using a pair of universal primers that are complementary to sequence present in each of the different nucleic acids in a nucleic acid population being amplified, although the remainder of the sequence in the different nucleic acids of the population being amplified differs in each nucleic acid (i.e., a polyclonal population of nucleic acids). In such instances, monoclonality of the amplicons generated from each different nucleic acid is often desirable because different characteristics of diverse nucleic acid molecules within a polyclonal population can complicate the interpretation of an assay, e.g., sequencing, data.

In some embodiments of the methods, as well as apparatuses, devices, systems, compositions, and kits for performing the methods, provided herein, a nucleic acid to be analyzed is amplified prior to conducting the analysis. In some embodiments, a nucleic acid to be analyzed is clonally amplified to generate a monoclonal, or substantially monoclonal, population of amplicons of the nucleic acid, for example, in a nucleic acid templating process. In some embodiments, different nucleic acids within a polyclonal population of a plurality of nucleic acids are clonally amplified to generate delimited monoclonal, or substantially monoclonal, populations of different nucleic acids.

In some embodiments of the methods, as well as apparatuses, devices, systems, compositions, and kits for performing the methods, provided herein, nucleic acid molecules in a sample are used to prepare a collection or library of nucleic acid molecules suitable for downstream sequencing. Some embodiments include a target enrichment step before, during, or after library preparation. Target nucleic acid molecules, including target loci or regions of interest, can be enriched, for example, through multiplex nucleic acid amplification or hybridization. A variety of methods can be used to perform multiplex nucleic acid amplification to generate amplicons, such as multiplex PCR, and can be used in any of the embodiments of the present methods. Enrichment by any method can be followed by a universal amplification reaction.

In some embodiments of the methods, as well as apparatuses, devices, systems, compositions and kits for performing the methods, provided herein, one or more nucleic acids to be analyzed, e.g., sequenced, is amplified in a templating process to generate a monoclonal, or substantially monoclonal, population of template nucleic acids. The templating methods, in combination with the apparatuses, devices, systems, compositions and kits provided herein, incorporate processes and compositions for generating, containing, isolating, transferring, replicating or manipulating substantially monoclonal populations of nucleic acids that are rapid, efficient and cost-effective while providing for significantly increased production of high-quality nucleic acid sequencing reads or nucleic acid sequencing reads of longer length with decreased numbers of duplicate, noninformative, erroneous or blank reads and decreased run times compared to existing methods. In some embodiments, the templating process generates one or more monoclonal, or substantially monoclonal, populations of template nucleic acids in which the nucleic acids are attached to one or more surfaces or supports, such as, for example, solid supports or surfaces. Template nucleic acid molecules may be immobilized on the surface or support by any method including but not limited to physical adsorption, by ionic or covalent bond formation, or combinations thereof. In some embodiments, a support, or site on a surface, is pre-seeded with one nucleic acid molecule, or a limited number of predominantly substantially identical or monoclonal nucleic acid molecules, from a collection of nucleic acids (e.g., a nucleic acid library, amplified targets or portions of a nucleic acid library or sample) to provide individual supports or sites (e.g., attachment sites that can be distinctly analyzed in downstream sequencing methods) attached to a single nucleic acid molecule or to a localized substantially monoclonal population of nucleic acids. Such pre-seeded supports or surfaces are readily manipulated and are used, for example, as a clean, confined, contained or separated source of separate single nucleic acid molecules or of two or more substantially identical or monoclonal nucleic acid molecules, that can be clonally amplified, for example, in templating reactions, to generate a relatively pure, confined, contained or separated collection of nucleic acid templates for use in a high-throughput sequencing workflow to improve sequencing results. Accordingly, in some embodiments or aspects of the methods of manipulating nucleic acids provided herein, a pre-seeding reaction is carried out before, or concurrently with, a templating reaction, for example, in a high-throughput sequencing workflow.

In some embodiments of the methods, as well as apparatuses, devices, systems, compositions and kits for performing the methods, provided herein, the amplification of a template nucleic acid on a surface or support, e.g., a solid surface or support, is performed in two or more reactions, including, for example, one or more pre-seeding reactions that generates one or more pre-seeded supports or surface sites with one template nucleic acid molecule attached thereto, or a substantially monoclonal population of template nucleic acid molecules attached thereto, followed by one or more templating reactions on the pre-seeded supports or sites that generate copies (e.g., at least 10× more copies) of the attached template nucleic acid molecule or molecules on the one or more supports or sites. Thus, in some embodiments, a templating reaction mixture includes one or more pre-seeded supports or surfaces. One advantage of performing a pre-seeding reaction and a templating reaction is that this workflow generates more high-quality sequencing reads in a high-throughput sequencing reaction. In some embodiments, nucleic acid molecules are amplified directly onto a support such as a site on a support that includes a plurality of sites, a bead or microparticle, or a reaction chamber of an array. For example, the nucleic acid molecules can be pre-seeded onto supports in reaction sites or chambers (e.g., wells or microwells) or can be pre-seeded onto supports in bulk in solution and then distributed into reaction sites, for example, on a solid support or surface. The different sites are optionally members of an array of sites. The array can include a two-dimensional array of sites on a surface (e.g., of a flow cell, electronic device, transistor chip, reaction chamber, channel, and the like), or a three-dimensional array of sites within a matrix or other medium (e.g., solid, semi-solid, liquid, fluid, and the like). In some embodiments, the wells or reactions sites contain one pre-seeded support per well or reaction site. In some embodiments, template nucleic acids attached to the pre-seeded supports that have been distributed into wells or reaction sites then undergo one or more templating reactions in which the templates are amplified on the supports to generate a monoclonal, or substantially monoclonal, population of template nucleic acids. Alternatively, nucleic acids are localized, deposited, or positioned at different sites prior to the pre-seeding reaction. In one example, supports can be distributed into an array of wells and nucleic acid molecules can be pre-seeded on the solid supports while they are held in place in an array of wells. In some embodiments, template nucleic acids that have been pre-seeded onto supports in wells or reaction sites then undergo one or more templating reactions in which the templates are amplified on the supports to generate a monoclonal, or substantially monoclonal, population of template nucleic acids. In some embodiments, methods for nucleic acid amplification include one or more, or two or more, or a plurality or population of surfaces or supports.

In some embodiments, a pre-seeding (or seeding) method provided herein includes hybridizing a nucleic acid molecule (e.g., a single-stranded nucleic acid) to a complementary nucleic acid, e.g., an oligonucleotide or primer, that is bound to and immobilized on a support or surface. Such methods are carried out under annealing conditions typically over a short time period. In some embodiments, the seeding method involves hybridizing under conditions in which the support, e.g., a solid support, such as a bead, particle, or site on a surface, will have only one nucleic acid molecule attached to it. Such conditions include, for example, contacting a population of nucleic acids (e.g., from a library, amplified targets or portions of a nucleic acid library or sample of nucleic acids) with a substantial excess of supports or sites relative to the number of nucleic acid molecules under annealing conditions. For example, in some embodiments a support-to-nucleic acid molecule ratio (or site-to-nucleic acid molecule) is selected to optimize the percentage of supports having a single template polynucleotide molecule or a monoclonal, or substantially monoclonal, population of template nucleic acid molecules attached thereto. For example, the pre-seeding can be carried out with a support-to-nucleic acid molecule (or site-to-nucleic acid molecule) ratio of at least about 1:1, 1.25:1, 1.5:1, 1.75:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 15:1, 20:1, 25:1, 50:1, 75:1, or 100:1. In some embodiments, the pre-seeding (or seeding) method further includes manipulation (e.g., conversion) of the library or sample nucleic acids prior to or simultaneously with hybridization of the template nucleic acids to primers immobilized on supports. Such manipulation can include, for example, addition of one or more adapter nucleotide sequences or nucleic acid amplification.

In some embodiments, one or more pre-seeded supports are formed during a pre-seeding (or seeding) reaction using a pre-seeding reaction mixture. In some embodiments, the pre-seeding reaction mixture includes some or all of the following: a population of nucleic acid molecules, one or more supports or surfaces, a polymerase, a population of first primers, nucleotides, a population of second primers, a divalent cation or a diffusion-limiting agent. In some embodiments, a pre-seeding reaction mixture includes one or more, or at least two, nucleic acid molecules, which can have the same or different sequences, a population of first primers (which may or may not be in solution, or some of which may be in solution and some of which may be immobilized to a support), a population of second primers (which may or may not be in solution) and, optionally, one or more supports or surfaces. In some embodiments, one or more supports or surfaces are introduced into the reaction mixture at a specific time during the pre-seeding reaction, for example, after one or more cycles of amplification of nucleic acid molecules to be attached to the supports or surfaces. In some embodiments, one or more supports or surfaces has a population of first primers, or a population of sequences contained in the first primer, attached thereto. In some embodiments, at least one, some, or all of the supports include a population of first primers, or a population of sequences contained in the first primer, that are substantially identical to each other. In some embodiments, all of the primers on the supports are substantially identical to each other or all include a substantially identical first primer sequence, or sequence contained in the first primer. In some embodiments, at least one of the supports includes two or more different primers attached thereto. For example, the at least one support can include a population of a first primer, or a population of sequences contained in the first primer, and a population of a second primer. The support can be attached to a universal primer. The universal primer optionally hybridizes (or is capable of hybridizing) to all, or substantially all, of the template nucleic acid molecules within the reaction mixture. The reaction mixture can include a first support covalently attached to a first target-specific primer and a second support covalently attached to a second target-specific primer, wherein the first and second target-specific primers are different from each other. Optionally, the first target-specific primer is substantially complementary to a first target nucleic acid sequence and the second target-specific primer is substantially complementary to a second target nucleic acid sequence, and wherein the first and second target nucleic acid sequences are different. In some embodiments, the reaction mixture includes multiple different supports or surfaces, for example, the pre-seeding reaction mixture includes one or more beads (such as particles, nanoparticles, microparticles, and the like) and at least two different template nucleic acid molecules are attached onto different beads, thereby forming at least two different beads, each of which is attached to a different template nucleic acid molecule. In some embodiments, the pre-seeding reaction mixture includes a single surface (for example, a planar-like surface, a flow cell, or array of reaction chambers) and at least two different template nucleic acid molecules are amplified onto two different regions, sites or locations on the surface, thereby forming a single surface attached to two or more template nucleic acid molecules. In some embodiments, the support or surface includes multiple instances of a second primer and the method includes hybridizing at least one extended first primer strand to a second primer of the support or surface as in bridge PCR. In some embodiments, the pre-seeding reaction mixture includes one or more, a plurality or a population of nucleic acid molecules, e.g., double-stranded or single-stranded nucleic acids, and one or more, or a plurality of, supports or surfaces having a plurality of first primers, or a plurality of sequences contained in a first primer, attached thereto, wherein the nucleic acid molecules contain a sequence of nucleotides substantially complementary, or substantially identical, to the first primer (i.e., a first primer binding sequence), and the pre-seeding reaction mixture optionally includes a polymerase and nucleotides. In some embodiments, the pre-seeding reaction mixture further includes a second primer, which can be in solution. The nucleic acid molecules can optionally contain a second primer-binding sequence. In some embodiments, a reaction mixture includes a population of first primers and a population of second primers that bind to sequences within the template nucleic acid molecules. The population of first primers can be identical, or substantially identical, copies or different sequences. The population of second primers can be identical, or substantially identical, copies or different sequences. In some embodiments, the population of first primers and optional second primers are universal primers (or contain sequence of a universal primer) and all copies of the first primers are identical and all copies of the second primers are identical. Thus, in some embodiments, the population of first primers and the population of second primers are both universal primers (or contain the sequence of a universal primer) that bind universal primer binding sequences on the template nucleic acid molecules. In some embodiments, the pre-seeding reaction mixture includes a recombinase and optionally a recombinase accessory protein.

In some embodiments, the pre-seeding or the templating reaction(s) use one or more enzymes capable of catalyzing polymerization of nucleotides. In any of the embodiments provided herein, the one or more enzymes capable of polymerization include at least one polymerase. In some embodiments, reactions are conducted with one type or a mixture of polymerases or ligases. In some embodiments, the at least one polymerase includes a thermostable or thermolabile polymerase. In some embodiments, the at least one polymerase includes a biologically active fragment of a DNA or RNA polymerase, or mutated version thereof, that maintains sufficient catalytic activity to polymerize or incorporate at least one nucleotide under any suitable conditions. The polymerase optionally can have, or lack, exonuclease activity. In some embodiments, the polymerase has 5' to 3' exonuclease activity, 3' to 5' exonuclease activity, or both. In some embodiments, the polymerase lacks any one or more of such exonuclease activities. Examples of polymerases include Taq DNA polymerase, T7 DNA polymerase, Sau DNA polymerase, Bst DNA polymerase, Bsu DNA polymerase, Klenow, and fragments and derivatives thereof. In some embodiments, the polymerase has strand-displacing activity. An exemplary polymerase is Bst DNA Polymerase (Exonuclease Minus), is a 67 kDa *Bacillus stearothermophilus* DNA Polymerase protein (large fragment), exemplified in accession number 2BDP_A, which has 5' to 3' polymerase activity and strand displacement activity but lacks 3' to 5' exonuclease activity. Other polymerases include Taq DNA polymerase I from *Thermus aquaticus* (exemplified by accession number 1TAQ), Eco DNA polymerase I from *Escherichia coli* (accession number P00582), Aea DNA polymerase I from *Aquifex aeolicus* (accession number 067779), or functional fragments or variants thereof. Another exemplary polymerase is Bsu DNA polymerase (large fragment (NEB)). Bsu DNA Polymerase I, Large Fragment retains the 5' to 3' polymerase activity of the *Bacillus subtilis* DNA polymerase I (1), but lacks the 5' to 3' exonuclease domain. In certain embodiments, the Bsu DNA Polymerase large fragment lacks 3' to 5' exonuclease activity. In certain embodiments, for example, where the reaction includes RPA, the one or more enzymes capable of polymerization include a T5 or T7 DNA polymerase. In some embodiments, the one or more enzymes capable of polymerization include a T5 or T7 DNA polymerase having one or more amino acid mutations that reduce the 3' to 5' exonuclease activity. In some embodiments, the T5 or T7 DNA polymerase having one or more amino acid mutations that reduce the 3 to 5' exonuclease activity does not contain an amino acid mutation that disrupts the processivity of the T5 or T7 DNA polymerase. In some embodiments, the T5 or T7 DNA polymerase includes one or more amino acid mutations that eliminate detectable 3' to 5' exonuclease activity; and wherein the one or more amino acid mutations do not disrupt processivity of the T5 or T7 DNA polymerase. In certain illustrative embodiments, pre-seeding or templating reaction mixture includes a Sau polymerase, T7 DNA polymerase with reduced 3' to 5' exonuclease activity, Bsu polymerase, or a combination thereof, which are especially well suited for an RPA reaction.

The pre-seeding reaction mixture, as well an any other amplification reaction in the methods provided here, including the templating reaction mixture, may include a source of nucleotides, or analogs thereof, that is used by a polymerase as substrates for an extension reaction. In some embodiments, the pre-seeding reaction mixture includes nucleotides (dNTPs) for strand extension of the template nucleic acid molecules resulting in one, or a substantially monoclonal population of the, template nucleic acid molecule sequence attached to one or more supports. In some embodiments, nucleotides are not extrinsically labeled. For example, the nucleotides can be naturally occurring nucleotides or synthetic analogs that do not include fluorescent moieties, dyes, or other extrinsic optically detectable labels. Optionally, the nucleotides do not include groups that terminate nucleic acid synthesis (e.g., dideoxy groups, reversible terminators, and the like). In other embodiments, the nucleotides include a label or tag. In some embodiments, a pre-seeding or templating reaction mixture includes one or more cofactors. Cofactors include, for example, a composition that enhances or regulates activity of another reaction component, e.g., an enzyme. In some embodiments, a cofactor includes one or more divalent cations. Examples of divalent cations include magnesium, manganese, and calcium. In various embodiments, the pre-seeding or templating reaction mixture includes a buffer containing one or more divalent cation. In illustrative embodiments, the buffer contains magnesium or manganese ions. In some embodiments, a pre-seeding reaction or a templating reaction is initiated by the addition of a cofactor, especially a divalent cation. In some embodiments, the pre-seeding or templating reaction mixture used herein for nucleic acid amplification may include at least one cofactor for recombinase assembly on nucleic acids or for homologous nucleic acid pairing.

Figure 53:
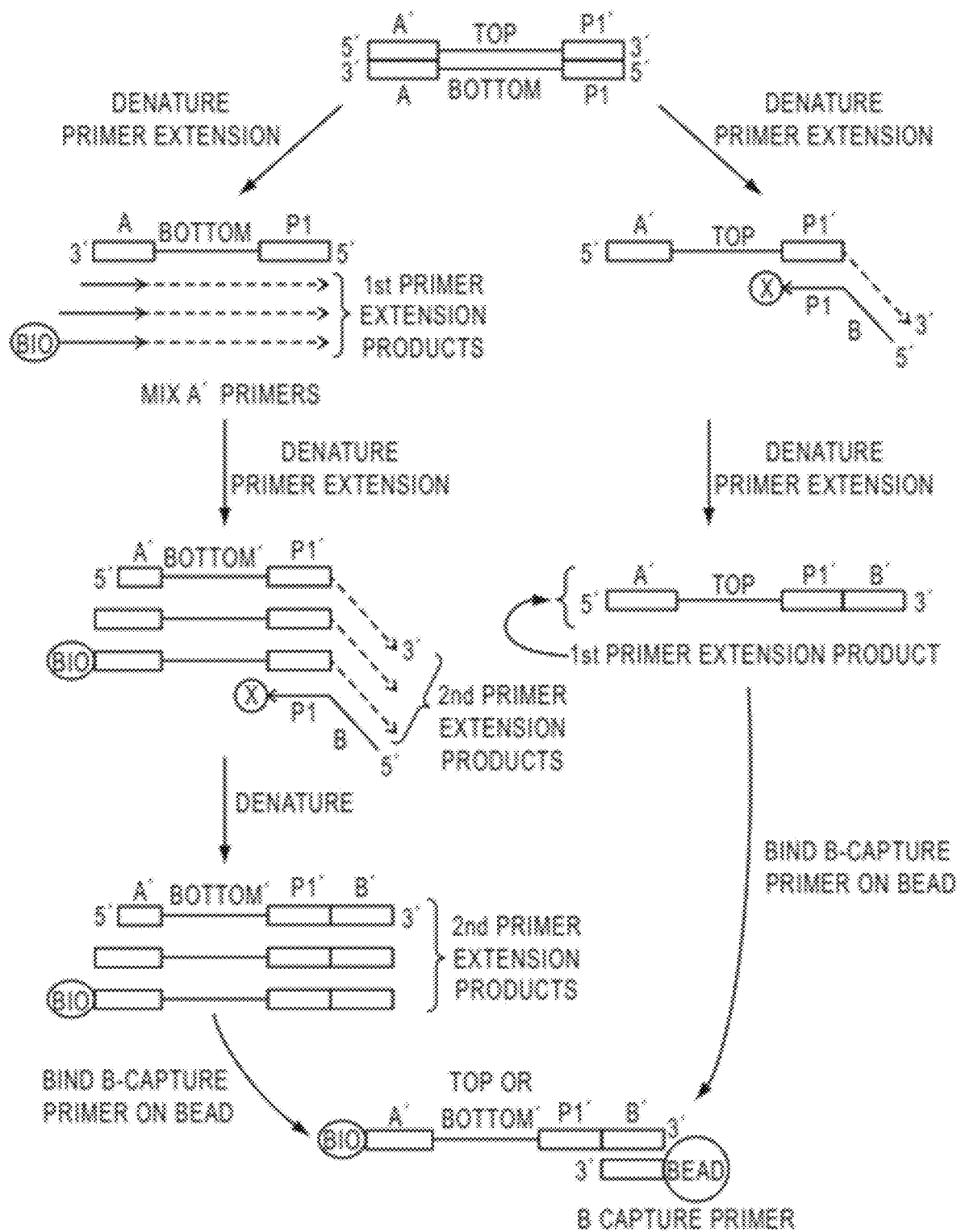
FIG. 53, FIG. 54, FIG. 55, FIG. 56, FIG. 57, FIG. 58, and FIG. 59 include illustrations of schema for seeding a support.

In some embodiments, the pre-seeding reaction includes (i) a plurality of nucleic acid molecules which include a target sequence and one or more adapter sequences (e.g., universal adapter sequences) on one or both ends, (ii) a plurality of soluble forward primers, (iii) a plurality of soluble reverse primers (which may be blocked or tailed primers), and (iv) a plurality of solid supports (for example included at the beginning of the reaction or at any other time during the reaction) having immobilized thereon capture primers that hybridize to an adapter sequence or to a complement of a sequence contained within a reverse primer. In some embodiments, the pre-seeding or templating reactions are conducted in a single reaction mixture with a plurality of nucleic acid molecules having the same or different target sequences. In some embodiments, individual nucleic acid molecules generated from a sample include a target sequence joined at the ends to at least one universal adaptor sequence (e.g., an A-adaptor or P1-adaptor sequences). In some embodiments, the nucleic acid molecules are double-stranded molecules having complementary top and bottom strands. In some embodiments, the pre-seeding reaction is conducted to amplify and attach one, or monoclonal, or substantially monoclonal, copies of a, nucleic acid molecule to a solid support using forward and reverse soluble primers that hybridize to the adaptor sequences (see, e.g., FIG. 4). Although FIG. 4 depicts a series of reactions for a single double-stranded nucleic acid molecule and a single bead within a single reaction mixture, the same single reaction mixture can contain a plurality of double-stranded nucleic acid molecules and a plurality of beads that are undergoing the same series of reactions to generate at least two beads each attached with one template nucleic acid, or a monoclonal, or substantially monoclonal, population of templates. Additionally, the bead can be attached to a plurality of B capture primers. Further, the bottom of FIG. 53 depicts a biotinylated primer extension product that binds to a B capture primer, but a non-biotinylated primer extension product can bind a B capture primer. Also, a mixture of biotinylated and non-biotinylated primer extension products can be attached to the plurality of B capture primers that are attached to the bead. In some embodiments, the single reaction mixture contains a plurality of nucleic acid molecules, wherein individual nucleic acid molecules having the same or different target sequences are attached to at least one universal adapter sequence.

Referring to an illustrative method such as depicted in FIG. 53, the nucleic acid molecules, having top and bottom strands, are denatured and the separated top and bottom strands are used in primer extension reactions using soluble primers (e.g., soluble A primers) and soluble blocked tailed primers (e.g., soluble blocked tailed P1/B primers), to generate a plurality of primer extension products having adapter sequences that can bind an immobilized B primer during the pre-seeding or templating reactions. The primer extension reactions generate different products for the two strands due to the different sequences and orientations of the top and bottom strands and differences in the primers used. In a first primer extension reaction, a complementary strand of the bottom strand is generated using a soluble primer that binds the A primer binding site. For illustration purposes in FIG. 53 (left) the soluble A' primer is complementary to the A adaptor sequence. In some embodiments, a mixture of varying length soluble A' primers is used for the first primer extension reaction. The mixture of soluble A' primers can vary in length at their 5' ends, 3' ends, or both 5' and 3' ends. For example, Primer Mix S (a mix of A' primers that can include various lengths of a 5' non-complementary sequence with or without a 5' biotin adduct (depicted as "Bio" in FIG. 53)) can be used in the primer extension reaction to generate one of several possible first extension products depending on which soluble A' primer is used for the first primer extension reaction (FIG. 53, left). For example, the first extension products contain, in a 5' to 3' direction, a complementary A-adaptor sequence (shown as A' in FIG. 53, left), a complementary bottom sequence (shown as BOTTOM' in FIG. 53, left), and a complementary P1 sequence (shown as P' in FIG. 53, left). In some embodiments, in a second primer extension reaction, the newly synthesized P1' sequence in the first extension product can bind to a soluble P1 primer to allow primer extension to occur from the 3' end of the P' sequence of the first primer extension product. The soluble P1 primer can be a tailed primer. The soluble P1 primer can carry a blocking moiety at its 3' end, wherein the blocking moiety can inhibit primer extension from the 3' end of the primer. Blocked primers can prevent the formation of primer dimer amplicons during the pre-seeding reaction which can generate lower quality sequencing reads and a reduction in the quantity of sequencing reads from template nucleic acid molecules. The soluble P1 primer can be a reverse tailed P1 primer which includes an attached 5' B adapter sequence such that primer extension of the first extension product, using the tailed primer P1 as a template, results in the addition of the complement of the B sequence (depicted as B' in FIG. 53 left) to the 3' end. In illustrative embodiments, the soluble P1 primer can have a 3' blocked end (shown as an encircled "X" in FIG. 53, left) to prevent extension from the 3' end of the soluble P1 primer (FIG. 53, left). The second primer extension reaction can generate a plurality of second extension products having various lengths, depending on which soluble A' primer was used in the first extension reaction. The plurality of second extension products contain, in a 5' to 3' direction, a complementary A-adaptor sequence (shown as A' in FIG. 53, left), a complementary bottom strand sequence (shown as BOTTOM' in FIG. 53, left), a complementary P1 sequence (shown as P' in FIG. 53, left), and a complementary B adaptor sequence (shown as B' in FIG. 53, left). The second primer extension products can include or lack a 5' biotin adduct (FIG. 53, left). The second extension reaction can generate a plurality of second extension products having different lengths, and which can include or lack a biotin adduct, and which include a B' adaptor sequence. Any of these second extension products can bind/hybridize to the B capture sequence which is immobilized to the solid surface (bead). The immobilized B primer can undergo a third primer extension reaction, thereby generating a third extension product which is immobilized to the bead, and is complementary to the second extension product (FIG. 53, bottom). The right side of FIG. 53 depicts the double-stranded nucleic acid undergoing denaturation, and a series of reactions for the top strand. In some embodiments, the P' adaptor sequence of the top strand can bind the soluble P1 primer and undergo a first primer extension reaction to generate a first extension product (FIG. 53, right). In some embodiments, the soluble P1 primer is a tailed primer. The soluble P1 primer can carry a blocking moiety at its 3' end, wherein the blocking moiety can inhibit primer extension from the 3' end of the primer (FIG. 53, right). The soluble P1 primer can be a tailed P1 primer which includes an attached 5' B adapter sequence such that primer extension, using the tailed primer P1 as a template, results in the addition of the complement of the B sequence (B') to the 3' end of the first extension product (FIG. 53, right). In illustrative embodiments, the soluble P1 primer can have a 3' blocked end (shown as an encircled "X" in FIG. 53, right) to prevent extension from the 3' end of the P1 primer (FIG. 53, right). The first primer extension reaction generates a plurality of first extension products which contain, in a 5' to 3' direction, an A' adaptor sequence, a top strand sequence, a P' adaptor sequence, and a B' adaptor sequence (FIG. 53, right). The first extension product, which includes a B' adaptor sequence, can bind/hybridize to the B capture sequence which is immobilized to the solid surface (bead). The immobilized B primer can undergo a second primer extension reaction, thereby generating a second extension product which is immobilized to the bead, and is complementary to the first extension product (FIG. 53, bottom).

Figure 5:
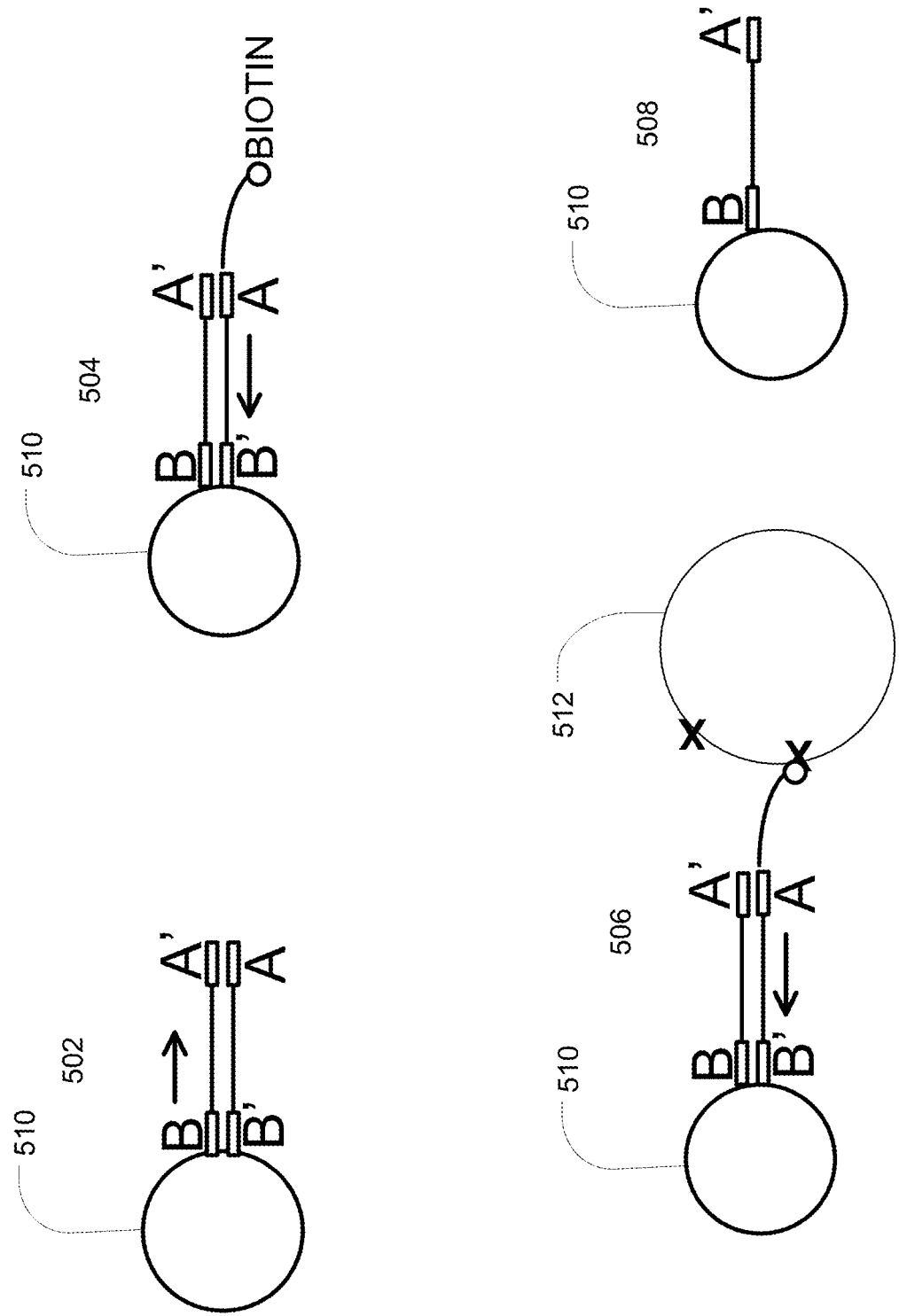
FIG. 5 illustrates example schema for preparing a bead assembly.
Figure 54:
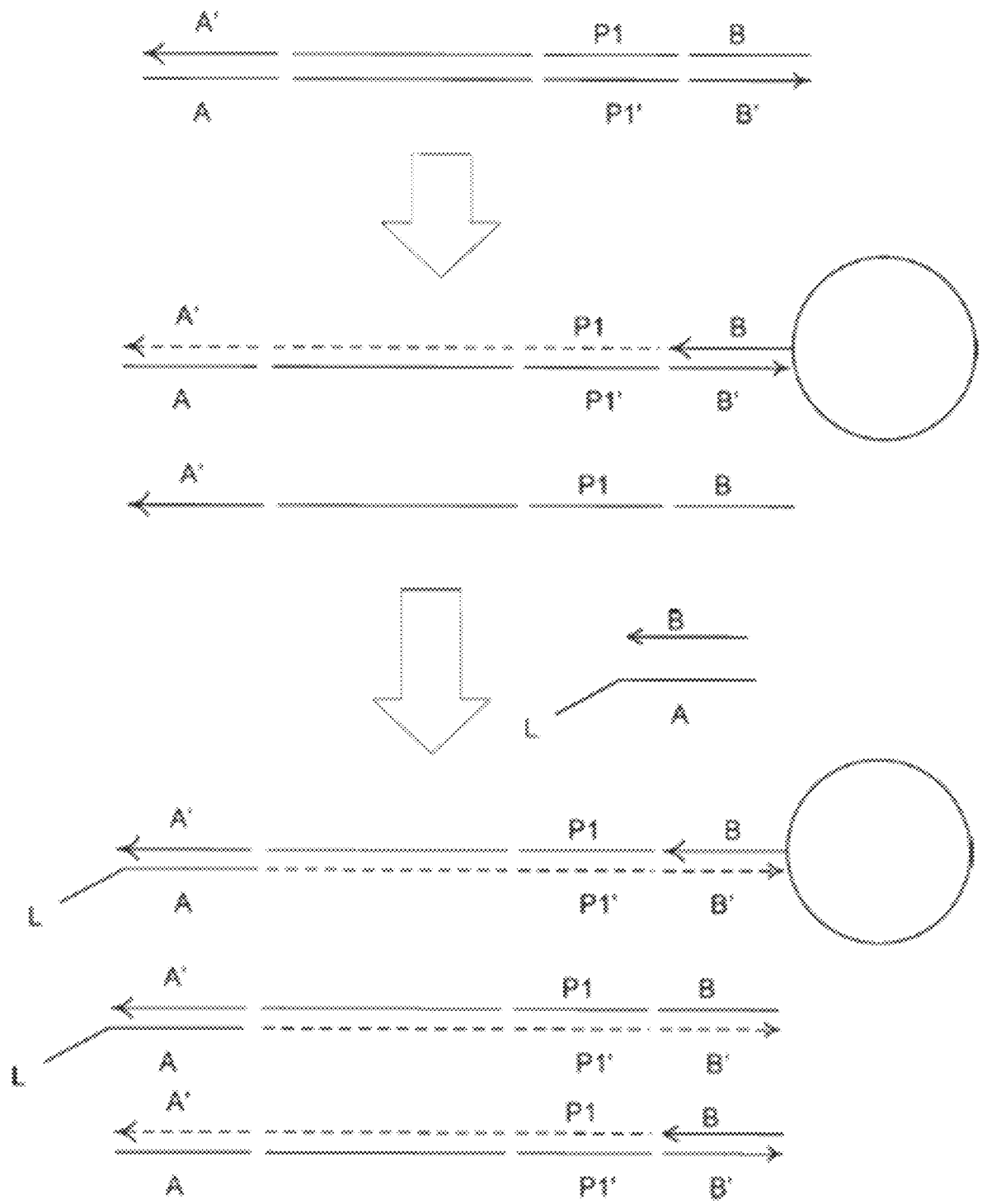

In some embodiments, a pre-seeding (or seeding) reaction can be performed as illustrated in FIG. 54. In this example, a target polynucleotide B-A' and its complement, a template polynucleotide (A-B'), are amplified in the presence of a bead support having a capture primer. The target polynucleotide has a capture portion (B) the same as or substantially similar to a sequence of the capture primer coupled to the bead support. Substantially similar sequences are sequences whose complements can hybridize to each of the substantially similar sequences. The bead support can have a capture primer that is the same sequence or a sequence substantially similar to that of the B portion of the target polynucleotide to permit hybridization of the complement of the capture portion (B) of the target polynucleotide with the capture primer attached to the bead support. Optionally, the target polynucleotide can include a second primer location (P1) adjacent to the capture portion (B) of the target polynucleotide and can further include a target region adjacent the primers and bounded by complement portion (A') to a sequencing primer portion (A) of the target polynucleotide. When amplified in the presence of the bead support including a capture primer, the template polynucleotide complementary to the target polynucleotide can hybridize with the capture primer (B). The target polynucleotide can remain in solution. The system can undergo an extension in which the capture primer B is extended complementary to the template polynucleotide yielding a target sequence bound to the bead support. One or more additional amplifications can be performed at this stage in the presence of the support having a capture primer. One or more further amplifications can be performed in the presence of a free primer (B), the bead support, and a free modified sequencing primer (A) a having a linker moiety (L) attached thereto. The primer (B) and the modified primer (L-A) can interfere with the free-floating target polynucleotide and template polynucleotide, hindering them from binding to the bead support and each other. In particular, the modified sequencing primer (A) having the linker moiety attached thereto can hybridize with the complementary portion (A') of the target polynucleotide attached to the bead support. Optionally, the linker modified sequencing primer L-A hybridized to the target polynucleotide can be extended forming a linker modified template polynucleotide. Such linker modified template polynucleotide hybridized to the target nucleic acid attached to the bead support can then be captured by a magnetic bead and used for magnetic sequestering (enriching) of the target polypeptide attached to the bead and loading of it into a sequencing device. The amplification or extensions can be performed using polymerase chain reaction (PCR) amplification, recombinase polymerase amplification (RPA), or other amplification techniques. In a particular example, each step of the scheme illustrated in FIG. 5 is performed using PCR amplification. Although FIG. 54 depicts a series of reactions for a single double-stranded nucleic acid molecule and a single bead within a single reaction mixture, the same single reaction mixture can contain a plurality of double-stranded nucleic acid molecules and a plurality of beads that are undergoing the same series of reactions to generate at least two beads each attached with one template nucleic acid, or a monoclonal, or substantially monoclonal, population of templates.

Figure 55:
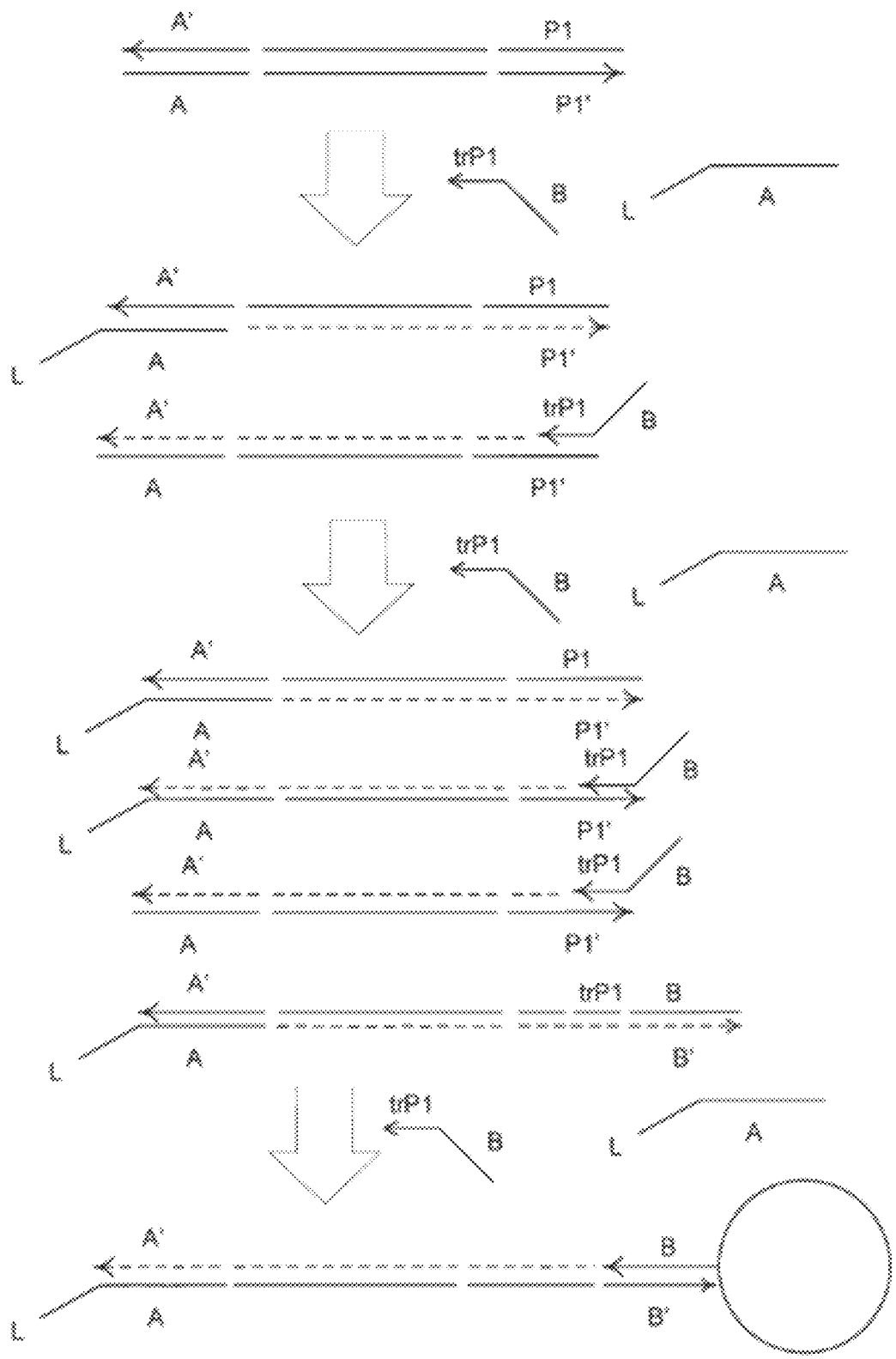

In some embodiments, a pre-seeding (or seeding) reaction can be performed as illustrated in FIG. 55. In this example, an alternative scheme includes a target polynucleotide (P1-A') and its complement template polynucleotide (A-P1'). The target polynucleotide and template polynucleotide are amplified in a solution including a linker modified sequencing primer (L-A) and a truncated P1 primer (trP1) having a portion having the sequence of the capture primer (B). In an example, the truncated P1 primer (trP1) includes a subset of the sequence of P1 or all of the sequence P1. During subsequent amplifications in the presence of the linker modified sequencing primer (L-A) and truncated P1 primer (trP1-B), a species includes a linker modified template polynucleotide (L-A-B') operable to hybridize with a bead support having a capture primer (B). Accordingly, the linker modified template polynucleotide (L-A-B') hybridizes with the capture primer (B) on the bead and is extended to form a target polynucleotide (B-A') attached to the bead support. The linker modified template polynucleotide hybridized to the target polynucleotide attached bead can be utilized to attach to a magnetic bead, which, for example, can be used to implement magnetic loading of the bead into a sequencing device or for enriching the nucleic acids attached to the bead. The linker moiety of the linker modified template polynucleotide can take various forms, such as biotin, which can bind to linker moieties attached to the magnetic bead, such as streptavidin. Each of the amplification reactions can be undertaken using polymerase chain reaction (PCR), recombinase-polymerase amplification (RPA), or other amplification techniques. In the example illustrated in FIG. 55, the scheme can be implemented using two or three cycles of PCR. Such a series of PCR reactions results in a greater percentage of bead supports having a single target polynucleotide attached thereto. As a result, more monoclonal populations can be generated, for example, in templating reactions for example, in wells in a sequencing device. Although FIG. 55 depicts a series of reactions for a single double-stranded nucleic acid molecule and a single bead within a single reaction mixture, the same single reaction mixture can contain a plurality of double-stranded nucleic acid molecules and a plurality of beads that are undergoing the same series of reactions to generate at least two beads each attached with one template nucleic acid, or a monoclonal, or substantially monoclonal, population of templates.

Figure 56:
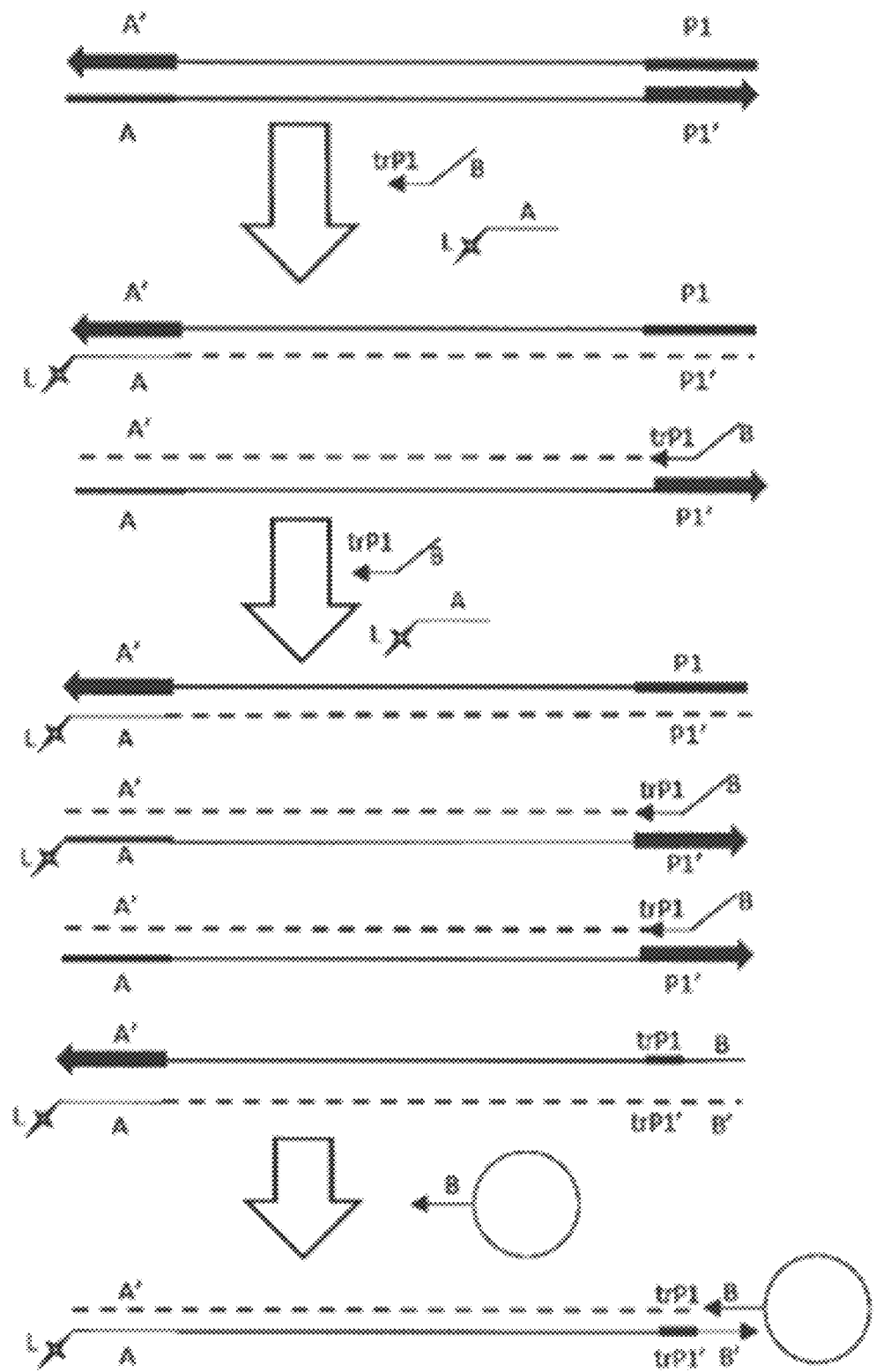

In some embodiments, a pre-seeding (or seeding) method can be performed as illustrated in FIG. 56. In this example, the method is designed to generate a desired support-attached nucleic acid molecule from a series of amplification cycles in which only one of the amplification products, which is the desired target nucleic acid, will attach to the support. The desired target contains a linker moiety, e.g., biotin, (labeled with the letter L in FIG. 56) attached to the 5' end of the nucleic acid and an adapter nucleotide sequence (labeled with the letter B' in FIG. 56) at the 3' end that is complementary to the primer (labeled with the letter B in FIG. 56) immobilized on the support (e.g., a bead). In contrast, the method shown in FIG. 55 generates two nucleic acid amplification products that hybridize to the support, only one of which has the desired linker moiety. In generating only one amplification product that will attach to the support, the method depicted in FIG. 56 avoids the production of supports that do not contain the desired target nucleic acid, for example, one lacking a linker moiety, which would not be used in downstream analyses. Thus, this method avoids excess utilization of supports and nucleic acids and ensures that only a single nucleic acid target molecule will hybridize to a support which is desirable to maintain a high level of monoclonality in subsequent templating amplifications using the supports that have only one nucleic acid template bound thereto. As illustrated in FIG. 56, the double-stranded nucleic acids (e.g., library nucleic acids) contain different adapter sequences at each end, shown as an A adapter sequence at the 5' end and a P1 adapter sequence at the 3' end (e.g., standard Ion Torrent A and P1 library adapters; Thermo Fisher Scientific). To begin the seeding process, the library nucleic acids are subjected to one cycle of amplification (i.e., denaturation, primer annealing and primer extension) in the presence of primers such as depicted in FIG. 56. Exemplary primers used in the amplification are a biotinylated primer A (forward primer) and reverse fusion primer. The fusion primer (e.g., a primer labeled trP1 in FIG. 56) is a fusion of a sequence that is complementary to a portion of the adapter sequence at the 3' end of the target nucleic acids and a B primer sequence that is identical to the sequence of the B primer immobilized on the supports. In the example shown in FIG. 56, trP1 is a 23 mer segment of the Ion P1 adapter with sequence of SEQ ID NO: 1). The fusion primer will hybridize and prime at the inner portion of the 3' adapter sequence of the library nucleic acid molecules, close to the library insert sequence, and does not hybridize at with the remainder of the adapter sequence at the extreme 3' end of the library nucleic acids. This forms a mismatch end between the fusion primer sequence and the very 3' end portion of the adapter on the library nucleic acids. As shown in FIG. 56, after two cycles of amplification (e.g., PCR), although four amplification products are generated, only one product will be able to seed (or hybridize) to the support (e.g., an Ion Sphere Particle). Thus, upon subsequent denaturation of the amplification products, a single strand of only one of the products will hybridize to the B primer on the support. This primer can be extended to form a double-stranded template nucleic acid in which one strand contains a linker moiety that can be used, for example, to bind the support-bound nucleic acid to a magnetic bead for use in enrichment or magnetic loading of template beads into a sequencing device. Although FIG. 56 depicts a series of reactions for a single double-stranded nucleic acid molecule and a single support within a single reaction mixture, the same single reaction mixture can contain a plurality of double-stranded nucleic acid molecules and a plurality of supports that are undergoing the same series of reactions to generate at least two supports each attached with a template nucleic acid.

Certain embodiments of the methods, as well as apparatuses, devices, systems, compositions, and kits for performing the methods, provided herein include a method for generating a nucleic acid template having a specific nucleotide sequence. Such a method is particularly useful in pre-seeding one or more, two or more, or a plurality of supports or surfaces with a single nucleic acid. In one embodiment, a method for generating a nucleic acid template having a specific nucleotide sequence includes (a) obtaining a nucleic acid, or an initial plurality or population of nucleic acids, containing a nucleic acid strand having a first sequence of contiguous nucleotides at the 5' end of the nucleic acid strand, a second sequence of contiguous nucleotides at the 3' end of the nucleic acid strand and a third nucleotide sequence positioned between the first and second sequences of contiguous nucleotides, wherein the first sequence of contiguous nucleotides and the second sequence of contiguous nucleotides are different from each other and, wherein the first sequences of contiguous nucleotides are substantially identical among a plurality or population of nucleic acids and the second sequences of contiguous nucleotides are substantially identical among a plurality or population of nucleic acids; (b) subjecting the nucleic acid, or initial plurality or population of nucleic acids, to a cycle of nucleic acid amplification in the presence of a first primer and a second primer, wherein the first primer includes a nucleotide sequence substantially identical to the first sequence of contiguous nucleotides and the second primer includes (i) a nucleotide sequence complementary to a portion of the second sequence of contiguous nucleotides at the 5' end of the second sequence of contiguous nucleotides and (ii) a fourth nucleotide sequence that is not complementary to the second sequence of contiguous nucleotides and that is linked to the sequence complementary to the portion of the second sequence of contiguous nucleotides at the 3'end of the complementary sequence, and the second primer does not contain a nucleotide sequence complementary to the 3' end of the second sequence of contiguous nucleotides; and (c) subjecting the products of the cycle of nucleic acid amplification of (b) to a cycle of nucleic acid amplification in the presence of the first and second primers to generate multiple different nucleic acid products wherein only one of the multiple different nucleic acid products of nucleic acid amplification of the nucleic acid or each separate nucleic acid in an initial plurality or population of nucleic acids in step (a) includes a sequence of nucleotides complementary to the fourth nucleotide sequence. When step (a) includes an initial plurality or population of nucleic acids, the method generates a population of different nucleic acids wherein each nucleic acid includes a sequence of nucleotides complementary to the fourth nucleotide sequence. In some embodiments, the method further comprises subjecting the products of the cycle of nucleic acid amplification of (c) to one or more cycles of nucleic acid amplification in the presence of the first and second primers to generate additional nucleic acid products containing a sequence of nucleotides complementary to the fourth nucleotide sequence. In some embodiments, a population of nucleic acids as set forth in step (a) is subjected to two or more cycles of nucleic acid amplification in the presence of one or more forward primers comprising an oligonucleotide sequence substantially identical to the first sequence of contiguous nucleotides and a reverse primer that is blocked at the 3' end and comprises an oligonucleotide sequence complementary to the second sequence of contiguous nucleotides that is linked at the 5'end of the oligonucleotide sequence to a fourth nucleotide sequence that is not complementary to the second sequence of contiguous nucleotides to generate nucleic acid products in which substantially all, or all, of the products include a sequence of nucleotides complementary to the fourth nucleotide sequence. In some embodiments of any of the methods for generating a nucleic acid template having a specific nucleotide sequence, the forward or first primer includes a modified nucleotide containing an attachment thereto. In some embodiments the attachment to the modified nucleotide comprises a linker moiety, e.g., biotin. In some embodiments, the sequence of the fourth nucleotide sequence is substantially identical to a sequence of a primer immobilized on one or more supports or surfaces, or sites on a surface, and the method can further include attaching the product comprising a sequence of nucleotides complementary to the fourth nucleotide sequence to the one or more supports, surfaces or sites on a surface through hybridization with the immobilized primer. In some embodiments the method further comprises isolating the nucleic acid strand attached to the support by removing the support from any other nucleic acids that are not bound to the support.

In some embodiments of the methods for generating a nucleic acid template having a specific nucleotide sequence or a population of two or more nucleic acid templates having a specific nucleotide sequence, one or more of the primers includes a modified nucleotide containing an attachment thereto. For example, in some embodiments, the forward primer or first primer, or the reverse or second primer, includes a modified nucleotide containing an attachment thereto. In some embodiments the attachment to the modified nucleotide includes a linker moiety, for example biotin. In some embodiments, one or more of the primers (e.g., the forward or first primer) includes a 3'-end nucleotide sequence substantially identical to the first nucleotide sequence, a 5'-end nucleotide sequence and a non-replicable moiety positioned between the 3'-end nucleotide sequence and the 5'-end nucleotide sequence. In embodiments in which the forward or first primer is one that includes a non-replicable moiety between a 3'-end nucleotide sequence substantially identical to the first nucleotide sequence and a 5'-end nucleotide sequence, the only product from the final nucleic acid amplification that includes a sequence of nucleotides complementary to the fourth nucleotide sequence also includes a single-stranded region at the 5'end that includes the non-replicable moiety and 5'-end nucleotide sequence of the first primer. In some embodiments the method further includes combining or contacting single-stranded nucleic acids of the products of the final cycle of amplification with a single-stranded oligonucleotide that is substantially identical to the fourth nucleotide sequence under annealing conditions thereby hybridizing the product(s) that includes a sequence of nucleotides complementary to the fourth nucleotide sequence to the single-stranded oligonucleotide that is substantially identical to the fourth nucleotide sequence to generate a partially double-stranded nucleic acid. In some embodiments the single-stranded oligonucleotide that is substantially identical to the fourth nucleotide sequence is attached to one or more, or a plurality of, supports or surfaces or sites on a surface. In some embodiments the support is a solid support. In particular embodiments the support is a particle or bead. In some embodiments the method further includes extending the 3' end of the oligonucleotide portion of the partially double-stranded nucleic acid(s) thereby generating an extended double-stranded nucleic acid(s) by synthesizing a nucleic acid strand that includes the single-stranded oligonucleotide that is substantially identical to the fourth nucleotide sequence and has a nucleotide sequence that is complementary to the product to which it is hybridized. In some embodiments the nucleic acid strand that includes the single-stranded oligonucleotide that is substantially identical to the fourth nucleotide sequence is attached to a support at the 5' end of the strand through the portion of the strand that is the oligonucleotide sequence. In some embodiments the method further includes isolating the nucleic acid strand(s) attached to the support(s) by collecting the support(s) or removing them from any other nucleic acids or reaction components that are not bound to the support(s).

In one embodiment, a method for pre-seeding, or seeding, a support includes (a) obtaining a nucleic acid containing a nucleic acid strand having a first sequence of contiguous nucleotides at the 5' end of the nucleic acid strand, a second sequence of contiguous nucleotides at the 3' end of the nucleic acid strand and a third nucleotide sequence positioned between the first and second sequences of contiguous nucleotides; (b) subjecting the nucleic acid to a cycle of nucleic acid amplification in the presence of a capture primer, wherein the capture primer includes a nucleotide sequence complementary to the second sequence of contiguous nucleotides and is attached to a support; and (c) subjecting the products of the nucleic acid amplification of (b) to a cycle of nucleic acid amplification in the presence of a capture primer that is not attached to a support and a first primer that includes a nucleotide sequence substantially identical to the first sequence of contiguous nucleotides. In some embodiments, the first primer is attached to a linker moiety.

In some embodiments, a pre-seeding (or seeding) method is performed essentially as illustrated in FIGS. 54-56 with the addition of one or more amplification (e.g., PCR) cycles in the method. Thus, in any such pre-seeding methods employing multiple cycles of amplification (e.g., PCR), two or more, e.g., 3, 4, 5 or more, cycles of amplification can be included in the pre-seeding method. For example, in instances where maximum possible nucleic acid library input is below optimal range, additional amplification cycle(s) may be included in the seeding process to generate a sufficient amount of template-seeded supports which may be used in further methods, including, for example, templating amplification to generate substantially monoclonal populations of nucleic acid templates and downstream sequencing processes. Such situations may include, for example, lower than expected library concentrations resulting from library preparation methods. Although in such situations it may be possible to increase library template copy number to more optimal levels by scaling up seeding reactions in order to accommodate larger library input volumes, this is sometimes not an available option due to volume constraints in a reaction vessel or handling.

Increased numbers of amplification cycle(s) may be included at any point in the pre-seeding method, e.g., before or after introducing supports having oligonucleotide primers attached thereto into the amplification scheme. For example, with reference to the method depicted in FIG. 56, if an additional amplification cycle is included prior to the point at which the support is introduced into the reaction mixture, a total of four of the amplification products will yield a nucleic acid strand that will hybridize to the B primer on the support, as compared to only one product yielding a strand that hybridizes in the scheme as shown without the addition of another cycle of amplification. Furthermore, each of the four product strands will include a linker moiety attached to the 5' end of the nucleic acid. Thus, after the added amplification cycle, when supports having B primers immobilized thereto are added to the reaction mixture, the next amplification cycle of denaturation, primer hybridization and primer extension will result in all four of the amplification product strands that include a sequence complementary to the B primers on the supports hybridizing to the supports and being extended, thereby seeding four supports as compared to one support. If an additional amplification cycle is included after the last amplification cycle shown in FIG. 56, in which supports having B primers attached thereto have been added to the reaction mixture, a total of four of the amplification products will yield a nucleic acid strand that will hybridize to the B primer on the support, as compared to only one product yielding a strand that hybridizes in the scheme as shown without the addition of another cycle of amplification. Furthermore, each of the four product strands will include a linker moiety attached to the 5' end of the nucleic acid. Thus, after the added amplification cycle, assuming that a sufficient number of supports having B primers immobilized thereto were added to the reaction mixture, a total of four supports will be seeded with nucleic acid templates, as compared to one seeded support if the additional amplification is not included. Therefore, by increasing the number of amplification cycles in pre-seeding methods such as these, a greater number of seeded supports is obtained from the same number of input library nucleic acid molecules.

In some embodiments, a pre-seeding (or seeding) method provided herein includes a combined process of attaching a nucleic acid to a support or surface through hybridization and, at the same time, amplifying the attached nucleic acid to a low level, for example, about 10 or more, 20 or more, 50 or more, 100 or more, 250 or more, 500 or more or 1000 or more copies. In some embodiments, a pre-seeding reaction generates a plurality of pre-seeded supports, surfaces, or sites on a surface, wherein individual pre-seeded supports, or sites in the plurality of pre-seeded supports, or sites on a surface include a plurality of first primers attached to the supports or sites, wherein the plurality of first primers have a substantially identical sequence, and wherein some of the plurality of the first primers are joined to a template nucleic acid molecule and some of the plurality of the first primers are not joined to a template nucleic acid molecule. In these embodiments, the pre-seeding reaction mixture typically includes some, or all, of the following: a population of nucleic acid molecules, a polymerase, nucleotides, a population of first primers, a population or plurality of supports or surfaces, or a cofactor such as a divalent cation. A variety of methods can be used to pre-seed supports with substantially monoclonal template nucleic acid molecules. As non-limiting examples, a pre-seeding reaction can be carried out using a recombinase-polymerase amplification (RPA) reaction, a template walking reaction, PCR, emulsion PCR, or bridge PCR. The pre-seeding reaction or a templating reaction can be performed in bulk in a solution. Furthermore, a pre-seeding reaction mixture or the templating reaction mixture can include a first universal primer attached to one or more supports, a second universal primer in solution (a soluble second universal primer), and a plurality of nucleic acid molecules where individual nucleic acid molecules are joined to at least one universal primer binding sequence(s) which may be added during library preparation, and where the universal primer binding sequence(s) bind the first and optional second universal primer(s). In some embodiments, the pre-seeding reaction or the templating reaction is performed in wells. In some embodiments, the pre-seeding reaction(s) and the templating reaction(s) are carried out using consecutive RPA reactions, wherein template nucleic acid molecules are washed away after the pre-seeding reaction before performing the templating reaction.

In some embodiments, different nucleic acid molecules are pre-seeded onto one or more different discrete surfaces or supports (e.g., beads or particles) without the need for compartmentalization prior to amplification. In other embodiments, the nucleic acid molecules are partitioned or distributed into emulsions prior to amplifying. In some embodiments, pre-seeding reactions can be carried out in parallel in a plurality of compartmentalized reaction volumes, as opposed to amplification within a single continuous liquid phase. Each reaction volume can include the pre-seeding reaction mixture. For example, the nucleic acid molecules can be distributed or deposited into an array of reaction chambers, or an array of reaction volumes, such that at least two such chambers or volumes in the array receive a single nucleic acid molecule. In some embodiments, a plurality of separate reaction volumes is formed. The reaction chambers (or reaction volumes) can optionally be sealed prior to amplification. Pre-seeding reactions can be performed in each of the reaction chambers to generate substantially monoclonal populations of template nucleic acid molecules. In another embodiment, the reaction mixture is compartmentalized or separated into a plurality of microreactors dispersed within a continuous phase of an emulsion. Each compartment or microreactor serves as an independent amplification reactor, thus the entire emulsion is capable of supporting many separate amplification reactions in separate (discontinuous) liquid phases in a single reaction vessel (e.g., an Eppendorf tube or a well). As used herein, the term "emulsion" includes any composition including a mixture of a first liquid and a second liquid, wherein the first and second liquids are substantially immiscible with each other. The compartmentalized or separate reaction volumes optionally do not mix or communicate, or are not capable of mixing or communicating, with each other. In such embodiments, a pre-seeding reaction mixture in the microreactors can be any of the pre-seeding reaction mixtures described herein. In some embodiments in which a reaction mixture is dispersed within an emulsion, the method further includes recovering from the emulsion at least some of the supports attached to substantially monoclonal populations of template nucleic acid molecules. In some embodiments, the method further includes depositing onto a surface at least some of the supports attached to the substantially monoclonal populations of template nucleic acid molecules. In some embodiments, the method further includes forming an array by depositing onto a surface at least some of the supports attached to the substantially monoclonal populations of template nucleic acid molecules.

In some embodiments, a pre-seeding reaction may generate supports having zero template nucleic acid molecules attached thereto (empty supports), other pre-seeded supports having one type of template nucleic acid molecule attached thereto, and other pre-seeded supports having more than one type of template nucleic acid molecule attached thereto. The number of template nucleic acid molecules attached to one or more pre-seeded supports is the pre-seeding number. In some of the embodiments of the pre-seeding methods, the pre-seeding number is 1 or is between about 1 and 150,000 template nucleic acid molecules, for example between about 1 and 100,000, 1 and 75,000, 1 and 50,000, 1 and 25,000, 1 and 10,000, 1 and 5,000, 1 and 2,500, 10 and 100,000, 10 and 75,000, 10 and 50,000, 10 and 25,000, 10 and 10,000, 10 and 5,000, or 10 and 2,500 template nucleic acid molecules. In some embodiments, after the pre-seeding reaction, a majority of any primers attached to a support are not bound to a template nucleic acid molecule. These unbound primers can be used in the subsequent templating reaction for further amplification of the template nucleic acid molecules. For example, after the pre-seeding reaction, at least 90%, 95%, 96%, 97%, 98%, or 99% of primers attached to a support are typically not bound to a template nucleic acid molecule or all but one of the primers attached to a support are not bound to a template nucleic acid molecule.

In some embodiments, the pre-seeding or templating reaction includes using PCR amplification methods. In some embodiments, the pre-seeding or templating reaction is carried out in a single round or cycle of PCR. In other embodiments, the pre-seeding or templating reaction is carried out in multiple rounds or cycles of PCR. For example, in some methods employing amplification (e.g., PCR) cycles, one or more, or two or more, cycles of PCR can be conducted in the absence (or presence) of supports to generate desired templates or amounts thereof, which can be followed by one, one or more, or two or more cycles of PCR in the presence of supports for seeding of desired template nucleic acids on the supports (see, e.g., FIG. 56). The methods can include diluting the amount of nucleic acid molecules that are reacted with the supports to reduce the percentage of supports that react with more than one nucleic acid molecule. In some embodiments, the nucleic acid molecules are diluted such that the pre-seeding reactions have a support-to-template nucleic acid molecule ratio that is selected to optimize the percentage of supports having one template nucleic acid molecule, or a substantially monoclonal population of template nucleic acid molecules, attached thereto. For example, the pre-seeding reaction can be carried out with a support-to-template nucleic acid molecule ratio of at least about 1:1, 1.25:1, 1.5:1, 1.75:1, 2:1, 2.5:1, 3:1, 3.5:1, 4:1, 4.5:1, 5:1, 5.5:1, 6:1, 6.5:1, 7:1, 7.5:1, 10:1, 15:1, 20:1, 25:1, 50:1, 75:1, and 100:1. In some embodiments, the PCR is performed in bulk in solution in a single reaction mixture. In some embodiments, the PCR is performed in wells or reaction chambers in a continuous solution. In some embodiments, PCR is performed in an emulsion where the PCR is carried out in a plurality of microreactors in an emulsion as described elsewhere herein.

In some embodiments, the pre-seeding or templating reaction includes template walking where portions of double-stranded nucleic acid molecules become dissociated such that a primer is bound to one of the strands to initiate a new round of replication (see, for example, U.S. Patent Publ. No. 2012/0156728, published Jun. 21, 2012, incorporated by reference herein in its entirety). Template walking reactions are typically performed at isothermal temperatures. In some embodiments, template walking is performed within an emulsion.

In some embodiments of the methods, as well as apparatuses, devices, systems, compositions, and kits for performing the methods, provided herein, the pre-seeding reaction mixture or the templating reaction mixture includes components to partially denature template nucleic acid molecules. In some embodiments, partially denaturing conditions include treating or contacting the template nucleic acid molecules to be amplified with one or more enzymes that are capable of partially denaturing the nucleic acid template, optionally in a sequence-specific or sequence-directed manner, as in an RPA reaction. In some embodiments, at least one enzyme catalyzes strand invasion or unwinding, optionally in a sequence-specific manner. Optionally, the one or more enzymes include one or more enzymes selected from the following: recombinases, topoisomerases, and helicases. In some embodiments, partially denaturing the template includes contacting the template with a recombinase and forming a nucleoprotein complex including the recombinase. Optionally, the template nucleic acid molecule is contacted with a recombinase in the presence of a first and optionally a second primer. Partially denaturing can include catalyzing strand exchange using the recombinase and hybridizing a first primer to the first primer binding sequence (or hybridizing a second primer to the second primer binding sequence). In some embodiments, partially denaturing includes performing strand exchange and hybridizing both a first primer to a first primer binding sequence and a second primer to a second primer binding sequence using the recombinase.

In some embodiments, partially denaturing the template nucleic acid molecule includes contacting the template with one or more recombinases or nucleoprotein complexes. At least one of the nucleoprotein complexes can include a recombinase. Not to be limited by theory, it is believed that the recombinase coats single-stranded DNA (ssDNA) to form a nucleoprotein filament strand which invades a double-stranded region of homology on template nucleic acid molecules. This creates a short hybrid and a displaced strand bubble known as a D-loop (see, e.g., U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308, herein incorporated by reference in their entireties). The free 3'-end of the hybridized primer is extended by DNA polymerases to synthesize a new complementary strand. The complementary strand displaces the originally paired partner strand of the template nucleic acid molecule as it is elongated. In an embodiment, one or more of a pair of primers are contacted with one or more recombinases before being contacted with a template nucleic acid molecule, which is optionally double-stranded. At least one of the nucleoprotein complexes can include a primer (e.g., a first primer or a second primer, or a primer including a sequence complementary to a corresponding primer binding sequence in the template). In some embodiments, partially denaturing the template includes contacting the template with a nucleoprotein complex including a primer. Partially denaturing can include hybridizing the primer of the nucleoprotein complex to the corresponding primer binding sequence in the template, thereby forming a primer-template duplex. In some embodiments, partially denaturing the template nucleic acid molecule includes contacting the template with a first nucleoprotein complex including a first primer. Partially denaturing can include hybridizing the first primer of the first nucleoprotein complex to the first primer binding sequence of the forward strand, thereby forming a first primer-template duplex. In some embodiments, partially denaturing the template includes contacting the template with a second nucleoprotein complex including a second primer. Partially denaturing can include hybridizing the second primer of the second nucleoprotein complex to the second primer binding sequence of the reverse strand, thereby forming a second primer-template duplex.

In some embodiments of pre-seeding or templating methods provide herein that include a population of immobilized first primers and a population of second primers in solution, not to be limited by theory, during the pre-seeding or templating reaction, a template nucleic acid is at least partially denatured, and a first primer binding site on the template binds to a first primer attached to a solid support. The first primer is used by a polymerase to generate a complementary strand to one strand of the template nucleic acid. That complementary strand is now covalently attached to the solid support through the primer. A second primer in solution is in a complex with the recombinase and binds to a primer binding site on the complementary strand, thus partially denaturing the bound template nucleic acid molecule. A polymerase uses the primer to synthesize a new strand, identical to the original template nucleic acid strand. In some such embodiments, this strand is then believed to be partially denatured by the binding of the complex of a recombinase and a nearby first primer attached to the solid support, and the polymerase synthesizes another complementary strand. Through repeated steps of this process, a substantially monoclonal population of template nucleic acid molecules is generated during some embodiments of a pre-seeding reaction or amplification during a templating reaction.

In some embodiments of the methods, as well as apparatuses, devices, systems, compositions and kits for performing the methods, provided herein, pre-seeding or templating includes partial denaturation or amplification, including any one or more steps or methods described herein, using a recombinase and optionally a recombinase accessory protein. The recombinase can include any agent that is capable of inducing, or increasing the frequency of occurrence, of a recombination event, including any event whereby two different polynucleotides strands are recombined with each other. The recombinase can be an enzyme that catalyzes homologous recombination. Suitable recombinases include RecA and its prokaryotic or eukaryotic homologues, or functional fragments or variants thereof, optionally in combination with one or more single-strand binding proteins (SSBs). In some embodiments, a homologous recombination enzyme includes an enzyme from any organism, including myoviridae (e.g., uvsX from bacteriophage T4, RB69, and the like) *Escherichia coli* (e.g., recA) or human (e.g., RAD51). In embodiments, the reaction mixture includes one or more recombinases selected from uvsX, RecA, RadA, RadB, Rad51, a homolog thereof, a functional analog thereof, or a combination thereof. In illustrative embodiments, the recombinase is uvsX. The UvsX protein can be present, for example, at 50-1000 ng/μl, 100-750 ng/μl, 200-600 ng/μl, or 250 to 500 ng/μl. In some embodiments of methods provided herein, a pre-seeding or templating reaction mixture includes one or more recombinase accessory proteins. For example, an accessory protein can improve the activity of a recombinase enzyme. In some embodiments, an accessory protein can bind single strands of template nucleic acid molecules or can load a recombinase onto a template nucleic acid molecule. Accessory proteins can originate, for example, from any bacteriophage, including a myoviral phage, or bacterial species. In some embodiments, methods for nucleic acid amplification can include single-stranded binding proteins, for example, myoviral gp32 (e.g., T4 or RB69). In some embodiments, reaction mixtures include proteins that improve recombinase loading onto a nucleic acid. For example, UvsY protein is a recombinase-loading protein. In some embodiments, UvsY can be present between about 20 and 500 ng/μl, for example, between about 20 and 250 ng/μl, 20 and 125 ng/μl or 75 and 125 ng/μl.

In some embodiments, pre-seeding or templating reaction mixtures can further include other components. For example, the compositions can include nucleotides, a population of first primers, optionally a second primer, cofactors, and a buffer. The population of first primers and optionally a population of second primers can be attached to the one or more supports. As a non-limiting example, the composition includes one or more supports, a recombinase such as uvsX, a polymerase such as Sau DNA polymerase, a recombinase-loading protein such as uvsY, a single-stranded binding protein such as gp32 protein, nucleotides, ATP, phosphocreatine, and creatine kinase. A reaction component composition can be in liquid form, or it can be in a solid form, such as a dried-down pellet form that can be rehydrated. A dehydrated pellet can include, for example, recombinase, an optional recombinase accessory protein, optionally gp32, DNA polymerase, dNTPs, ATP, optionally phosphocreatine, an optional crowding agent, and optionally creatine kinase. Rehydration buffer can include, for example, Tris buffer, potassium acetate salt, and optionally a crowding agent such as PEG. The DNA polymerase can be for example, T4 or T7 DNA polymerase, and can further include thioredoxin when the polymerase is T7 DNA polymerase. In some embodiments, when a dehydrated pellet is used that includes reaction mixture components, the pellet is rehydrated with a rehydration buffer and template nucleic acid molecules, primers, and additional nuclease-free water are added to a final volume. Furthermore, components of the compositions can be split up such that any combination of the components can be in a pellet or liquid form, and one or more combinations of the rest of the components can be in one or more separate pellet or liquid forms. Such combinations can form kits or vials that include at least two of such combinations. For example, a kit or vial can include a pellet that includes all the reaction mixture components except for the polymerase enzyme, which can be provided in a separate pellet or liquid in a vial, for example, in a kit. In one non-limiting example, a composition includes a population of nucleic acid molecules, a polymerase, a recombinase, a forward primer, a reverse primer, nucleotides, and a buffer. In some embodiments, the composition includes a nucleic acid molecule, a forward primer, a reverse primer, uvsX recombinase, uvsY recombinase loading protein, gp32 protein, Sau DNA polymerase, dNTPs, ATP, phosphocreatine, and creatine kinase. In some embodiments, a composition includes at least two different nucleic acid molecules with both a first primer binding sequence and a second primer binding sequence, a recombinase, a recombinase accessory protein, a polymerase, a first universal primer, a second universal primer, dNTPs, and a buffer. In some embodiments, the composition further includes one or more supports. In illustrative embodiments, the composition includes at least two different template nucleic acid molecules with both a first primer binding sequence and a second primer binding sequence, uvsX recombinase, uvsY recombinase loading protein, gp32 protein, Sau DNA polymerase, ATP, phosphocreatine, creatine kinase, a first universal primer attached to a bead support, a second universal primer, and a buffer.

In some embodiments of the methods, as well as apparatuses, devices, systems, compositions and kits for performing the methods, provided herein, a templating reaction (e.g., one, one or more, two, or two or more, templating reaction(s)) is performed after a pre-seeding reaction wherein the template nucleic acid molecules on the pre-seeded surfaces or supports are amplified or further amplified (herein referred to as the templating reaction). The pre-seeded solid supports are typically generated in a pre-seeding reaction that is separate from the templating reaction. Generally, in such embodiments, the templating reaction mixture does not include additional template nucleic acid molecules in solution such that the template nucleic acid molecules attached to the one or more pre-seeded supports are the predominant or only source of template nucleic acid molecules in the templating reaction mixture before the templating reaction is initiated. In some embodiments, template nucleic acid molecules are present in solution in the reaction mixture when the templating reaction is initiated. In some embodiments, one or more washes are carried out on the one or more pre-seeded supports before introducing them into the templating reaction mixture. In some embodiments, two or more reactions are performed in a templating method.

In some embodiments, one or more templating reactions are performed (or the templating reaction is performed in two steps of two separate amplifications, e.g., two separate RPA reactions). In some embodiments, two or more separate reactions are performed in a templating method. For example, in some methods provided herein, a first, or initial, templating reaction is performed and is followed by a second or subsequent templating reaction. The initial templating reaction, in some instances, includes one or more supports to which one or more template polynucleotides is/are attached that were generated in a separate pre-seeding process prior to initiation of the templating reaction. The initial templating reaction includes amplification of the one or more template polynucleotides on the pre-seeded supports, for example, using a recombinase and polymerase (i.e., RPA) under substantially isothermal conditions. In such embodiments, the separate templating or RPA reactions can be performed for the same or different amounts of time. An initial first templating reaction that is followed by a second or subsequent templating reaction is typically conducted for a shorter time period than the duration of a subsequent second templating reaction. For example, an initial first templating reaction, that is followed by a second or subsequent templating reactions may be conducted for about 1-10 minutes, about 1-9 minutes, about 1-8 minutes, about 1-7 minutes, about 1-6 minutes, about 1-5 minutes, about 1-4 minutes, about 1-3 minutes, about 1-2.5 minutes, about 1-2 minutes, about 1-1.5 minutes, about 2-10 minutes, about 2-9 minutes, about 2-8 minutes, about 2-7 minutes, about 2-6 minutes, about 2-5 minutes, about 2-4 minutes, about 2-3 minutes, about 2-2.5 minutes, about 2.5-10 minutes, about 2.5-9 minutes, about 2.5-8 minutes, about 2.5-7 minutes, about 2.5-6 minutes, about 2.5-5 minutes, about 2.5-4 minutes or about 2.5-3 minutes. In some examples, an initial first templating reaction, that is followed by a second or subsequent templating reactions, may be conducted for less than about 15 minutes, less than about 10 minutes, less than about 5 minutes, less than about 4 minutes, less than about 3 minutes, less than about 2.5 minutes, less than about 2 minutes, less than about 1.5 minutes or less than about 1 minute. In one non-limiting example, an initial templating reaction is conducted using RPA at about 40° C. for about 2.5 minutes. In some embodiments, an initial, or first templating reaction, is terminated or limited prior to initiation of a second or subsequent templating reaction. For example, a terminating composition, such as a templating reaction inhibitor, may be added to an initial, or first, templating reaction that inhibits or stops the reaction or prevents the reaction from continuing. Examples of templating reaction inhibitors include, but are not limited to, compositions that inhibit one or more components of a nucleic acid amplification reaction, e.g., a polymerase inhibitor or a recombinase inhibitor, or limit a component of the reaction that is required for the reaction to proceed. For example, in an initial templating reaction that includes RPA, a templating reaction inhibitor may be a chelating agent, such as a metal or cation chelating agent, e.g., EDTA, that binds to cations, such as magnesium, that may be required for a recombinase-mediated reaction in recombinase-polymerase amplification. In another example, a templating reaction can be limited or discontinued by removing reaction components such as by washing of a templating reaction site, e.g., reaction chamber or well, with a solution that does not contain one or more components required for the templating reaction. For example, a templating reaction site may be washed, or flushed, with a solution lacking a recombinase, a polymerase, cations, nucleotides, or other components of an RPA reaction used in a templating reaction. In some embodiments, a second or subsequent templating reaction that follows an initial or first templating reaction is initiated or facilitated by addition, or contacting, of one or more templating reaction components to the template-bound supports that had been subjected to the initial, or first, templating reaction. For example, in a second or subsequent templating reaction that includes recombinase-polymerase nucleic acid amplification, one or more of the following components may be added to, or contacted with, the template-bound supports: a recombinase, polymerase, nucleotides or a cation. A second or subsequent templating reaction that follows a first, or initial, templating reaction is typically conducted for a longer time period than the duration of a first templating reaction. For example, a second or subsequent templating reaction that follows a first templating reaction may be conducted for about 5-60 minutes, about 5-50 minutes, about 5-45 minutes, about 5-40 minutes, about 5-35 minutes, about 5-30 minutes, about 5-25 minutes, about 5-20 minutes, about 5-15 minutes, about 5-10 minutes, about 10-60 minutes, about 10-50 minutes, about 10-45 minutes, about 10-40 minutes, about 10-35 minutes, about 10-30 minutes, about 10-25 minutes, about 10-20 minutes, about 10-15 minutes, about 15-60 minutes, about 15-50 minutes, about 15-45 minutes, about 15-40 minutes, about 15-35 minutes, about 15-30 minutes, about 15-25 minutes, about 15-20 minutes, about 20-60 minutes, about 20-50 minutes, about 20-45 minutes, about 20-40 minutes, about 20-35 minutes, about 20-30 minutes or about 20-25 minutes. In some examples, a second or subsequent templating reaction that follows a first, or initial, templating reaction may be conducted for at least about 60 minutes, at least about 55 minutes, at least about 50 minutes, at least about 45 minutes, at least about 40 minutes, at least about 35 minutes, at least about 30 minutes, at least about 25 minutes, at least about 20 minutes, less than 2 minutes, less than 1.5 minutes or less than 1 minute. In one non-limiting example, a second or subsequent templating reaction is conducted using RPA at about 40° C. for about 20 minutes. In some embodiments, a second or subsequent templating reaction is terminated, discontinued, or limited at a set time, for example, as described for an initial or first templating reaction.

One advantage of including two or more reactions in a templating process to generate substantially monoclonal populations of nucleic acids is that it facilitates control of template amplification that can reduce or prevent polyclonality in the nucleic acid populations. For example, an initial, or first, amplification of a template polynucleotide on a pre-seeded support that is limited in amount or duration can limit the amount of free template nucleic acid available to move or migrate into another templating reaction site. The initial or first templating reaction provides for binding of replicated template nucleic acids to additional immobilization primers on a pre-seeded support or surface or surface site and thus provides an environment that is less open for template nucleic acid diffusion to occur in a second or subsequent templating reaction amplification.

In some embodiments of pre-seeding or templating methods provided herein, including, for example, embodiments in which two or more reactions are performed in a templating method, one or more of the reactions includes one or more diffusion-limiting agents. Inclusion of a diffusion-limiting agent may be advantageous when amplifying two or more template nucleic acid molecules within a single continuous liquid phase of a reaction mixture. The diffusion-limiting agent can further prevent or slow diffusion of template nucleic acid molecules or amplified polynucleotides produced via replication of at least some portion of a template nucleic acid molecule within a templating or pre-seeding reaction mixture, thus preventing or reducing the transfer of a nucleic acid in one templating reaction for the generation of a monoclonal template population into another templating reaction for the generation of a different monoclonal template population and thereby reducing formation of polyclonal contaminants during nucleic acid amplification in a templating or pre-seeding reaction. A diffusion-limiting agent thus can prevent or reduce formation of polyclonal contaminants without requiring compartmentalization of the pre-seeding or templating reaction mixture by physical means or encapsulation means (e.g., emulsions) during the amplification. In some embodiments, a diffusion-limiting agent is included in a first, or initial, templating reaction. In some embodiments, a diffusion-limiting agent is included in a first, or initial, templating reaction but is not included in a second or subsequent templating reaction. In some embodiments, a diffusion-limiting agent is included in a first, or initial, templating reaction and in one or more subsequent templating reactions. In some embodiments, a diffusion-limiting agent included in one or more reactions is one or more sieving agents, e.g., a polymer, such as methyl cellulose, or that provides a matrix having a plurality of pores. The sieving agent can be any agent that is effective in sieving, and restricting or slowing the migration of, one or more template nucleic acid molecules or polynucleotides present in the pre-seeding or templating reaction mixture, such as, for example, amplification reaction products or template nucleic acid molecules. Thus, a sieving agent can reduce Brownian motion of a polynucleotide. In some embodiments, the sieving agent is a polymer compound. By way of non-limiting examples, the sieving agent can include polysaccharides, polypeptides, organic polymers, or any other suitable polymer. In some embodiments, a sieving agent is one or more of the following polymers: cellulose, dextran, starch, glycogen, agar, chitin, pectin, or agarose. In some embodiments, the sieving agent includes a cellulose derivative, such as sodium carboxy methyl cellulose, sodium carboxymethyl 2-hydroxyethyl cellulose, methyl cellulose, hydroxyl ethyl cellulose, 2-hydroxypropyl cellulose, carboxy methyl cellulose, hydroxyl propyl cellulose, hydroxyethyl methyl cellulose, hydroxybutyl methyl cellulose, (hydroxypropyl)methyl cellulose or hydroxyethyl ethyl cellulose, or a mixture including any one or more of such polymers. In some embodiments, the pre-seeding reaction mixture includes a crowding agent. For example, a crowding agent can increase the concentration of one or more components in a nucleic acid amplification reaction by generating a crowded reaction environment. In some embodiments, the pre-seeding or templating reaction mixture includes both a sieving agent or diffusion-limiting reagent or a crowding agent. Diffusion-limiting agents include diffusion-reducing agents. A diffusion-reducing agent includes any compound that reduces migration of template nucleic acid molecules or polynucleotides from a region of higher concentration to one having a lower concentration. In some embodiments, a diffusion-reducing agent includes any compound that reduces migration of any component of a nucleic acid amplification reaction irrespective of size.

In some embodiments, a diffusion-limiting agent included in one or more reactions is a drag compound. The term "drag compound" and its variants refers to any composition, e.g., a chemical composition, that can be attached to nucleic acids and retard their diffusion through a reaction mixture, but still permit nucleic acid synthesis to proceed using such polynucleotide, primer, template or amplification product in a nucleic acid synthesis reaction. For example, a drag compound can provide hydrodynamic drag when attached to a nucleic acid by altering the overall size, length, radius, shape, or electrical charge of the modified nucleic acid compared to the nucleic acid lacking the attached compound. In some embodiments, a drag compound attached to a nucleic acid can alter interaction between the nucleic acid and an aqueous medium compared to the interaction between the aqueous medium and a nucleic acid lacking the attached compound. Attachment of such drag compounds to nucleic acids within a synthesis reaction typically reduces the mobility of such nucleic acids in the reaction mixture and can be useful in preventing cross-contamination of amplification products or templates between different synthetic reactions occurring with the same reaction mixture. For example, a drag compound may be a compound that binds or attaches to template nucleic acids during a templating reaction, e.g., during template nucleic acid amplification, to reduce mobility of the template nucleic acids in a templating reaction mixture. In some embodiments, the template nucleic acids are modified to include a moiety (referred to as a "drag tag") that binds to a drag compound. For example, an affinity moiety, such as a linker moiety, may be attached to the nucleic acids and the drag compound is one that is a binding partner moiety, e.g., a receptor-type moiety, that binds to the affinity moiety. In one non-limiting example, template nucleic acids are attached to a biotin moiety that can bind an avidin-like moiety (for example, streptavidin or a derivative thereof, e.g., neutravidin) that serves as a drag compound included in one or more templating or pre-seeding reactions. In some embodiments, a drag compound is included in a first, or initial, templating reaction. In some embodiments, a drag compound is included in a first, or initial, templating reaction but is not included in a second or subsequent templating reaction. In some embodiments, a drag compound is included in a first, or initial, templating reaction and in one or more subsequent templating reactions. In some embodiments, the diffusion-reducing agent or sieving agent includes polyacrylamide, agar, agarose, or a cellulose polymer such as hydroxyethyl cellulose (HEC), methylcellulose (MC), or carboxymethyl cellulose (CMC).

In some embodiments of templating methods provided herein, a templating reaction includes an RPA reaction. The templating reaction mixture typically includes all or some of the following: one or more pre-seeded solid supports that include a population of attached substantially identical first primers and have substantially monoclonal template nucleic acid molecules, e.g., one template molecule (or more than one template molecule), attached thereto, a polymerase, a recombinase, an optional single-stranded binding protein, an optional recombinase loading protein, an optional second or reverse primer, which can be attached to the solid support or is in solution, dNTPs, ATP, a buffer, and optionally one or both of phosphocreatine and creatine kinase. A divalent cation, such as $MgCl_2$ or $Mg(OAc)_2$, can be added to start the reaction. In some embodiments, the buffer includes a crowding agent, such as PEG, Tris buffer, or a potassium acetate salt or a diffusion-limiting agent, e.g., a sieving agent or drag compound. In some embodiments, a forward primer binding sequence on template nucleic acid molecules is complementary or identical to at least a portion of a forward primer, and a reverse primer binding sequence on the template nucleic acid molecules is complementary or identical to at least a portion of a reverse primer. In some embodiments, the templating reaction includes a bulk amplification (e.g., a bulk isothermal amplification) or is performed in reaction chambers, e.g., wells of a multi-well solid support or surface.

In some embodiments, compositions, as well as systems, methods, kits and apparatuses relating to the compositions, include a templating reaction mixture including a population of pre-seeded supports, nucleotides, a recombinase, and a polymerase, wherein the pre-seeded supports each have one, or more than one, e.g., between 10 and 50,000, substantially monoclonal template nucleic acid molecules including a first primer attached thereto and further include attached first primers that are attached to the pre-seeded support and are not bound to template nucleic acid molecules. In some embodiments, the reaction mixture does not include a cation capable of initiating a recombinase-polymerase amplification reaction, or at least 95% of the template nucleic acid molecules in the reaction mixture are attached to the one or more supports. In some embodiments, the templating reaction mixture further includes a cation capable of initiating a recombinase-polymerase amplification reaction. In some embodiments, the template nucleic acid molecules include two or more template nucleic acid molecules with different sequences. In some embodiments, the templating reaction mixture includes a recombinase-accessory protein. In further embodiments, the recombinase-accessory protein is a single-stranded binding protein or a recombinase-loading protein. In some embodiments, the pre-seeded supports are generated in a pre-seeding reaction including a PCR cycle or a recombinase-polymerase amplification (RPA) reaction. In some embodiments, an RPA reaction is performed by incubating an RPA reaction mixture for 2 to 5 minutes at a temperature between 35° C. and 45° C.

Since, in some embodiments of methods provided herein, the pre-seeding method can include an RPA reaction or the templating process can include more than one RPA reaction, the methods may include sequential RPA reactions. For example, a first RPA reaction can be a pre-seeding reaction, followed by a second RPA templating reaction. In another example, a pre-seeding reaction can be one or more PCR cycles or cycles of non-isothermal amplification which is followed by one or more templating reactions involving RPA reactions. The RPA reactions can be carried out under the same conditions. However, in some embodiments, a pre-seeding RPA reaction, or an initial templating RPA reaction that is followed by one or more subsequent templating RPA reactions, is carried out such that less amplification cycles occur, than for the templating RPA reaction or the templating reaction(s) occurring subsequent to an initial templating RPA reaction. For example, a pre-seeding RPA reaction can be carried out for less time than a templating RPA reaction that amplifies template nucleic acid molecules attached to pre-seeded solid supports generated by the pre-seeded RPA reaction. As non-limiting illustrative examples, a pre-seeding RPA reaction, or an initial templating RPA reaction that will be followed by one or more templating RPA reactions, is carried out, for example, for about 2 to 5 minutes to generate one or more, e.g., a population of, pre-seeded supports or templated supports, which are then subjected to a templating RPA reaction that is carried out for between about 10 and 60 minutes. In some of these non-limiting illustrative examples, reaction components including template nucleic acids are washed away from the pre-seeded solid supports before the templating RPA reaction.

In some embodiments, the pre-seeding reaction mixture or the templating reaction mixture is pre-incubated under conditions that inhibit premature reaction initiation. For example, one or more components in the pre-seeding reaction mixture can be withheld from a reaction vessel to prevent premature reaction initiation. In some embodiments, to start the reaction, a divalent cation is added (e.g., magnesium or manganese). In another example, the reaction mixture is pre-incubated at a temperature that inhibits enzyme activity, for example at about 0-15° C. or about 15-25° C. The reaction is then incubated at a higher temperature to increase enzymatic activity. In illustrative embodiments, the pre-seeding reaction mixture or templating reaction mixture is not exposed to a temperature above 42° C. during the reaction. In some embodiments, a pre-seeding or templating reaction is carried out under isothermal conditions. In some embodiments, isothermal conditions include a reaction subjected to a temperature variation which is constrained within a limited range during at least some portion of the amplification (or the entire amplification process), including for example a temperature variation that is equal to or less than about 10° C., or about 5° C., or about 1-5° C., or about 0.1-1° C., or less than about 0.1° C. The temperature of the isothermal reaction can be typically between about 15° C. and 65° C., for example between about 15° C. and 55° C., between about 15° C. and 45° C., between about 15° C. and 37° C., between about 30° C. and 60° C., between about 40° C. and 60° C., between about 55° C. and 60° C., between about 35° C. and 45° C., or between about 37° C. and 42° C. In other embodiments, the pre-seeding reaction is not exposed to a temperature above 40° C., 41° C., 42° C., 43° C., 45° C., or 50° C. Accordingly, in certain embodiments, the reaction mixture is not exposed to hot start conditions. In some embodiments, the methods are performed without subjecting double-stranded template nucleic acid molecules to extreme denaturing conditions during amplification. For example, the methods can be performed without subjecting the nucleic acid template(s) to temperatures equal to or greater than the $T_m$ of the template(s) during amplification. In some embodiments, the methods are performed without contacting the template(s) with chemical denaturants such as NaOH, urea, guanidium, and the like, during amplification.

In some embodiments, after performing a templating method, the templated surface or support or sites have at least 50,000, 75,000, 100,000, 125,000, 150,000, 200,000, 250,000, 300,000, 350,000, 400,000, 450,000, 500,000, 600,000, 700,000, 800,000, 900,000 or $10^6$ substantially monoclonal template nucleic acid molecules attached to each templated support, surface or site. In some embodiments, after performing a templating method, the templated surface or support or sites have between about 50,000 and 500,000 substantially monoclonal template nucleic acid molecules attached to each templated support, for example between about 50,000 and 400,000, between about 50,000 and 300,000, between about 50,000 and 200,000, between about 50,000 and 100,000, between about 100,000 and 400,000, between about 100,000 and 300,000, between about 100,000 and 200,000 or between about 150,000 and 300,000 substantially monoclonal template nucleic acid molecules attached to each templated support.

In some embodiments methods for generating one or more templated supports or surfaces, such as, for example, solid supports, include, for example: a) forming a templating reaction mixture by combining one or more pre-seeded supports, nucleotides, a recombinase, and a polymerase, wherein the one or more pre-seeded supports include a population of attached substantially identical first primers and have one template molecule attached thereto or have substantially monoclonal template nucleic acid molecules attached thereto, wherein the one or more pre-seeded supports are formed in a separate pre-seeding reaction that precedes a templating reaction, wherein the template nucleic acid molecules include a proximal segment including the first primer, which, in some embodiments, does not include 100 or more identical nucleotides, wherein the proximal segment attaches a template nucleic acid segment to a pre-seeded solid support, and wherein the pre-seeded supports further include attached first primers that are not bound to template nucleic acid molecules, wherein the templating reaction mixture further includes a population of substantially identical second primers, which can be soluble or in solution, and wherein the template nucleic acid molecules include a primer binding site for the second primer at or near the terminal end that is opposite the proximal segment; and b) performing one or more templating reactions. In some embodiments, in performing a templating reaction, the templating reaction mixture is incubated under isothermal conditions to amplify the template nucleic acid molecules to generate one or more templated surfaces or supports. Addition of a cation to a templating reaction mixture is included in some templating reactions. In some embodiments, the template nucleic acid molecules are not present in solution in the reaction mixture when the templating reaction is initiated. In some embodiments, the template nucleic acid molecules comprise two or more template nucleic acid molecules with different sequences. At least 100 times as many substantially monoclonal template nucleic acid molecules are present on the templated supports as were present on the pre-seeded supports in some embodiments of the methods.

The templating reaction can be preceded by a pre-seeding method in which the one or more pre-seeded supports, or population of pre-seeded supports, used in forming the templating reaction mixture are generated. The pre-seeding method includes using a pre-seeding reaction mixture under pre-seeding conditions to generate pre-seeded supports having one template molecule or a plurality, for example between 10 to 100,000 substantially monoclonal template nucleic acid molecules, comprising the first primer attached thereto, and comprising attached first primers that are not bound to template nucleic acid molecules. Typically, the pre-seeding reaction includes incubating a pre-seeding reaction mixture comprising a population of nucleic acid molecules and a population of supports or surfaces comprising a population of attached substantially identical first primers. In some embodiments, the population of nucleic acid molecules comprises a plurality of nucleic acid molecules which include a target sequence and one or more universal adaptor sequences. For example, each nucleic acid molecule of the plurality contains, with respect to one of the strands of the molecule, a first sequence of contiguous nucleotides at the 5' end of the molecule (e.g., a first adapter), a second sequence of contiguous nucleotides at the 3' end of the molecule (e.g., a second adapter) and a third nucleotide sequence, e.g., a target sequence, positioned between the first and second sequences of contiguous nucleotides, wherein the first sequence of contiguous nucleotides and the second sequence of contiguous nucleotides are different, the first sequence of contiguous nucleotides of the nucleic acid molecules are substantially identical and the second sequence of contiguous nucleotides of the nucleic acid molecules are substantially identical among the population of nucleic acid molecules. One of the sequences of contiguous nucleotides at an end of the nucleic acid molecules (e.g., an adapter sequence) typically is complementary to at least a portion of the first primers attached to the supports, or a sequence of contiguous nucleotides complementary to at least a portion of the first primers attached to the supports is added to an end of the nucleic acid molecules in a pre-seeding reaction. In some embodiments, the incubation in a pre-seeding reaction includes a cycle of amplification (e.g., PCR) under conditions in which the nucleic acids anneal to the first primers attached to the supports. The pre-seeding reaction mixture, in some embodiments, includes components (e.g., one or more polymerases, dNTPs) for extension of a first primer hybridized to a nucleic acid. In some embodiments, the pre-seeding reaction includes one or more cycles of nucleic acid amplification (e.g., including denaturing, primer annealing and primer extension) in which a sequence of contiguous nucleotides complementary to at least a portion of the first primers attached to the supports is added to an end of the nucleic acid molecules, for example, when the nucleic acid molecules do not comprise such a sequence of contiguous nucleotides. In such embodiments, the one or more cycles of amplification can be performed in the absence or presence of supports or surfaces comprising a population of attached first primers. In instances in which the one or more cycles of amplification are performed in the absence of supports or surfaces comprising a population of attached first primers, the supports or surfaces are added to the pre-seeding reaction mixture after generation of nucleic acids having an end comprising a sequence of contiguous nucleotides complementary to at least a portion of the first primers attached to the supports. In some embodiments, the pre-seeding reaction includes one or more cycles of amplification in the presence of the nucleic acids and one or more primers in solution, including, for example, a primer comprising a first primer sequence or a primer that is a second primer in the absence or presence of supports or surfaces having a plurality of first primers attached thereto which, in some embodiments, can be followed by one or more cycles of amplification (e.g., denaturation, primer annealing and primer extension) in the presence of supports or surfaces having a plurality of first primers attached thereto. In some embodiments, one or more cycles of amplification during a pre-seeding reaction are conducted under isothermal conditions. For example, in some embodiments, one or more cycles of amplification in a pre-seeding reaction include RPA. In some embodiments of the methods, the pre-seeding reaction conditions comprise a cycle of amplification including about 2 minutes at about 98° C. followed by about 5 minutes at about 56° C. to about 58° C. In some embodiments, the pre-seeding reaction condition comprise one or more cycles (e.g., 2 cycles) of amplification including about 15 seconds at about 98° C. followed by about 2 minutes at about 58° C., in the presence of a primer comprising a first primer sequence or a second primer in solution, which can be performed in the presence or absence of supports or surfaces. This, in some embodiments, is followed by a cycle of amplification including about 2 minutes at about 98° C. followed by about 5 minutes at about 56° C. to about 58° C. in the presence of supports or surfaces having a plurality of first primers attached thereto. In some embodiments of the methods, the pre-seeding reaction conditions comprise incubating the pre-seeding reaction mixture for about 2 to 5 minutes under isothermal conditions. In some embodiments, the pre-seeded supports are generated using a first recombinase-polymerase amplification (RPA) reaction and the templating reaction includes a second RPA reaction, and optionally, third or more RPA reaction, in the method. In some embodiments, the first RPA reaction is performed by incubating an RPA reaction mixture for 2 to 5 minutes at a temperature between 35° C. and 45° C. In some embodiments of the methods, the pre-seeding reaction mixture or the templating reaction mixture in the method further comprise a recombinase-accessory protein, such as, for example, a single-stranded binding protein or a recombinase-loading protein. The templating reaction mixture or the pre-seeding mixture in some embodiments of the methods is incubated at a temperature between 35° C. and 45° C. In some embodiments, the templating reaction mixture is incubated for between 10 and 60 minutes. Examples of pre-seeding and templating methods suitable for use in methods, as well as apparatuses, devices, systems, compositions and kits for performing the methods, provided herein include, but are not limited to, pre-seeding and templating methods described in PCT International Publication no. WO2019/094524, U.S. Patent Application Publication no. US2019/0194719 and U.S. patent application Ser. No. 16/403,339 the disclosure of each of which is incorporated herein in its entirety by reference thereto.

In some embodiments, the one or more templated solid supports are used in a sequencing reaction to determine the sequences of the template nucleic acid molecules. In further embodiments, the templated solid supports are templated beads and the sequencing includes distributing the beads in wells of a solid support or surface before a sequencing reaction is performed. In some embodiments, the one or more templated solid supports include a first templated solid support that is attached with a substantially monoclonal population of template nucleic acid molecules having a first sequence, and at least one other templated solid support that is attached with a substantially monoclonal population of template nucleic acid molecules having a second sequence, wherein the sequence of the first attached template nucleic acid molecules differ from the sequence of the second attached template nucleic acid molecules.

In some embodiments of the methods for generating one or more templated supports or surfaces, such as, for example, solid supports provided herein, at least some, most, substantially all, or all of the template nucleic acids attached to the templated support or supports generated in the method contain at least one modified nucleotide that includes an attachment, e.g., a first linker moiety, thereto. Such methods may further include linking the templated support(s) to a second support, e.g., a bead, having a moiety (e.g., a binding partner or second linker moiety) to which the modified nucleotide(s) of the nucleic acids attached to the templated support can bind, link or attach via the attachment or linker of the modified nucleotide(s) thereby forming a support assembly of the templated support and the second support. In some embodiments of these methods, the support assembly is separated from any elements that do not include a second support thereby separating the support assembly away from any such elements and forming an enriched population of templated supports. In some embodiments, the second support comprises a magnetic component (e.g., a magnetic bead) and the support assembly is separated from elements that do not include the magnetic support by applying a magnetic field to the support assembly. In some embodiments of the methods, the separated support assembly is further subjected to conditions under which the templated support is released from the second support and is analyzed in further methods, e.g., sequencing methods.

In some embodiments, after conducting the pre-seeding (seeding) or templating reactions, particles, e.g., beads, having on their surface a moiety that binds to or attaches to a linker (e.g., biotin) on the template nucleic acids are used to directly capture and enrich the seeded template nucleic acids. For example, in some embodiments, template nucleic acids carrying a biotin adduct that are generated in seeding reactions using soluble blocked tailed primers, (e.g., P1/B primers as depicted in FIG. 53), or a biotinylated primer (e.g., primer A as depicted in FIG. 56), are hybridized to a primer immobilized to a support which is then extended to form a double-stranded template molecule bound to the support. The seeded support is then contacted with particles having a moiety to which the biotin binds (e.g., streptavidin-coated beads, such as magnetic beads, which bind the template nucleic acid via the biotin adduct to form a bead assembly (see FIG. 58) whereby the seeded support is thus captured. The bead assembly may then be separated from any other reaction components, for example, by pelleting the bead assemblies with a magnet. Subsequent detachment of the streptavidin-coated bead from the template nucleic acid (e.g., by denaturation of the double-stranded template that is bound to the solid support) and removal of the template nucleic acid bound to the solid support from the detached bead yields an enriched collection of single-stranded template-bound solid supports. Excess streptavidin-coated magnetic beads may be included in the capture process to ensure that all of the template nucleic acid-seeded supports are captured. Any seeding amplification reaction products carrying a linker (e.g., biotin) but that are not bound to supports that may be captured by magnetic beads and eluted therefrom along with seeded supports can be separated from the seeded supports in further downstream processing (e.g., in loading the seeded supports into reaction sites, such as microwells on a surface, e.g., a chip, for sequencing of the template bound to solid supports) as described herein.

Figure 58:
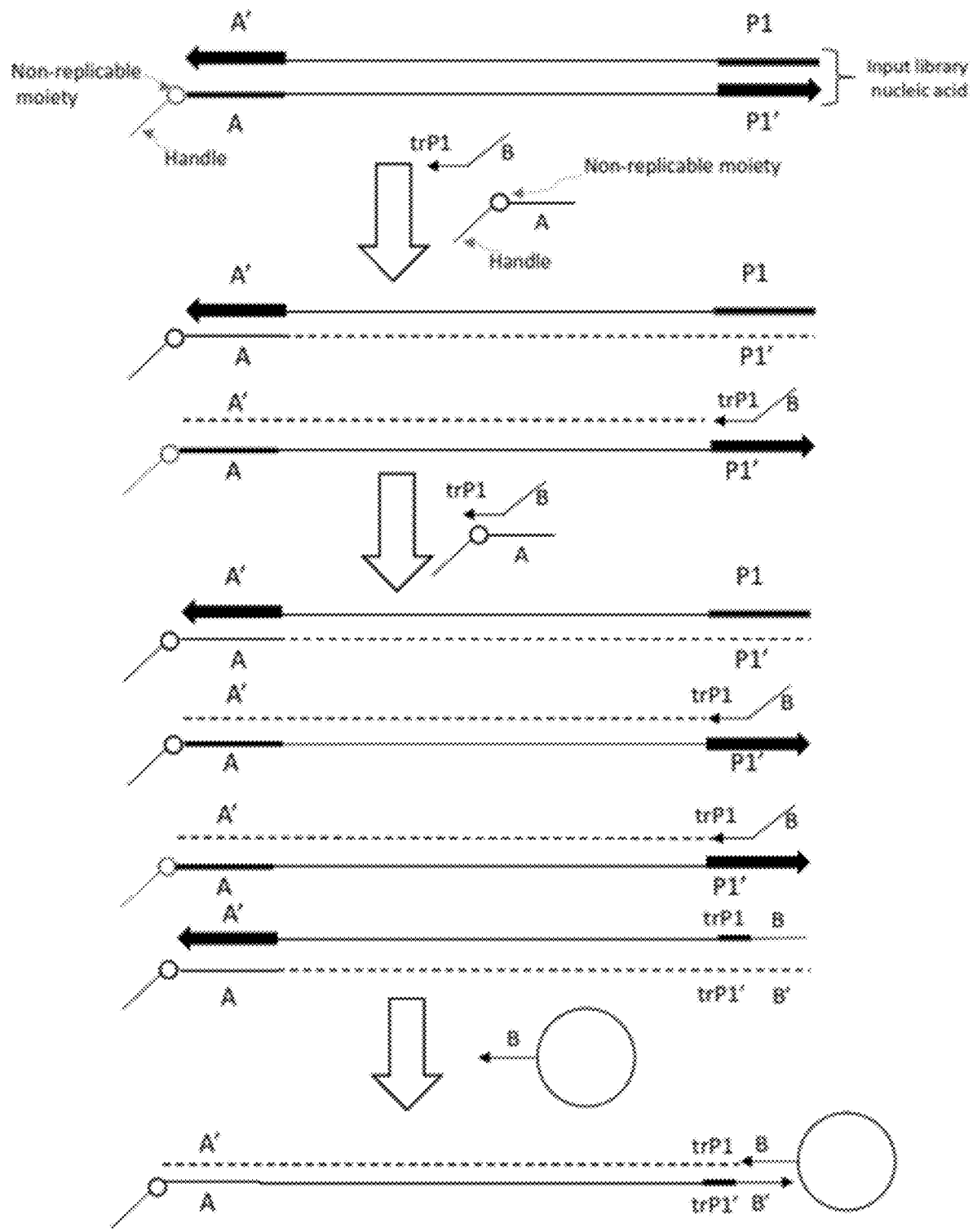
Figure 59:
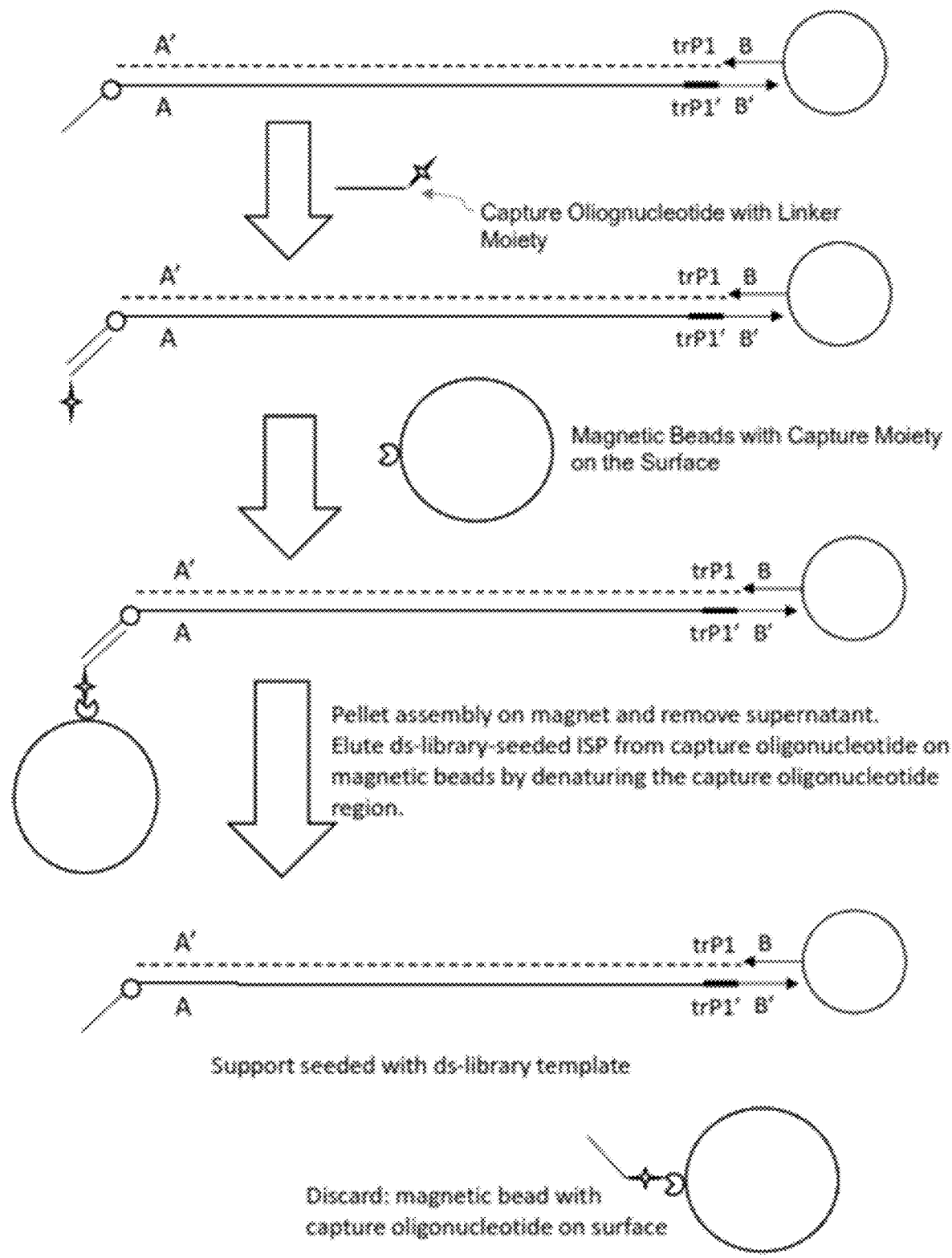

In some embodiments, a pre-seeding (or seeding) method can be performed as illustrated in FIG. 59. In this example, the method is designed to generate a desired solid support-attached nucleic acid molecule from a series of cycles of amplification of the target nucleic acid in which only one of the amplification products, which is the desired target nucleic acid, will attach to the support. The desired target contains a single-stranded sequence of nucleotides referred to as a "handle" portion at the 5' end of the nucleic acid and an adapter nucleotide sequence (labeled with the letter B' in FIG. 59) at the 3' end that is complementary to the primer (labeled with the letter B in FIG. 58) immobilized on the support. As shown in FIG. 58, the double-stranded nucleic acids (e.g., library nucleic acids) contain adapter sequences at each end, such as, for example, an A adapter sequence at the 5' end and a P1 adapter sequence at the 3' end (standard Ion Torrent A and P1 library adapters; Thermo Fisher Scientific). In some instances, as depicted in FIG. 58, the input library may already have a handle configuration on the A adapter. If the input library does not have a handle configuration on the A adapter, it can be added in amplification reactions of the library that include a primer that contains, in the 5' to 3' direction, a handle nucleotide sequence, a non-replicable moiety (e.g., a polymerase stop site) and an A adaptor sequence. To begin the pre-seeding amplification reactions, the library is subjected to one cycle of amplification (i.e., denaturation, primer annealing and primer extension) in the presence of primers such as depicted in FIG. 58. Exemplary primers used in the amplification are a primer A (forward primer), which has at its 5' end a polymerase stop site and a handle sequence located 5' of the non-replicable moiety, and a reverse fusion primer. The non-replicable moiety of the handle-containing primer can be any composition that cannot be replicated by a polymerase. Such non-replicable moieties include, e.g., any moiety that cannot support template-based nucleotide polymerization by a polymerase. For example, the non-replicable moiety can include a non-nucleotidyl moiety (e.g., PEG or other carbon-based spacer), amino acid or nucleotide analog that is not recognized by the polymerase used to perform the primer extension. Examples of primers containing non-replicable moieties are described, for example, in International Application publication no. WO2014/062717, the disclosure of which is incorporated in its entirety herein by reference thereto. When the handle-containing primer is used in template-dependent nucleic acid synthesis by a polymerase, the polymerase cannot extend the synthesized nucleic acid strand beyond the non-replicable moiety. This typically results in the cessation or termination of nucleic acid synthesis, and the non-replicable moiety serves as a polymerase stop site. The fusion primer (e.g., a primer labeled trP1 in FIG. 58) is a fusion of a sequence that is complementary to a portion of the adapter sequence at the 3' end of the target nucleic acids and a B primer that is identical to the primer immobilized on the solid supports. In the example shown in FIG. 58, trP1 is a 23 mer segment of the Ion P1 adapter. The fusion primer will hybridize and prime at the inner portion of the 3' adapter sequence of the library nucleic acid molecules, close to the library insert sequence, and does not hybridize with the remainder of the adapter sequence at the extreme 3' end of the library nucleic acids. This forms a mismatch end between the fusion primer sequence and the very 3' end portion of the adapter on the library nucleic acids. As shown in FIG. 58, after two cycles of amplification (e.g., PCR), although four amplification products are generated, only one product will be able to seed (or hybridize) to the support (e.g., an Ion Sphere Particle). Thus, upon subsequent denaturation of the amplification products, a single strand of only one of the products will hybridize to the B primer on the support. This primer can be extended to form a double-stranded template nucleic acid in which one strand contains a handle that can be used, for example, in the binding of the support-bound nucleic acid to a capture moiety (e.g., a capture moiety bound to a magnetic bead) for use in enrichment or magnetic loading of wells.

In some embodiments of the pre-seeding (or seeding) method depicted in FIG. 58, the primer containing a handle sequence includes, in the 3' to 5' direction, a first sequence of nucleotides that is complementary to the sequence of a first double-stranded adapter on one end of the library DNA amplicons, a polymerase stop site, and a second sequence of nucleotides (a handle sequence) that is at least partially complementary or fully complementary to the first sequence of nucleotides. The handle sequence may be, for example, complementary to a portion of the first sequence of nucleotides but, within that portion, contain one or more mismatch bases that are not complementary to the bases in the corresponding positions of that portion of the first sequence of nucleotides. Under certain permissive conditions, the first sequence of nucleotides and the second sequence of nucleotides will hybridize to each other to form a hairpin structure. However, under conditions for the amplification reactions that occur during the seeding process in, e.g., a method such as that depicted in FIG. 58, the first and second sequences of nucleotides of the handle-containing primer will not hybridize. Instead, under such non-permissive conditions, hybridization of the first sequence of nucleotides of the primer to the complementary adapter sequence (e.g., A adapter) of the library amplicons will be favored and occur, and the handle sequence will extend, at the site of polymerase stop moiety, from the duplex of the A adapter and first nucleotide sequence of the primer as a single-stranded portion that is not duplicated in the seeding amplification reactions. Permissive conditions under which the first and second sequences of nucleotides of the handle-containing primer can hybridize may include, for example, relatively low temperatures, such as temperatures that are lower than the temperatures at which the seeding amplification reactions are conducted or lower than standard PCR operating temperatures. Low temperatures include temperatures substantially or significantly lower than the Tm for a duplex, double-stranded nucleic acid of the A adapter and first nucleotide sequence of the primer. In some embodiments, the Tm of a duplex nucleic acid of the first and second sequences of nucleotides of the handle-containing primer is substantially or significantly less than the Tm of a duplex nucleic acid of the A adapter and first nucleotide sequence of the primer. For example, the Tm of the hybrid formed between the first and second sequences of nucleotides of the handle-containing primer can be less than about 50° C., 45° C., 40° C., 35° C., 30° C., 25° C., 20° C. or lower. Another example of permissive conditions is relatively high salt concentrations, e.g., NaCl concentrations of 0.25M, 0.3M, 0.4M, 0.5M, 0.75M, 1M or higher. Non-permissive conditions can include, for example, higher temperatures (e.g., temperatures significantly greater than the Tm of a hybrid formed between the first and second sequences of nucleotides of the handle-containing primer) or low or absent levels of salt (e.g., NaCl concentrations of 0.2M, 0.1M, 0.05 M, 0.001M or lower).

In some embodiments, after conducting the seeding (or pre-seeding) method as depicted in FIG. 58, the seeded supports are enriched through separation from other reaction components. In one method of enrichment, the seeded supports are indirectly captured via a linker moiety (such as biotin, for example) that attaches to the handle of the double-stranded target template on the supports. Beads having a moiety (e.g., streptavidin) that in turn binds to or attaches to the linker attached to the template nucleic acid can be used to enrich the seeded supports. For example, as depicted in FIG. 59, an oligonucleotide (i.e., a "capture" oligonucleotide) that is complementary to the handle sequence on the support-bound template target nucleic acids and that is attached to a linker moiety (e.g., a biotin adduct) is contacted with the seeded supports and with beads (e.g., magnetic beads) having streptavidin coated surfaces. This results in an indirect capturing of the support-bound double-stranded target template nucleic acids through the formation of a bead assembly. In the case of magnetic beads, the assembly can be pelleted on a magnet and the supernatant containing any other reaction components is removed. In some embodiments, the capturing process is conducted under conditions in which the first and second sequences of nucleotides that are at least partially complementary of a free handle-containing primer will hybridize, e.g., permissive conditions. Under such conditions, free handle-containing primers that are present will be in a hairpin configuration which will not hybridize with the capture oligonucleotide. Thus, the free handle-containing primers will not be captured by the streptavidin-coated magnetic beads.

Figure 57:
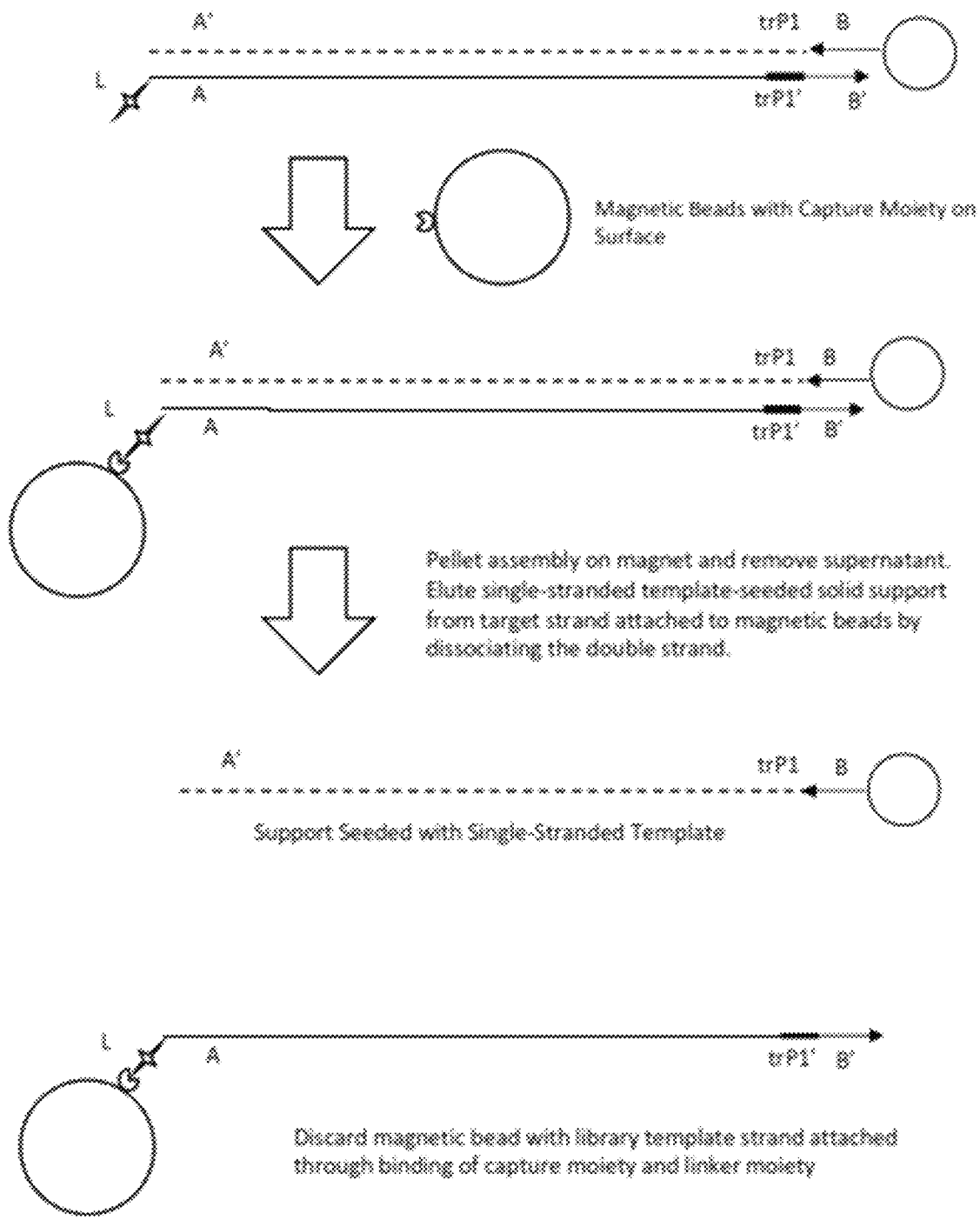

The process by which template nucleic acids bound to supports are linked to magnetic beads illustrated in FIG. 59 is referred to as an indirect capture method, whereas the process depicted in FIG. 57 by which support-bound template nucleic acids are linked to magnetic beads is referred to as a direct capture method. As shown in FIG. 57, a streptavidin-coated magnetic bead binds to a biotin linker moiety that is directly attached to the strand of the template duplex that is hybridized to a strand that is an extended primer immobilized to a support. In contrast, in the indirect capture method shown in FIG. 59, the streptavidin-coated magnetic bead binds to a biotinylated capture oligonucleotide that is not a strand of the support-bound template duplex but instead is hybridized to a single-stranded handle extending from the duplex. Thus, the bead assemblies formed upon capture of seeded supports by magnetic beads in the direct and indirect capture methods are different. In some instances, the difference in the bead assemblies may affect the association between hybridized strands of the support-bound template duplex. For example, force exerted on a template strand directly linked to a magnetic bead by movement of the bead may at times be in opposition to the force exerted on the strands of the duplex by movement of the seeded support. Such forces may have a greater effect on the associated template duplex strands than they would on a template duplex in which the magnetic bead is indirectly linked to a template duplex strand through a capture oligonucleotide. The extent of the effect may be influenced by one or more factors, e.g., length of the template hybrid, the salt concentration of the medium, temperature and the amount of mixing, transferring, etc. of the bead assemblies during capture and enrichment. As the effect of such forces on a support-bound target template duplex increases, so does the possibility that the template duplex strands may dissociate. Dissociation of template duplexes during the enrichment process could result in decreases in enriched seeded support yield or a greater percentage of longer template duplexes being enriched. However, the short hybrid between the capture oligonucleotide and the handle portion of one of the template duplex strands of a bead assembly formed in the indirect capture method is likely to dissociate more readily and rapidly than the template duplex thereby releasing the magnetic bead and eliminating that force on the template duplex. Additionally, the short nucleic acid sequences of the capture oligonucleotide and the handle portion of a template duplex strand may tend to associate more readily than longer template duplex strands that have separated, which may mitigate any potential decrease in enriched seeded support yield. Thus, capture method and capture conditions can be selected to match desired seeded template duplex lengths and seeded support yields. Generally, in order to optimize the yield of seeded supports when using a direct capture method, bead assemblies generated by such methods are handled using more gentle conditions, e.g., slow pipetting and gentle mixing, as opposed to vigorous conditions, e.g., vortexing. Seeded support yields when using an indirect capture method to generate bead assemblies generally are not adversely affected by more vigorous handling of the bead assemblies.

In some embodiments of an indirect capture method of enriching pre-seeded supports, the captured seeded supports are eluted from the capture oligonucleotide bound to the magnetic beads by denaturing the relatively small region of hybridization between the capture oligonucleotide and the handle sequence on the template nucleic acid under conditions in which the double-stranded template nucleic acids bound to seeded supports do not denature. Such conditions can be determined, for example, by exploiting the differences in the melting temperatures (Tm) of the short hybrid formed by the handle sequence and capture oligonucleotide (e.g., Tm of about 32° C. in high salt buffer) and the double-stranded target template nucleic acids (e.g., Tm greater than 32° C.) bound to the supports. For example, in some embodiments, any moderate denaturing condition, e.g., increased temperature (e.g., gentle heating to greater than 35° C., such as 42° C. for about 5 minutes), lower salt concentrations (e.g., low TE, addition of water) or physical disturbance or agitation (e.g., vortexing, pipetting) can be used to dissociate the capture oligonucleotide-handle sequence hybrid without disrupting the double stranded support-bound template nucleic acids. The magnetic beads bound to capture oligonucleotides are discarded leaving the enriched double-stranded templates bound to the seeded supports. In embodiments in which the first and second sequences of nucleotides of the handle-containing primer are not complementary, and do not hybridize to form a hairpin structure under any conditions used in the seeding process, excess capture oligonucleotide and excess streptavidin-coated magnetic beads may be included in the capture process to ensure that all of the template nucleic acid-seeded supports are captured. Any handle-containing primers and seeding amplification reaction products not bound to supports that may be captured by magnetic beads and eluted therefrom along with seeded supports can be separated from the seeded supports in further downstream processing (e.g., in loading the seeded supports into reaction sites or chambers, such as microwells on a surface, e.g., a chip, for templating reactions or sequencing of the template bound to solid supports) as described herein.

In contrast to the enrichment method depicted in FIG. 57, which yields a single-stranded template bound to a support after denaturation to remove the magnetic bead, the enrichment method depicted in FIG. 59 yields a double-stranded template bound to a support after denaturation to remove the magnetic bead. In some embodiments, having a double-stranded template attached to a support facilitates detection of an error that may have occurred during the seeding process, eliminating results of any downstream analysis of an error-containing template-seeded support from consideration, and thereby reduces error in the overall results of, for example, sequencing of a population or plurality of seeded templates. For example, in some instances it may be possible for an error in polymerization to occur during template-dependent extension of a primer immobilized on a support in generating a double-stranded template bound to the support. If an error of this type occurs, and only single-stranded seeded templates result from subsequent capture and enrichment of the seeded supports, such as depicted in FIG. 57, the only template sequence that is available for use in downstream processes (for example in templating amplification and sequencing) will contain an error. In this case, templates amplified from the seeded supports will be a monoclonal population of sequences containing the error and sequencing of the templates will yield reads that are identical. If, instead, a double-stranded seeded template results from an indirect capture and enrichment, such as is depicted in FIG. 59, both strands, i.e., one being the extended immobilized primer having the error and one being the original template that hybridized to the immobilized primer that does not have the error, are available for further processing and analysis. This effectively dilutes the template error from 100%, in the case of having only a single-stranded seed template, to about 50% (i.e., the seeding error rate is reduced by about 50%). Because the templates amplified from such a double-stranded seeded support will produce a polyclonal population of sequences (i.e., some sequences (~50%) having the error and some sequences (~50%) not having the error), the error can be detected in downstream analysis, such as sequencing. Sequence reads from sequencing of that polyclonal population can be eliminated from consideration in analysis of the sequence results of a plurality of nucleic acid template populations. Thus, if there are no other errors in the templates bound to other supports being sequenced, the sequencing error rate for the remainder of the templates will in effect be 0%.

In some embodiments, a method of generating one or more, or a plurality of template nucleic acid populations, for example, monoclonal, or substantially monoclonal nucleic acid populations is provided that includes (a) obtaining a plurality of supports wherein each support has a plurality of single-stranded oligonucleotide primers immobilized thereto and a template nucleic acid attached to the support, wherein the template nucleic acid comprises a sequence of contiguous nucleotides at one end of the strand that is the oligonucleotide primer sequence; (b) subjecting the template nucleic acids attached to the plurality of supports to one or more, or two or more isothermal nucleic acid amplifications (e.g., RPA reactions) in the presence of a first primer in solution, wherein the first primer comprises a sequence of nucleotides that is complementary to a primer-binding sequence of the attached nucleic acid strand at the end of the strand opposite to the end having a sequence of contiguous nucleotides that is the oligonucleotide primer sequence. In some embodiments of the method, the one or more, or two or more, isothermal nucleic acid amplifications are carried out within a single continuous liquid phase of a single reaction mixture. In some embodiments, the nucleic acids attached to the supports are subjected to at least two isothermal nucleic acid amplification reactions wherein the second amplification generates at least 1000-fold more, at least 100,000-fold more, or at least 1,000,000-fold more, nucleic acids attached to a support than were attached after the first amplification. In some embodiments, in step (b) a first isothermal nucleic acid amplification is performed in the presence of (i) a first primer that is attached to a linker moiety or affinity moiety in solution and (ii) a composition that attaches to or binds the linker moiety or affinity moiety and the method further comprises: (c) discontinuing the first isothermal amplification of (b) and removing the composition that attaches to the linker moiety or affinity moiety of the first primer and (d) subjecting the template nucleic acids attached to the plurality of supports to a second isothermal nucleic acid amplification in the presence of a first primer in solution and in the absence of the composition that attaches to the linker moiety thereby generating monoclonal, or substantially monoclonal, populations of template nucleic acids attached to the supports, wherein the first primer present in the second isothermal nucleic acid amplification is attached to a linker moiety (or affinity moiety) or is not attached to a linker moiety (or affinity moiety). In some embodiments, one or more of the isothermal amplifications is conducted in the presence of a diffusion-limiting agent, e.g., a polymer, e.g., cellulose or methyl cellulose. In some embodiments, the first or second isothermal nucleic acid amplification is/are recombinase-polymerase amplifications. In some embodiments, the first or second isothermal amplification is/are conducted in the presence of a diffusion-limiting agent, e.g., a polymer, e.g., cellulose or methyl cellulose. In some embodiments, the plurality of supports of step (a) having a template nucleic acid attached to the support is obtained by a method including (1) obtaining a population of nucleic acids in which each nucleic acid includes a nucleic acid strand comprising a first sequence of contiguous nucleotides at the 5' end of the nucleic acid strand, wherein the first sequence of contiguous nucleotides optionally comprises a first linker moiety attached thereto, a second sequence of contiguous nucleotides at the 3' end of the nucleic acid strand and a third nucleotide sequence positioned between the first and second sequences of contiguous nucleotides, wherein the first sequence of contiguous nucleotides and the second sequence of contiguous nucleotides are different and the first sequences of contiguous nucleotides are substantially identical and the second sequences of contiguous nucleotides are substantially identical and, wherein, in some embodiments, the third nucleotide sequence positioned between the first and second sequences of contiguous nucleotides differs among the population of nucleic acids, (2) contacting single strands of the population of nucleic acids with supports under annealing conditions to generate supports having single-stranded nucleic acids attached thereto through hybridization with the second sequence of contiguous nucleotides, wherein the supports comprise a plurality of primer oligonucleotides having a nucleotide sequence complementary to the second sequence of contiguous nucleotides immobilized thereto, (3) extending the immobilized primers of the support that are hybridized to a nucleic acid strand to generate double-stranded nucleic acids attached to the supports wherein the double-stranded nucleic acids comprise an extended strand that is directly attached to the support and a strand that is hybridized to the attached strand and (4) separating the strands of the double-stranded nucleic acids. In some embodiments, the number of supports in step (2) exceeds the number of nucleic acid molecules by a factor of at least 2, or a factor of at least 5. In some embodiments, the number of supports in step (2) exceeds the number of nucleic acid molecules by a factor of at least 2, or at least 2.5, or at least 3, or at least 3.5, or at least 4, or at least 4.5, or at least 5, or at least 5.5, or at least 6, or at least 6.5, or at least 7, or at least 7.5, or at least 10, or at least 15, or at least 20, or at least 25.

In some embodiments, the method of generating one or more, or a plurality of template nucleic acid populations, for example, monoclonal, or substantially monoclonal, nucleic acid populations attached to supports or surfaces includes transferring one or more, or a plurality of supports or surfaces having one, one or more, or a plurality of nucleic acids attached thereto to one or more, or a plurality of reaction sites or chambers (e.g., wells) on a surface. In one example, such a method includes transferring one or more, or a plurality of, supports having a plurality of single-stranded oligonucleotide primers immobilized thereto and a template nucleic acid attached thereto that comprises a sequence of contiguous nucleotides at one end of the nucleic acid that is the oligonucleotide primer sequence to a surface comprising reaction sites whereby the supports having nucleic acids attached thereto are loaded into separate sites. In some embodiments, after the supports having a template nucleic acid attached thereto are loaded into separate reaction sites, the nucleic acids are subjected to one or more, or two or more, isothermal nucleic acid amplification reactions (e.g., RPA reactions). In some embodiments the method further comprises subjecting the amplified nucleic acids attached to the supports to nucleic acid sequencing. In some embodiments the sequencing process produces at least about 45 million sequence reads which are at least 100, at least 200, or at least 300 nucleotides in length. In some embodiments the sequencing process produces at least 60 million sequence reads which are at least 300 nucleotides in length. In some embodiments the sequencing process produces at least about 45 million or about 80 million sequence reads which are at least 100 nucleotides in length. In some embodiments the sequencing process produces at least 80 million sequence reads between about 100 and about 400 nucleotides in length.

In some embodiments, the method of generating one or more, or a plurality of template nucleic acid populations, for example, monoclonal, or substantially monoclonal, nucleic acid populations, attached to supports or surfaces includes forming a plurality of captured supports prior to subjecting template nucleic acids attached to the plurality of supports to one or more, or two or more isothermal nucleic acid templating amplifications. For example, in one such method, supports in the plurality of supports have a double-stranded, or partially double-stranded, template nucleic acid attached thereto, wherein each double-stranded, or partially double-stranded, template nucleic acid comprises (1) an attached strand that is directly attached to the support (e.g. an extended primer strand) and a strand that is hybridized to the attached strand, and (2) a linker moiety or a single-stranded overhang nucleotide sequence on the strand that is hybridized to the attached strand. This method comprises (i) generating a plurality of captured supports by contacting the plurality of supports with a capture moiety that binds to the linker moiety (or affinity moiety), or with an oligonucleotide complementary to the single-stranded overhang nucleotide sequence and a capture moiety, wherein the oligonucleotide complementary to the single-stranded overhang nucleotide sequence hybridizes to the single-stranded overhang and comprises a linker moiety to which the capture moiety binds; (ii) collecting the captured supports; and (iii) separating the supports having template nucleic acids attached thereto from the capture moiety or from the oligonucleotide complementary to the single-stranded overhang nucleotide sequence. In some embodiments of the method, each support of the plurality of supports of step (i) has only one double-stranded, or partially double-stranded, template nucleic acid attached to the support. In some embodiments, the capture moiety is attached to a bead or particle and, after collecting the captured supports, the supports having template nucleic acids attached thereto are separated from the capture moiety attached to the bead or particle by dissociating the strands of the double-stranded template nucleic acids thereby generating a plurality of supports attached to single-stranded template nucleic acids or by dissociating the hybrid of the oligonucleotide complementary to the single-stranded overhang nucleotide sequence and the single-stranded overhang thereby generating a plurality of supports attached to partially double-stranded template nucleic acids containing a single-stranded overhang nucleotide sequence. In some embodiments, prior to subjecting the template nucleic acids attached to the plurality of supports to the first isothermal nucleic amplification, the supports attached to template nucleic acids that have been separated from the capture moiety attached to the bead or particle are transferred to a surface comprising reaction sites (e.g., wells) and loaded into separate reaction sites. In some embodiments, the supports are transferred to a surface comprising reaction sites in a method comprising combining the supports having nucleic acids attached thereto with magnetic beads wherein the nucleic acids on the supports do not attach to the magnetic beads and delivering the combined supports having nucleic acids attached thereto and magnetic beads to the surface comprising reaction sites and applying a magnetic field to the surface whereby the supports having nucleic acids attached thereto are loaded into separate reaction sites. In some embodiments, the bead or particle to which the capture moiety is attached is a magnetic support and the captured supports comprise template nucleic acid-bound support-magnetic support assemblies, and collecting the captured supports in step (ii) comprises applying a magnetic field to the assemblies thereby separating the assemblies from elements that do not include a magnetic support. In some embodiments of this method of generating one or more, or a plurality of template nucleic acid populations attached to supports that includes forming a plurality of captured supports, the supports have a partially double-stranded template nucleic acid attached thereto, wherein each partially double-stranded template nucleic acid comprises (1) an attached strand that is directly attached to the support (e.g. an extended primer strand) and a strand that is hybridized to the attached strand, and (2) a single-stranded overhang nucleotide sequence on the strand that is hybridized to the attached strand. In one example of such an embodiment, the partially double-stranded template nucleic acid is generated in a method comprising: (A) subjecting an initial population of nucleic acid molecules to a cycle of nucleic acid amplification in the presence of a first primer and a second primer, wherein: (1) each of the plurality of nucleic acids comprises a nucleic acid strand having a first sequence of contiguous nucleotides at the 5' end of the strand, a second sequence of contiguous nucleotides at the 3' end of the strand and a third nucleotide sequence positioned between the first and second nucleotide sequences, wherein the first nucleotide sequence and second nucleotide sequence are different from each other, and wherein the first nucleotide sequences of the population of nucleic acid molecules are substantially identical and the second nucleotide sequences of the population of nucleic acid molecules are substantially identical among the population, (2) the first primer comprises a 3'-end nucleotide sequence substantially identical to the first nucleotide sequence, a 5'-end nucleotide sequence and a non-replicable moiety positioned between the 3'-end nucleotide sequence and the 5'-end nucleotide sequence, and (3) the second primer comprises (i) a nucleotide sequence complementary to a portion of the second nucleotide sequence at the 5' end of the second nucleotide sequence and (ii) a fourth nucleotide sequence that is not complementary to the second nucleotide sequence and that is linked to the sequence complementary to the portion of the second nucleotide sequence at the 3'end of the complementary sequence, and wherein the second primer does not contain a nucleotide sequence complementary to the 3' end of the second nucleotide sequence; (B) subjecting the products of the cycle of amplification of step (A) to a cycle of nucleic acid amplification in the presence of the first and second primers to generate multiple different products, wherein only one of the multiple different nucleic acid products from nucleic acid amplification in step (B) of each separate nucleic acid molecule in the initial population of nucleic acid molecules from step (A) comprises a strand having a sequence of nucleotides at the 3' end that is complementary to the fourth nucleotide sequence and a single-stranded region at the 5' end that includes the non-replicable moiety and 5'-end nucleotide sequence of the first primer; (C) contacting single strands of the nucleic acid products of step (B) with supports having immobilized thereto a plurality of single-stranded oligonucleotide primers that are substantially identical to the fourth nucleotide sequence under annealing conditions thereby hybridizing single strands of the nucleic acid products of step (B) that comprise a sequence of nucleotides complementary to the fourth nucleotide sequence to the single-stranded oligonucleotide that is substantially identical to the fourth nucleotide sequence to generate supports attached to template nucleic acids that comprise a partially double-stranded nucleic acid; and (D) extending the 3' end of the immobilized oligonucleotide primer portion of the partially double-stranded nucleic acids by template-dependent nucleic acid synthesis to generate extended double-stranded nucleic acids wherein extension of the immobilized oligonucleotide primer portion continues to the point of the non-replicable moiety present on the template strand to which the extension strand is hybridized and then discontinues resulting in partially double-stranded nucleic acids containing a single-stranded overhang nucleotide sequence that includes the 5'-end nucleotide sequence of the first primer, thereby producing a plurality of supports having template nucleic acids attached thereto, wherein each support has a different partially double-stranded template nucleic acid attached thereto. In some embodiments of this method, the 5'-end nucleotide sequence of the first primer and the 3'-end nucleotide sequence of the first primer are at least substantially complementary to each other.

In some embodiments, supports or surfaces used in pre-seeding or templating methods described herein are transferred to reaction sites or chambers, for example, microwells on a surface, e.g., a chip or semiconductor chip, for further downstream processing (e.g., for templating reactions or sequencing of the template bound to supports). One method provided herein for transferring supports or surfaces having one, or one or more, or a plurality of nucleic acid templates attached thereto wherein the nucleic acid templates have an attached first linker moiety includes coupling a magnetic support, e.g., bead, having a second linker moiety to the nucleic acid templates through attachment of the second linker moiety to the first linker moiety thereby forming a template-attached support-magnetic support assembly (e.g., a bead or support assembly), and depositing the support into a reaction site or chamber, e.g., a well, of a surface, e.g., a sequencing device, using a magnetic field. In some such embodiments, supports or surfaces having one, or one or more, or a plurality of nucleic acid templates attached thereto wherein the nucleic acid templates have an attached first linker moiety are generated in a method that comprises generating a template nucleic acid including a capture sequence portion, a template portion, and a primer portion, capturing the template nucleic acid on a support coupled to a capture primer complementary to the capture sequence portion, the capture primer hybridizing to the capture sequence portion of the template nucleic acid, extending the capture primer complementary to the template nucleic acid to form a target nucleic acid complementary to and hybridized to the template nucleic acid, separating the hybridized template nucleic acid and the target nucleic acid, hybridizing a linker modified primer to the target nucleic acid on the support, the linker modified primer including a linker moiety, extending the linker modified primer complementary to the target nucleic acid, coupling a magnetic support, e.g., bead, to the linker moiety, the magnetic support having a second linker moiety attaching to the linker moiety, and depositing the support into a reaction site or chamber, e.g., a well, of a surface, e.g., a sequencing device, using a magnetic field. In some embodiments the method further comprises separating the template nucleic acid and the sequence target nucleic acid to release the magnetic support from the support complex. In some embodiments separating includes denaturing, e.g., heat denaturing, enzymatic denaturing, denaturing in the presence of an ionic solution. In some embodiments the method further comprises washing the magnetic supports from the surface having the reaction sites.

In some embodiments of the methods, as well as apparatuses, devices, systems, compositions and kits for performing the methods, provided herein, one or more monoclonal, or substantially monoclonal, populations of template nucleic acids attached to templated supports or surfaces or sites, wherein the populations of template nucleic acids are generated in pre-seeding or templating methods as described herein, are sequenced using methods, apparatuses, devices, systems, compositions and kits described herein.

Sequencing

Following loading of target sequence on a sensor device and templating to form monoclonal populations of target sequences, nucleotide solutions of individual types of nucleotide can flow sequentially through a flow cell of the sensor device. Signals responsive to the nucleotide flow can be measured from the sensor device. Such signals can be used for base calling to determine a base order. The order of smaller sequences can be aligned and analyzed to determine aligned reads and variant calls.

The nucleotide solutions can be provided through the flow cell of the sensor device in a flow order that enhances performance, such as read length, of the system. For example, a flow order described in U.S. Pat. No. 9,428,807, granted Aug. 30, 2016, which is incorporated herein by reference, can be followed.

Example nucleotide flow, signal detection, and signal processing to detect bases can be performed as described in U.S. Pat. No. 10,241,075, granted Mar. 26, 2019, which is incorporated herein by reference in its entirety.

Performance Definitions and Parameters

The above systems and methods provide desirable technical advantages including performance and automation. In particular, the above systems can perform sequencing operations from extracted DNA or RNA samples to aligned reads or variant call in a desirably short time with limited human intervention. For example, once the samples and consumables (reagent strips, pipette tips, sensor device, and adaptors, etc.) are provided to the instrument, the instrument can perform the sequencing and data processing without further manual intervention. In an example, a user unskilled in sample processing for nucleic acid analysis can setup the sequencing system and direct the system to perform a sequencing analysis without further intervention.

In an example, the system and methods provide for runs and analysis with a raw read accuracy (accuracy of a base called sequence measured by aligning to a reference sequence) of at least 98.5%. For example, the raw read accuracy can beat least 99.0%, such as at least 99.1% or even 99.2%. In an example, the raw read accuracy is not greater than 99.99%.

In a further example, the system and method provide for runs and analysis with a Q20 mean read length (Q20 MRL) of at least 100 b. Q20 read length is the number of the bases from a beginning of the read that the phred quality score is at least 20 for all bases. Q20 mean read length is the average of Q20 read length over all sequences. In an example, the Q20 MRL is at least 100 b. For example, the Q20 MRL is in a range of 100 b to 450 b, such as a range of 102 b to 300 b or a range of 104 b to 300 b.

In an additional example, the system and method provide for runs and analysis having a uniformity of at least 95%. For example, the uniformity can be in a range of 96% to 99.9%, such as a range of 96% to 98%.

In another example, the system and method provide for runs and analysis having a sensitivity of at least 80%. Sensitivity is the number of true positive calls divided by number of all true variants in a control sample. Such sensitivity can be further determined for control samples provided at a percent of limit of detection, which is the lowest % of variant that can be detected by the sequencing data. For example, the sensitivity can be at least 90%. In an example, the sensitivity can be in a range of 90% to 100%, such as a range of 90% to 99% or a range of 94% to 99%. In particular, a copy number variant sensitivity can be in a range of 80% to 100%, such as a range of 90% to 100% or a range of 95% to 100%.

In a further example, the system and method provide for runs and analysis having a Median of the Absolute values of all Pairwise Differences (MAPD) of less than 0.5. Median of the Absolute values of all Pairwise Differences MAPD between log 2 ratios per tile for a given run. Tiles roughly correspond to amplicons in an Ion AmpliSeq™ assay. Each pair is defined as adjacent in terms of genomic distance. MAPD is a per-sequencing run estimate of copy number variability, similar to standard deviation (SD). For example, the MAPD is in a range of 0.5 to 0.001, such as a range of 0.5 to 0.01 or a range of 0.4 to 0.01.

In an additional example, the system and method provide for runs and analysis having an average percent reads on target of at least 97%, such as in a range of 98% to 100%, such as a range of 98% to 99.9% or a range of 98.1% to 99.9%. The average percent reads on target is the percentage of filtered reads mapped to any targeted region relative to all reads mapped to the reference. A read is considered on target if at least one aligned base overlaps at least one target region.

Ina further example, the system and method provide for runs and analysis having at total reads in a range of 13 million bases to 100 million bases, such as a range of 13 million bases to 60 million bases, or a range of 14.5 million bases to 25 million bases. In another example, the system and methods provide for runs and analysis having a mapped reads/library in a range of 5M to 20M, such as a range of 5M to 14M. In an additional example, the total reads per lane for sensor devices including a multilane flow cell can be in a range of 0.5 million bases to 48 million bases, such as 0.5 million bases to 14 million bases.

In an additional example, the system and method provide for runs and analysis having a bar code (BC) imbalance of not greater than 80%. BC is the barcode with min mapped reads/average mapped reads.

In another, the system and method provide for runs and analysis having read coverage per library of at least 25K, such as a read coverage in a range of 25K to 100K or a range of 25K to 50K. Read coverage/library is a number of reads mapped to an amplicon.

In a further example, the system and method provide for runs and analysis having a coverage depth or at least 800, such as a coverage depth in a range of 800 to 5000, a range of 800 to 4000, or a range of 1000 to 3500. Coverage depth is the average number of reads of all targeted reference bases. This is the total number of base reads on target divided by the number of targeted bases and therefore includes any bases that had no coverage.

In an additional example, the system and methods provide for runs and analysis having an unaligned read length of at least 75 bp, such as a range of 75 bp to 200 bp or a range of 75 bp to 110 bp. The unaligned read length is the average read length of reads that do not align to reference.

In another example, the system and methods provide for runs and analysis having a molecular coverage per library in a range of 100 to 10000, such as a range of 250 to 10000, a range of 300 to 10000, or a range of 300 to 5000. The molecular coverage per library is a number of molecular families mapped to an amplicon.

In a further example, the system and methods provide for runs and analysis having end to end reads of at least 90%. End to end reads is reads that read end to end after quality filter. i.e. reads that reported the 3' adapter at the end of the read.

In an additional example, the system and methods provide for runs and analysis having positive predictive value in of at least 90%, such as in a range of 90% to 100%, a range of 92% to 99%, or a range of 94% to 99%. The positive predictive value is the probability that a reported variant is a true variant in the sample.

In a further example, the system and method provide for runs and analysis having a specificity of not greater than 1 FP per normal sample. The specificity is, for control samples with known true variants, the number of true negative calls divided by (number of all true negative calls+number of false positive calls).

EXAMPLES

Example 1—Pre-Seeding ISPs with a Single-Cycle PCR Followed by Isothermal Amplification In this method, solid supports (Ion Torrent Ion Sphere Particles (ISPs)) were pre-seeded with monoclonal templates and distributed into wells of an Ion Torrent semiconductor sequencing chip before an isothermal amplification (templating reaction) for downstream next-generation sequencing. The pre-seeded ISPs were compared to no template control ("NTC") ISPs, which had the same template polynucleotides in solution during the templating reaction instead of before the templating reaction and during the pre-seeding reaction. Sequencing results from the different amplification reactions were compared using various metrics.

Generating Template Nucleic Acid Molecules

DNA was amplified from genomic DNA using PCR primers 1, 12, and 13 from the Oncomine Focus Assay (OFA) (Thermo Fisher Scientific, Waltham, Mass.). Adapters that facilitated binding to immobilized primer B and a primer A in solution used in the seeding reaction were added to the amplicons during 10 cycles of a second tailed PCR. The amplification generated 3 templates: OFA 1 AB, 19.2 ng/µl (148 nM); OFA 12 AB, 15.6 ng/µl (100 nM); and OFA 13 AB, 17.2 ng/µl (76 nM).

Pre-Seeding Reaction

Dilutions of the OFA 1 AB, OFA 12 AB, and OFA 13 AB templates were made and used to generate separate pre-seeded P1 ISPs in a pre-seeding reaction. The pre-seeding reaction included 6.67 µl P1 ISPs with immobilized primer B (400,000,000 ISPs), 88.33 µl 1× Platinum HiFi Mix (Thermo Fisher Scientific, Waltham, Mass.), and 5 µl of the appropriate template dilution to generate a desired number of substantially monoclonal template molecules (copy numbers 70, 665, and 4,170 for P1 ISPs). The ISP pre-seeding reaction mixtures were placed in a thermocycler for a denaturation step of 98° C. for 2 min followed by 98° C. for 25 sec and 56° C. for 10 min to generate pre-seeded ISPs. To check the relative sizes of the ISPs, 1 µl of each of the pre-seeded P1 ISPs was diluted in 999 µl Annealing Buffer (Ion PGM™ Hi-Q™ View Sequencing Solutions, (Part No. A30275)) and analyzed using a Guava easyCyte Flow Cytometer (EMD Millipore, Billerica, Mass.). The NTC P1 ISPs were also analyzed for relative size in the absence of bound template.

The remaining pre-seeded P1 ISPs were washed twice in Ion OneTouch Wash Solution wash buffer in a total volume of 1 ml. After the first wash, the samples were centrifuged at >21,000 g for 8 min and the supernatant was removed to leave ~100 µl. After the second wash and centrifugation, the supernatant was removed to leave ~50 µl sample in the tube. The sample was then treated with 300 µl of freshly prepared melt off solution (125 mM NaOH, 0.1% Tween 20) and thoroughly vortexed before incubation for 5 minutes at room temperature. These samples were then washed three times with nuclease-free (NF) $H_2O$ in a final volume of 1 ml. After each wash, the samples were centrifuged at >21,000 g for 8 min and the supernatants were removed to leave 100 µl. To check the size of the pre-seeded P1 ISPs after the last wash, 1 µl of each of the pre-seeded P1 ISPs was diluted in 99 µl Annealing Buffer and analyzed using a Guava easyCyte Flow Cytometer. The NTC P1 ISPs were also analyzed for relative size in the absence of bound template.

Determining the Numbers of Copies on the Pre-Seeded P1 ISPs

Based on the counts from the Guava easyCyte Flow Cytometer of the samples after washing, dilutions were made of the pre-seeded P1 ISPs to give 50,000, 5,000, 500, or 50 ISPs/µl. These dilutions were used in a qPCR reaction as follows: 10 µl Fast SYBR (Thermo Fisher Scientific, Waltham, Mass.), 0.2 µl 10 µM Truncated PCR A Primer (SEQ ID NO: 2), 0.2 µl 10 µM Truncated PCR B Primer (SEQ ID NO: 3), 2 µl pre-seeded P1 ISPs, and 7.6 µl NF $H_2O$. The reaction mixes were placed in a real-time PCR instrument for a denaturation step of 95° C. for 20 sec followed by 40 cycles of 95° C. for 3 sec and 60° C. for 30 sec. The $C_t$ of each qPCR reaction was compared to $C_t$ values of qPCR reactions with known numbers of molecules to calculate the number of copies of monoclonal template on each ISP. Samples with the same amount of template pre-seeded were combined to obtain an average number of copies per ISP for each group.

The pre-seeded ISPs with the same number of copies of each monoclonal template were pooled, i.e. the ISPs that had been pre-seeded with 82 copies of OFA 1 AB, OFA 12 AB, or OFA 13 AB were all pooled and similarly the ISPs pre-seeded with 775 copies of the templates were pooled and the ISPs pre-seeded with 5,400 copies of the templates were pooled.

Cassette Loading

Ion Torrent 541 chips were washed with 100 µl of 100 mM NaOH for 60 seconds, rinsed with 200 µl nuclease-free water, rinsed with 200 µl isopropyl alcohol, and aspirated dry. To load the chip, ISPs (500,000,000 NTC ISPs or pooled, pre-seeded ISPs) were vortexed, brought to 45 µl with Annealing Buffer (Ion PI™ Hi-Q™ Sequencing 200 Kit, Ion Torrent), and injected into the treated chip through the loading port. The chip was centrifuged for 2 minutes at 1424 rcf. 1 ml of foam (980 µl 50% Annealing Buffer with 20 µl 10% Triton X-100 were combined, 1 ml of air was pipetted in, and foam was further mixed by pipette for 5 seconds) was injected into the chip and the excess was aspirated. 200 µl of a 60% Annealing Buffer/40% isopropyl alcohol flush solution was injected into the chip and the chip was aspirated to dryness. The chip was rinsed with 200 µl Annealing Buffer and the chip was vacuumed dry. For the chips with pre-seeded ISPs, 40 µl of PBST was added to the chip and each port was filled with 35 µl PBST. For the chip with NTC ISPs, 5 µl of 100 pM library (equal parts OFA 1 AB, OFA 12 AB, and OFA 13 AB) was added to 110 µl Annealing Buffer to make a library mix. 40 µl of the library mix was added to the chip and each port was filled with 35 µl library mix. The chips were placed on a thermocycler and cycled one time at 95° C. for 1 minute, then 37° C. for 2 minutes, then 4° C. The chips were rinsed once with 200 µl Annealing Buffer and left wet.

Templating Reaction and Sequencing

An Ion PGM™ Template IA Pellet was rehydrated with 871 µl of Ion PGM™ Rehydration Buffer, vortexed thoroughly, and spun briefly. Each chip was injected with 40 µl pellet IA solution and the displaced Annealing Buffer was aspirated from the exit port. 20 µl pellet IA solution was added to the loading port and the chips were spun for 2 minutes at 1424 rcf. To activate the pellet IA solution, 218.2 µl Ion PGM™ Start Solution was combined with 8 µl Primer A and added to the pellet IA solution. The activated pellet IA solution was vortexed and spun briefly. To each chip, 60 µl of activated pellet IA solution was injected and the displaced fluid was aspirated. Each chip had an additional 35 µl of pellet IA solution added to each port. The chips were placed on a thermocycler set to 40° C., covered, and incubated for 15 minutes. The chips were rinsed with 200 µl 10.5 M EDTA under vacuum and aspirated dry. The chips were rinsed with 200 µl Annealing Buffer under vacuum and aspirated dry. The chips were rinsed twice with 200 µl 1% SDS under vacuum and aspirated dry. The chips were rinsed with 200 µl Flush solution (50% isopropyl alcohol/50% Annealing Buffer) under vacuum and aspirated dry. Then the chips were rinsed with 200 µl Annealing Buffer and aspirated dry. To each chip 40 µl primer mix (250 µl Sequencing Primer and 250 µl Annealing Buffer) was injected into the flow cell and 35 µl primer mix were added to each port. The chips were placed on a thermocycler and cycled one time at 95° C. for 2 minutes, then 37° C. for 2 minutes, then 4° C. The chips were rinsed once with 200 µl Annealing Buffer and aspirated. To each chip, 60 µl Enzyme Mix was added (60 µl Annealing Buffer and 6 µl PSP4 enzyme) and incubated for 5 minutes. The chips were vacuum dried and 100 µl Annealing Buffer was added immediately. The chips were loaded onto the Ion Proton System for sequencing. The Ion Proton System was initialized with Hi-Q 200 materials and sequencing was performed using 400 flows.

Results

Figure 61A:
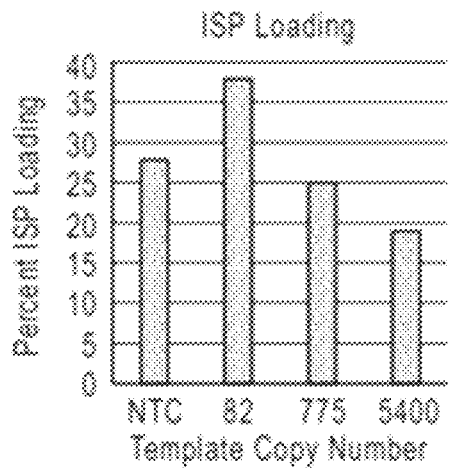
FIG. 61A-F include graphs illustrating parameters responsive to template copy number.
Figure 61B:
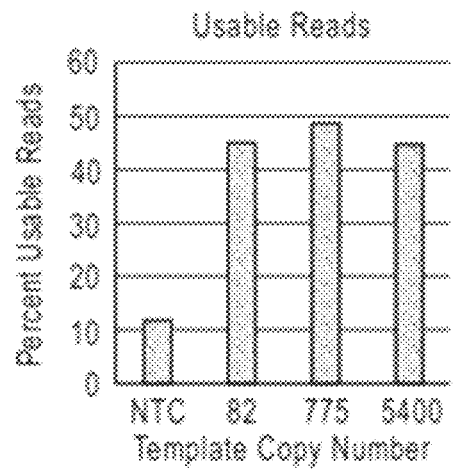
Figure 61C:
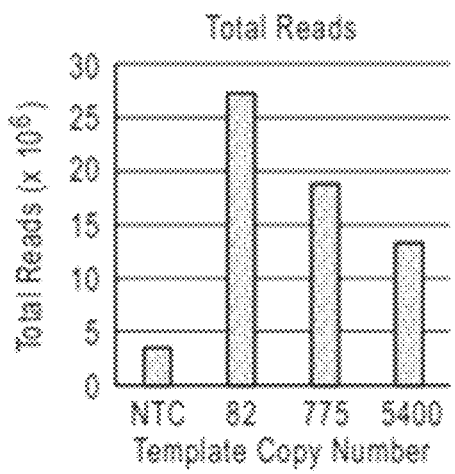
Figure 61D:
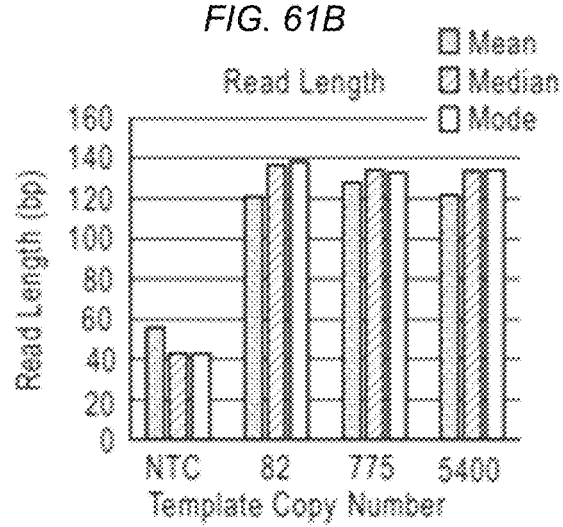
Figure 61E:
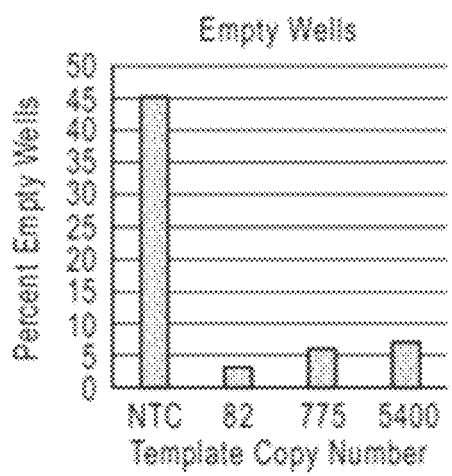
Figure 61F:
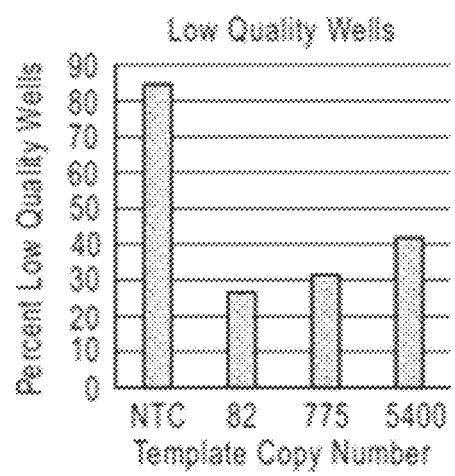

Pre-seeding the ISPs with monoclonal templates and then loading the pre-seeded onto an Ion Torrent sequencing chip generated better sequencing metrics than the NTC ISPs, which had monoclonal templates attached and amplified in one reaction. The percentage of ISP loaded increased with 82 copies of template pre-seeded onto the ISPs although higher levels of pre-seeding decreased the percentage of ISP loaded below the NTC ISPs (FIG. 61A). The percentage of usable reads increased with the pre-seeded ISPs (FIG. 61B). The pre-seeded ISPs also had up to a 9-fold increase in total reads relative to the NTC ISPs and greater than 2-fold increases in the mean, median, and mode of the read lengths (FIGS. 61C-61D). All the pre-seeded ISPs showed lower percentages of low-quality wells and wells with no template (FIGS. 61E-61F). This example demonstrates that ISPs can be pre-seeded with monoclonal template nucleic acid molecules in a method where templating is performed on ISPs distributed within the wells of an Ion Torrent chip, to achieve improved sequencing data.

Example 2—Generation of Substantially Monoclonal Template Nucleic Acid Populations on Supports Pre-Seeding/Seeding In a PCR tube, 1.2 billion copies of Ion Ampliseq Exome library (20 µL 100 pM, with standard Ion Torrent A and P1 library adapters) was mixed with 3 µL 3 µM biotin-TPCRA (sequence 5'biotin—SEQ ID NO: 2) and 3 µL 1.5 M B-trP1 (trP1 is a 23 mer segment of the Ion P1 adapter having sequence of SEQ ID NO: 1; B is a primer sequence attached to Ion Torrent Ion Sphere Particles (ISPs)) primers, and 9 µL Ion Ampliseq HiFi Master Mix 5× or other suitable polymerase-containing mixture, e.g., a mixture lacking a 3'-5'exonuclease activity. The volume was filled up to 45 µL with 10 µL nuclease-free water. The tube was thermocycled on a thermocycler with the following temperature profile: 2 min at 98° C., 2 cycles of [15 sec at 98° C.-2 min at 58° C.], final hold at 10° C. After the thermocyling, 6 billion ISPs (75 µL 80 million/µL), and 6 µL Ion Ampliseq HiFi Master Mix 5× were added to the tube. 5 µL nuclease-free water was also added to bring up total volume to 131 µL. The solution was mixed well and the tube was returned to the thermocycler. A third cycle of amplification was performed with the following temperature profile: 2 min at 98° C., 5 min at 56° C., final hold at 10° C. After thermocycling, 5 µL EDTA 0.5M was added and mixed to stop the reaction.

Enriching of the ISPs

MyOne Streptavidin C1 beads (120 µL) were transferred into a separate tube and the tube was placed on a magnet to pellet the magnetic beads. The supernatant was discarded and the tube was removed from the magnet. The beads were washed by resuspending in 150 µL Ion Torrent Annealing Buffer, then pelleting on a magnet. The supernatant was discarded, and the wash was repeated one more time with 150 µL Annealing Buffer. After discarding supernatant from the second wash, the washed MyOne C1 beads were resuspended with 50 µL Annealing Buffer. The whole content of the washed MyOne C1 in Annealing Buffer was transferred to the thermocycled PCR tube containing library and ISPs. The pipette volume was set to 160 µL, and the contents were mixed slowly by pipetting up and down three times at 1 sec per aspiration or dispensing motion. The mixture was allowed to sit at room temperature for 30 min without agitation to allow magnetic beads to capture library seeded ISPs. The tube was then put on a magnet to pellet magnetic beads and the supernatant was discarded. Tween-20 (25 µL 0.1%) in water was added to the pellet. The mixture was vortexed vigorously to elute seeded ISPs from MyOne C1 beads. The tube was pulse spun then returned to magnet. The supernatant (eluent) containing seeded ISPs was collected in a fresh tube for downstream chip loading and amplification steps.

Chip Preparation and Magnetic Loading of IPS onto Chips

An Ion Torrent semiconductor chip containing reaction chamber microwells chip was rinsed 2× with 200 µL NF water. Dynabeads M-270 streptavidin (150 µL; Thermo Fisher Scientific), which are magnetic beads with streptavidin bound to the surface thereof, were transferred to a tube which was then placed in a magnet to pellet magnetic beads. The supernatant was discarded and the tube was removed from the magnet. The following was then added to the tube containing the M-270 pelleted beads: 20 µL ISP mixture from the seeding process, 9 µL 5× Annealing Buffer, and 16 µL nuclease-free water for a total 45 µL. Alternatively, 20 ul of ISP/Library mixture was mixed with 3.2 uL 10× annealing buffer 3 uL concentrated M270 magnetic beads and 5.8 uL water for a total of 32 ul. The mixture was mixed to resuspend the M-270 pellet, and slowly injected into the chip through the loading port. A magnet placed beneath the chip was swept across the chip back and forth repeatedly to load ISPs into chip microwells. The magnetic loading sweeping was performed for 40 minutes at 30 sec/sweep. After loading, a 15 mL falcon tube containing 5 mL 1% SDS was vigorously shaken to generate a dense foam, 800 µL of which was then injected through the chip to remove magnetic beads from the chip flow cell. Flow through at the chip exit was discarded. Annealing Buffer (200 µL) was then injected through the chip, and the flow through was discarded. The chip was vacuumed dry from the chip exit. Flush (200 µL of 60% Annealing Buffer, 40% IPA) was injected through the chip which was then vacuumed dry. Annealing Buffer (200 µL) was injected to fill the chip flow cell, and the flow through was discarded at the chip exit. The chip was left filled with Annealing Buffer until ready to amplify in downstream amplification steps.

Amplification

First Step Amplification

For each chip being amplified, 1.1 uL biotinylated primer A (100 uM) and 1 uL blocking molecule (10 mg/mL Neutravidin rehydrated in buffer) were combined in a tube and incubated on ice for >15 minutes. Rehydration buffer (871 µL) was added to 1× IA pellet (PN 100032944) containing reaction components for conducting recombinase-polymerase amplification (e.g., recombinase, polymerase, single-strand binding protein, nucleotides, buffers, and other ingredients) from the ION PGM™ TEMPLATE IA 500 kit. The solution was pulse vortexed 10× and quick spun to collect tube contents. The rehydrated contents (referred to as "pellet solution", at roughly 900 ul) were kept on ice during the process. For each Ion Torrent chip, 60 µL of rehydrated IA pellet solution was slowly injected into the chip. The displaced annealing buffer was aspirated from the exit port. The chip was incubated with rehydrated IA pellet solution at RT for 4 minutes.

For each chip being amplified, 90 uL of rehydrated IA pellet solution was transferred to a new tube. The previously prepared biotinylated primer A and neutravidin blocking molecule (2.1 uL) was added and pulse mixed. A start solution (30 µL), containing an aqueous solution of 28 mM Mg(OAc)$_2$, 10 mM Tris acetate and 3.75% (V/V) methyl cellulose, was added to the tube of rehydrated IA pellet solution, pulse vortexed 10× and quick spun to form an activated amplification solution in a ~120 uL total volume. For each chip, ~60 µL activated amplification solution was slowly injected into the chip. All displaced fluid was aspirated from both ports. Next, 25 µL of remaining activated amplification solution was added to each chip port. Chips were placed onto a hot plate (thermocycler) set to 40° C. The chips were covered with a pipette tip box lid or similar cover (not the heated thermocycler cover) and allowed to incubate for 2.5 minutes.

Short Reaction Stop and Clean Between Amplification Steps

Amplified chips were taken off the hot plate or thermocycler. While vacuuming the exit port, 200 µL 0.5 M EDTA pH 8 (VWR E522-100ML) was injected into the chip and the chip was then aspirated to dry using a vacuum. In some methods, EDTA was not added to the chip and instead annealing buffer was injected into the chip to discontinue the reaction. While vacuuming the exit port, 200 µL 1× AB was injected into the chip which was then aspirated to dry. The addition of AB was repeated two more times and the chip was left filled for the 2nd step amplification. (The AB was vacuumed out twice and the third addition of AB was left in the chip.)

Second Step Amplification (No Blocker)

For each chip, 60 uL rehydrated pellet solution was slowing injected into the chip. The displaced annealing buffer was aspirated from the exit port. The chip was incubated with pellet solution at RT for 4 minutes. For each chip being prepared, 90 uL of rehydrated pellet solution was transferred to a fresh tube. Biotinylated Primer A (1.1 uL of 100 uM) was added and the tube pulse vortexed and spun. Start solution (30 µL) was added to the tube containing rehydrated pellet solution and Primer A and was pulse vortexed 10× and quick spun to generate an activated amplification solution. Approximately 60 µL activated amplification solution was injected into the chip. Displaced fluid was aspirated from both ports. An additional 25 µL of remaining amplification solution was added to each port. Chips were placed onto a hot plate (thermocycler) set to 40° C. The chips were covered with a pipette tip box lid or similar cover and allowed to incubate for 20 minutes.

Reaction Stop and Clean Up

Chips that had been subjected to amplification reactions were placed near a hood equipped with a vacuum. While vacuuming the exit port, 200 µL 0.5 M EDTA pH 8 was added and the chips were aspirated to dry the chips. In some methods, EDTA was not added to the chip and instead annealing buffer was injected into the chip to discontinue the reaction. While vacuuming the exit port, 200 µL 1× AB was added and then aspirated to dry the chip. While vacuuming the exit port, 200 µL 1% SDS solution in water (Ambion PN AM9822) was added and then aspirated to dry the chip. The SDS wash was repeated. While vacuuming the exit port, 200 µL formamide was added. The chip was incubated 3 minutes at 50° C., then aspirated to dry the chip. While vacuuming the exit port, 200 µL Flush (50% IPA/50% AB) solution was added. The chip was aspirated to dry. While vacuuming the exit port, 200 µL annealing buffer was added. The chip was left in 1×AB until ready for priming.

On Chip Sequencing Primer Hybridization and Enzyme Reaction

A tube containing Ion sequencing primer (100 uM) was thawed. For each chip being sequenced, a primer mixture of 40 uL annealing buffer and 40 uL sequencing primer was prepared and vortexed well. The chip was aspirated to dry then 80 µL of primer mixture was added to the chip (50 µL in flow cell, 15 µL in each port). The chip was placed on a thermocycler and incubated at 50° C. for 2 min, 20° C. for 5 min. 200 µL 1× AB was injected while vacuuming the exit port. An enzyme mixture was prepared with 60 µL annealing buffer and 6 µL sequencing enzyme (Ion PSP4 Sequencing Polymerase). The ports were cleaned and vacuumed to dry the chip from the inlet port. Enzyme mixture (60 µL) was added to the chip and incubated at RT for 5 minutes. The chip was aspirated to dry. AB (100 µL of 1×) was injected to fill the chip immediately. The ports were cleaned, the back of the chip was dried, and the chip was loaded on the Ion Torrent Proton (Thermo Fisher Scientific) apparatus for sequencing of the library nucleic acids.

Figure 60:
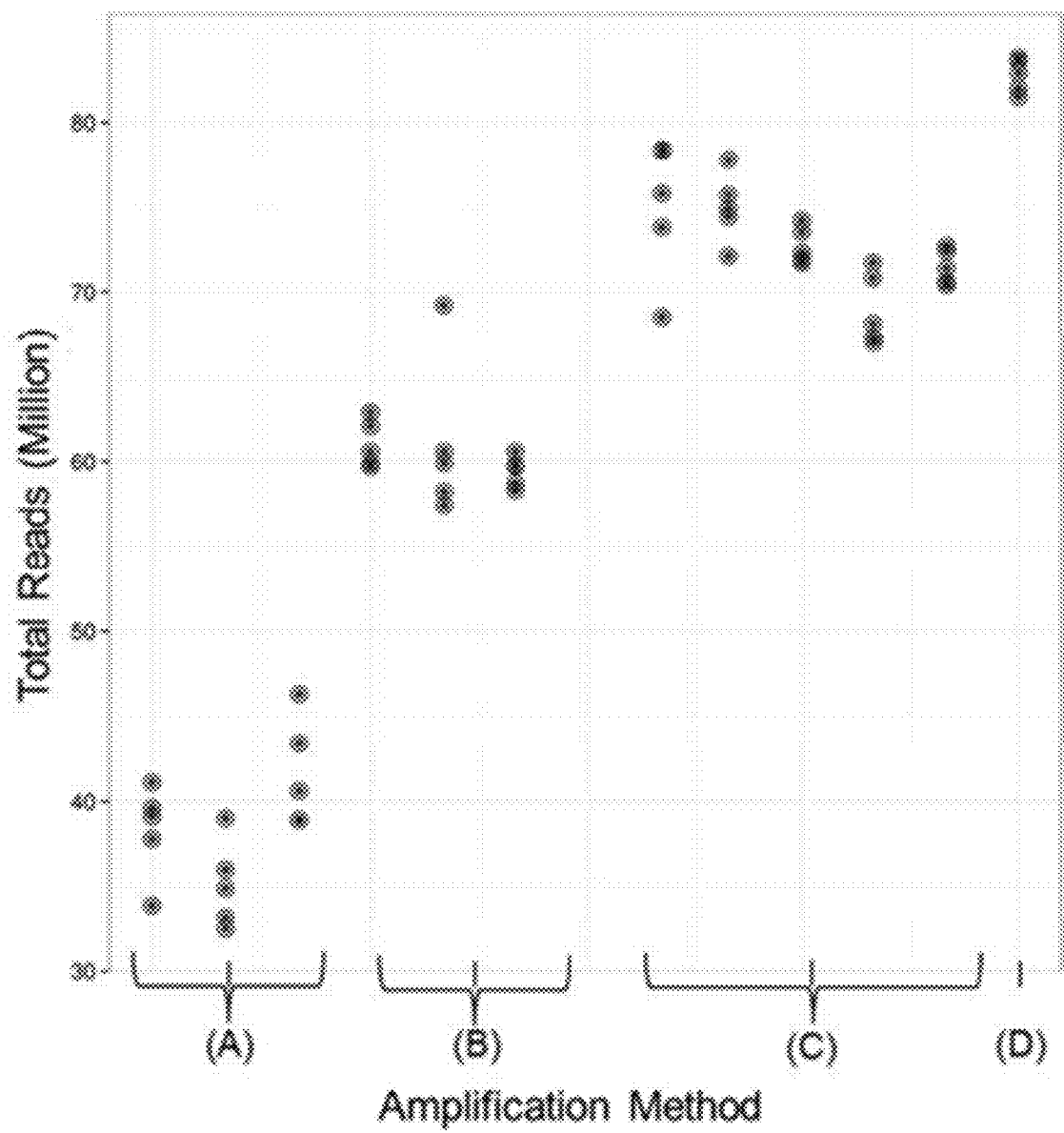
FIG. 60 includes a graph indicating a total number of reads resulting from various amplification methods.

Example 3—Comparison of Sequencing Results Using Different Nucleic Acid Manipulation Methods FIG. 60 shows the total usable reads for groups of nucleic acid sequencing runs of nucleic acid templates generated using four different amplification conditions (A-D in the figure). In method A, non-templated Ion Sphere Particles (ISPs) were loaded into microwells of Ion Torrent 541 chips according to methods described in Example 2 herein. Subsequently, library molecules (a 110-bp hg19 fragment library) with adaptors complementary to the ISP primer were hybridized to the pre-loaded ISPs with a single 95° C. 1 min/37° C. 1 min thermocycling step following injection of the library amplicons into the chip. Following library hybridization, amplification was performed using a single-step RPA templating amplification method essentially as described in Example 2. The primers were not biotinylated. Method B employed two important changes to amplification protocol A: 1) an additional amplification step (a "first" amplification step) prior to the templating amplification and 2) incorporation of neutravidin and biotinylated solution primers in the added first amplification step. In this example, the first amplification step, which is an isothermal RPA amplification, is 2.5 minutes and contains an equivalent concentration of biotinylated solution primer and neutravidin. The second amplification step is 15 minutes and does not contain neutravidin. In this method, the first amplification step serves to locally amplify template copies while adding drag (via neutravidin) to limit well-2-well diffusion of nascent strands. After 2.5 minutes, enough local copies are created that the drag component is no longer needed. The second amplification step was then carried out as described in Example 2. In Methods C and D, a 220-bp hg19 Ampliseq Exome Library was used. Method C improves upon method B by replacing the library hybridization method in methods A and B, with a solution-based pre-amplification ISP enrichment method as described in Example 6 herein. Thus, instead of performing all steps in wells, the first step of hybridizing the library to the ISPs was done in solution, then magnetic beads were added to the tube, the template-containing ISPs were enriched, and then separated from the magnetic beads and loaded into the wells for the 2-step amplification as was done in Method B. The pre-amplification enrichment method enables loading of ISPs with single library template copies. Finally, amplification method D, which was carried out according to Method C, employed a modified ISP primer sequence compared with method C. The modified primer, AV4, has the sequence of SEQ ID NO: 4. As shown in FIG. 60, the combination of improvements made from Methods A-D enable total reads equivalent to sequencing carried out on template nucleic acids amplified through emulsion PCR.

Example 4. Template Nucleic Acid Seeding Method and Indirect Capture of Seeded Supports In this method (which is illustrated in FIG. 58) of seeding solid supports with target template nucleic acids, a series of amplification reactions of adapter-modified nucleic acid library molecules is conducted to generate a single amplification product that is capable of attaching to a solid support through hybridization to a primer immobilized on the support. The product includes a single-stranded 5' end overhang, referred to as a "handle" that provides a short sequence that can be hybridized with a capture oligonucleotide for use in enriching the target template nucleic acid-bound supports.

Seeding Method

PCR amplification mixture was prepared by combining library DNA with polymerase and two primers: (1) a primer having a sequence of nucleotides that includes, in the 3' to 5' direction, a nucleotide sequence complementary to the sequence of a first double-stranded adapter on one end of the library DNA amplicons, a polymerase stop site and a sequence of nucleotides (a handle sequence) that is not complementary to library amplicon sequences and (2) a fusion primer having a sequence of nucleotides that includes, in the 5' to 3' direction, a nucleotide sequence identical to the sequence of a primer immobilized to solid supports to which template target nucleic acids would be seeded fused to a nucleotide sequence complementary to a portion of the sequence of a double-stranded adapter on the end of the library DNA amplicons opposite to the end at which the first adapter, to which the first primer is complementary, is located. Libraries were generated using the Oncomine™ Comprehensive Assay v3 (Life Technologies Corporation, Carlsbad, Calif.) and Oncomine focus Assay library preparation protocols according to manufacturer's instructions. The first primer was a TPCRA primer (SEQ ID NO: 2) with a handle sequence at the 5' end of the primer and a polymerase stop site located between the handle and TPCRA sequences. The second primer was a fusion of an AV4 primer sequence (SEQ ID NO: 4) to the trP1 sequence (trP1 is a 23 mer segment of the Ion P1 adapter of SEQ ID NO: 1). In a 0.2 ml PCR tube, 30 µl of 100 pM library, 3 µl of 3 pM handle-TPCRA primer, 3 µl of 1.5 pM AV4-trP1 fusion primer and 9 µl of Ion Ampliseq 5× HiFi PCR Master Mix, or other suitable polymerase-containing mixture, e.g., a mixture lacking a 3'-5'exonuclease activity, were added and briefly mixed and quick spun. The 45-µl content in the PCR tube was thermocycled in a thermocycler with the following profile: 98° C. for 2 min, then two cycles of 98° C. for 15 sec-64° C. for 90 sec-58° C. for 2 min followed by a 10° C. hold. The tube was removed from the thermocycler and 6 billion (54.5 µL at 110 M/µL) Ion Sphere Particles (ISPs; Thermo Fisher Scientific) and 6 µL of 5× HiFi PCR master mix, or other suitable polymerase-containing mixture, e.g., a mixture lacking a 3'-5'exonuclease activity, were added to the mixture. The tube was briefly mixed and spun down. The total 105.5 µL mixture in the PCR tube was placed in a thermocycler again, and thermocycled with the following profile: 98° C. 2 min-56° C. 5 min-10° C. hold.

Capture and Enrichment of Seeded Supports

A biotinylated capture oligonucleotide complementary to the handle of the handle-TPCRA primer was added to the PCR tube taken from the thermocycler and the tube was vortexed thoroughly and spun down. The tube was allowed to incubate at room temperature for 5 min. In a separate tube, 120 µL MyOne C1 magnetic beads was added. The magnetic beads were washed twice with 150 µL Annealing Buffer, and then resuspended in 50 µL Annealing Buffer. The washed magnetic beads in 50 µL suspension were combined with the PCR reaction tube containing capture oligonucleotide after 5 min incubation. The whole content was gently mixed by slowly pipetting up and down 3 times. The tube was allowed to incubate at room temperature without agitation for 30 min. After 30 min incubation, the tube was carefully placed on a magnetic stand (or a magnetic plate) to pellet the MyOne C1 beads with library seeded ISPs assembly attached. Supernatant was removed without disturbing the pellet. To the pellet, 25 µL water was added to elute the target template-seeded ISPs. The tube was vortexed vigorously and quickly spun down. The tube was placed on a magnetic stand again to pellet. The supernatant containing the enriched target template-seeded ISPs was transferred to a fresh tube and was ready for use in further analysis, e.g., sequencing.

For analysis of the yield of the enriched seeded ISPs, 1 µL of the product was serially diluted by 100,000-fold in Ion Annealing Buffer. SYBR™ Gold Nucleic Acid Gel Stain (Thermo Fisher Scientific, S11494) was used at 0.5× in the final dilution to stain the ISPs. The SYBR Gold stained ISP dilution was measured on Guava easyCyte flow cytometer (Luminex Corporation, Austin, Tex.) to analyze the concentration and the total yield of enriched ISPs in the undiluted sample. The yield for an Oncomine Focus Assay library and an Oncomine™ Comprehensive Assay v3 (Life Technologies Corporation, Carlsbad, Calif.) was measured to be 475 million and 383 million ISPs, respectively.

Templating Amplification and Sequencing of Library Nucleic Acids

The enriched seeded ISPs were loaded onto an Ion™ semiconductor chip (Life Technologies, Carlsbad, Calif.) containing reaction chamber microwells. The loading process was as described in Example 2. The following were added to a tube containing 150 µL Dynabeads M-270 streptavidin (Thermo Fisher Scientific): 20 µL ISP mixture from the seeding process, 9 µL 5× Annealing Buffer, and 16 µL nuclease-free water for a total 45 µL. The mixture was mixed to resuspend the M-270 pellet, and slowly injected into the chip through the loading port. A magnet placed beneath the chip was swept across the chip back and forth repeatedly to load ISPs into chip microwells. After loading, the magnetic beads and excess ISPs were removed from the chip flow cell. The nucleic acids on the seeded ISPs in the microwells were then subjected to a two-step amplification process with a short reaction stop and chip washing between the two amplification reactions as described in Example 6.

ISPs containing amplified templates were sequenced using the Ion Proton (Thermo Fisher Scientific) system. A tube containing Ion sequencing primer (100 uM) was thawed. For each chip being sequenced, a primer mixture of 40 uL annealing buffer and 40 uL sequencing primer was prepared and vortexed well. The chip was aspirated to dry then 80 µL of primer mixture was added to the chip (50 µL in flow cell, 15 µL in each port). The chip was placed on a thermocycler and incubated at 50° C. for 2 min, 20° C. for 5 min. 200 µL 1× AB was injected while vacuuming the exit port. An enzyme mixture was prepared with 60 µL annealing buffer and 6 µL sequencing enzyme (Ion PSP4 Sequencing Polymerase). The ports were cleaned and vacuumed to dry the chip from the inlet port. Enzyme mixture (60 µL) was added to the chip and incubated at RT for 5 minutes. The chip was aspirated to dry. Annealing buffer (100 µL of 1×) was injected to fill the chip immediately. The ports were cleaned, the back of the chip was dried, and the chip was loaded on the Ion Proton apparatus for sequencing of the library nucleic acids. The mean read lengths for sequence reads of the Oncomine Focus Assay library and the Oncomine Comprehensive Assay v3 library were 113 bp and 109 bp, respectively. The majority (99%) of the identified reads aligned to the target region.

Example 5

A library is prepared automatically from four samples using an OFA assay. The library is applied to a single lane of a four lane ION Torrent chip in an automated process described above in Example 2. A variant call report is provided in 13.8 hours with 14.7 million reads. The run had a raw read accuracy of 98.98% and a Q20 MRL of 110 bp.

Example 6

A library is prepared automatically from six samples using an OCAv3 assay with both DNA and RNA. The library is applied to four lanes of an ION Torrent chip in an automated process described above in Example 2. A variant call report is provided in 30.3 hours with 56.2 million reads. The run had a raw read accuracy of 99.05% and a Q20 MRL of 107 bp.

Example 7

A library is prepared automatically from four samples using an TCR Beta-LR assay. The library is applied to one lane of an ION Torrent chip in an automated process described above in Example 2. A variant call report is provided in 18.7 hours with 14.6 million reads. The run had a Q20 MRL of 292 bp.

Example 8

Two libraries are prepared automatically, a first from four samples using an OFA assay, and a second from four samples using TCR-Beta-LR assay. The libraries are applied to separate lanes of an ION Torrent chip in an automated process described above in Example 2. A variant call report is provided in 22.1 hours with respective reads in each lane of 13.5 million reads and 11.7 million reads. The first lane including the first library provided a raw read accuracy of 99.1% and a Q20 MRL of 112 bp. The second lane with the second library run had a Q20 MRL of 275 bp.

Example 9

A set of 6 runs is performed, each utilizing a library prepared automatically from four samples using an OFA assay and applied to a single lane of a four lane ION Torrent chip in an automated process described above in Example 2. A variant call report is provided in 13.8 hours. The runs provided mean performance as follows:

|  | Mean | CV (%) |
| --- | --- | --- |
| Raw Accuracy | 99.2 | 0.1 |
| Q20 MRL | 104.5 | 0.5 |
| Total Reads (M) | 13.1 | 4.4 |
| Uniformity_of_base_coverage | 98.6 | 0.4 |
| Average Percent reads on target | 98.1 | 0.1 |

Example 9

A set of 4 runs is performed, each utilizing a library prepared automatically from six samples derived from FFPE DNA/RNA and using an OCAv3 assay and applied to four lanes of an ION Torrent chip in an automated process described above in Example 2. A variant call report is provided in 30.8 hours. The runs provided mean performance as follows:

| Metric | Average | % cv | |
| --- | --- | --- | --- |
| Total reads/Lane | 12.9M | 12.10 | 11.7% |
| DNA-Amplicon uniformity | 95.1% | 1.4% | |
| DNA - Mapped reads | 6022807 | 16.2% | |
| DNA - Coverage depth | 1465 | 13.9% | |
| DNA - MAPD | 0.316 | 9.3% | |
| DNA - Unaligned RL | 100.6 | 4.1% | |
| BC imbalance | <80% | — | |

Nucleotide Sequences

| SEQ ID NO | NUCLEOTIDE SEQUENCE |
| --- | --- |
| 1 | CCTCTCTATGGGCAGTCGGTGAT |
| 2 | CCATCTCATCCCTGCGTGTC |
| 3 | CCTATCCCTGTGTGCCTTG |
| 4 | ATTCGAGCTGTTCATCTGTATCTTGCGCTACCAA |

In a first aspect, a sequencing system comprises an automated sequencing instrument adapted to determine variant calls for one or more extracted polynucleotide samples with a performance of at least 98.5% raw read accuracy and a run time in a range of 5 hours to 14 hours to determine variant calls when sequencing 4 extracted polynucleotide samples using a targeted assay with one DNA pool per sample and an average amplicon size in a range of 100 to 120 bases.

In a second aspect, a sequencing system comprises an automated sequencing instrument adapted to determine variant calls for one or more extracted polynucleotide samples with a performance of at least 98.5% raw read accuracy and a run time in a range of 15 hours to 24 hours to determine variant calls when sequencing 32 extracted polynucleotide samples using a targeted assay with one DNA pool per sample and an average amplicon size in a range of 100 to 120 bases.

In a third aspect, a sequencing system comprises an automated sequencing instrument adapted to determine variant calls for one or more extracted polynucleotide samples with a performance of at least 98.5% raw read accuracy and a run time in a range of 20 hours to 30 hours to determine variant calls when sequencing 6 extracted polynucleotide samples using a targeted assay with two DNA pools and two RNA pools per sample and an average amplicon size in a range of 100 to 120 bases.

In a fourth aspect, sequencing system comprises an automated sequencing instrument adapted to determine variant calls for one or more extracted polynucleotide samples with a performance of at least 98.5% raw read accuracy and a run time in a range of 20 hours to 28 hours to determine variant calls when sequencing 12 extracted polynucleotide samples using a targeted assay with one DNA pool per sample and an average amplicon size in a range of 190 to 220 bases.

In a fifth aspect, a sequencing system comprises an automated sequencing instrument adapted to determine variant calls for one or more extracted polynucleotide samples with a performance of at least 98.5% raw read accuracy and a run time in a range of 15 hours to 24 hours to concurrently determine variant calls when sequencing 8 extracted polynucleotide samples based on first and second assays, a first set of 4 extracted polynucleotide samples of the 8 extracted polynucleotide samples using the first assay with one DNA pool per sample and an average amplicon size in a range of 100 to 120 bases, a second set of 4 extracted polynucleotide samples of the 8 extracted polynucleotide samples using the second assay with one DNA per sample and an average amplicon size in a range of 190 to 220 bases.

In an example of the first aspect, the run time is in a range of 5 hours to 12 hours.

In an example of the first through fifth aspects and the above examples, the raw read accuracy is at least 99.0% Raw Read Accuracy. For example, the raw read accuracy is at least 99.1%.

In another example of the first through fifth aspects and the above examples, the performance is further characterized by a Q20 median read length of at least 100 bases and not greater than 450 bases. For example, the Q20 median read length is at least 102 bases and not greater than 300 bases. In another example, the Q20 median read length is at least 104 bases and not greater than 300 bases.

In a further example of the first through fifth aspects and the above examples, the performance is further characterized by a uniformity of at least 97%. For example, the uniformity is at least 98%. In another example, the uniformity is at least 98.5%.

In an additional example of the first through fifth aspects and the above examples, the performance is further characterized by an average percent reads on target of at least 97%. For example, the average percent reads on target is at least 98%. In an example, the average percent reads on target is at least 98.1%.

In another example of the first through fifth aspects and the above examples, the performance is further characterized by a total reads in a range of 13 million bases to 100 million bases. For example, the total reads is in a range of 13 million bases to 60 million bases. In an example, the total reads is in a range of 14.5 million bases to 25 million bases.

In an sixth aspect, a method for sequencing includes providing to a sequencing instrument 4 extracted polynucleotide samples, a sequencing substrate, and reagents for an assay with one DNA pool per sample and an average amplicon size in a range of 100 to 120 bases; generating with the sequencing instrument a plurality of polynucleotides derived from the assay; sequencing with the sequencing instrument the plurality of polynucleotides with a raw read accuracy of at least 98.5%; and preparing with the sequencing instrument a variant call report based on the sequencing; wherein the generating, the sequencing, and the preparing are performed in a run time within a range of 5 hours to 14 hours.

In an example of the sixth aspect, the run time is in a range of 5 hours to 12 hours.

In another example of the sixth aspect and the above examples, the raw read accuracy is at least 99.1%. For example, the raw read accuracy is at least 99.2%.

In a further example of the sixth aspect and the above examples, the performance is further characterized by a Q20 median read length of at least 100 bases and not greater than 300 bases. For example, the Q20 median read length is at least 102 bases and not greater than 300 bases. In an example, the Q20 median read length is at least 104 bases and not greater than 300 bases.

In an additional example of the sixth aspect and the above examples, the performance is further characterized by a uniformity of at least 97%. For example, the uniformity is at least 98%. In another example, the uniformity is at least 98.5%.

In another example of the sixth aspect and the above examples, the performance is further characterized by an average percent reads on target of at least 97%. For example, the average percent reads on target is at least 98%. In an example, the average percent reads on target is at least 98.1%.

In a further example of the sixth aspect and the above examples, the performance is further characterized by a total reads in a range of 13 million bases to 100 million bases. For example, the total reads is in a range of 14 million bases to 60 million bases. In an example, the total reads is in a range of 14.5 million bases to 25 million bases.

In a seventh aspect, a method for sequencing includes providing to a sequencing instrument, reagent solutions for a first type of assay, reagent solutions for a second type of assay, a sequencing substrate having a plurality of lanes, and at least two polynucleotide samples; generating with the sequencing instrument a first plurality of polynucleotides derived from at least a first polynucleotide sample of the at least two purified polynucleotide samples and the first type of assay; generating with the sequencing instrument a second plurality of polynucleotides derived from at least a second polynucleotide sample of the at least two purified polynucleotide samples and the second type of assay; loading the first plurality of polynucleotides into a first lane of the plurality of lanes of the sequencing substrate; loading the second plurality of polynucleotides into a second lane of the plurality of lanes of the sequencing substrate; sequencing with the sequencing instrument the first and second pluralities of polynucleotides; and preparing with the sequencing instrument a variant call report in a run time within a range of 10 hours to 24 hours following providing, the sequencing having a performance characterized by a raw read accuracy of at least 98.5% for at least one of the first and second pluralities of polynucleotides.

In an eighth aspect, a sequencing instrument comprises an automated system to concurrently generate a first population of polynucleotides from a first purified sample and a first assay type and generate a second population of polynucleotides from a second purified sample and a second assay type different from the first assay type, and a sequencing apparatus to simultaneously sequence the first population of polynucleotides and the second population of polynucleotides.

In a ninth aspect, a method of sequencing a plurality of samples includes generating automatically using a sequencing instrument a first population of polynucleotides from an assay and a first sample; loading the first population of polynucleotides into a first lane of a multilane sequencing substrate using the sequencing instrument; sequencing the first population of polynucleotides using the multilane sequencing substrate and the sequencing instrument; generating automatically using a sequencing instrument a second population of polynucleotides from a second assay and a second sample following sequencing the first population of polynucleotides; loading the second population of polynucleotides into a second lane of the multilane sequencing substrate using the sequencing instrument; and sequencing the second population of polynucleotides using the multilane sequencing substrate and the sequencing instrument.

In a tenth aspect, a system includes a sequencing instrument adapted to receive one or more extracted polynucleotide samples and generate a variant call report, wherein: a run time between receipt of the one or more extracted polynucleotide samples and generation of the variant call report when sequencing using assay including one polynucleotide pool per sample run on the sequencing instrument is between about 5 hours to 14 hours; the system does not require any manual intervention to generate the variant call report other than providing the one or more extracted polynucleotide samples, a set of consumables, and a run plan.

In an eleventh aspect, an integrated automated system for nucleic acid processing and analysis includes components for preparing nucleic acid templates from one or more samples containing nucleic acids; components for attaching the nucleic acid templates to one or more surfaces; components for amplifying the nucleic acid templates on the one or more surfaces; components for generating nucleic acid sequences complementary to the nucleic acid templates through nucleotide polymerization; components for detecting nucleotides polymerized in generating nucleic acid sequences complementary to the nucleic acid templates; and components for identifying nucleotides polymerized in generating nucleic acid sequences complementary to the nucleic acid templates; wherein the integrated automated system requires only one intervention step by a human user.

In an example of the eleventh aspect, the integrated automated system further includes components for analyzing the identified nucleotides to determine the sequences of the nucleic acid templates.

In another example of the eleventh aspect and the above examples, the integrated automated system further includes the human user is unskilled in sample nucleic acid processing and analysis as performed by the system.

In a further example of the eleventh aspect and the above examples, the integrated automated system further includes the system is capable of processing and analyzing nucleic acids to generate at least about 12 million nucleic acid sequence reads from each of four or more different samples simultaneously.

In an additional example of the eleventh aspect and the above examples, the integrated automated system further includes the system is capable of processing and analyzing nucleic acids to generate at least about 1 million nucleic acid sequence reads from each of 96 or more different samples simultaneously.

In another example of the eleventh aspect and the above examples, the integrated automated system further includes the system is capable of processing and analyzing nucleic acids to generate at least about 0.5 million nucleic acid sequence reads from each of 48 or more different samples simultaneously.

In a further example of the eleventh aspect and the above examples, the majority of the nucleic acid sequence reads each comprise at least about 350 nucleotides.

In an additional example of the eleventh aspect and the above examples, the components for preparing the nucleic acid templates comprise a system for amplifying nucleic acids of at least one of the one or more samples in a single amplification reaction mixture using two or more different pairs of amplification primers. For example, the components for preparing the nucleic acid templates comprise a system for amplifying nucleic acids of at least one of the one or more samples in a single amplification reaction mixture using 50 or more different pairs of amplification primers.

In another example of the eleventh aspect and the above examples, the components for preparing the nucleic acid templates are capable of preparing templates from RNA or DNA.

In a further example of the eleventh aspect and the above examples, the components for preparing the nucleic acid templates comprise a system for amplifying nucleic acids of at least one of the one or more samples in a single amplification reaction mixture using two or more different pairs of amplification primers. For example, the system is capable of processing nucleic acids from four or more samples to generate at least 12 million nucleic acid sequence reads in about 5 to 14 hours.

In a twelfth aspect, an automated method for processing a sample for nucleic acid analysis includes providing a sample comprising nucleic acid; and inputting the sample to the system of the above aspects and allowing the system to process the sample. For example, the system provides a variant call report in a run time of 5 to 14 hours when an assay having one DNA pool per sample and an average amplicon size in a range of 100 to 120 bases is used.

In a thirteenth aspect an integrated sample processing device for automated nucleic acid analysis includes a user input module, a nucleic acid library preparation unit, a nucleic acid templating unit, a nucleotide polymerization signal detection unit, a nucleotide polymerization signal data processing unit, a nucleotide polymerization data analysis unit, and a control unit; wherein the device is configured for automated sample processing with only one intervention step by a user unskilled in sample processing for nucleic acid analysis.

In an example of the thirteenth aspect, the device is capable of providing a variant call report in a run time of 5 to 14 hours when, for four samples, an assay having one DNA pool per sample and an average amplicon size in a range of 100 to 120 bases is used.

In another example of the thirteenth aspect and the above examples, the user instruction input unit comprises a touchscreen user interface.

In a further example of the thirteenth aspect and the above examples, the nucleic acid library preparation unit comprises a well plate disposed on an instrument deck.

In an additional example of the thirteenth aspect and the above examples, the nucleic acid library preparation unit comprises a pipetting robot.

In another example of the thirteenth aspect and the above examples, the nucleic acid templating unit comprises a magnetic loading apparatus.

In a further example of the thirteenth aspect and the above examples, the signal detection unit comprises an electronic interface to interact with a sensor device.

In an additional example of the thirteenth aspect and the above examples, the signal data processing unit and the analysis unit are implemented in computational devices.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A sequencing system comprising an automated sequencing instrument including a preparation deck to prepare one or more extracted polynucleotide samples for loading, a loading station to load the one or more modified extracted polynucleotides on a substrate, and a sequencing station, the sequencing station to detect nucleotide incorporation using ion-sensitive field effect transistors, the automated sequencing instrument adapted to determine variant calls for the one or more extracted polynucleotide samples with a performance of at least 98.5% raw read accuracy and a run time in a range of 5 hours to 14 hours to determine variant calls when sequencing 4 extracted polynucleotide samples using a targeted assay with one DNA pool per sample and an average amplicon size in a range of 100 to 120 bases.

2. The sequencing system of claim 1, wherein the run time is in a range of 5 hours to 12 hours.

3. The sequencing system of claim 1, wherein the raw read accuracy is at least 99.0%.

4. The sequencing system of claim 3, wherein the raw read accuracy is at least 99.1%.

5. The sequencing system of claim 1, wherein the performance is further characterized by a Q20 median read length of at least 100 bases and not greater than 450 bases.

6. The sequencing system of claim 5, wherein the Q20 median read length is at least 102 bases and not greater than 300 bases.

7. The sequencing system of claim 6, wherein the Q20 median read length is at least 104 bases and not greater than 300 bases.

8. The sequencing system of claim 1, wherein the performance is further characterized by a uniformity of at least 97%.

9. The sequencing system of claim 8, wherein the uniformity is at least 98%.

10. The sequencing system of claim 9, wherein the uniformity is at least 98.5%.

11. The sequencing system of claim 1, wherein the performance is further characterized by an average percent reads on target of at least 97%.

12. The sequencing system of claim 11, wherein the average percent reads on target is at least 98%.

13. The sequencing system of claim 12, wherein the average percent reads on target is at least 98.1%.

14. The sequencing system of claim 1, wherein the performance is further characterized by a total reads in a range of 13 million bases to 100 million bases.

15. The sequencing system of claim 14, wherein the total reads is in a range of 13 million bases to 60 million bases.

16. The sequencing system of claim 15, wherein the total reads is in a range of 14.5 million bases to 25 million bases.

* * * * *

```
                            SEQUENCE LISTING

<160> NUMBER OF SEQ ID NOS: 4

<210> SEQ ID NO 1
    <211> LENGTH: 23
    <212> TYPE: DNA
    <213> ORGANISM: Artificial Sequence
    <220> FEATURE:
    <223> OTHER INFORMATION: Synthetic DNA

<400> SEQUENCE: 1
cctctctatg ggcagtcggt gat                                              23

<210> SEQ ID NO 2
    <211> LENGTH: 20
    <212> TYPE: DNA
    <213> ORGANISM: Artificial Sequence
    <220> FEATURE:
    <223> OTHER INFORMATION: Synthetic DNA

<400> SEQUENCE: 2
ccatctcatc cctgcgtgtc                                                  20

<210> SEQ ID NO 3
    <211> LENGTH: 20
    <212> TYPE: DNA
    <213> ORGANISM: Artificial Sequence
    <220> FEATURE:
    <223> OTHER INFORMATION: Synthetic DNA

<400> SEQUENCE: 3
cctatcccct gtgtgcccttg                                                 20

<210> SEQ ID NO 4
    <211> LENGTH: 34
    <212> TYPE: DNA
    <213> ORGANISM: Artificial Sequence
    <220> FEATURE:
    <223> OTHER INFORMATION: Synthetic DNA

<400> SEQUENCE: 4
attcgagctg ttcatctgta tcttgcgcta ccaa                                  34
```